US012673071B2

(12) United States Patent
Huang et al.

(10) Patent No.: US 12,673,071 B2
(45) Date of Patent: Jul. 7, 2026

(54) ANTI-BCMA ANTIBODIES AND CHIMERIC ANTIGEN RECEPTORS

(71) Applicant: SHANGHAI ABELZETA LTD., Shanghai (CN)

(72) Inventors: Jiaqi Huang, Rockville, MD (US); Yihong Yao, Rockville, MD (US); Shigui Zhu, Rockville, MD (US); Xin Yao, Rockville, MD (US); Yun Ji, Shanghai (CN); Wei Xue, Shanghai (CN); Yutian Wei, Shanghai (CN); Cheng Chen, Shanghai (CN); Chaocan Zhang, Shanghai (CN)

(73) Assignee: Shanghai AbelZeta Ltd., Shanghai (CN)

( * ) Notice: Subject to any disclaimer, the term of this patent is extended or adjusted under 35 U.S.C. 154(b) by 797 days.

(21) Appl. No.: 17/924,410

(22) PCT Filed: May 7, 2021

(86) PCT No.: PCT/US2021/031299

§ 371 (c)(1),
(2) Date: Nov. 10, 2022

(87) PCT Pub. No.: WO2021/231213

PCT Pub. Date: Nov. 18, 2021

(65) Prior Publication Data

US 2023/0181640 A1 Jun. 15, 2023

(30) Foreign Application Priority Data

May 11, 2020 (CN) ......................... 202010394296.5

(51) Int. Cl.
*A61K 40/11* (2025.01)
*A61K 35/17* (2015.01)
*C07K 16/28* (2006.01)

(52) U.S. Cl.
CPC .......... *A61K 35/17* (2013.01); *C07K 16/2878* (2013.01); *C07K 2317/33* (2013.01); *C07K 2317/622* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 5,350,674 | A | 9/1994 | Boenisch et al. |
| 5,399,346 | A | 3/1995 | Anderson et al. |
| 5,580,859 | A | 12/1996 | Felgner et al. |
| 5,585,089 | A | 12/1996 | Queen et al. |
| 5,585,362 | A | 12/1996 | Wilson et al. |
| 5,589,466 | A | 12/1996 | Felgner et al. |
| 6,326,193 | B1 | 12/2001 | Liu et al. |
| 8,575,317 | B2 | 11/2013 | Kuramochi et al. |
| 10,988,546 | B2 | 4/2021 | Kinneer et al. |
| 2015/0218267 | A1 | 8/2015 | Brodeur et al. |
| 2017/0298119 | A1 | 10/2017 | Wollacott et al. |
| 2019/0112382 | A1 | 4/2019 | Oden et al. |

FOREIGN PATENT DOCUMENTS

| | | | |
|---|---|---|---|
| CA | 3070539 | A1 | 2/2019 |
| CA | 3095827 | A1 | 10/2019 |
| CN | 105777911 | A | 7/2016 |
| CN | 108350076 | A | 7/2018 |
| JP | 2017515470 | A | 6/2017 |
| WO | 0129058 | A1 | 4/2001 |
| WO | 0196584 | A2 | 12/2001 |
| WO | 2010/056898 | A2 | 5/2010 |
| WO | 2015/158671 | A1 | 10/2015 |
| WO | 2016/150899 | A2 | 9/2016 |
| WO | 2016/207304 | A2 | 12/2016 |
| WO | 2017/189959 | A1 | 11/2017 |
| WO | 2019/025983 | A1 | 2/2019 |
| WO | 2019196713 | A1 | 10/2019 |

OTHER PUBLICATIONS

Lerner Nature 1982; 299:592-596, see p. 595-596.*
Ferrara et al, 2015 mAB, v. 7 p. 32-41.*
Edwards et al., JMB 2003, v.334, pp. 103-118.*
Marino et al.: "A complex water network contributes to high-affinity binding in an antibody-antigen interface": Data in Brief 6 (2016) 394-397.
Zhang et al: "Research Progresson in B-Cell Maturation Antigen Based Tumor Immunotherapy": Pharmaceutical Biotechnology: 2018, 25(1): 1-6.
International Search Report and Written Opinion of PCT/US21/31299 mailed Oct. 14, 2021.
Ma et al: "Chimeric antigen receptor T cell targeting B cell maturation antigen immunotherapy is promising for multiple myeloma", Annals of Hematology, vol. 98, No. 4, 2019, pp. 813-822. [10 pages].
Bird et al. "Single-Chain Antigen-Binding Proteins", Science, 1988, 242:423-426 [4 pages].
Bowie et al. "Deciphering the Message in Protein Sequences: Tolerance to Amino Acid Substitutions", Science, 247: 1306-1310 (1990) [5 pages].

(Continued)

*Primary Examiner* — Michail A Belyavskyi
(74) *Attorney, Agent, or Firm* — LEASON ELLIS LLP

(57) ABSTRACT

Anti-BCMA antibodies and chimeric antigen receptors (CARs) are provided. Immune cells expressing the anti-BCMA CAR can be used to treat cancer. The anti-BCMA antibodies and CARs can recognize the extracellular domains of human BCMA. The anti-BCMA CAR T cells show specific cytotoxicity towards BCMA-positive target cells.

14 Claims, 52 Drawing Sheets

Specification includes a Sequence Listing.

(56) References Cited

OTHER PUBLICATIONS

Cunningham et al. "High-Resolution Epitope Mapping of hGH-Receptor Interactions by Alanine-Scanning Mutagenesis", Science, 244: 1081-1085 (1989) [5 pages].
Gonnet et al. "Exhaustive Matching of the Entire Protein Sequence Database", Science 256:1443-45 (1992). [3 pages].
Huston et al. "Protein engineering of antibody binding sites: Recovery of specific activity in an anti-digoxin single-chain Fv analogue produced in*Escherichia coli*", Proc. Natl. Acad. Sci. USA, 1988, 85:5879-5883. [5 pages].
Iwasaki et al. "Importance of cynomolgus monkeys in development of monoclonal antibody drugs", Drug Metabolism and Pharmacokinetics, vol. 34, No. 1, 2019, pp. 55-63. [9 pages].
Kabat et al. "Sequences of Proteins of Immunological Interest", NIH Publ. No. 91-3242, vol. I, 5th edition, pp. 647-669 (1991) [25 pages].
Kufer et al. "A revival of bispecific antibodies", 2004, Trends Biotechnol. 22(5):238-244 [7 pages].
Munson et al. "Ligand: A versatile computerized approach for characterization of ligand-binding systems", Anal. Biochem., 107:220 (1980). [20 pages].
Pearson. "Using the FASTA program to search protein and DNA sequence databases", Methods Mol. Biol. 243:307-31 (1994). [25 pages].
Rosenberg et al. "Use of Tumor-Infiltrating Lymphocytes and Interleukin-2 in the Immunotherapy of Patients with Metastatic Melanoma", New Eng. J. of Med. 319: 1676, 1988 [5 pages].
Tutt et al. "Trispecific F(ab')3 derivatives that use cooperative signaling via the TCR/CD3 complex and CD2 to activate and redirect resting cytotoxic T cells", 1991, J. Immunol. 147:60-69 [10 pages].
UI-TEI et al. "Sensitive Assay of RNA interference in *Drosophila* and Chinese hamster cultured cells using firefly luciferase gene as target", 2000, FEBS Letters, 479:79-82 [4 pages].
Ward et al. "Binding activities of a repertoire of single immunoglobulin variable domains secreted from *Escherichia coli*", Nature, 341:544-546 (1989) [3 pages].

* cited by examiner

| Balb/c: #5061, #5062, #5063, #5064, #5065 | SJL: #5066, #5067, #5068, #5069, #5070 |
|---|---|

| The first fusion F0109 |
|---|
| Balb/c: #5065: plate #1-#20 |
| SJL #5067: plate #21-#40 |

①

| 6G10 bound to human BCMA ECD-Fc, Cyno BCMA ECD-Fc and K562-BCMA+ cells |
|---|
| 34D1 bound to human BCMA ECD-Fc and K562-BCMA+ cells and did not bind to Cyno BCMA ECD-Fc |

②

6G10-ID7 bound to human BCMA ECD-Fc, Cyno BCMA ECD-Fc and K562-BCMA+ cells

Small-batch antibody production and antibody identification

Sequencing of variable regions

6G10-1D7 was monoclonal according to sequencing

Expression and activity identification of chimeric antibodies

| The second fusion F0227 |
|---|
| Balb/c: #5063: plate #41-#60 |
| SJL #5068: plate #61-#80 |

①

No positive clones were obtained

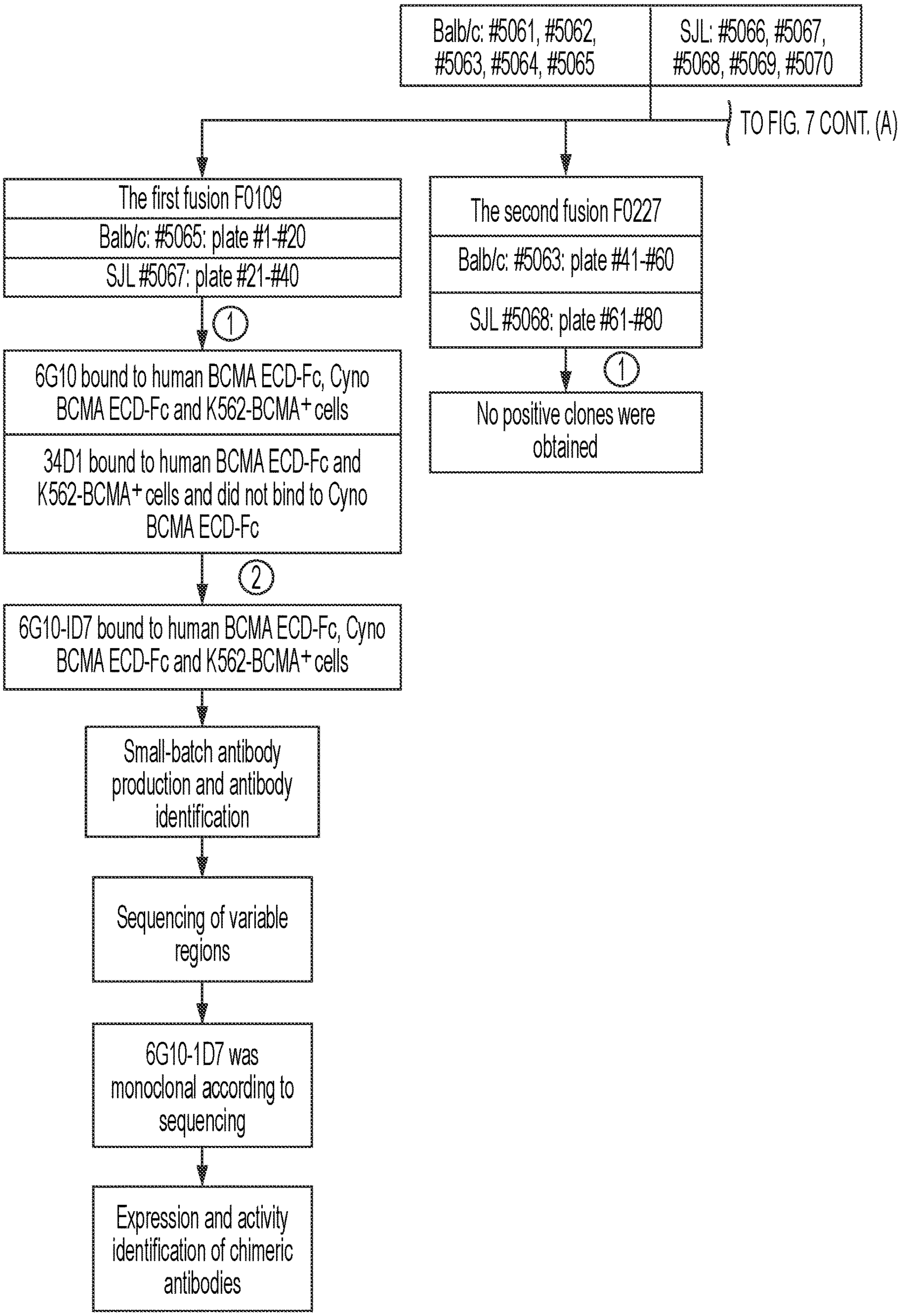

FIG. 7

FROM TO FIG.7 CONT. (B)

The fourth fusion F0614

Balb/c: #5061: plate #101-#120

SJL #5066: plate #121-#140

①

151A9, 156E11, 149H4, 143D6 and 154B8 bound to human BCMA ECD-Fc, Cyno BCMA ECD-Fc and L-BCMA⁺ cells 152D8 bound to human BCMA ECD-Fc and L-BCMA⁺ cells; and did not bind to Cyno BCMA ECD-Fc

②

143D6F4, 151A9A4 and 152D8E8 bound to human BCMA ECD-Fc, Cyno BCMA ECD-Fc and L-BCMA⁺ cells Small-batch antibody production and antibody identification Sequencing of variable regions 143D6F4, 151A9A4 and 152D8E8 were monoclonal according to sequencing ① Screening of parent clones
② Screening of subclones

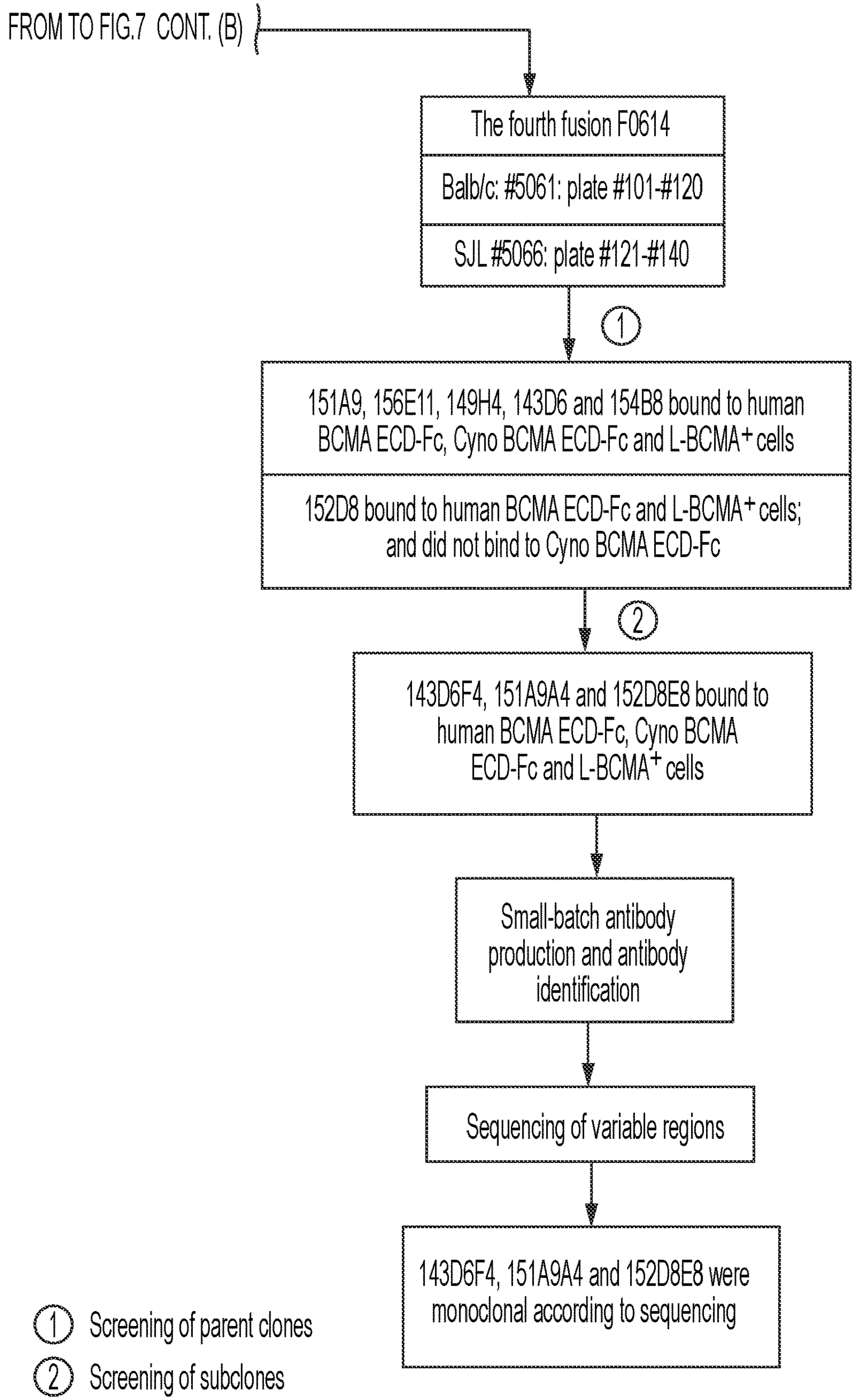

FIG. 7 CONT.

| | EC50 |
|---|---|
| mAb001 | 0.03389 |
| mAb002 | 0.03194 |
| mAb003 | 0.05809 |
| mAb004 | 0.03804 |
| mAb005 | 0.1341 |
| mAb006 | 0.02926 |
| mAb007 | 0.2061 |
| mAb008 | 0.1548 |
| mIgG | |
| anti-hBCMA | 0.2735 |

| | EC50 |
|---|---|
| mAb009 | 0.03296 |
| mAb010 | 0.1828 |
| mAb011 | 0.1493 |
| mAb012 | 0.1691 |
| mAb013 | ~~18.41~~ |
| mIgG | ~~0.8441~~ |
| anti-hBCMA | 0.2646 |

| | EC50 |
|---|---|
| mAb001 | ~~13.05~~ |
| mAb002 | 0.02307 |
| mAb003 | 0.06225 |
| mAb004 | ~~1.857e+006~~ |
| mAb005 | 0.1440 |
| mAb006 | 0.01939 |
| mAb007 | 0.1732 |
| mAb008 | ~~0.001885~~ |
| mIgG | ~~0.03709~~ |
| anti-hBCMA | ~~233.4~~ |

| | EC50 |
|---|---|
| mAb009 | 0.03289 |
| mAb010 | 0.1806 |
| mAb011 | 0.1739 |
| mAb012 | 0.1495 |
| mAb013 | 164.9 |
| mIgG | 3.029 |
| anti-hBCMA | ~2.548e-009 |

| | EC50 |
|---|---|
| mAb001 | ~~0.1266~~ |
| mAb002 | ~~78.35~~ |
| mAb003 | ~~0.006461~~ |
| mAb004 | ~~0.0003199~~ |
| mAb005 | ~~0.004793~~ |
| mAb006 | ~~~15844~~ |
| mAb007 | ~~~28208~~ |
| mAb008 | ~~~25476~~ |
| mIgG | ~~492860~~ |
| anti-hTACI | 0.04574 |

| | EC50 |
|---|---|
| mAb010 | ~~15.02~~ |
| mAb011 | ~~1.350~~ |
| mAb012 | |
| mAb013 | ~~0.9491~~ |
| mIgG | ~~6.189~~ |
| anti-hTACI | 0.03524 |

| | EC50 |
|---|---|
| mAb001 | 0.7084 |
| mAb002 | 1.878 |
| mAb003 | ~~28.60~~ |
| mAb004 | 3.007 |
| mAb005 | 3.608 |
| mAb006 | 2.709 |
| mAb007 | 6.345 |
| mAb008 | 1.546 |
| mIgG | ~~74.61~~ |
| anti-hBCMA | 1.840 |

| | EC50 |
|---|---|
| mAb009 | 3.190 |
| mAb010 | 3.042 |
| mAb011 | 4.854 |
| mAb012 | 5.802 |
| mAb013 | ~~1.474e-007~~ |
| anti-hBCMA | 2.484 |
| mIgG | ~~45.75~~ |

| | EC50 |
|---|---|
| mAb001 | 0.2527 |
| mAb002 | 1.989 |
| mAb003 | ~44960 |
| mAb004 | 2.089e+006 |
| mAb005 | |
| mAb006 | 0.003097 |
| mAb007 | 0.02591 |
| mAb008 | 0.4556 |
| mIgG | 48.80 |
| anti-hBCMA | ~2373 |

| | EC50 |
|---|---|
| mAb009 | ~~73.58~~ |
| mAb010 | ~~5.254e+006~~ |
| mAb011 | ~~1.527~~ |
| mAb012 | ~~2.092e+006~~ |
| mAb013 | |
| anti-hBCMA | ~~0.003068~~ |
| mIgG | ~~0.0004735~~ |

| | anti-hBCMA | mAb001 |
|---|---|---|
| IC50 | 0.5314 | 0.7312 |

| | mIgG | anti-hBCMA | mAb001 |
|---|---|---|---|
| IC50 | ~~1.518~~ | 0.4138 | 0.4658 |

ANTI-BCMA ANTIBODIES AND CHIMERIC ANTIGEN RECEPTORS

SEQUENCE LISTING

This application contains a Sequence Listing which has been filed electronically in ASCII format and is hereby incorporated by reference in its entirety. Said ASCII copy, created on May 7, 2021, is named 11299-009938-WO0_ST25.txt and is 91 KB in size.

TECHNICAL FIELD

The present invention relates to anti-BCMA antibodies and chimeric antigen receptors (CARs), and preparation and applications thereof.

BACKGROUND

Multiple myeloma (MM) is the second most common hematological malignant tumor next to non-Hodgkin's lymphoma. In recent years, although great progress has been made in chemotherapy, proteasome inhibitors, immunomodulators (thalidomide derivatives) and CD38 targeting antibodies, almost all patients will eventually relapse. Therefore, there is an urgent need for new therapeutic regimens.

B-cell maturation antigen (BCMA), also known as a tumor necrosis factor receptor superfamily member 17, is a membrane protein widely expressed on mature B cells. An important feature of BCMA is that BCMA is highly expressed on all MM cells, and not expressed in other normal tissues (except plasma cells). Therefore, BCMA has become a popular target for many pharmaceutical companies and research institutions to treat relapsed or refractory multiple myeloma (R/R MM patients).

At present, the immunotherapies developed for the BCMA target mainly fall into three categories: chimeric antigen receptor T cell (CAR-T) therapy, bispecific antibodies (BsAb) and antibody drug conjugates (ADC). A CAR-T (bb2121) jointly developed by Celgene and Bluebird Bio, has entered the phase 3 clinical stage. The current bispecific antibodies targeting BCMA have one end binding to BCMA, and the other end binding to a CD3 T cell receptor on the surface of the T cell, thereby recruiting T cells to tumor cells which then can kill the tumor cells. It was reported that the optimal dose of AMG-420 (Amgen) can reach 70% ORR when treating patients with R/R MM. In the aspect of ADC, GSK-2857916 from GlaxoSmithKline (GSK) has been used in multiple clinical trials to treat different types of MM patients. Among them, the key clinical trial for the treatment of R/R MM patients as a ¾-line therapy has obtained interim results. The results recently published in Blood Cancer Journal showed that the ORR of the patients treated with GSK-2857916 was 60%, the complete response rate (CRR) reached 15%, and the progression-free survival (PFS) reached 12 months.

Nevertheless, the therapies available for the treatment of R/R MM patients are still limited, and new drugs and methods for the treatment of R/R MM patients still need to be developed in this field.

SUMMARY

The present disclosure provides for an anti-BCMA antibody, or an antigen-binding portion thereof, comprising a light chain variable region ($V_L$) and a heavy chain variable region ($V_H$).

The present disclosure provides for a chimeric antigen receptor (CAR), comprising an anti-BCMA antigen-binding region which comprises a light chain variable region ($V_L$) and a heavy chain variable region ($V_H$).

The light chain variable region may comprise three CDRs, CDR1, CDR2 and CDR3, having amino acid sequences about 80% to about 100% identical to the amino acid sequences set forth in (i) SEQ ID NOs: 76, 77 and 78, respectively, (ii) SEQ ID NOs: 82, 83 and 84, respectively, (iii) SEQ ID NOs: 88, 89 and 90, respectively, (iv) SEQ ID NOs: 94, 95 and 96, respectively, (v) SEQ ID NOs: 100, 101 and 102, respectively, (vi) SEQ ID NOs: 106, 107 and 108, respectively, (vii) SEQ ID NOs: 112, 113 and 114, respectively, (viii) SEQ ID NOs: 118, 119 and 120, respectively, or (ix) SEQ ID NOs: 124, 125 and 126, respectively.

The heavy chain variable region may comprise three complementarity determining regions (CDRs), CDR1, CDR2 and CDR3, having amino acid sequences about 80% to about 100% identical to the amino acid sequences set forth in (i) SEQ ID NOs: 79, 80 and 81, respectively, (ii) SEQ ID NOs: 85, 86 and 87, respectively, (iii) SEQ ID NOs: 91, 92 and 93, respectively, (iv) SEQ ID NOs: 97, 98 and 99, respectively, (v) SEQ ID NOs: 103, 104 and 105, respectively, (vi) SEQ ID NOs: 109, 110 and 111, respectively, (vii) SEQ ID NOs: 115, 116 and 117, respectively, (viii) SEQ ID NOs: 121, 122 and 123, respectively, or (ix) SEQ ID NOs: 127, 128 and 129, respectively.

The $V_L$ and $V_H$ may be as follows: (i) the $V_L$ may comprise three CDRs, CDR1, CDR2 and CDR3, having amino acid sequences about 80% to about 100% identical to the amino acid sequences set forth in SEQ ID NOs: 76, 77 and 78, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 79, 80 and 81, respectively; (ii) the $V_L$ may comprise three CDRs, CDR1, CDR2 and CDR3, having amino acid sequences about 80% to about 100% identical to the amino acid sequences set forth in SEQ ID NOs: 82, 83 and 84, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 85, 86 and 87, respectively; (iii) the $V_L$ may comprise three CDRs, CDR1, CDR2 and CDR3, having amino acid sequences about 80% to about 100% identical to the amino acid sequences set forth in SEQ ID NOs: 88, 89 and 90, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 91, 92 and 93, respectively; (iv) the $V_L$ may comprise three CDRs, CDR1, CDR2 and CDR3, having amino acid sequences about 80% to about 100% identical to the amino acid sequences set forth in SEQ ID NOs: 94, 95 and 96, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 97, 98 and 99, respectively; (v) the $V_L$ may comprise three CDRs, CDR1, CDR2 and CDR3, having amino acid sequences about 80% to about 100% identical to the amino acid sequences set forth in SEQ ID NOs: 100, 101 and 102, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 103, 104 and 105, respectively; (vi) the $V_L$ may comprise three CDRs, CDR1, CDR2 and CDR3, having amino acid sequences about 80% to about 100% identical to the amino acid sequences set forth in SEQ ID NOs: 106, 107 and 108, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 109, 110 and 111, respectively; (vii) the $V_L$ may comprise three CDRs, CDR1, CDR2 and CDR3, having amino acid sequences about 80% to about 100% identical to the amino acid sequences set forth in SEQ ID NOs: 112, 113 and 114, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 115, 116 and 117, respectively; (viii) the $V_L$ may comprise three CDRs, CDR1, CDR2 and CDR3, having amino acid sequences about 80% to about 100% identical to the amino acid sequences set forth in SEQ ID NOs: 118, 119 and 120, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 121, 122 and 123, respectively; or (ix) the $V_L$ may comprise three CDRs, CDR1, CDR2 and CDR3, having amino acid sequences about 80% to about 100% identical to the amino acid sequences set forth in SEQ ID NOs: 124, 125 and 126, respectively; the $V_H$ may comprise three complementarity determining regions (CDRs), CDR1, CDR2 and CDR3, having amino acid sequences about 80% to about 100% identical to the amino acid sequences set forth in SEQ ID NOs: 127, 128 and 129, respectively.

The $V_L$ and $V_H$ may have amino acid sequences about 80% to about 100% identical to amino acid sequences set forth in (i) SEQ ID NO: 53 and SEQ ID NO: 54, respectively, (ii) SEQ ID NO: 55 and SEQ ID NO: 56, respectively, (iii) SEQ ID NO: 57 and SEQ ID NO: 58, respectively, (vi) SEQ ID NO: 59 and SEQ ID NO: 60, respectively, (v) SEQ ID NO: 61 and SEQ ID NO: 62, respectively, (vi) SEQ ID NO: 63 and SEQ ID NO: 64, respectively, (vii) SEQ ID NO: 65 and SEQ ID NO: 66, respectively, (viii) SEQ ID NO: 67 and SEQ ID NO: 68, respectively, or (ix) SEQ ID NO: 69 and SEQ ID NO: 70, respectively.

The $V_L$ may comprise an amino acid sequence about 80% to about 100% identical to any one of the amino acid sequences set forth in SEQ ID NOs: 53, 55, 57, 59, 61, 63, 65, 67 and 69. The $V_H$ may comprise an amino acid sequence about 80% to about 100% identical to any one of the amino acid sequences set forth in SEQ ID NOs: 54, 56, 58, 60, 62, 64, 66, 68 and 70.

The antibody or antigen-binding portion thereof may be (a) a whole immunoglobulin molecule; (b) an scFv; (c) a Fab fragment; (d) an F(ab')2; or (e) a disulfide linked Fv.

The present antibody or antigen-binding portion thereof may comprise at least one constant domain selected from: a) an IgG constant domain; and (b) an IgA constant domain.

The present antibody or antigen-binding portion thereof may comprise at least one human constant domain.

The present disclosure provides for an antibody conjugate that comprises the present antibody or antigen-binding portion thereof, linked with a conjugate moiety. The conjugate moiety may be a detectable marker, a drug, a toxin, a cytokine, a radionuclide, an enzyme, a targeting moiety, and combinations thereof. In one embodiment, the antibody conjugate is an antibody drug conjugate (ADC).

Also encompassed by the present disclosure is a composition comprising the present antibody or antigen-binding portion thereof, and a pharmaceutically acceptable carrier.

The present disclosure provides for a composition comprising the present CAR or immune cells, and a pharmaceutically acceptable carrier.

The present disclosure provides for a nucleic acid encoding the present antibody or antigen-binding portion thereof (or encoding the CAR), a vector comprising the present nucleic acid, and a cell comprising the present vector.

In the CAR, the anti-BCMA antigen-binding region may be a single-chain variable fragment (scFv) that specifically binds BCMA.

The CAR may further comprise one or more of the following:

(a) a signal peptide, (b) a hinge region, (c) a transmembrane domain, (d) a co-stimulatory region, and (e) a cytoplasmic signaling domain.

The co-stimulatory region of the CAR may comprise a co-stimulatory region of 4-1BB (CD137), CD28, OX40, CD2, CD7, CD27, CD30, CD40, CD70, CD134, PD1, Dap10, CDS, ICAM-1, LFA-1 (CD11a/CD18), ICOS (CD278), NKG2D, GITR, TLR2, or combinations thereof.

The cytoplasmic signaling domain of the CAR may comprise a cytoplasmic signaling domain of CD3ζ.

The hinge region of the CAR may comprise a hinge region of Ig4, CD8, CD28, CD137, or combinations thereof.

The transmembrane domain of the CAR may comprise a transmembrane domain of CD8, CD28, CD3c, CD45, CD4, CD5, CD9, CD16, CD22, CD33, CD37, CD64, CD80, CD86, CD134, CD137, CD154, or combinations thereof.

The present disclosure provides for an immune cell expressing the CAR. The immune cell may be a T cell, a natural killer (NK) cell, a natural killer T cell, a lymphoid progenitor cell, a hematopoietic stem cell, a stem cell, a macrophage, or a dendritic cell.

The present disclosure provides for a method of treating cancer. The method may comprise administering the present immune cell or composition to a subject in need thereof.

The cancer may be a hematologic cancer. The cancer may be a plasma-cell malignancy. The cancer may be a BCMA-positive malignancy. The cancer may be multiple myeloma (MM), or plasma cell leukemia.

The immune cell may be administered by infusion, injection, transfusion, implantation, and/or transplantation. The immune cell may be administered intravenously, subcutaneously, intradermally, intranodally, intratumorally, intramedullary, intramuscularly, or intraperitoneally. In one embodiment, the immune cell is administered via intravenous infusion.

The immune cell may be allogeneic or autologous to the subject.

The subject may be a human or a mammal. The present antibodies, antigen-binding portions thereof, CARs, compositions and methods may be used in all vertebrates, e.g., mammals and non-mammals, including human, mice, rats, guinea pigs, hamsters, dogs, cats, cows, horses, goats, sheep, pigs, monkeys, apes, gorillas, chimpanzees, rabbits, ducks, geese, chickens, amphibians, reptiles and other animals.

An object of the present disclosure is to provide a BCMA antibody, and preparation and application thereof.

In a first aspect of the present disclosure, a BCMA antibody is provided, wherein the antibody comprises heavy chain variable ($V_H$) regions encoded by nucleotide sequences shown in SEQ ID NO: 1, 3, 5, 7, 9, 10, 11, 12, 14, 15, 16, 17, 19, 20, 21, 22, 24, 26, 28, 30, 32, 34 and 37 and light chain variable ($V_L$) regions encoded by nucleotide sequences shown in SEQ ID NO: 2, 4, 6, 8, 13, 18, 23, 25, 27, 29, 31, 33, 35, 36 and 38.

Alternatively, the antibody comprises heavy chains with amino acid sequences as shown in SEQ ID NO: 39, 41, 43, 45, 47 and 49 and light chains with amino acid sequences as shown in SEQ ID NO: 40, 42, 44, 46, 48, 50 and 51.

Alternatively, the antibody comprises $V_H$ regions with amino acid sequences as shown in SEQ ID NO: 54, 56, 58, 60, 62, 64, 66, 68 and 70 and $V_L$ regions with amino acid sequences as shown in SEQ ID NO: 53, 55, 57, 59, 61, 63, 65, 67 and 69.

Any of the foregoing amino acid sequences may include a derivative sequence that optionally adds, deletes, modifies and/or substitutes at least one amino acid and can retain the binding affinity of BCMA.

In certain embodiments, the antibody comprises $V_H$ regions and $V_L$ regions encoded by nucleotide sequences shown below:

| Hybridoma No. | Nucleotide sequences encoding $V_H$ regions | Nucleotide sequences encoding $V_L$ regions |
|---|---|---|
| 6G10-1D7 (CP01) | SEQ ID NO: 1 | SEQ ID NO: 2 |
| 99B3G3 (CP02) | SEQ ID NO: 3 | SEQ ID NO: 4 |
| 102A12H6 | SEQ ID NO: 5 | SEQ ID NO: 6 |
| 105C10F1(CP03) | SEQ ID NO: 7 | SEQ ID NO: 8 |
| 107A11F1 | SEQ ID NO: 9 | SEQ ID NO: 13 |
| | SEQ ID NO: 10 | |
| | SEQ ID NO: 11 | |
| | SEQ ID NO: 12 | |
| 107B11E1 | SEQ ID NO: 14 | SEQ ID NO: 18 |
| | SEQ ID NO: 15 | |
| | SEQ ID NO: 16 | |
| | SEQ ID NO: 17 | |
| 107A9A4 | SEQ ID NO: 19 | SEQ ID NO: 23 |
| | SEQ ID NO: 20 | |
| | SEQ ID NO: 21 | |
| | SEQ ID NO: 22 | |
| 113B3F12 | SEQ ID NO: 24 | SEQ ID NO: 25 |
| 100H2D12C6 | SEQ ID NO: 3 | SEQ ID NO: 4 |
| 109C5F3C1(CP06) | SEQ ID NO: 26 | SEQ ID NO: 27 |
| 143D6F4(CP07) | SEQ ID NO: 28 | SEQ ID NO: 29 |
| 151A9A4(CP08) | SEQ ID NO: 30 | SEQ ID NO: 31 |
| 152D8E8(CP09) | SEQ ID NO: 32 | SEQ ID NO: 33 |
| 1O7A11F1B7(CP04) | SEQ ID NO: 34 | SEQ ID NO: 35 |
| | | SEQ ID NO: 36 |
| 107A9A4D2 | SEQ ID NO: 34 | SEQ ID NO: 35 |
| | | SEQ ID NO: 36 |
| 107B11E1D7(CP05) | SEQ ID NO: 37 | SEQ ID NO: 38 |
| 97B8G8D12 | SEQ ID NO: 3 | SEQ ID NO: 4 |

In certain embodiments, the antibody is a murine antibody.

In certain embodiments, the antibody comprises heavy chains and light chains with amino acid sequences shown below:

| Hybridoma No. | Amino acid sequences of heavy chains | Amino acid sequences of light chains |
|---|---|---|
| 6G10-1D7 (CP01) | SEQ ID NO: 39 | SEQ ID NO.: 40 |
| 99B3G3(CP02) | SEQ ID NO: 41 | SEQ ID NO: 42 |
| 105C10F1(CP03) | SEQ ID NO: 43 | SEQ ID NO: 44 |
| 113B3F12 | SEQ ID NO: 45 | SEQ ID NO: 46 |
| 107B11E1D7(CP05) | SEQ ID NO: 47 | SEQ ID NO: 48 |
| 107A9A4D2 | SEQ ID NO: 49 | SEQ ID NO: 50 |
| | | SEQ ID NO: 51 |

In certain embodiments, the antibody is a chimeric antibody.

In certain embodiments, the antibody comprises $V_H$ regions and $V_L$ regions with amino acid sequences shown below:

| Antibody | Amino acid sequences of VH regions | Amino acid sequences of VL regions |
|---|---|---|
| CP01 | SEQ ID NO: 54 | SEQ ID NO.: 53 |
| CP02 | SEQ ID NO: 56 | SEQ ID NO: 55 |
| CP03 | SEQ ID NO: 58 | SEQ ID NO: 57 |
| CP04 | SEQ ID NO: 60 | SEQ ID NO: 59 |
| CP05 | SEQ ID NO: 62 | SEQ ID NO: 61 |
| CP06 | SEQ ID NO: 64 | SEQ ID NO: 63 |
| CP07 | SEQ ID NO: 66 | SEQ ID NO: 65 |
| CP08 | SEQ ID NO: 68 | SEQ ID NO: 67 |
| CP09 | SEQ ID NO: 70 | SEQ ID NO: 69 |

In certain embodiments, the antibody is a single-chain antibody.

In certain embodiments, the antibody binds to a human BCMA protein and/or a machin BCMA protein.

In certain embodiments, the antibody binds to an extracellular domain of the BCMA protein.

In certain embodiments, the antibody does not bind to a tumor necrosis factor receptor superfamily 13B.

In certain embodiments, the antibody further comprises heavy chain constant regions and/or light chain constant regions.

In certain embodiments, the heavy chain constant regions are of human or mouse origin.

In certain embodiments, the heavy chain constant regions are heavy chain IgG1 constant regions of a human antibody.

In certain embodiments, the light chain constant regions are of human or mouse origin.

In certain embodiments, the light chain constant regions are light chain kappa constant regions of a human antibody.

In certain embodiments, the number of the added, deleted, modified and/or substituted amino acids is 1 to 5 (e.g., 1 to 3, 1 to 2, or 1).

In certain embodiments, the derivative sequence that adds, deletes, modifies and/or substitutes at least one amino acid and can retain the binding affinity of BCMA is an amino acid sequence with at least 80%, 85%, 90%, 91%, 92%, 93%, 94%, 95%, 96%, 97%, 98% or 99% of homology or sequence similarity.

In certain embodiments, the antibody is selected from animal-derived antibodies, chimeric antibodies, humanized antibodies, fully human antibodies, or combinations thereof.

In certain embodiments, the ratio of the immunogenicity Z1 of the chimeric antibodies in humans to the immunogenicity Z0 of non-chimeric antibodies (such as murine antibodies) in humans (Z1/Z0) is 0 to 0.5, 0 to 0.2, or 0 to 0.05 (e.g., 0.001 to 0.05).

In certain embodiments, the antibody is a partially or fully humanized or fully human monoclonal antibody.

In certain embodiments, the antibody is a double-chain antibody, or a single-chain antibody.

In certain embodiments, the antibody is an antibody full-length protein or an antigen-binding fragment.

In certain embodiments, the antibody is a bispecific antibody or a multispecific antibody.

In certain embodiments, the antibody is a monoclonal antibody or polyclonal antibody.

In a second aspect of the present disclosure, a recombinant protein is provided, which comprises:

(i) The antibody described in the first aspect of the present disclosure; and (ii) An optional tag sequence for assisting expression and/or purification.

In certain embodiments, the tag sequence includes a 6×His tag.

In certain embodiments, the recombinant protein (or polypeptide) comprises a fusion protein.

In certain embodiments, the recombinant protein is a monomer, dimer, or multimer.

In a third aspect of the present disclosure, a chimeric antigen receptor (CAR) fusion protein is provided, which from an N-terminal to a C-terminal, comprises:

(i) scFv targeting BCMA, (ii) A transmembrane domain, (iii) At least one costimulatory domain, and (iv) An activation domain.

The scFv targeting BCMA comprises $V_H$ regions with amino acid sequences as shown in SEQ ID NO: 54, 56, 58, 60, 62, 64, 66, 68 and 70 and $V_L$ regions with amino acid sequences as shown in SEQ ID NO: 53, 55, 57, 59, 61, 63, 65, 67 and 69.

In certain embodiments, the scFv comprises $V_H$ regions and $V_L$ regions with amino acid sequences shown below:

| Antibody | Amino acid sequences of VH regions | Amino acid sequences of VL regions |
|---|---|---|
| CP01 | SEQ ID NO: 54 | SEQ ID NO.: 53 |
| CP02 | SEQ ID NO: 56 | SEQ ID NO: 55 |
| CP03 | SEQ ID NO: 58 | SEQ ID NO: 57 |
| CP04 | SEQ ID NO: 60 | SEQ ID NO: 59 |
| CP05 | SEQ ID NO: 62 | SEQ ID NO: 61 |
| CP06 | SEQ ID NO: 64 | SEQ ID NO: 63 |
| CP07 | SEQ ID NO: 66 | SEQ ID NO: 65 |
| CP08 | SEQ ID NO: 68 | SEQ ID NO: 67 |
| CP09 | SEQ ID NO: 70 | SEQ ID NO: 69. |

In certain embodiments, the CAR fusion protein has a structure shown in the following Formula I:

$$L\text{-}scFv\text{-}H\text{-}TM\text{-}C\text{-}CD3\zeta \quad (I)$$

where,

Each "-" is independently a linking peptide or a peptide bond;

L is an optional signal peptide sequence;

scFv is scFv targeting BCMA;

H is an optional hinge region;

TM is a transmembrane domain;

C is a costimulatory signal molecule; and

CD3ζ is a cytoplasmic signal transduction sequence of CD3ζ.

In certain embodiments, the L is a signal peptide of a protein selected from the group consisting of: CD8, GM-CSF, CD4, CD137 or combinations thereof.

In certain embodiments, the L is a signal peptide derived from CD8.

In certain embodiments, the amino acid sequence of the signal peptide is shown in SEQ ID NO: 52.

In certain embodiments, the scFv has a structure as shown in the following Formula II or III:

$$VL - L1 - VH \quad (II)$$

$$VH - L2 - VL \quad (III)$$

where $V_L$ is a light chain variable region;

$V_H$ is a heavy chain variable region;

L1 and L2 are each independently a linking peptide.

In certain embodiments, the amino acid sequence of the linking peptide is as shown in SEQ ID NO: 71.

In certain embodiments, the H is a hinge region of a protein selected from the group consisting of: CD8, CD28, CD137, or combinations thereof. In certain embodiments, the H is a hinge region derived from CD8. In certain embodiments, the amino acid sequence of the hinge region is as shown in SEQ ID NO: 72.

In certain embodiments, the TM is a transmembrane region of a protein selected from the group consisting of: CD28, CD3 epsilon, CD45, CD4, CD5, CD8, CD9, CD16, CD22, CD33, CD37, CD64, CD80, CD86, CD134, CD137, CD154, or combinations thereof.

In certain embodiments, the TM includes a transmembrane region derived from CD8. In certain embodiments, the amino acid sequence of the transmembrane region is as shown in SEQ ID NO: 73.

In certain embodiments, the C is a costimulatory signal molecule of a protein selected from the group consisting of: OX40, CD2, CD7, CD27, CD28, CD30, CD40, CD70, CD134, 4-1BB(CD137), PD1, Dap10, CDS, ICAM-1, LFA-1 (CD11a/CD18), ICOS (CD278), NKG2D, GITR, TLR2, or combinations thereof. In certain embodiments, the C includes a costimulatory signal molecule derived from 4-1BB. In certain embodiments, the amino acid sequence of the costimulatory signal molecule is as shown in SEQ ID NO: 74.

In certain embodiments, the cytoplasmic signaling sequence of CD3ζ is as shown in SEQ ID NO: 75.

In a fourth aspect of the present disclosure, a polynucleotide is provided, which encodes a polypeptide such as:

(1) The antibody as described in the first aspect of the present disclosure;

(2) The recombinant protein as described in the second aspect of the present disclosure; and (3) The CAR fusion protein as described in the third aspect of the present disclosure.

In certain embodiments, the polynucleotides encoding the $V_H$ regions of the antibody are as shown in SEQ ID NO. 1, 3, 5, 7, 9, 10, 11, 12, 14, 15, 16, 17, 19, 20, 21, 22, 24, 26, 28, 30, 32, 34 and 37; and/or the polynucleotides encoding the $V_L$ regions of the antibody are as shown in SEQ ID NO: 2, 4, 6, 8, 13, 18, 23, 25, 27, 29, 31, 33, 35, 36 and 38.

In certain embodiments, the polynucleotides encoding the $V_H$ regions and the polynucleotides encoding the $V_L$ regions are shown below:

| Hybridoma No. | Nucleotide sequences encoding $V_H$ regions | Nucleotide sequences encoding $V_L$ regions |
|---|---|---|
| 6G10-1D7 (CP01) | SEQ ID NO: 1 | SEQ ID NO.: 2 |
| 99B3G3(CP02) | SEQ ID NO: 3 | SEQ ID NO: 4 |
| 102A12H6 | SEQ ID NO: 5 | SEQ ID NO: 6 |
| 105C10F1(CP03) | SEQ ID NO: 7 | SEQ ID NO: 8 |
| 107A11F1 | SEQ ID NO: 9 | SEQ ID NO: 13 |
| | SEQ ID NO: 10 | |
| | SEQ ID NO: 11 | |
| | SEQ ID NO: 12 | |
| 107B11E1 | SEQ ID NO: 14 | SEQ ID NO: 18 |
| | SEQ ID NO: 15 | |
| | SEQ ID NO: 16 | |
| | SEQ ID NO: 17 | |
| 107A9A4 | SEQ ID NO: 19 | SEQ ID NO: 23 |
| | SEQ ID NO: 20 | |
| | SEQ ID NO: 21 | |
| | SEQ ID NO: 22 | |
| 113B3F12 | SEQ ID NO: 24 | SEQ ID NO: 25 |
| 100H2D12C6 | SEQ ID NO: 3 | SEQ ID NO: 4 |
| 109C5F3C1(CP06) | SEQ ID NO: 26 | SEQ ID NO: 27 |

-continued

| Hybridoma No. | Nucleotide sequences encoding $V_H$ regions | Nucleotide sequences encoding $V_L$ regions |
|---|---|---|
| 143D6F4(CP07) | SEQ ID NO: 28 | SEQ ID NO: 29 |
| 151A9A4(CP08) | SEQ ID NO: 30 | SEQ ID NO: 31 |
| 152D8E8(CP09) | SEQ ID NO: 32 | SEQ ID NO: 33 |
| 107A11F1B7(CP04) | SEQ ID NO: 34 | SEQ ID NO: 35 |
| | | SEQ ID NO: 36 |
| 107A9A4D2 | SEQ ID NO: 34 | SEQ ID NO: 35 |
| | | SEQ ID NO: 36 |
| 107B11E1D7(CP05) | SEQ ID NO: 37 | SEQ ID NO: 38 |
| 97B8G8D12 | SEQ ID NO: 3 | SEQ ID NO: 4. |

In a fifth aspect of the present disclosure, a vector is provided, which contains any of the polynucleotides in the fourth aspect of the present disclosure.

In certain embodiments, the vector includes a bacterial plasmid, a bacteriophage, a yeast plasmid, a plant cell virus, a mammalian cell virus such as an adenovirus or a retrovirus, or any other vector.

In certain embodiments, the vector includes a lentiviral vector.

In a sixth aspect of the present disclosure, a genetically engineered host cell is provided, which comprises the vector described in the fifth aspect of the present disclosure, or is integrated with an exogenous polynucleotide described in the fourth aspect of the present disclosure in the genome, or expresses the antibody described in the first aspect of the present disclosure, the recombinant protein described in the second aspect of the present disclosure, or the CAR fusion protein in the third aspect of the present disclosure.

In certain embodiments, the cell is an isolated cell, and/or a genetically engineered cell.

In certain embodiments, the immune cells are derived from humans or non-human mammals (such as mice).

In certain embodiments, the cells include T cells and NK cells.

In certain embodiments, the host cell is an engineered immune cell.

In certain embodiments, the engineered immune cell includes a T cell or an NK cell, such as, (i) a chimeric antigen receptor T cell (CAR-T cell); or (ii) a chimeric antigen receptor NK cell (CAR-NK cell).

In a seventh aspect of the present disclosure, an antibody conjugate is provided, which comprises:

(a) an antibody portion, which is selected from the group consisting of: the antibody as described in the first aspect of the present disclosure; and (b) a conjugating portion conjugated to the antibody portion, which is selected from the group consisting of: detectable markers, drugs, toxins, cytokines, radionuclides, enzymes, or combinations thereof.

In certain embodiments, the antibody portion is conjugated to the conjugating portion via a chemical bond or a linker.

In certain embodiments, the antibody conjugate is an antibody drug conjugate.

In an eighth aspect of the present disclosure, a method for preparing an engineered cell is provided. The engineered cell expresses the antibody described in the first aspect of the present disclosure, the recombinant protein described in the second aspect of the present disclosure, or the CAR fusion protein described in the third aspect of the present disclosure. The following steps are comprised: transducing the polynucleotide described in the fourth aspect of the present disclosure or the vector described in the fifth aspect of the present disclosure into a host cell, thereby obtaining an engineered cell.

In certain embodiments, the method further comprises a step of detecting the function and effectiveness of the obtained engineered cell.

In a ninth aspect of the present disclosure, a pharmaceutical composition is provided, which comprises the antibody described in the first aspect of the present disclosure, the recombinant protein described in the second aspect of the present disclosure, the CAR fusion protein described in the third aspect of the present disclosure, the vector described in the fifth aspect of the present disclosure, the host cell described in the sixth aspect of the present disclosure, or the antibody conjugate described in the seventh aspect of the present disclosure, and a pharmaceutically acceptable carrier, diluent or excipient.

In certain embodiments, the pharmaceutical composition is a liquid preparation.

In certain embodiments, the pharmaceutical composition is an injection.

In certain embodiments, the pharmaceutical composition further comprises an anti-tumor second active ingredient, such as a second antibody or a chemotherapeutic agent.

In certain embodiments, the chemotherapeutic agent is docetaxel, carboplatin, or a combination thereof.

In the tenth aspect of the present disclosure, a use of an active ingredient is provided. The active ingredient is selected from the group consisting of: the antibody described in the first aspect of the present disclosure, the recombinant protein described in the second aspect of the present disclosure, the CAR fusion protein described in the third aspect of the present disclosure, the vector described in the fifth aspect of the present disclosure, the host cell described in the sixth aspect of the present disclosure, or the antibody conjugate described in the seventh aspect of the present disclosure, and is used for (a) preparing diagnostic reagents or kits; and/or (b) preparing drugs or preparations for preventing and/or treating cancers or tumors.

In certain embodiments, the tumor is a BCMA-positive tumor.

In certain embodiments, the tumors are hematological tumors, solid tumors, or combinations thereof.

In certain embodiments, the hematological tumor is acute myelocytic leukemia (AML), multiple myeloma (MM), chronic lymphocytic leukemia (CLL), acute lymphatic leukemia (ALL), diffuse large B cell lymphoma (DLBCL), or combinations thereof.

In certain embodiments, the solid tumor is gastric cancer, peritoneal metastasis of gastric cancer, liver cancer, kidney tumor, lung cancer, carcinoma of small intestine, bone cancer, prostate cancer, colorectal cancer, breast cancer, colon cancer, cervical cancer, ovarian cancer, lymphoma cancer, nasopharynx cancer, adrenal gland tumor, bladder tumor, non-small cell lung cancer (NSCLC), brain glioma, endometrial cancer, testicular cancer, colorectal cancer, urinary tract tumor, thyroid cancer, or combinations thereof.

In certain embodiments, the tumor is multiple myeloma.

In certain embodiments, the diagnostic reagent is a test piece or a test plate.

In certain embodiments, the diagnostic reagent or kit is used for: (1) detecting BCMA proteins in the sample; (2) detecting endogenous BCMA proteins in tumor cells; and/or (3) detecting tumor cells expressing BCMA proteins.

In an eleventh aspect of the present disclosure, a method for in vitro detection (including diagnostic or non-diagnostic) of BCMA proteins in a sample is provided, which comprises steps of: (1) in vitro, contacting the sample with the antibody described in the first aspect of the present disclosure, the recombinant protein described in the second aspect of the present disclosure, or the antibody conjugate described in the seventh aspect of the present disclosure; and (2) detecting whether an antigen-antibody complex is formed, if yes, which means BCMA proteins exist in the sample.

In a twelfth aspect of the present disclosure, a test plate is provided, which comprises a substrate (support plate) and a test strip. The test strip comprises the antibody described in the first aspect of the present disclosure, the recombinant protein described in the second aspect of the present disclosure, or the antibody conjugate in the seventh aspect of the present disclosure, or combinations thereof.

In a thirteenth aspect of the present disclosure, a kit is provided, which may comprise: (1) a first container, which comprises the antibody described in the first aspect; and/or (2) a second container, which comprises a secondary antibody against the antibody described in the first aspect of the present disclosure.

The kit may comprise the test plate described in the twelfth aspect of the present disclosure.

In a fourteenth aspect of the present disclosure, a method for preparing a recombinant polypeptide is provided, which comprises steps of: (a) culturing the host cell described in the sixth aspect of the present disclosure under conditions suitable for expression; (b) isolating a recombinant polypeptide from the culture, the recombinant polypeptide being the antibody described in the first aspect of the present disclosure or the recombinant protein described in the second aspect of the present disclosure.

In a fifteenth aspect of the present disclosure, a method for treatment of a disease is provided. The method may comprise administering to a subject in need thereof an effective dose of the antibody described in the first aspect of the present disclosure, the recombinant protein described in the second aspect of the present disclosure, the antibody conjugate described in the seventh aspect of the present disclosure, the host cell in the sixth aspect of the present disclosure or the pharmaceutical composition described in the ninth aspect of the present disclosure, or a combination thereof.

In certain embodiments, the disease is a BCMA-positive cancer/tumor.

DETAILED DESCRIPTION

Figure 1:
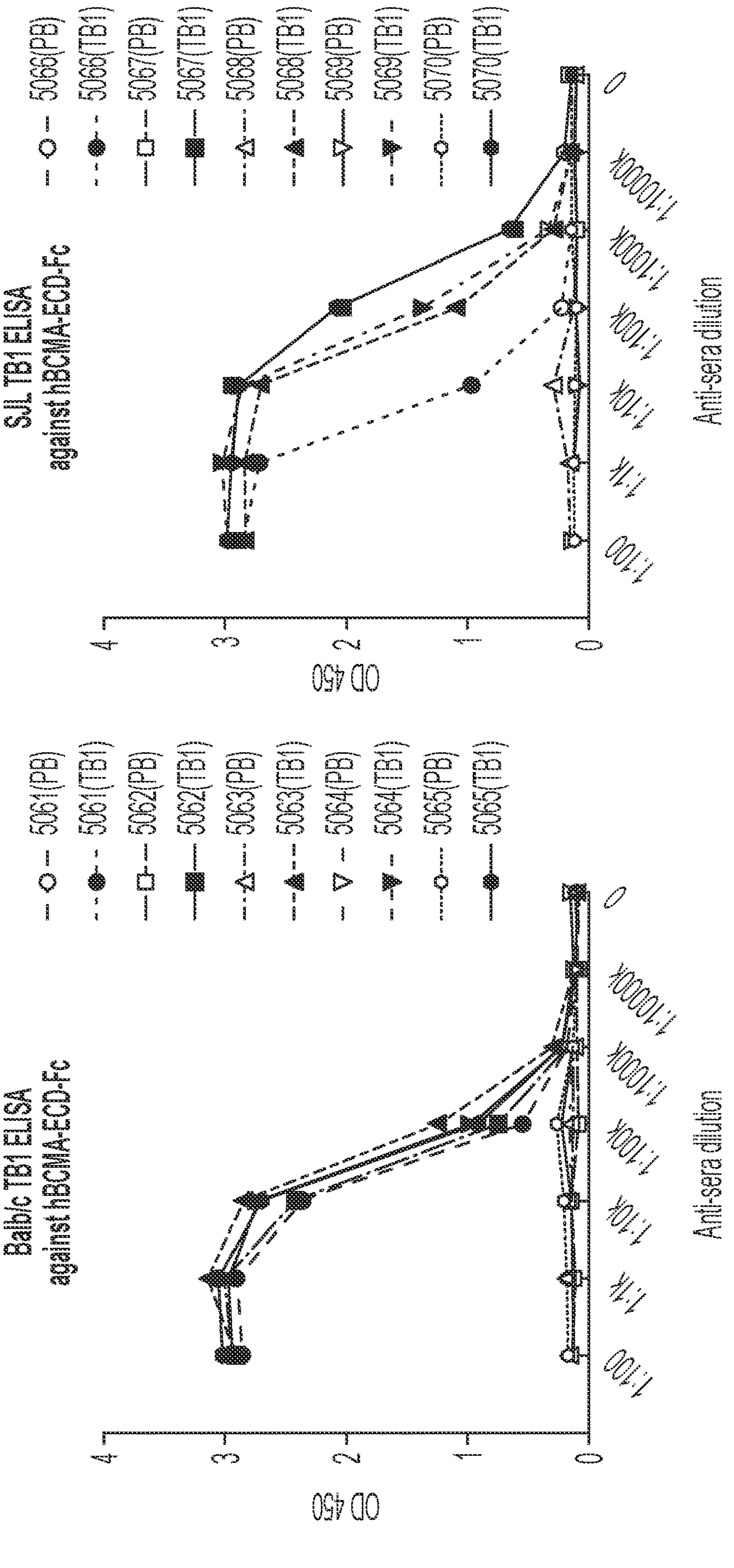
FIG. 1 shows ELISA analysis on the binding titers of mouse serum to hBCMA-ECD-Fc and cynoBCMA-ECD-Fc after the first booster immunization.
Figure 1:
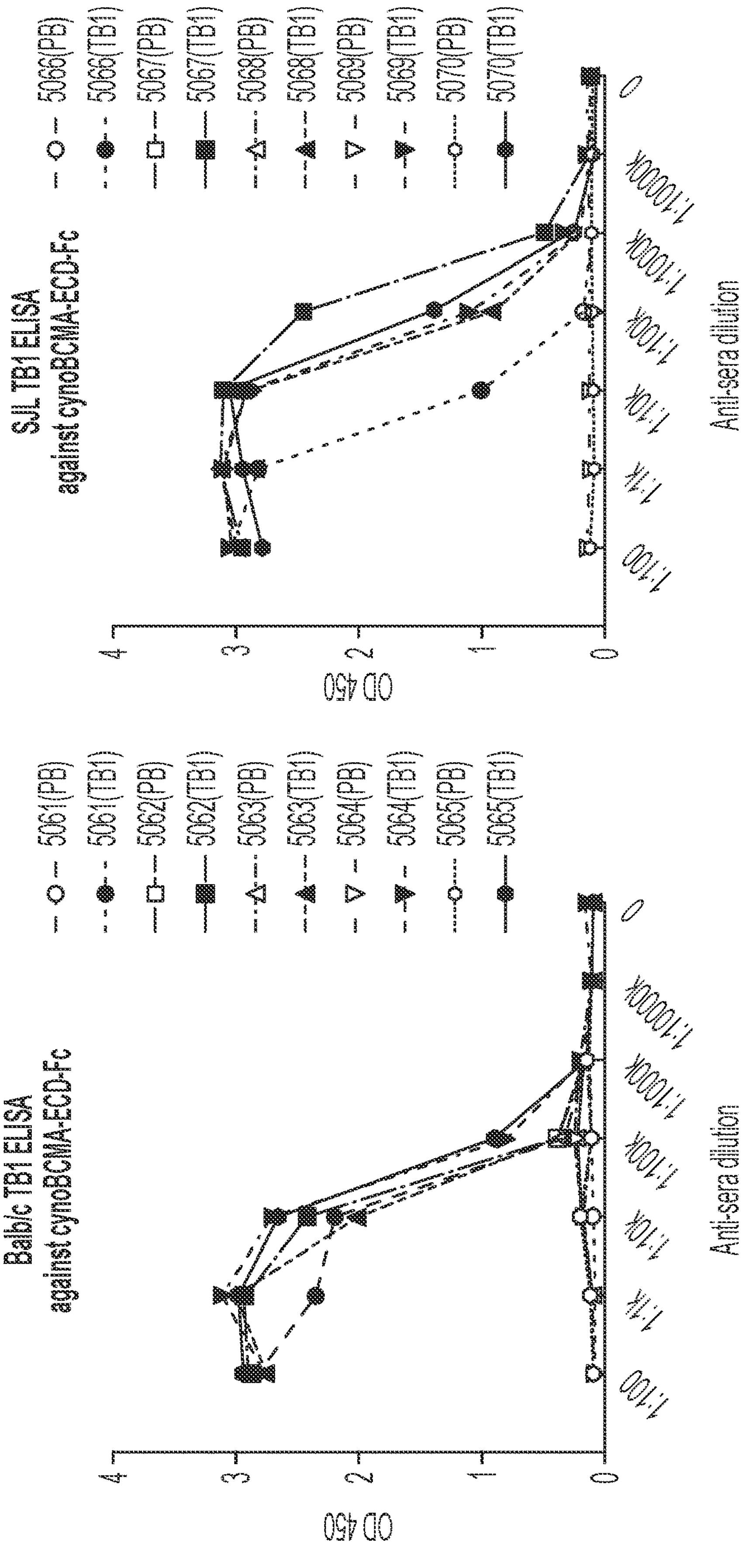

The present disclosure relates to anti-BCMA antibodies, antibody fragments (e.g., antigen-binding portions of the antibody) and chimeric antigen receptors that may be used in various therapeutic, prophylactic, diagnostic and other methods.

The antibodies, or antigen-binding portions thereof, include, but are not limited to, humanized antibodies, human antibodies, monoclonal antibodies, chimeric antibodies, polyclonal antibodies, recombinantly expressed antibodies, as well as antigen-binding portions of the foregoing. An antigen-binding portion of an antibody may include a portion of an antibody that specifically binds to BCMA.

The present disclosure provides methods of treating a disease such as cancer in a subject by administering to the subject the present antibody or antigen-binding portion thereof, or immune cells comprising the present chimeric antigen receptors, in an effective amount.

Also encompassed by the present disclosure is a method of blocking the function of BCMA in a mammal comprising administering to the mammal a composition comprising the present antibodies, or antigen-binding portions thereof, or immune cells comprising the present chimeric antigen receptors.

Another method of the disclosure relates to inhibiting the growth and/or differentiation of cells expressing BCMA, comprising contacting the cells with the present antibody or antigen-binding fragment, or immune cells comprising the present chimeric antigen receptors.

After extensive and in-depth research and mass screening, a number of anti-BCMA monoclonal antibodies were obtained. The present disclosure further provides the construction of chimeric antigen receptors targeting BCMA and a preparation method and activity identification of T cells expressing the chimeric antigen receptors targeting BCMA. Specifically, the inventors successfully screened nine strains of hybridoma cells (6G10-1D7, 99B3G3, 105C10F1, 113B3F12, 109C5F3C1, 143D6F4, 151A9A4, 107B11E1D7 and 107A9A4D2), and the antibodies they secreted recognize soluble extracellular domains of human BCMA (e.g., on the cell membrane surface). The antibodies secreted by 6G10-1D7, 99B3G3, 109C5F3C1, 143D6F4, 151A9A4, 107B11E1D7 and 107A9A4D2 can also cross-recognize the soluble extracellular domains of machin BCMA molecules. Anti-BCMA chimeric antigen receptors (CARs) have also been constructed. These CARs have different reactivity to BCMA-positive target cells and have desirable specific cytotoxicity towards target cells.

The fusion protein (hBCMA-ECD-Fc) of human BCMA extracellular domain (Met1-Ala54) and human IgG1 Fc fragment (Pro100-Lys330) was used to immunize mice. The hybridoma technology was used to screen for monoclonal antibodies against human BCMA. The antibody must be able to cross-recognize machin BCMA (cynoBCMA-ECD-Fc) and not recognize tumor necrosis factor receptor superfamily member 13B (TACI, which shares a common ligand with BCMA).

The present disclosure provides for an anti-BCMA antibody, or an antigen-binding portion thereof, comprising a light chain variable region ($V_L$) and a heavy chain variable region ($V_H$).

The present disclosure provides for a chimeric antigen receptor (CAR), comprising an anti-BCMA antigen-binding region which comprises a light chain variable region ($V_L$) and a heavy chain variable region ($V_H$).

In certain embodiments, the anti-BCMA antigen-binding region (or the anti-BCMA antibody, or an antigen-binding portion thereof) includes a light chain variable region comprising an amino acid sequence about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the amino acid sequence set forth in SEQ ID NOs: 53, 55, 57, 59, 61, 63, 65, 67 and 69.

In certain embodiments, the anti-BCMA antigen-binding region (or the anti-BCMA antibody, or an antigen-binding portion thereof) includes a heavy chain variable region comprising an amino acid sequence about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100% identical to the amino acid sequence set forth in SEQ ID NOs: 54, 56, 58, 60, 62, 64, 66, 68 and 70.

In certain embodiments, the anti-BCMA antigen-binding region (or the anti-BCMA antibody, or an antigen-binding portion thereof) includes a light chain variable region ($V_L$) and a heavy chain variable region ($V_H$), where the $V_L$ and $V_H$ comprise/have amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to amino acid sequences set forth in (i) SEQ ID NO: 53 and SEQ ID NO: 54, respectively, (ii) SEQ ID NO: 55 and SEQ ID NO: 56, respectively, (iii) SEQ ID NO: 57 and SEQ ID NO: 58, respectively, (vi) SEQ ID NO: 59 and SEQ ID NO: 60, respectively, (v) SEQ ID NO: 61 and SEQ ID NO: 62, respectively, (vi) SEQ ID NO: 63 and SEQ ID NO: 64, respectively, (vii) SEQ ID NO: 65 and SEQ ID NO: 66, respectively, (viii) SEQ ID NO: 67 and SEQ ID NO: 68, respectively, or (ix) SEQ ID NO: 69 and SEQ ID NO: 70, respectively.

A light chain variable region of the anti-BCMA antigen-binding region (or the anti-BCMA antibody, or an antigen-binding portion thereof) can comprise one, two, or three complementarity determining regions (CDRs) that are about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in (i) SEQ ID NOs: 76, 77 and 78, respectively, (ii) SEQ ID NOs: 82, 83 and 84, respectively, (iii) SEQ ID NOs: 88, 89 and 90, respectively, (iv) SEQ ID NOs: 94, 95 and 96, respectively, (v) SEQ ID NOs: 100, 101 and 102, respectively, (vi) SEQ ID NOs: 106, 107 and 108, respectively, (vii) SEQ ID NOs: 112, 113 and 114, respectively, (viii) SEQ ID NOs: 118, 119 and 120, respectively, or (ix) SEQ ID NOs: 124, 125 and 126, respectively.

A heavy chain variable region of the anti-BCMA antigen-binding region (or the anti-BCMA antibody, or an antigen-binding portion thereof) can comprise one, two, or three complementarity determining regions (CDRs) that are about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in (i) SEQ ID NOs: 79, 80 and 81, respectively, (ii) SEQ ID NOs: 85, 86 and 87, respectively, (iii) SEQ ID NOs:

91, 92 and 93, respectively, (iv) SEQ ID NOs: 97, 98 and 99, respectively, (v) SEQ ID NOs: 103, 104 and 105, respectively, (vi) SEQ ID NOs: 109, 110 and 111, respectively, (vii) SEQ ID NOs: 115, 116 and 117, respectively, (viii) SEQ ID NOs: 121, 122 and 123, respectively, or (ix) SEQ ID NOs: 127, 128 and 129, respectively.

In certain embodiments, a light chain variable region of the anti-BCMA antigen-binding region (or the anti-BCMA antibody, or an antigen-binding portion thereof) comprises three CDRs (CDR1, CDR2 and CDR3) that are identical to the amino acid sequences set forth in (i) SEQ ID NOs: 76, 77 and 78, respectively, (ii) SEQ ID NOs: 82, 83 and 84, respectively, (iii) SEQ ID NOs: 88, 89 and 90, respectively, (iv) SEQ ID NOs: 94, 95 and 96, respectively, (v) SEQ ID NOs: 100, 101 and 102, respectively, (vi) SEQ ID NOs: 106, 107 and 108, respectively, (vii) SEQ ID NOs: 112, 113 and 114, respectively, (viii) SEQ ID NOs: 118, 119 and 120, respectively, or (ix) SEQ ID NOs: 124, 125 and 126, respectively; and a heavy chain variable region of the anti-BCMA antigen-binding region (or the anti-BCMA antibody, or an antigen-binding portion thereof) includes three CDRs (CDR1, CDR2 and CDR3) that are identical to the amino acid sequences set forth in (i) SEQ ID NOs: 79, 80 and 81, respectively, (ii) SEQ ID NOs: 85, 86 and 87, respectively, (iii) SEQ ID NOs: 91, 92 and 93, respectively, (iv) SEQ ID NOs: 97, 98 and 99, respectively, (v) SEQ ID NOs: 103, 104 and 105, respectively, (vi) SEQ ID NOs: 109, 110 and 111, respectively, (vii) SEQ ID NOs: 115, 116 and 117, respectively, (viii) SEQ ID NOs: 121, 122 and 123, respectively, or (ix) SEQ ID NOs: 127, 128 and 129, respectively.

In certain embodiments, the anti-BCMA antigen-binding region (or the anti-BCMA antibody, or an antigen-binding portion thereof) comprises a light chain variable region ($V_L$) and a heavy chain variable region ($V_H$), where, (i) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 76, 77 and 78, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 79, 80 and 81, respectively;

(ii) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 82, 83 and 84, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 85, 86 and 87, respectively;

(iii) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 88, 89 and 90, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 91, 92 and 93, respectively;

(iv) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 94, 95 and 96, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 97, 98 and 99, respectively;

(v) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 100, 101 and 102, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 103, 104 and 105, respectively;

(vi) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 106, 107 and 108, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 109, 110 and 111, respectively;

(vii) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 112, 113 and 114, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 115, 116 and 117, respectively;

(viii) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 118, 119 and 120, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 121, 122 and 123, respectively; or (ix) the $V_L$ comprising three CDRs, CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 124, 125 and 126, respectively; the $V_H$ comprising three complementarity determining regions (CDRs), CDR1, CDR2 and CDR3, having amino acid sequences about 80% to about 100%, at least or about 70%, at least or about 75%, at least or about 80%, at least or about 85%, at least or about 90%, at least or about 95%, at least or about 99%, at least or about 81%, at least or about 82%, at least or about 83%, at least or about 84%, at least or about 85%, at least or about 86%, at least or about 87%, at least or about 88%, at least or about 89%, at least or about 90%, at least or about 91%, at least or about 92%, at least or about 93%, at least or about 94%, at least or about 95%, at least or about 96%, at least or about 97%, at least or about 98%, at least or about 99%, or about 100%, identical to the amino acid sequences set forth in SEQ ID NOs: 127, 128 and 129, respectively.

In certain embodiments, the CDR, $V_H$ and/or $V_L$ have sequence variations. For example, the CDR, $V_H$ or $V_L$, in which 1, 2 3, 4, 5, 6, 7 or 8 residues, or less than 20%, less than 30%, or less than about 40%, of total residues in the CDR, $V_H$ or $V_L$, are substituted or deleted can be present in an antibody (or antigen-binding portion thereof) or CAR that binds BCMA.

Also within the scope of the disclosure are antibodies or antigen-binding portions thereof, or CAR, in which specific amino acids have been substituted, deleted or added. These alternations do not have a substantial effect on the peptide's biological properties such as binding activity. For example, antibodies or antigen-binding portions thereof, or CAR, may have amino acid substitutions in the framework region, such as to improve binding to the antigen. In another example, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al., Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256:1443-45 (1992).

The present peptides may be the functionally active variant of antibodies or antigen-binding portions thereof, or CAR, disclosed herein, e.g., with less than about 30%, about 25%, about 20%, about 15%, about 10%, about 5% or about 1% amino acid residues substituted or deleted but retain essentially the same immunological properties including, but not limited to, binding to BCMA.

The antibodies or antigen-binding portions thereof, or CAR, may also include variants, analogs, orthologs, homologs and derivatives of peptides, that exhibit a biological activity, e.g., binding of BCMA. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

The antibody, or antigen-binding portion thereof, can be derivatized or linked to another functional molecule. For example, an antibody, or antigen-binding portion thereof, can be functionally linked (by chemical coupling, genetic fusion, noncovalent interaction, etc.) to one or more other molecular entities, such as another antibody, a detectable agent, an immunosuppressant, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. Cytotoxic agents may include radioactive isotopes, chemotherapeutic agents, and toxins such as enzymatically active toxins of bacterial, fungal, plant, or animal origin, and fragments thereof. Such cytotoxic agents can be coupled to the antibodies, or antigen-binding portion thereof, of the present disclosure using standard procedures, and used, for example, to treat a patient indicated for therapy with the antibody.

One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Useful detectable agents with which a protein can be derivatized (or labeled) include fluorescent agents, various enzymes, prosthetic groups, luminescent materials, bioluminescent materials, and radioactive materials. Non-limiting, exemplary fluorescent detectable agents include fluorescein, fluorescein isothiocyanate, rhodamine, and phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

The antibodies can be full-length or can include a fragment (or fragments) of the antibody having an antigen-binding portion, including, but not limited to, Fab, F(ab')2, Fab', F(ab)', Fv, single chain Fv (scFv), bivalent scFv (bi-scFv), trivalent scFv (tri-scFv), Fd, dAb fragment (e.g., Ward et al., Nature, 341:544-546 (1989)), an isolated CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present disclosure. Bird et al. Science, 1988, 242:423-426. Huston et al., Proc. Natl. Acad. Sci. USA, 1988, 85:5879-5883.

The present antibody or antigen-binding portion thereof may comprise at least one constant domain, such as, (a) an IgG constant domain; (b) an IgA constant domain, etc.

All antibody isotypes are encompassed by the present disclosure, including IgG (e.g., IgG1, IgG2, IgG3, IgG4), IgM, IgA (IgA1, IgA2), IgD or IgE. The antibodies or antigen-binding portions thereof may be mammalian (e.g., mouse, human) antibodies or antigen-binding portions thereof. The light chains of the antibody may be of kappa or lambda type.

The antibodies or antigen-binding portions thereof of the present disclosure may be monospecific, bi-specific or multi-specific. Multi-specific or bi-specific antibodies or fragments thereof may be specific for different epitopes of one target polypeptide (e.g., BCMA) or may contain antigen-binding domains specific for more than one target polypeptide (e.g., antigen-binding domains specific for BCMA and another antigen). In one embodiment, a multi-specific antibody or antigen-binding portion thereof comprises at least two different variable domains, wherein each variable domain is capable of specifically binding to a separate antigen or to a different epitope on the same antigen. Tutt et al., 1991, J. Immunol. 147:60-69. Kufer et al., 2004, Trends Biotechnol. 22:238-244. The present antibodies can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for BCMA, and the other arm of the immunoglobulin is specific for a second therapeutic target or is conjugated to a therapeutic moiety as described herein.

The antibodies or antigen-binding portions thereof described herein are useful as affinity purification agents. In this process, the antibodies or fragments thereof are immobilized on a solid phase such a Protein A resin, using methods well known in the art.

The present anti-BCMA antibodies or antigen-binding portions thereof are also useful in diagnostic assays to detect and/or quantify BCMA protein, for example, detecting BCMA expression in specific cells, tissues, or serum.

The antibodies or antigen-binding portions thereof described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

Antibody

The term "antibody" or "immunoglobulin" may mean a heterotetrameric glycoprotein of about 150,000 daltons with the same structural characteristics, which comprises two identical light chains (L) and two identical heavy chains (H). Each light chain is linked to a heavy chain by means of a covalent disulfide bond, and the number of disulfide bonds between the heavy chains of different immunoglobulin isotypes is different. Each heavy chain and light chain also have regularly spaced intrachain disulfide bonds. Each heavy chain has a variable region (VH) at one end, followed by a plurality of constant regions. Each light chain has a variable region (VL) at one end and a constant region at the other end; the constant region of the light chain is opposite to the first constant region of the heavy chain, and the variable region of the light chain is opposite to the variable region of the heavy chain. Special amino acid residues form interfaces between the variable regions of the light and heavy chains.

The term "variable" may mean that certain parts of the variable regions of the antibody are different in sequence, which forms the binding and specificity of various specific antibodies to specific antigens thereof. Nevertheless, the variability is not uniformly distributed in the variable regions of the entire antibody and is concentrated in three fragments of the complementarity determining regions (CDR) or hypervariable regions in the light chain and heavy chain variable regions. The more conserved parts of the variable regions are called framework regions (FRs). The variable regions of the natural heavy chains and light chains each contain four FRs, which are roughly in a β-folded configuration and are linked by three CDRs, which form an adapter ring. In some cases, a partial β-folded structure can be formed. The CDRs in each chain are closely joined together by means of the FRs and form antigen binding sites of the antibody together with the CDRs of another chain (see Kabat et al., NIH Publ. No. 91-3242, Volume I, pages 647-669 (1991)). Constant regions do not directly participate in the binding of antibodies to antigens, but they exhibit different effector functions, such as participating in antibody-dependent cytotoxicity of the antibody.

The "light chains" of vertebrate antibodies (immunoglobulins) can be classified into one of two distinct categories (called κ and λ) based on the amino acid sequences in their constant regions. According to the amino acid sequences of heavy chain constant regions of immunoglobulins, the immunoglobulins can be classified into different types. There are mainly five types of immunoglobulins: IgA, IgD, IgE, IgG, and IgM, some of which can be further divided into subclasses (isotypes), such as IgG1, IgG2, IgG3, IgG4, IgA, and IgA2. The heavy chain constant regions corresponding to different types of immunoglobulins are called α, δ, ε, γ and μ, respectively. The subunit structures and three-dimensional configurations of different types of immunoglobulins are well known to those skilled in the art.

Generally, the antigen-binding properties of an antibody can be described by 3 specific regions located in the heavy chain and light chain variable regions, which are called variable regions (CDRs) and space this fragment into four framework regions (FRs). The amino acid sequences of the four FRs are relatively conservative and do not directly participate in the binding reaction. These CDRs form a circular structure and are close to each other in the space structure by means of the β-folds formed by the FRs among the CDRs. The CDRs on the heavy chains and the corresponding CDRs on the light chain constitute antigen binding sites of the antibody. The amino acid sequences of the same type of antibody can be compared to determine which amino acids constitute the FRs or CDRs.

The present disclosure not only includes a complete antibody, but also includes immunologically active antibody fragments or fusion proteins formed by the antibody and other sequences. Therefore, the present disclosure also includes fragments, derivatives and analogs of the antibody.

In the present disclosure, antibodies include murine, chimeric, humanized or fully human antibodies prepared by technologies well known to those skilled in the art. Recombinant antibodies, such as chimeric and humanized monoclonal antibodies, comprise a human portion and a non-human portion, can be obtained through standard DNA recombination techniques, and are all useful antibodies. A chimeric antibody is a molecule in which different parts are derived from different animal species, such as a chimeric antibody with variable regions of a mouse-derived monoclonal antibody, and constant regions of a human-derived immunoglobulin (see U.S. Pat. Nos. 4,816,567 and 4,816,397 for example, incorporated herein by reference in their entirety). A humanized antibody may refer to an antibody molecule derived from non-human species and comprising one or more complementarity determining regions (CDRs) derived from non-human species and framework regions derived from human immunoglobulin molecules (see U.S. Pat. No. 5,585,089, incorporated herein by reference in its entirety). These chimeric and humanized monoclonal antibodies can be prepared using DNA recombination techniques well known in the art.

In the present disclosure, antibodies can be monospecific, bispecific, trispecific, or multispecific.

In the present disclosure, the antibody also includes its conservative variants, which means that compared with the amino acid sequences of the antibody provided by the present disclosure, at most 10, at most 8, at most 5, or at most 3 amino acids are substituted by amino acids with similar properties to form polypeptides. For example, the conservative variant polypeptides may be produced by amino acid substitutions according to Table A.

TABLE A

| Initial residue | Representative substitution | Exemplary substitution |
|---|---|---|
| Ala (A) | Val; Leu; Ile | Val |
| Arg(R) | Lys; Gin; Asn | Lys |
| Asn (N) | Gln; His; Lys; Arg | Gln |
| Asp (D) | Glu | Glu |
| Cys (C) | Ser | Ser |
| Gin (Q) | Asn | Asn |
| Glu (E) | Asp | Asp |
| Gly (G) | Pro; Ala | Ala |
| His (H) | Asn; Gln; Lys; Arg | Arg |
| He (I) | Leu; Val; Met; Ala; Phe | Leu |
| Leu (L) | Ile; Val; Met; Ala; Phe | Ile |
| Lys (K) | Arg; Gin; Asn | Arg |
| Met (M) | Leu; Phe; He | Leu |
| Phe (F) | Leu; Val; He; Ala; Tyr | Leu |
| Pro (P) | Ala | Ala |
| Ser (S) | Thr | Thr |
| Thr(T) | Ser | Ser |
| Trp (W) | Tyr; Phe | Tyr |
| Tyr(Y) | Trp; Phe; Thr; Ser | Phe |
| Val (V) | Ile; Leu; Met; Phe; Ala | Leu |

Anti-BCMA Antibody

The present disclosure provides an antibody against BCMA and with high specificity and high affinity, which comprises heavy chains and light chains, the heavy chains contain amino acid sequences of VH regions, and the light chains contain amino acid sequences of VL regions.

In certain embodiments, the antibody comprises $V_H$ regions and $V_L$ regions encoded by nucleotide sequences shown below:

| Hybridoma No. | Nucleotide sequences encoding $V_H$ regions | Nucleotide sequences encoding $V_L$ regions |
|---|---|---|
| 6G10-1D7 (CP01) | SEQ ID NO: 1 | SEQ ID NO: 2 |
| 99B3G3 (CP02) | SEQ ID NO: 3 | SEQ ID NO: 4 |
| 102A12H6 | SEQ ID NO: 5 | SEQ ID NO: 6 |
| 105C10F1 (CP03) | SEQ ID NO: 7 | SEQ ID NO: 8 |
| 107A11F1 | SEQ ID NO: 9 | SEQ ID NO: 13 |
| | SEQ ID NO: 10 | |
| | SEQ ID NO: 11 | |
| | SEQ ID NO: 12 | |
| 107B11E1 | SEQ ID NO: 14 | SEQ ID NO: 18 |
| | SEQ ID NO: 15 | |
| | SEQ ID NO: 16 | |
| | SEQ ID NO: 17 | |
| 107A9A4 | SEQ ID NO: 19 | SEQ ID NO: 23 |
| | SEQ ID NO: 20 | |
| | SEQ ID NO: 21 | |
| | SEQ ID NO: 22 | |
| 113B3F12 | SEQ ID NO: 24 | SEQ ID NO: 25 |
| 100H2D12C6 | SEQ ID NO: 3 | SEQ ID NO: 4 |
| 109C5F3C1 (CP06) | SEQ ID NO: 26 | SEQ ID NO: 27 |
| 143D6F4 (CP07) | SEQ ID NO: 28 | SEQ ID NO: 29 |
| 151A9A4 (CP08) | SEQ ID NO: 30 | SEQ ID NO: 31 |
| 152D8E8 (CP09) | SEQ ID NO: 32 | SEQ ID NO: 33 |
| 107A11F1B7 (CP04) | SEQ ID NO: 34 | SEQ ID NO: 35 |
| | | SEQ ID NO: 36 |
| 107A9A4D2 | SEQ ID NO: 34 | SEQ ID NO: 35 |
| | | SEQ ID NO: 36 |
| 107B11E1D7 (CP05) | SEQ ID NO: 37 | SEQ ID NO: 38 |
| 97B8G8D12 | SEQ ID NO: 3 | SEQ ID NO: 4 |

In certain embodiments, the antibody is a murine antibody.

In certain embodiments, the antibody comprises heavy chains and light chains with amino acid sequences shown below:

| Hybridoma No. | Amino acid sequences of heavy chains | Amino acid sequences of light chains |
|---|---|---|
| 6G10-1D7 (CP01) | SEQ ID NO: 39 | SEQ ID NO: 40 |
| 99B3G3 (CP02) | SEQ ID NO: 41 | SEQ ID NO: 42 |
| 105C10F1 (CP03) | SEQ ID NO: 43 | SEQ ID NO: 44 |
| 113B3F12 | SEQ ID NO: 45 | SEQ ID NO: 46 |
| 107B11E1D7 (CP05) | SEQ ID NO: 47 | SEQ ID NO: 48 |
| 107A9A4D2 | SEQ ID NO: 49 | SEQ ID NO: 50 |
| | | SEQ ID NO: 51 |

In certain embodiments, the antibody is a chimeric antibody.

In certain embodiments, the antibody comprises $V_H$ regions and $V_L$ regions with amino acid sequences shown below:

| Antibody | Amino acid sequences of $V_H$ regions | Amino acid sequences of $V_L$ regions |
|---|---|---|
| CP01 | SEQ ID NO: 54 | SEQ ID NO: 53 |
| CP02 | SEQ ID NO: 56 | SEQ ID NO: 55 |
| CP03 | SEQ ID NO: 58 | SEQ ID NO: 57 |
| CP04 | SEQ ID NO: 60 | SEQ ID NO: 59 |
| CP05 | SEQ ID NO: 62 | SEQ ID NO: 61 |
| CP06 | SEQ ID NO: 64 | SEQ ID NO: 63 |
| CP07 | SEQ ID NO: 66 | SEQ ID NO: 65 |
| CP08 | SEQ ID NO: 68 | SEQ ID NO: 67 |
| CP09 | SEQ ID NO: 70 | SEQ ID NO: 69 |

The CDR sequences of antibodies CP01-CP09 are shown below.

| Name | CDR | SEQ ID No: | Sequence |
|---|---|---|---|
| CP01 VL | | 53 | DIVMTQSQRFMSTSVGDRVSITCKASQSVGTAVAWYQQTPGQFPKLLIYSTSNRYTGVPDRFTGSGSGTDFTLTISNMQSEDLADYFCQQYSTYPLTFGSGTKLELK |
| | CDR-L1 | 76 | KASQSVGTAVA |
| | CDR-L2 | 77 | STSNRYT |
| | CDR-L3 | 78 | QQYSTYPLT |
| CP01 VH | | 54 | EVQLQQSGPELVKPGASMKISCKASDYSFTDYIMTWVKQSHGKNLEWIGLINPYNGGTTYNQKFKDKATFTVDKSSTTAYMDLLSLTSEDSAVYYCARRGITTDYYTMDYWGQGTSVTVSS |
| | CDR-H1 | 79 | DYIMT |
| | CDR-H2 | 80 | LINPYNGGTTYNQKFKD |
| | CDR-H3 | 81 | RGITTDYYTMDY |
| CP02 VL | | 55 | DIVMTQSPSSLAMSVGQKVTMSCKSSQSLLNSSIQKNYLAWYQQKPGQSPKLLVYFASTRESGVPDRFIGSGSGTDFTLTISSVQAEDLADYFCQQHYSSPLTFGAGTKLELK |
| | CDR-L1 | 82 | KSSQSLLNSSIQKNYLA |
| | CDR-L2 | 83 | FASTRES |
| | CDR-L3 | 84 | QQHYSSPLT |
| CP02 VH | | 56 | EVQLQQSGPVLVKPGASVKMSCKASGYTFTDLYMNWVKQSHGKSLEWIGVINPYNGGTSYNQKFKAKATLTVDKSSITAYMELNSLTSEDSAVYYCARGDSIYVMDYWGQGTSVTVSS |
| | CDR-H1 | 85 | DLYMN |
| | CDR-H2 | 86 | VINPYNGGTSYNQKFKA |
| | CDR-H3 | 87 | GDSIYVMDY |
| CP03 VL | | 57 | DIVMTPSQKFMSTSVGDRVSVTCKASQNVGTNVAWYQQKPGQSPKALIYSASYRYSGVPDRFTGSGSGTDFTLTISNVQSEDLAEYFCQHYNSYPFTFGSGTKLEIK |
| | CDR-L1 | 88 | KASQNVGTNVA |
| | CDR-L2 | 89 | SASYRYS |
| | CDR-L3 | 90 | QHYNSYPFT |
| CP03 VH | | 58 | EVKLLQSGGGLVQPGGSLKLSCAASGIDFSRYWMSWVRRAPGKGLEWIGEINPDSSTINYAPSLKDKFIISRDAAKNTLYLQMSKVRSEDTALYYCATLYYDYDGDYAMDYWGQGTSVTVSS |
| | CDR-H1 | 91 | RYWMS |
| | CDR-H2 | 92 | EINPDSSTINYAPSLKD |
| | CDR-H3 | 93 | LYYDYDGDYAMDY |
| CP04 VL | | 59 | DIVMTQSPSSLAMSVGQKVTMSCKSSQSLLNSSIQKNYLAWYQQKPGQSPKLLIYFASTRESGVPDRFIGSGSGTDFTLTISSVQAEDLADYFCQQHYSTPLTFGAGTKLELK |
| | CDR-L1 | 94 | KSSQSLLNSSIQKNYLA |
| | CDR-L2 | 95 | FASTRES |
| | CDR-L3 | 96 | QQHYSTPLT |
| CP04 VH | | 60 | EVQLQQSGPVLVKPGASVKMSCKASGYTFTDLYMNWLKQSHGKRLEWIGVINPYNGGTSYNQKFKGKATLTVDKSSSTAYMDLNSLTSEDSAVYYCARGDSIYVMDYWGQGTSFTVSS |
| | CDR-H1 | 97 | DLYMN |
| | CDR-H2 | 98 | VINPYNGGTSYNQKFKG |
| | CDR-H3 | 99 | GDSIYVMDY |
| CP05 VL | | 61 | ENVLTQSPAIMSASPGEKVTMTCSASSSVSYMHWYQQKSSTSPKLWIYDTSKLSSGVPGRFSGSGSGKSYSLTISSMEAEDVATYYCFQGSGYPLFTFGSGTKLEIK |
| | CDR-L1 | 100 | SASSSVSYMH |
| | CDR-L2 | 101 | DTSKLSS |
| | CDR-L3 | 102 | FQGSGYPLFT |
| CP05 VH | | 62 | EVQLQQSGPVLVKPGASVKMSCKASGYTFTDLYMNWLKQSHGKRLEWIGVINPYNGGTSYNQKFKGKATLTVDKSSSTAYMDLNSLTSEDSAVYYCARGDSIYVMDYWGQGTSFTVSS |
| | CDR-H1 | 103 | DLYMN |
| | CDR-H2 | 104 | VINPYNGGTSYNQKFKG |
| | CDR-H3 | 105 | GDSIYVMDY |

-continued

| Name | CDR | SEQ ID No: | Sequence |
|---|---|---|---|
| CP06 VL | | 63 | DIVMTQSPSSLALSVGQKVTMSCKSSQSLLDNSNQKHYLAWYQQKPGQSPKLLVYFASTRESGVPDRFIGSGSGTDFTLTISSVQAEDLADYFCQQHYTAPLTFGAGTKLALK |
| | CDR-L1 | 106 | KSSQSLLDNSNQKHYLA |
| | CDR-L2 | 107 | FASTRES |
| | CDR-L3 | 108 | QQHYTAPLT |
| CP06 VH | | 64 | EVQLQQSGPVLVKPGASVKMSCKVSGYTFTDYYMNWVKQSHGKSLEWIGVITPYNGANRYNQKFKGKATLTVDKSSSTAYMEVSSLTSEDSAVYYCARGDSIYVMDYWGQGTSVIVSS |
| | CDR-H1 | 109 | DYYMN |
| | CDR-H2 | 110 | VITPYNGANRYNQKFKG |
| | CDR-H3 | 111 | GDSIYVMDY |
| CP07 VL | | 65 | DIVMTQSPSSLAMSVGQKVTMSCKSSQSLLNSSIQKNYLAWYQQKPGQSPKLLVYFASTRESGVPDRFIGSGSGTDFTLTISSVQAEDLADYFCQQHYSTPLTFGGGTKLELK |
| | CDR-L1 | 112 | KSSQSLLNSSIQKNYLA |
| | CDR-L2 | 113 | FASTRES |
| | CDR-L3 | 114 | QQHYSTPLT |
| CP07 VH | | 66 | EVQLQQSGPVLVKPGASVKMSCKASGYTFTDYSLNWVKQSHGKSLEWIGVVNPYNGGTSHNQKFKGKATLTVDKSSSTAYMELNSLTSEDSAVYYCARPDSIYVMDYWGQGTSVTVSS |
| | CDR-H1 | 115 | DYSLN |
| | CDR-H2 | 116 | VVNPYNGGTSHNQKFKG |
| | CDR-H3 | 117 | PDSIYVMDY |
| CP08 VL | | 67 | DIVMTQSPSSLAMSVGQKVTMSCKSSQSLLNSNIQKNYLAWYQQKPGQSPKLLVYFASTRESGVPDRFIGSGSGTDFTLTISSVQAEDLADYFCQQHYSTPLTFGAGTKLELK |
| | CDR-L1 | 118 | KSSQSLLNSNIQKNYLA |
| | CDR-L2 | 119 | FASTRES |
| | CDR-L3 | 120 | QQHYSTPLT |
| CP08 VH | | 68 | EVQLQQSGPVLVKPGASVKMSCKASGYTFTDYSLNWVKQSHGKSLEWIGVVNPYNGGTTYNQKFKGKATLTVDKSSSTAYMELNSLTSEDSAVYYCARPDSIYVMDSWGQGTSVTVSS |
| | CDR-H1 | 121 | DYSLN |
| | CDR-H2 | 122 | VVNPYNGGTTYNQKFKG |
| | CDR-H3 | 123 | PDSIYVMDS |
| CP09 VL | | 69 | DIKMTQSPSSMYVSLGERVTITCKASQDINRNLSWFQQKPGKSPKTLIYRANRLVDGVPLRFSGSGSGQDYSLTISSLEYEDMGIYYCLQYDEFPRTFGGGTKLEIK |
| | CDR-L1 | 124 | KASQDINRNLS |
| | CDR-L2 | 125 | RANRLVD |
| | CDR-L3 | 126 | LQYDEFPRT |
| CP09 VH | | 70 | QVTLKESGPGILQSSQTLSLTCSFSGFSLNTSGMGVNWIRQSSGKDLEWLAHIYWNDDKRYNPSLKSRLTISKDTSRNQVFLRITSVDATDTATYFCCRSRLSFDYWGHGTTLTVSS |
| | CDR-H1 | 127 | TSGMGVN |
| | CDR-H2 | 128 | HIYWNDDKRYNPSLKS |
| | CDR-H3 | 129 | SRLSFDY |

In certain embodiments, the antibody is a single-chain antibody.

In certain embodiments, any of the foregoing amino acid sequences also includes a derivative sequence that optionally adds, deletes, modifies and/or substitutes at least one amino acid and can retain the binding affinity of BCMA.

In certain embodiments, the sequence formed by addition, deletion, modification and/or substitution of at least one amino acid sequence may have a homology of at least 80%, at least 85%, at least 90%, or at least 95% of amino acid sequences. The number of the added, deleted, modified and/or substituted amino acid residues can be 1 to 7, 1 to 5, 1 to 3, or 1 to 2.

The antibody provided by the present disclosure can be a double-chain or single-chain antibody, and can be selected from animal-derived antibodies, chimeric antibodies and humanized antibodies, a human-animal chimeric antibody, or a fully humanized antibody.

The antibody derivatives provided by the present disclosure can be single-chain antibodies and/or antibody fragments, such as: Fab, Fab', (Fab')2 or other antibody derivatives known in the art and any one or more of IgA, IgD, IgE, IgG and IgM antibodies or antibodies of other subtypes.

Among them, the animal may be a mammal, such as a mouse.

The antibody provided by the present disclosure can be a chimeric antibody, humanized antibody, or CDR-grafted and/or -modified antibody that targets human BCMA.

Specifically, in the embodiments of the present application, four rounds of hybridoma cell fusion were carried out. A total of 14 hybridoma cells (6G10-1D7, 99B3G3, 102A12H6, 107A11F1, 107A9A4, 107B11E1, 100H2D12C6, 105C10F1, 113B3F12, 109C5F3C1, 97B8G8D12, 143D6F4, 151A9A4 and 152D8E8) were selected for antibody production and purification in small batches. Among them, 13 of the 14 clones (except 97B8G8D12) all successfully generated corresponding antibodies. Except 152D8E8 (CP09), the remaining 12 hybridoma antibodies all could bind to the soluble extracellular domains of human BCMA molecules. Except 105C10F1(CP03), 152D8E8(CP09) and 113B3F12, the remaining 10 hybridoma antibodies all could cross-recognize the soluble extracellular domains of machin BCMA molecules. Except 102A12H6 and 152D8E8 (CP09), the remaining 11 hybridoma antibodies all could recognize the extracellular domains of human BCMA molecules on the cell surface.

17 strains of hybridoma cells in total were sequenced for antibody variable regions. 12 strains of the hybridoma cells were monoclonal according to the sequencing: 6G10-1D7, 99B3G3, 102A12H6, 100H2D12C6, 105C10F1, 113B3F12, 109C5F3C1, 97B8G8D12, 143D6F4, 151A9A4, 152D8E8 and 107B11E1D7, of which 99B3G3, 100H2D12C6 and 97B8G8D12 had the same sequence in the antibody variable regions. Five strains of the hybridoma cells were polyclonal according to the sequencing: 07A11F1, 107A9A4, 107B11E1, 107A9A4D2 and 107A11F1B7, of which 107A11F1, 107A9A4 and 107B11E1 each had four heavy chains and a light chain; and 107A9A4D2 and 107A11F1B7 each had a heavy chain and two light chains, and had the same sequence. Five strains of monoclonal hybridoma cells (6G10-1D7, 99B3G3, 105C10F1, 113B3F12 and 107B11E1D7) and a strain of polyclonal hybridoma cell (107A9A4D2) were selected for chimeric antibody expression. Among them, 107A9A4D2VH was paired and expressed with 107A9A4D2VL-1 and 107A9A4D2VL-2, respectively. The detection results of ELISA and flow cytometry showed that the chimeric antibodies of the hybridomas 6G10-1D7, 99B3G3, 105C10F1 and 107B11E1D7 all bound to the soluble extracellular domains of human BCMA molecules on the cell surface. The chimeric antibodies formed by pairing of the heavy chain 107A9A4D2VH and the light chain 107A9A4D2VL-2 of the hybridoma 107A9A4D2 all bound to the soluble extracellular domains of the human BCMA molecules on the cell surface. The chimeric antibodies formed by pairing of 107A9A4D2VH and 107A9A4D2VL-1 did not bind to the soluble extracellular domains of the human BCMA molecules on the cell surface.

Antibody Preparation

The sequence of the DNA molecule of the antibody or its fragments provided by the present disclosure can be obtained by conventional techniques, such as PCR amplification or genomic library screening. In addition, the coding sequences of the light chains and the heavy chains may also be fused together to form a single-chain antibody.

Once relevant sequences are obtained, the relevant sequences can be obtained in large batches by recombination. Generally, the relevant sequences are obtained by cloning the relevant sequences into vectors, then transferring the relevant sequences into cells, and then isolating the relevant sequences from the proliferated host cells by conventional methods.

In addition, artificial synthesis methods can be used to synthesize the relevant sequences, especially when the fragment length is short. Generally, a fragment with a long sequence can be obtained by synthesizing a plurality of small fragments first and then linking the small fragments.

At present, a DNA sequence encoding the antibody (or fragment or derivative thereof) provided by the present disclosure can be obtained completely through chemical synthesis. The DNA sequence can then be introduced into various existing DNA molecules (or such as vectors) and cells known in the art. In addition, mutations can be introduced into the protein sequences of the present disclosure by chemical synthesis.

The present disclosure also relates to vectors containing the foregoing appropriate DNA sequences and appropriate promoters or control sequences. These vectors can be used to transform appropriate host cells so that they can express proteins.

The host cells can be prokaryotic cells, such as bacterial cells; or lower eukaryotic cells, such as yeast cells; or higher eukaryotic cells, such as mammalian cells. The animal cells may include (but are not limited to): CHO—S and HEK-293 cells.

Normally, the obtained host cells are cultured and transformed under the conditions suitable for expression of the antibody provided by the present disclosure. Then conventional immunoglobulin purification steps, such as protein A-Sepharose, hydroxyapatite chromatography, gel electrophoresis, dialysis, ionization exchange chromatography, hydrophobic chromatography, molecular sieve chromatography or affinity chromatography and other conventional isolation and purification methods well known to those skilled in the art, are used for purification to obtain the antibody provided by the present disclosure.

The obtained monoclonal antibody can be identified by conventional means. For example, the binding specificity of the monoclonal antibody can be determined by immunoprecipitation or in vitro binding test (such as radioimmunoassay (RIA) or enzyme-linked immunosorbent assay (ELISA)). The binding affinity of the monoclonal antibody, for example, can be determined by the Scatchard analysis of Munson et al., Anal. Biochem., 107:220 (1980).

The antibody provided by the present disclosure may be expressed in a cell, or on a cell membrane, or secreted out of a cell. If necessary, a recombinant protein can be isolated and purified through various isolation methods by employing the physical, chemical, and other properties of the recombinant protein. These methods are well known to those skilled in the art. Examples of these methods include, but are not limited to: conventional renaturation treatment, treatment with a protein precipitation agent (salting-out method), centrifugation, osmotic bacteriostasis, ultrasonic treatment, ultracentrifugation, molecular sieve chromatography (gel filtration), adsorption chromatography, ion exchange chromatography, high performance liquid chromatography (HPLC) and various other liquid chromatography techniques and combinations of these methods.

Antibody-Drug Conjugate (ADC)

The present disclosure further provides an antibody-drug conjugate (ADC) based on the antibody provided by the present disclosure.

Typically, the ADC comprises the antibody and an effector molecule, and the antibody is conjugated, e.g., chemically conjugated, to the effector molecule. The effector molecule may be a drug with therapeutic activity. Further, the effector molecule may be one or more of toxic proteins, chemotherapeutics, small-molecule drugs or radionuclides.

The antibody provided by the present disclosure and the effector molecule may be conjugated by means of a coupling agent. Examples of the coupling agent include one or more of non-selective coupling agents, coupling agents using a carboxyl group, peptide chains, and coupling agents using a disulfide bond. The non-selective coupling agent refers to a compound that makes the effector molecule and the antibody form a covalent bond, such as glutaraldehyde. The coupling agents using a carboxyl group can be any one or more of cis-aconitic anhydride coupling agents (e.g., cis-aconitic anhydride) and acyl hydrazone coupling agents (the coupling site is acyl hydrazone).

Some residues on the antibody (e.g., Cys or Lys) may be used to link a variety of functional groups, including imaging reagents (e.g., chromophoric groups and fluorescent groups), diagnostic reagents (e.g., MRI contrast agents and radioisotopes), stabilizers (e.g., glycol polymers) and therapeutic agents. The antibody can be conjugated to a functional agent to form an antibody-functional agent conjugate. Functional agents (e.g., drugs, detection reagents and stabilizers) may be conjugated (covalently linked) to the antibody. The functional agent may be linked to the antibody directly or indirectly by means of a linker.

An antibody can be conjugated to a drug to form an antibody drug conjugate (ADC). Typically, the ADC comprises a linker located between the drug and the antibody. The linker can be a degradable or a non-degradable linker. The degradable linker is typically easily degraded in the intracellular environment, for example, the linker is degraded at the target site, so that the drug is released from the antibody. Suitable degradable linkers include, for example, enzymatically degraded linkers, which include peptidyl-containing linkers that can be degraded by intracellular proteases (e.g., lysosomal proteases or endosomal proteases), or sugar linkers, for example, glucuronide-containing linkers that can be degraded by glucosidase. The peptidyl linkers may include, for example, dipeptides, such as valine-citrulline, phenylalanine-lysine or valine-alanine. Other suitable degradable linkers include, for example, pH-sensitive linkers (e.g., linkers that are hydrolyzed when the pH is less than 5.5, such as hydrazone linkers) and linkers that will be degraded under reducing conditions (e.g., disulfide bond linkers). A non-degradable linker typically releases a drug under the condition that the antibody is hydrolyzed by protease.

Before linking the antibody, the linker may have an active reactive group that can react with some amino acid residues where the linking is achieved through the active reactive group. Sulfhydryl-specific active reactive groups include: for example, maleimide compounds, halogenated amides (e.g., iodinated, brominated, or chlorinated); halogenated esters (e.g., iodinated, brominated, or chlorinated); halogenated methyl ketones (e.g., iodinated, brominated, or chlorinated), benzyl halides (e.g., iodinated, brominated, or chlorinated); vinyl sulfone, and pyridyl disulfide; mercury derivatives such as 3,6-di-(mercury methyl) dioxane, with the counter ion being acetate, chloride ion or nitrate; and poly(methylene dimethyl sulfide ether) thiosulfonate. The linker may include, for example, maleimide linked to the antibody by thiosuccinimide.

The drug can be any drug, which is cytotoxic, inhibits cell growth or is immunosuppressive. In an implementation manner, a linker links an antibody and a drug, and the drug has a functional group that can form a bond with the linker. For example, the drug may have an amino group, a carboxyl group, a sulfhydryl group, a hydroxyl group, or a keto group that can form a bond with the linker. In the case where the drug is directly linked to the linker, the drug has a reactive active group before being linked to the antibody.

Useful drug categories include, for example, anti-tubulin drugs, DNA minor groove binders, DNA replication inhibitors, alkylating reagents, antibiotics, folate antagonists, anti-metabolites, chemotherapy sensitizers, topoisomerase inhibitors and *Vinca* alkaloids. Examples of particularly useful cytotoxic drugs include, for example, DNA minor groove binders, DNA alkylating reagents and tubulin inhibitors. Typical cytotoxic drugs include, for example, auristatins, camptothecins, duocarmycins, etoposides, maytansines and maytansinoids compounds (e.g., DM1 and DM4), taxanes, benzodiazepines or benzodiazepine containing drugs (e.g., pyrrolidine [1,4] benzodiazepine (PBDs), indolinobenzodiazepines and oxazolidinobenzodiazepines) and vinca alkaloids.

The drug-linker may be used to form ADC in a simple step. In other implementation manners, bifunctional linker compounds can be used to form ADCs in a two-step or multi-step process. For example, a cysteine residue reacts with the reactive part of the linker in the first step, and in the subsequent step, the functional group on the linker reacts with the drug, thereby forming an ADC.

Generally, a functional group on the linker is selected to facilitate the specific reaction with an appropriate reactive group on the drug portion. As a non-limiting example, the azide-based portion can be used to specifically react with the reactive alkynyl group on the drug portion. The drug is covalently bound to the linker through the 1,3-dipolar cycloaddition between the azide and the alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, such as N-hydroxysuccinimide ester (suitable for reacting with amines and alcohols). These and other linking strategies, such as those described in "Bioconjugate Techniques," Second Edition (Elsevier), are well known to those skilled in the art. Those skilled in the art can understand that, for the selective reaction between the drug portion and the linker, when reactive functional groups in a complementary pair are selected, each member of the complementary pair can be used in both the linker and the drug.

The present disclosure further provides a method for preparing an ADC, which may further comprise binding an antibody to a drug-linker compound under conditions sufficient to form an antibody-drug conjugate (ADC).

In some implementation manners, the method provided by the present disclosure comprises binding an antibody to a bifunctional linker compound under conditions sufficient to form an antibody-linker conjugate. In these implementation manners, the method provided by the present disclosure further comprises binding the antibody linker conjugate to the drug portion under conditions sufficient to covalently link the drug portion to the antibody by means of a linker.

In some implementation manners, the antibody-drug conjugate ADC is as shown in the following molecular formula:

$$Ab \text{—}(LU\text{—}D)_p$$

where, Ab is an antibody, LU is a linker, D is a drug, and the subscript p is a value selected from 1 to 8.

Chimeric Antigen Receptor (CAR)

The chimeric antigen receptor (CAR) provided by the present disclosure may comprise an extracellular domain, a transmembrane domain and an intracellular domain. The extracellular domain may comprise a target-specific binding element (also known as an antigen binding domain). The intracellular domain may comprise a costimulatory signaling region and a ζ chain portion. The costimulatory signaling region may refer to a part of the intracellular domain that comprises costimulatory molecules. The co-stimulatory molecules are cell surface molecules required for effective response of lymphocytes to antigens, rather than antigen receptors or ligands thereof.

A linker may be incorporated between the extracellular domain and the transmembrane domain of the CAR, or between the cytoplasmic domain and the transmembrane domain of the CAR. The term "linker" may refer to any oligopeptide or polypeptide that functions to link the transmembrane domain to the extracellular domain or cytoplasmic domain of the polypeptide chain. The linker may comprise 0 to 300 amino acids, 2 to 100 amino acids, or 3 to 50 amino acids.

In certain embodiments, the extracellular domain of the CAR includes an antigen-binding domain targeting BCMA. When the CAR is expressed in T cells, antigen recognition can be performed based on the antigen binding specificity. When the T cells bind to antigens associated therewith, the T cells will affect the tumor cells, such as causing the tumor cells not to grow, or resulting in tumor cell death, which can reduce or eliminate the patient's tumor burden.

The antigen binding domain may be fused with one or more intracellular domains from the costimulatory molecule and the ζ chain. In one embodiment, the antigen binding domain is fused with the intracellular domain formed by combination of the 4-1BB signaling domain and the CD3ζ signal domain.

The terms "antigen-binding domains" and "single-chain antibody fragments" may refer to Fab fragments, Fab' fragments, $F(ab')_2$ fragments, or single Fv fragments, which have antigen-binding activity. The Fv antibody comprises antibody VH regions and VL regions, but no constant regions, and has the smallest antibody fragment of all antigen binding sites. Generally, the Fv antibody further comprises a polypeptide linker between the VH and VL domains, and can form a structure required for antigen binding. The antigen binding domain is generally a scFv (single-chain variable fragment). The size of the scFv is generally ⅙ of a complete antibody. The single-chain antibody may be an amino acid chain sequence encoded by a nucleotide chain. In certain embodiments, the scFv specifically recognizes BCMA.

For hinge regions and transmembrane regions (transmembrane domains), a CAR may be designed to include transmembrane domains fused to the extracellular domains of the CAR. In an implementation manner, a transmembrane domain that is naturally associated with one of the domains in the CAR is used. In some examples, modification can be performed by selecting transmembrane domains or replacing amino acids to avoid binding such domains to the transmembrane domains of the same or different surface membrane proteins, thereby minimizing interaction with other members of the receptor complex.

The intracellular domains in the CAR may include 4-1BB signaling domains and CD3ζ signaling domains.

Based on the light chains and heavy chains of the 9 antibodies obtained through screening in the present disclosure, 18 chimeric antigen receptors (CARs) were constructed. These CARs have different reactivities to BCMA-positive target cells and have a desirable specific killing ability to the target cells. Specifically, the foregoing nine antibodies comprise $V_H$ regions and $V_L$ regions with amino acid sequences shown below:

| Antibody | Amino acid sequences of $V_H$ regions | Amino acid sequences of $V_L$ regions |
|---|---|---|
| CP01 | SEQ ID NO: 54 | SEQ ID NO: 53 |
| CP02 | SEQ ID NO: 56 | SEQ ID NO: 55 |
| CP03 | SEQ ID NO: 58 | SEQ ID NO: 57 |
| CP04 | SEQ ID NO: 60 | SEQ ID NO: 59 |
| CP05 | SEQ ID NO: 62 | SEQ ID NO: 61 |
| CP06 | SEQ ID NO: 64 | SEQ ID NO: 63 |
| CP07 | SEQ ID NO: 66 | SEQ ID NO: 65 |
| CP08 | SEQ ID NO: 68 | SEQ ID NO: 67 |
| CP09 | SEQ ID NO: 70 | SEQ ID NO: 69 |

In certain embodiments, the gene structure of a CAR may comprise a leader sequence (signal peptide), an antigen recognition sequence, a linker region, a transmembrane region, a costimulatory factor signal region, and a CD3zeta signaling region, and the linking sequence is as follows:

[CD8 LS]-[VL-Linker-VH]-[hinge-CD8TM]-[4-1BB]-[CD3zeta] or

[CD8 LS]-[VH-Linker-VL]-[hinge-CD8TM]-[4-1BB]-[CD3zeta].

The present disclosure has identified the correlation between the expression time and expression intensity of different CAR structures on the cell membrane surface after virus infection, and then identified the differences in the easiness of expression of different CAR structural proteins. This finding indicates a difference between the expression level of the CAR protein on the membrane surface and the persistence of in vivo activity of CART under the same infection conditions of different CAR structures.

Vector

The nucleic acid sequences encoding desired molecules can be obtained using recombinant methods known in the art, such as, for example, by screening a library from cells expressing the gene, by obtaining the gene from a vector known to include the gene, or by using standard techniques to isolate the gene directly from the cells and tissues that contain the gene. Optionally, the gene of interest can be synthesized and produced The present disclosure also provides a vector into which an expression cassette provided by the present disclosure is inserted. Vectors derived from retroviruses such as lentiviruses are suitable vehicles to achieve long-term gene transfer because they allow long-term, stable integration of transgenes and propagation of the transgenes in daughter cells. Lentiviral vectors have advantages over vectors derived from oncogenic retroviruses such as murine leukemia viruses, because they can transduce non-proliferating cells, such as hepatocytes. They also have the advantage of low immunogenicity.

The expression cassettes or nucleic acid sequences in the present disclosure may be operably linked to promoters and incorporated into expression vectors in general. The vectors are suitable for replication and integration of eukaryotic cells. A typical cloning vector comprises a transcription and translation terminator, an initial sequence and a promoter that can be used to regulate the expression of expected nucleic acid sequences.

The expression constructs may also use standard gene delivery protocols for nucleic acid immunization and a gene therapy. The method of gene delivery is known in the art. See, for example, U.S. Pat. Nos. 5,399,346, 5,580,859 and 5,589,466. In certain embodiments, the present disclosure provides a gene therapy vector.

The nucleic acid can be cloned into many types of vectors. For example, the nucleic acid can be cloned into such vectors, which include, but are not limited to, plasmids, phagemids, phage derivatives, animal viruses, and cosmids. Specific vectors of interest include expression vectors, replication vectors, probe generation vectors, and sequencing vectors.

Further, the expression vectors can be provided to cells in the form of viral vectors. The viral vector technology is well known in the art and is described in, for example, Sambrook et al. (2001, Molecular Cloning: A Laboratory Manual, Cold Spring Harbor Laboratory, New York) and other virology and molecular biology manuals. Viruses that can be used as vectors include, but are not limited to, retroviruses, adenoviruses, adeno-associated viruses, herpes viruses, and lentiviruses. Generally, a suitable vector comprises an origin of replication that functions in at least one organism, a promoter sequence, a convenient restriction enzyme site, and one or more selectable markers (e.g., WO01/96584; WO01/29058; and U.S. Pat. No. 6,326,193).

Many virus-based systems have been developed for transferring genes into mammalian cells. For example, retroviruses provide a convenient platform for gene delivery systems. Techniques known in the art can be used to insert selected genes into vectors and package the selected genes into retroviral particles. The recombinant virus can then be isolated and delivered to target cells in vivo or ex vivo. Many retroviral systems are known in the art. In some implementation manners, adenoviral vectors are used. Many adenoviral vectors are known in the art. In an implementation manner, lentiviral vectors are used.

Additional promoter elements, such as enhancers, can regulate the frequency of transcription initiation. Generally, they are located in the 30-110 bp region upstream of the start site, although it has recently been shown that many promoters also contain functional elements downstream of the start site. The spacing between promoter elements is often flexible in order to maintain the promoter function when the elements are inverted or moved relative to one another. In a thymidine kinase (tk) promoter, the spacing between promoter elements can be increased by 50 bp before the activity begins to decrease. Depending on the promoter, it appears that individual elements can act cooperatively or independently to initiate transcription.

An example of a suitable promoter is an immediate early cytomegalovirus (CMV) promoter sequence. The promoter sequence is a strong constitutive promoter sequence capable of driving high-level expression of any polynucleotide sequence operably linked to the promoter sequence. Another example of a suitable promoter is an elongation growth factor $-1\alpha$(EF-$1\alpha$). Nevertheless, other constitutive promoter sequences can be used, too, including but not limited to simian virus 40 (SV40) early promoters, mouse mammary tumor viruses (MMTV), human immunodeficiency virus (HIV) long terminal repeat (LTR) promoters, MoMuLV promoters, avian leukemia virus promoters, Epstein-Barr virus immediate early promoters, Rous sarcoma virus promoters, and human gene promoters, such as but not limited to actin promoters, myosin promoters, heme promoters and creatine kinase promoters. Inducible promoters are also considered as part of the present disclosure. The use of an inducible promoter provides a molecular switch that can turn on the expression of a polynucleotide sequence operably linked to the inducible promoter when such expression is expected, or turn off the expression when such expression is unexpected. Examples of inducible promoters include, but are not limited to, metallothionein promoters, glucocorticoid promoters, progesterone promoters and tetracycline promoters.

In order to evaluate the expression of a CAR polypeptide or part thereof, an expression vector introduced into a cell may also contain either or both of a selectable marker gene or a reporter gene, so as to identify and select expression cells from the transfected or infected cell population searched by means of viral vectors. In other aspects, the selectable marker can be carried on a single fragment of DNA and used in a co-transfection procedure. The flanks of both the selectable marker and reporter gene may have appropriate regulatory sequences so as to be expressed in the host cell. Useful selectable markers include, for example, antibiotics resistance genes, such as neo, etc.

Reporter genes may be used to identify potentially transfected cells and to evaluate the functionality of regulatory sequences. Generally, the reporter genes are the following genes: they are not present in recipient organisms or tissues or are expressed by the recipient organisms or tissues, and encode polypeptides whose expression is clearly indicated by some easily detectable properties such as enzyme activity. After DNA has been introduced into a receptor cell, the expression of the reporter genes is determined at an appropriate time. Suitable reporter genes may include genes encoding luciferase, β-galactosidase, chloramphenicol acetyltransferase, secreted alkaline phosphatase or green fluorescent protein (e.g., Ui-Tei et al., 2000, FEBS Letters, 479:79-82). Suitable expression systems are well known and can be prepared using known techniques or obtained commercially. Generally, a construct with a minimum of 5 flanking regions that shows the highest level of reporter gene expression is identified as a promoter. Such a promoter region can be linked to a reporter gene and used to evaluate the ability of a reagent to regulate the promoter-driven transcription.

Methods for introducing genes into cells and expressing genes into cells are known in the art. In the content of an expression vector, the vector can be easily introduced into a host cell by any method in the art, for example, mammal, bacteria, yeast or insect cells. For example, the expression vector can be transferred into the host cell by physical, chemical or biological means.

The physical methods for introducing polynucleotides into host cells include calcium phosphate precipitation, lipofection, particle bombardment, microinjection, electroporation, etc. Methods for producing cells that comprise vectors and/or exogenous nucleic acids are well known in the art. See, for example, Sambrook, et al (2001, Molecular Cloning: A Laboratory Manual, Cold Spring Harbor Laboratory, New York). A method for introducing polynucleotides into host cells is calcium phosphate transfection.

Biological methods for introducing polynucleotides of interest into host cells include the use of DNA and RNA vectors. Viral vectors, especially retroviral vectors, have become the most widely used methods for inserting genes into mammalian cells such as human cells. Other viral vectors can be derived from lentiviruses, poxviruses, herpes simplex viruses I, adenoviruses, adeno-associated viruses, etc. See, for example, U.S. Pat. Nos. 5,350,674 and 5,585,362.

Chemical means for introducing polynucleotides into host cells include colloidal dispersion systems, such as macromolecular complexes, nanocapsules, microspheres, and beads; and lipid-based systems, including oil-in-water emulsions, micelles, mixed micelles, and liposomes. Exemplary colloidal systems used as delivery vehicles in vitro and in vivo are liposomes (e.g., artificial membrane vesicles).

In the case of using a non-viral delivery system, an exemplary delivery tool is a liposome. The use of a lipid preparation is considered to introduce nucleic acids into host cells (in vitro, ex vivo or in vivo). On the other hand, the nucleic acids can be associated with lipids. Lipid-associated nucleic acids can be encapsulated in the aqueous interior of liposomes, dispersed in the lipid bilayer of liposomes, and attached to liposomes via linking molecules associated with both liposomes and oligonucleotides, trapped in liposomes, complexed with liposomes, dispersed in a solution containing lipids, mixed with lipids, combined with lipids, contained in lipids as a suspension, contained in micelles or complexed with micelles, or associated with lipids by other methods. The lipids, lipids/DNA or lipids/expression vectors associated with the composition are not limited to any specific structure in the solution. For example, they can exist in a bilayer structure, as micelles or have a "collapsed" structure. They can also simply be dispersed in a solution, possibly forming aggregates in uneven sizes or shapes. Lipids are fatty substances and can occur naturally or be synthesized. For example, lipids include fat droplets, which naturally occur in cytoplasm and in compounds containing long-chain aliphatic hydrocarbons and their derivatives such as fatty acids, alcohols, amines, amino alcohols and aldehydes.

In certain embodiments, the vector is a lentiviral vector.

Therapeutic Applications of CAR T

The present disclosure includes therapeutic applications using cells (e.g., T cells) transduced with a lentiviral vector (LV) encoding the expression cassette of the present disclosure. The transduced T cells can target BCMA, a marker of tumor cells, synergistically activate T cells and give arise to immune responses of the T cells, thereby significantly improving the killing efficiency of the T cells to tumor cells.

Therefore, the present disclosure further provides a method for stimulating T cell-mediated immune responses to mammalian target cell populations or tissues, which comprises the step of administering the CAR-T cells of the present disclosure to the mammal.

In an implementation manner, the present disclosure includes a cell therapy that isolates the patient's autologous T cells (or heterologous donors), activates and genetically modifies them to produce CAR-T cells, and then injects them into the same patient. In this way, the probability of suffering from graft-versus-host diseases is extremely low, and the antigen is recognized by T cells in a non-MHC-restricted manner. Further, one CAR-T can treat all cancers that express the antigen. Not like an antibody therapy, CAR-T cells can be replicated in vivo, producing long-term persistence that can lead to sustained tumor control.

In an implementation manner, the CAR-T cells provided by the present disclosure can undergo a stable expansion of T cells in vivo for a continuously extendable length of time. Further, the CAR-mediated immune response can be part of an adoptive immunotherapy step, in which CAR-modified T cells induce an immune response specific to the antigen-binding domain in the CAR. For example, CAR-T cells against BCMA arouse a specific immune response against cells that express BCMA.

Although the data disclosed herein specifically disclose a lentiviral vector comprising anti-BCMA scFv, a hinge, a transmembrane region, and 4-1BB and CD3ζ signaling domains, the present disclosure should be construed as including any number of changes in each of the components of the construct.

Treatable cancers include tumors that have not been vascularized or substantially have not been vascularized, as well as vascularized tumors. Cancers may include non-solid tumors (such as hematological tumors, such as leukemia and lymphoma) or may include solid tumors. The types of cancers treated with the CAR, antibody, or an antigen-binding portion thereof, provided by the present disclosure include but are not limited to carcinoma, blastoma and sarcoma, and some leukemia or lymphoid malignancies, benign and malignant tumors such as sarcoma, carcinoma and melanoma, also include adult tumors/cancers and pediatric tumors/cancers.

Hematological cancers are cancers of blood or bone marrow. Examples of hematological (or hematogenic) cancers include leukemia, including acute leukemia (such as acute lymphoblastic leukemia, acute myeloblastic leukemia, acute myelogenous leukemia, and myeloblastic, promyelocytic, myelomonocytic, monocytic erythrocytic leukemia), chronic leukemia (such as chronic myeloblastic (granulocytic) leukemia, chronic myelogenous leukemia, and chronic lymphocytic leukemia), polycythemia vera, lymphoma, Hodgkin's disease, non-Hodgkin's lymphoma (painless and high-grade form), multiple myeloma, Waldenstrom's macroglobulinemia, heavy chain disease, myelodysplastic syndrome, hairy cell leukemia and myelodysplasia.

A solid tumor is an abnormal mass of tissue that generally does not contain a cyst or fluid area. Solid tumors can be benign or malignant. Different types of solid tumors are named after the types of cells that form the solid tumors (such as sarcoma, carcinoma and lymphoma). Examples of solid tumors such as sarcoma and carcinoma include fibrosarcoma, myxosarcoma, liposarcoma, mesothelioma, lymphoid malignancy, pancreatic cancer and ovarian cancer.

The CAR-modified T cells may also be used as a type of vaccine for mammalian ex-vivo immunization and/or in vivo therapy. Preferably, the mammal is a human.

For ex vivo immunization, at least one of the following items occurs in vitro before the cells are administered into the mammal: i) amplifying cells, ii) introducing the nucleic acids that encode CARs into the cells, and/or iii) cryopreserving the cells.

Ex vivo procedures are well known in the art and will be more fully discussed below. In brief, cells are isolated from a mammal (preferably a human) and genetically modified (i.e., transduced or transfected in vitro) with the vectors expressing the CARs disclosed herein. The CAR-modified cells can be administered to mammalian recipients to provide therapeutic benefits. The mammalian recipients can be humans, and the CAR-modified cells can be autologous relative to the recipients. Optionally, the cells can be allogeneic, syngeneic or xenogeneic relative to the recipients.

In addition to using cell-based vaccines for ex vivo immunization, the present disclosure also provides compositions and methods for in vivo immunization to cause immune responses against antigens in patients.

The present disclosure provides a method for treating tumors, which comprises administering to a subject in need thereof a therapeutically effective dose of the CAR-modified T cells provided by the present disclosure.

The CAR-modified T cells provided by the present disclosure can be administered alone or administered as a pharmaceutical composition in combination with a diluent and/or other components such as IL-2, IL-17 or other cytokines or cell populations. In brief, the pharmaceutical composition provided by the present disclosure may comprise a target cell population as described herein, combined with one or more of pharmaceutically or physiologically acceptable vectors, diluents or excipients. Such composition may comprise a buffer solution such as neutral buffer saline and sulfate buffer; carbohydrates such as glucose, mannose, sucrose, dextran and mannitol; proteins; polypeptides or amino acids such as glycine; antioxidants; chelating agents such as EDTA or glutathione; adjuvants (e.g., aluminum hydroxides); and preservatives. The composition may be suitable for intravenous administration.

The pharmaceutical composition provided by the present disclosure can be administered in a manner suitable for the disease to be treated (or prevented). The number and frequency of administrations will be determined by factors such as the patient's condition, and the type and severity of the patient's disease—although an appropriate dose can be determined by clinical trials.

When "immunologically effective dose," "anti-tumor effective dose," "tumor-suppressive effective dose" or "therapeutic dose" is indicated, the precise dose of the composition to be administered can be determined by the physician, who considers the age, weight, tumor size, degree of infection or metastasis and individual difference of disease in the patient (subject). It may generally be indicated that the pharmaceutical composition comprising the T cells described herein can be administered at a dose of $10^4$ to $10^9$ cells/kg of body weight, or at a dose of $10^5$ to $10^6$ cells/kg of body weight (including all integer values within those ranges). The T cell composition may also be administered multiple times at these doses. Cells can be administered by using well-known injection techniques in immunotherapy (see, for example, Rosenberg et al., New Eng. J. of Med. 319:1676, 1988). The optimal dose and therapeutic regimen for a specific patient can be easily determined by those skilled in the medical field by monitoring the patient's signs of disease and thus adjusting the treatment.

The administration of the composition by the subject can be carried out in any convenient manner, including by spraying, injection, swallowing, infusion, implantation or transplantation. The composition described herein can be administered to the patient subcutaneously, intracutaneously, intratumorally, intranodally, intraspinally or intramuscularly, or by intravenous injection (i.v.), or intraperitoneally. In an implementation manner, the T cell composition provided by the present disclosure is administered to the patient by intradermal or subcutaneous injection. In certain embodiments, the T cell composition is administered by intravenous injection (i.v.). The T cell composition may be directly injected into a tumor, lymph node or infection position.

In certain embodiments, cells activated and expanded using the methods described herein or other methods known in the art to expand T cells to a therapeutic level are administered to the patient in combination with any number of relevant treatment forms (e.g., before, at the same time or after). The treatment forms include but are not limited to treatment with the following reagents: The reagents include, for example, an antiviral therapy, cidofovir and interleukin-2, cytarabine (also known as ARA-C) or natalizumab for MS patients or erfazumab monoclonal treatment for psoriasis patients or other treatments for PML patients. In a further implementation manner, the T cells provided by the present disclosure can be used in combination with the following: chemotherapy, radiation, immunosuppressors, such as cyclosporine, azathioprine, methotrexate, mycophenolate and FK506, antibodies or other immunotherapeutics. In certain embodiments, the cell composition provided by the present disclosure is administered to the patient in combination with bone marrow transplantation, chemotherapeutic agents such as fludarabine, an external beam radiotherapy (XRT), cyclophosphamide (e.g., before, at the same time or after). For example, the subject can undergo the standard treatment of high-dose chemotherapy followed by peripheral blood stem cell transplantation. In certain embodiments, after the transplantation, the subject receives an injection of expanded immune cells according to the present disclosure. In certain embodiments, the expanded cells are administered before or after a surgery.

The foregoing therapeutic dose administered to the patient will vary with the precise nature of the condition being treated and the receiver of the treatment. The dosage ratio of human administration can be implemented according to the practice accepted in the art. Generally, $1\times10^6$ to $1\times10^{10}$ modified T cells (e.g., CAR-T20 cells) can be administered to the patient by venous re-transfusion per treatment or per course of treatment.

CART Preparation

The present disclosure provides CAR-T cells, as well as a pharmaceutically acceptable carrier, diluent or excipient. In an implementation manner, the preparation is a liquid preparation. In one embodiment, the preparation is an injection. In one embodiment, the concentration of the CAR-T cells in the preparation is $1\times10^3$ to $1\times10^8$ cells/ml, or $1\times10^4$ to $1\times10^7$ cells/ml.

In certain embodiments, the preparation may comprise a buffer solution such as neutral buffer saline and sulfate buffer saline; carbohydrates such as glucose, mannose, sucrose, dextran and mannitol; proteins; polypeptides or amino acids such as glycine; antioxidants; chelating agents such as EDTA or glutathione; adjuvants (e.g., aluminum hydroxide); and preservatives. The preparation may be suitable for intravenous administration.

Pharmaceutical Composition

The present disclosure further provides a composition. In certain embodiments, the composition is a pharmaceutical composition, which contains the foregoing antibody or active fragments thereof, fusion proteins thereof, ADCs thereof or corresponding CAR-T cells, and a pharmaceutically acceptable carrier. Generally, these substances can be prepared in a non-toxic, inert and pharmaceutically acceptable aqueous carrier medium, with pH of about 5 to 8, or about 6 to 8, although the pH value may vary with the nature of the prepared substances and the diseases to be treated. The prepared pharmaceutical composition can be administered by conventional routes, including (but not limited to): intratumoral, intraperitoneal, intravenous, or topical administration.

The antibody described in the present disclosure can also be used in a cell therapy for intracellular expression of nucleotide sequences. For example, the antibody is used in a chimeric antigen receptor T cell immunotherapy (CAR-T).

The pharmaceutical composition provided by the present disclosure can be directly used to bind TF protein molecules, and thus can be used to prevent and treat tumors and other diseases. In addition, other therapeutic agents can also be used at the same time.

The pharmaceutical composition provided by the present disclosure contains a safe and effective dose (e.g., 0.001-99 wt %, 0.01-90 wt %, or 0.1-80 wt %) of the foregoing monoclonal antibody provided by the present disclosure (or conjugate thereof) and a pharmaceutical acceptable carrier or excipient. Such carriers include (but are not limited to): saline, buffer solutions, glucose, water, glycerol, ethanol, and combinations thereof. The pharmaceutical preparation should match the way of administration. The pharmaceutical composition provided by the present disclosure can be prepared in the form of injections, for example, from physiological saline or an aqueous solution containing glucose and other adjuvants by conventional methods. The pharmaceutical composition such as an injection or a solution should be manufactured under sterile conditions. The dosage of the active ingredient is a therapeutically effective dose, for example, about 1 mg/kg of body weight to about 5 mg/kg of body weight per day. In addition, the polypeptide provided by the present disclosure may also be used together with other therapeutic agents.

The use of a pharmaceutical composition is to administer a safe and effective dose of an immunoconjugate to a mammal, where the safe and effective dose is generally at least about 10 mg/kg of body weight, and in most cases, it does not exceed about 50 mg/kg of body weight. For example, the dose is about 10 mg/kg of body weight to about 20 mg/kg of body weight. Of course, the specific dose should also consider factors such as the route of administration and the patient's health status, which are all within the skills of skilled physicians.

Detection Purposes and Kits

The antibodies or conjugates thereof provided by the present disclosure can be used in detection applications, for example, used to detect samples, thereby providing diagnostic information.

The specimens (samples) may include cells, tissue samples, and biopsy specimens. The term "biopsy" may include all types of biopsy known to those skilled in the art. Therefore, the biopsy may include, for example, a tumor resection sample, and a tissue sample prepared by an endoscopic method or a puncture or needle biopsy of an organ.

The samples may include fixed or preserved cell or tissue samples.

The present disclosure further provides a kit containing the antibody (or fragment thereof), or CAR, of the present disclosure. In an embodiment, the kit further comprises a container, an operating manual, a buffer agent, etc. In an embodiment, the antibody can be attached to a test plate.

The present disclosure further provides a use of the antibody. For example, the antibody is used to prepare a diagnostic preparation or a drug for preventing and/or treating the BCMA-positive cancer/tumor.

The antibodies provided by the present disclosure may recognize soluble extracellular domains of human BCMA molecules on the cell membrane surface. Some antibodies can also cross-recognize the soluble extracellular domains of machin BCMA molecules.

The CAR-T cells provided by the present disclosure do not recognize tumor necrosis factor receptor superfamily member 13B.

The CAR-T cells provided by the present disclosure have desirable specific cytotoxicity toward BCMA-positive target cells.

The following examples of specific aspects for carrying out the present disclosure are offered for illustrative purposes only, and are not intended to limit the scope of The present disclosure in any way.

General Materials and Methods

The materials and methods used in the Examples are as follows:

1 Sources of Cells and Mice

K562-BCMA$^+$: K562-BCMA-B22D8 (provided by Cellular Biomedicine Group)

K562 (ATCC; provided by Cellular Biomedicine Group)

L-BCMA$^+$: L-BCMA-1E6-A4 (provided by Cellular Biomedicine Group)

L Cells (mouse fibroblast, ATCC: cat. CRL-2648™; lot, 63903687; provided by Cellular Biomedicine Group)

Sp2/0-Ag14 cell (ATCC; provided by ChemPartner)

Balb/c mice (Shanghai Slac)

SJL mice (Shanghai Slac)

2 Main Reagents

TABLE 1

| Reagents | | | |
| --- | --- | --- | --- |
| Name | Manufacturer | Goods No. | Batch No. |
| hBCMA-ECD-Fc | ChemPartner | — | 171030004 |
| cynoBCMA-ECD-Fc | ChemPartner | — | 171030003 |
| Recombinant hFc fusion protein control (NC-Fc) | ChemPartner | — | — |
| Recombinant human TACI/TNFRSF13B Fc chimeric protein, CF (hTACI-ECD-Fc) | R&D Systems | 174-TC | EFN0417051 |
| Tool antibody (tAb, anti-hBCMA) | Biolegend | 357502 | B206531 |
| mIgG | Invitrogen | 026502 | 1623974A |

3 Main Laboratory Instruments

TABLE 2

| Laboratory instruments | | |
| --- | --- | --- |
| Name | Manufacturer | Model |
| Microplate reader | Molecular Devices | Plus 384 |
| ELISA microplate washer | BioTek | ELx406UCWS |
| Centrifuge | Eppendorf | 5810R |
| Flow cytometer | BD | FACSVerse |

4 Experimental Design 4.1 Mouse Immunization and Serum Titer Detection

Five Balb/c mice and five SJL mice were divided into two groups and immunized with hBCMA-ECD-Fc according to Table 3. As shown in Table 4, booster immunization should be performed at least twice after the first immunization (the third booster immunization uses K562-BCMA$^+$ cells). After immunization, ELISA and FACS were used to detect the titer of mouse serum. After the serum titer met the requirements (ELISA reaches 1:10,000 dilution or FACS reaches 1:1,000 dilution), hybridoma cell fusion screening was performed.

TABLE 3

| Mouse immunization groups | | | |
| --- | --- | --- | --- |
| Animal Species | Qty | Immunization Method | Reference Number |
| Balb/c mouse | 5 | Intrapertitoneal injection | 5061, 5062, 5063, 5064, 5065 |
| SJL mouse | 5 | Intrapertitoneal injection | 5066, 5067, 5068, 5069, 5070 |

TABLE 4

| Immunization strategy | |
|---|---|
| Day 0 | Draw blood before immunization (PB, 15-30 μl of serum/mouse) The first immunization: hBCMA-ECD-Fc, 50 μg/mouse (CFA adjuvant) |
| Day 14 | Booster immunization: hBCMA-ECD-Fc, 25 μg/mouse (IFA adjuvant) |
| Day 21 | Draw blood from mice (TB1, 15-30 μl of serum/mouse) |
| Day 22 | Detect serum titer by ELISA/FACS |
| Day 35 | Booster immunization: hBCMA-ECD-Fc, 25 μg/mouse (IFA adjuvant) |
| Day 42 | Draw blood from mice (TB2, 15-30 μl of serum/mouse) |
| Day 43 | Detect serum titer by ELISA/FACS |
| Day 56 | Pre-fusion immunization: hBCMA-ECD-Fc, 25 μg/mouse (IFA adjuvant) |
| Day 60 | Electro-fusion of hybridoma cells |

4.2 Screening of Hybridoma Cell Strains 4.2.1 Fusion of Hybridoma Cells

Through FACS detection, the mouse with the highest serum titer (Balb/c and SJL each one) was determined, and the spleen and lymph node lymphocytes and Sp2/0-Ag14 cells were fused by the electrofusion method to obtain hybridoma cells.

4.2.2 Monoclonal Screening of Hybridoma Cells

After red blood cell lysis, the fusion cells of each mouse were spread on 96-well plates, $2.5\times10^6$ cells per plate, 20 plates in total. Primary screening was carried out after 10 days: the binding ability of the medium supernatant to hBCMA-ECD-Fc protein was detected by ELISA, and the clones with a positive test result were transferred to a 24-well plate for multiplication culture.

For the cells after multiplication culture, ELISA was used to detect the binding ability of the medium supernatant to hBCMA-ECD-Fc and cynoBCMA-ECD-Fc, and FACS was used to detect the binding ability of the medium supernatant to L-BCMA$^+$ cells (secondary screening). In the end, the clones with strong binding to L-BCMA$^+$ cells were selected to conduct subclonal screening.

4.2.3 Subclonal Screening of Hybridoma Cells

The monoclonal cells obtained in 4.2.2 were spread on two 96-well plates, the ELISA and FACS screening processes in 4.2.2 were repeated and the in the end, subclonal cell strains were obtained. The target clones were transferred to culture bottles for multiplication culture, a seed bank was established and 4 to 6 units of cells under each strain were cryopreserved ($0.5\text{-}1\times10^7$ cells/unit).

4.3 Production and Purification of Hybridoma Antibodies

Monoclonal cells that bind to both human and machin BCMA were selected for small-batch trial production. Cells were cultured in 250 to 500 ml cell culture shake flasks, and the produced antibodies were purified by Protein A affinity column and treated with endotoxin removal in sequence, and 3 to 5 mg of antibodies were obtained for characteristic analysis.

4.4 Identification of Purified Hybridoma Antibodies

Antibody identification includes the following three points:

a) Analysis of the binding specificity to hBCMA-ECD-Fc, cynoBCMA-ECD-Fc and hTACI-ECD-Fc (ELISA)
b) Analysis of the binding ability to L cells and L-BCMA$^+$ cells (FACS)
c) Analysis of the competitive binding to soluble BCMA (FACS)

4.5 Sequencing of Antibody Variable Regions

Extract the RNA of the hybridoma cell of the target clone, reversely transcribe the RNA into cDNA, amplify the antibody VH/VL gene fragments by PCR, and sequence to obtain the gene sequences of the antibody variable regions of the target clone.

4.6 Expression Identification of Chimeric Antibodies

Clone the antibody VH regions obtained from sequencing to an IgG1,κ recombinant antibody heavy chain expression vector and clone the VL regions to an IgG1,κ recombinant antibody light chain expression vector to construct expression plasmids of a chimeric antibody, and meanwhile use the two plasmids to transfect HEK 293T cells. Collect the supernatant of the culture after culturing for three days. Determine the binding abilities of the supernatant to hBCMA-ECD-Fc(ELISA) and L-BCMA$^+$ cells (FACS).

Example 1 Mouse Immunization and Serum Titer Detection

Mouse immunization was performed. Three booster immunizations and fours fusions were conducted. As shown in Table 5, the first two booster immunizations used hBCMA-ECD-Fc to immunize mice, and then F0109 and F0227 were fused. The third booster immunization used K562-BCMA$^+$ cells to immunize mice and then F0508 and F0614 were fused.

TABLE 5

Timetable of mouse immunization and fusion

| Strain | Mouse # | Prime | $1^{st}$ boost | bleed 1 | $2^{nd}$ boost | bleed 2 | $3^{rd}$ boost | bleed 3 | Final boost | Fusion | Note |
|---|---|---|---|---|---|---|---|---|---|---|---|
| Balb/c | 5061 | Nov. 7, 2017 | Nov. 21, 2017 | Nov. 28 2017 | Dec. 12, 2017 | Dec. 19, 2017 | Mar. 20, 2018 | Mar. 27, 2018 | Jun. 11, 2018 | Jun. 14, 2018 | F0614 |
| | 5062 | Nov. 7, 2017 | Nov. 21, 2017 | Nov. 28, 2017 | Dec. 12 2017 | Dec. 19, 2017 | X | X | Jan. 5, 2018 | X | dead after final boost |
| | 5063 | Nov. 7, 2017 | Nov. 21, 2017 | Nov. 28, 2017 | Dec. 12, 2017 | Dec. 19, 2017 | X | X | Feb. 23, 2018 | Feb. 27, 2018 | F0227 |
| | 5064 | Nov. 7, 2017 | Nov. 21, 2017 | Nov. 28, 2017 | Dec. 12, 2017 | Dec. 19, 2017 | Mar. 20, 2018 | Mar. 27, 2018 | May 4, 2018 | May 8, 2018 | F0508 |
| | 5065 | Nov. 7, 2017 | Nov. 21, 2017 | Nov. 28, 2017 | Dec. 12, 2017 | Dec. 19, 2017 | X | X | Jan. 5, 2018 | Jan. 9, 2018 | F0109 |
| SJL | 5066 | Nov. 7, 2017 | Nov. 21, 2017 | Nov. 28, 2017 | Dec. 12, 2017 | Dec. 19, 2017 | Mar. 20, 2018 | Mar. 27, 2018 | Jun. 11, 2018 | Jun. 14, 2018 | F0614 |
| | 5067 | Nov. 7, 2017 | Nov. 21, 2017 | Nov. 28, 2017 | Dec. 12, 2017 | Dec. 19, 2017 | X | X | Jan. 5, 2018 | Jan. 9, 2018 | F0109 |

TABLE 5-continued

| Timetable of mouse immunization and fusion | | | | | | | | | | | |
|---|---|---|---|---|---|---|---|---|---|---|---|
| Strain | Mouse # | Prime | $1^{st}$ boost | bleed 1 | $2^{nd}$ boost | bleed 2 | $3^{rd}$ boost | bleed 3 | Final boost | Fusion | Note |
| | 5068 | Nov. 7, 2017 | Nov. 21, 2017 | Nov. 28, 2017 | Dec. 12, 2017 | Dec. 19, 2017 | X | X | Feb. 23, 2018 | Feb. 27, 2018 | F0227 |
| | 5069 | Nov. 7, 2017 | Nov. 21, 2017 | Nov. 28, 2017 | Dec. 12, 2017 | Dec. 19, 2017 | Mar. 20, 2018 | Mar. 27, 2018 | May 4, 2018 | May 8, 2018 | F0508 |
| | 5070 | Nov. 7, 2017 | Nov. 21, 2017 | Nov. 28, 2017 | Dec. 12, 2017 | Dec. 19, 2017 | X | X | Feb. 23, 2018 | X | dead after final boost |
| Immusource: | | | hBCMA-ECD-Fc | | | | K562BCMA$^+$ cell line | | | | |

The results of ELISA analysis of mouse serum titers after the first booster immunization are shown in FIG. 1. After the first booster immunization using hBCMA-ECD-Fc, ELISA detected that the sera of the 10 mice at a dilution of 1:10 k all had a binding ability to hBCMA-ECD-Fc and cynoBCMA-ECD-Fc, of which the titer of SJL #5066 was relatively low and the remaining nine mice had similar titers.

Figure 2:
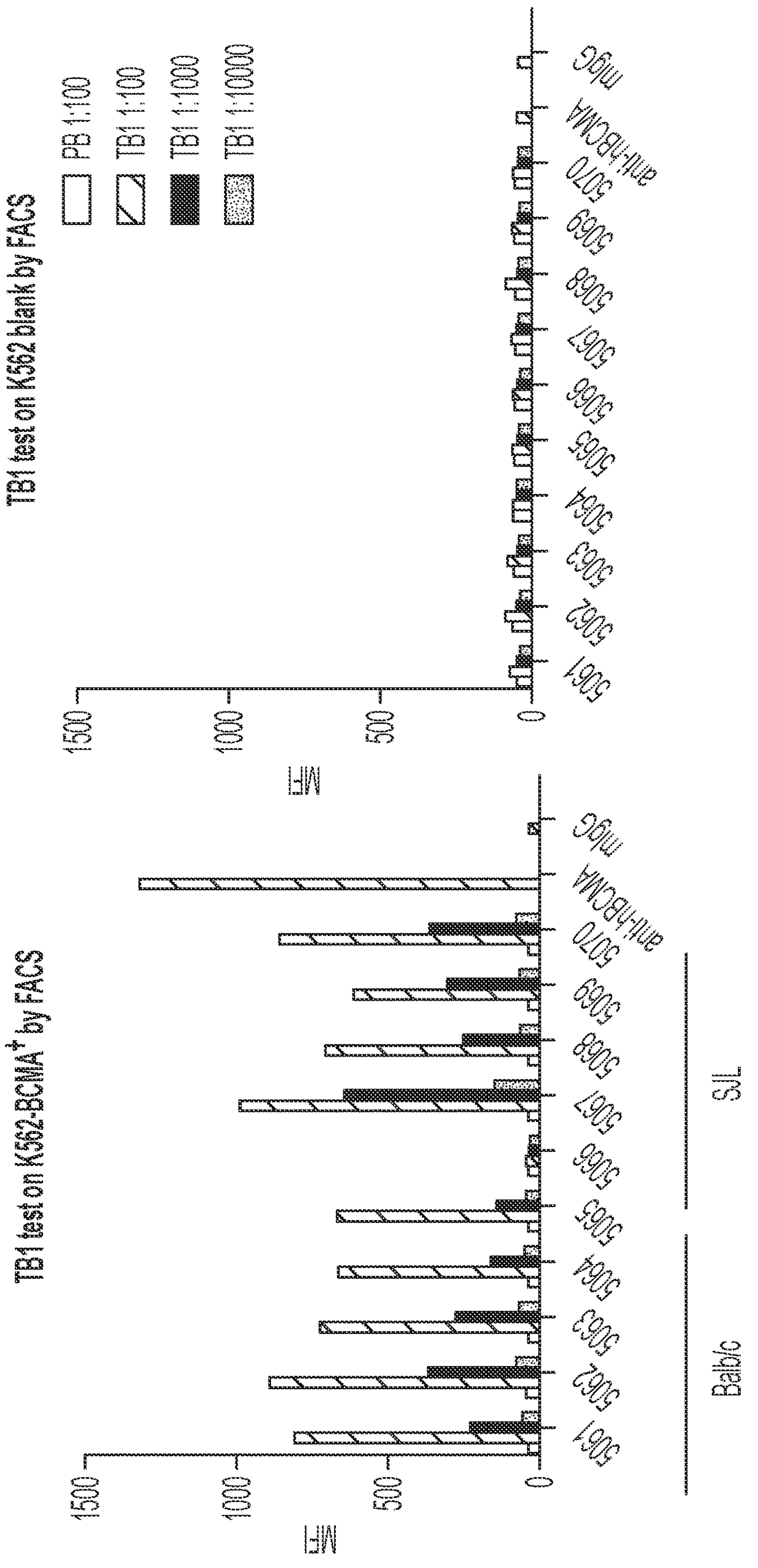
FIG. 2 shows flow cytometry analysis on the binding titers of mouse serum to K562-BCMA+ and K562 cells after the first booster immunization.

The FACS detection results are as shown in FIG. 2. Except JL #5066, the sera of the remaining mice at a dilution of 1:1,000 all had a strong binding ability to K562-BCMA$^+$.

Figure 3:
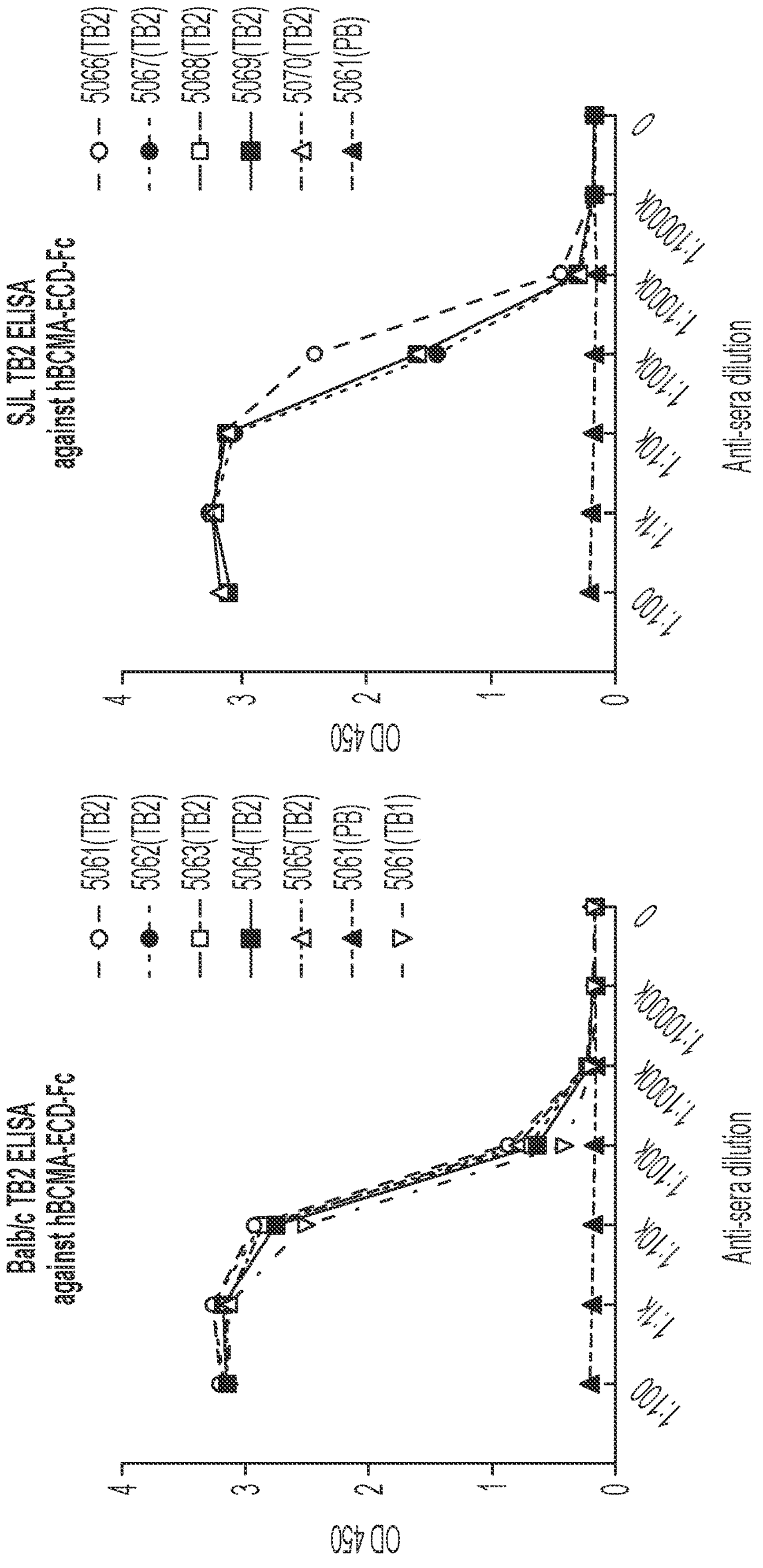
FIG. 3 shows ELISA analysis on the binding titers of mouse serum to hBCMA-ECD-Fc and cynoBCMA-ECD-Fc after the second booster immunization.
Figure 3:
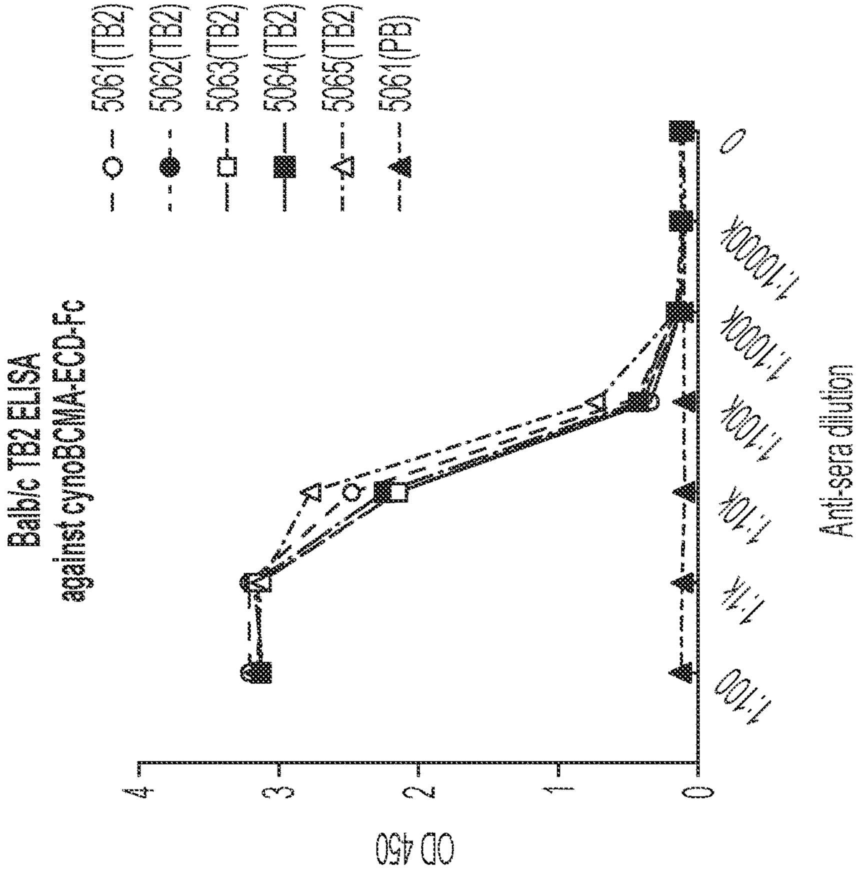
Figure 3:
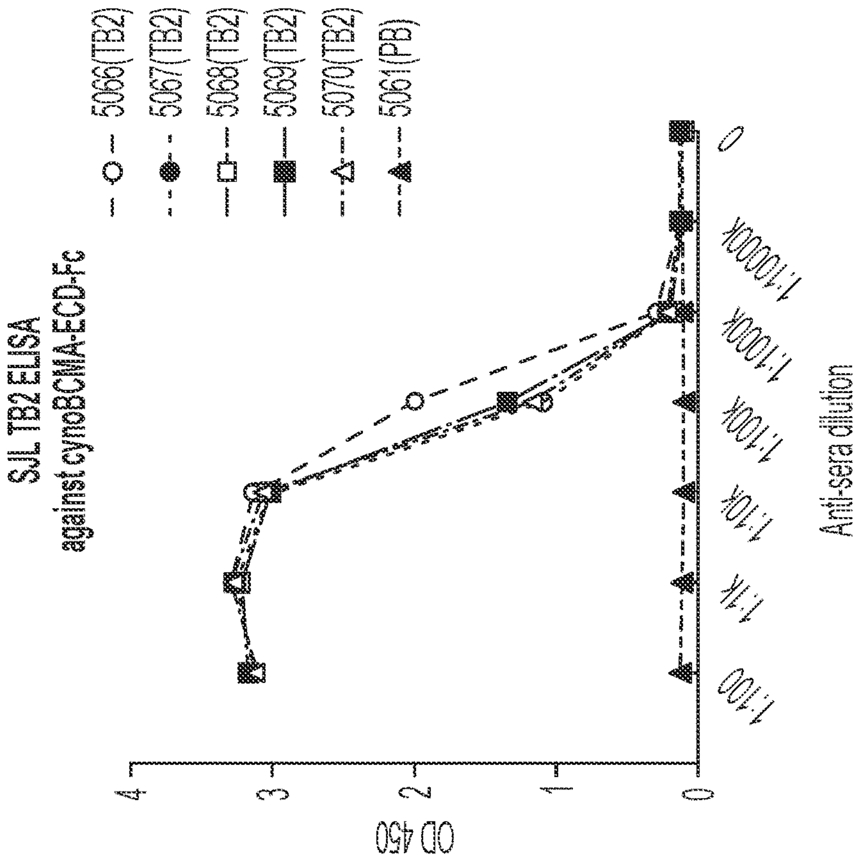

The results of ELISA analysis of mouse serum titers after the second booster immunization are shown in FIG. 3. After the second booster immunization using hBCMA-ECD-Fc, ELISA detected that the sera of the 10 mice at a dilution of 1:10 k all had a desirable binding ability to hBCMA-ECD-Fc and cynoBCMA-ECD-Fc and had similar titers.

Figure 4:
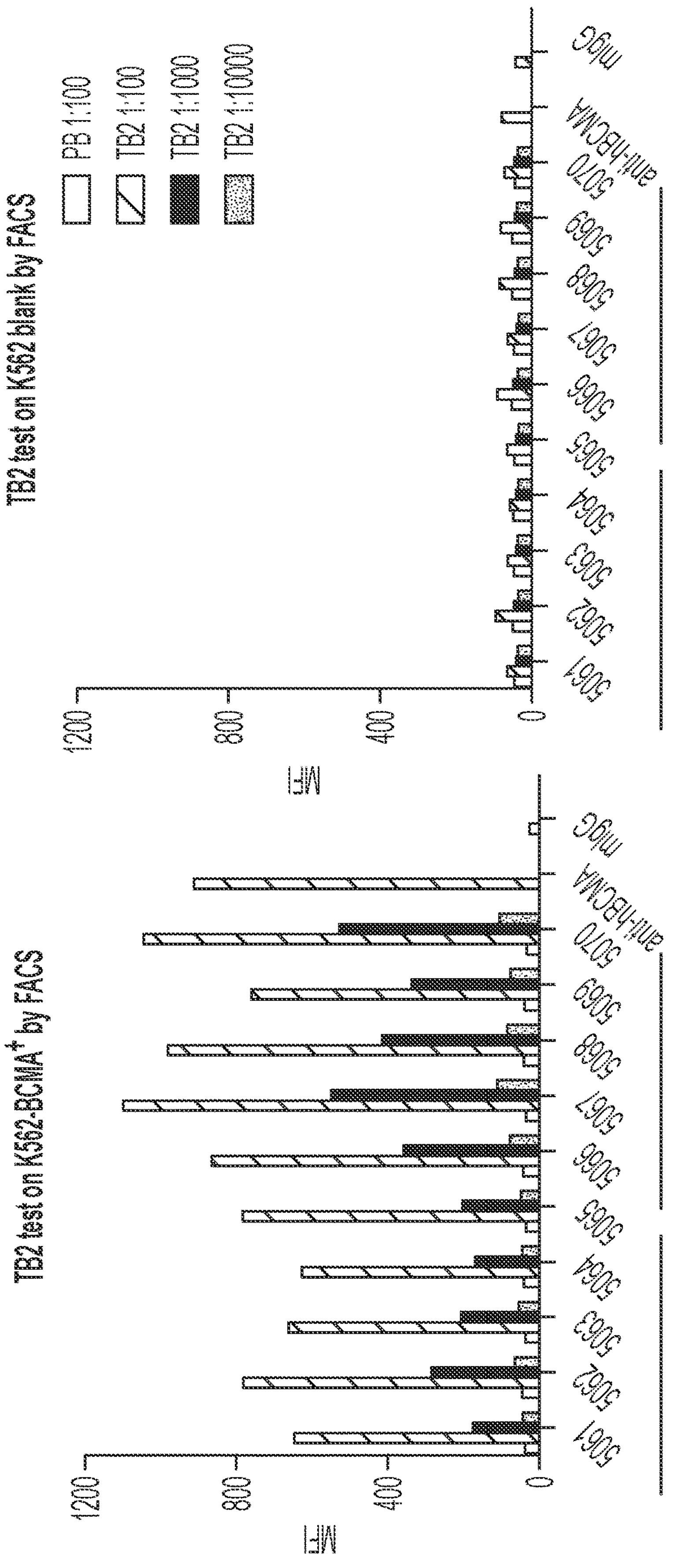
FIG. 4 shows flow cytometry analysis on the binding titers of mouse serum to K562-BCMA+ and K562 cells after the second booster immunization.

The FACS detection results are as shown in FIG. 4. The sera of the ten mice at a dilution of 1:1,000 all bound to K562-BCMA$^+$. In the two groups of mice, Balb/c #5062 and SJL #5067 had the highest titers.

Because mouse Balb/c #5062 died before fusion and after immunization, mice Balb/c #5065 and SJL #5067 were selected to conduct the first fusion F0109. Because mouse SJL #5070 died before fusion and after immunization, mice Balb/c #5063 and SJL #5068 were selected to conduct the second fusion F0227 (this fusion did not obtain positive clones when screened).

As F0109 only generated one clone and F0227 did not generate a positive clone, K562-BCMA$^+$ cells were used to conduct the third booster immunization. Mouse serum (TB2-2) was taken before immunization and mouse serum (TB3) was taken after one week of immunization.

Figure 5:
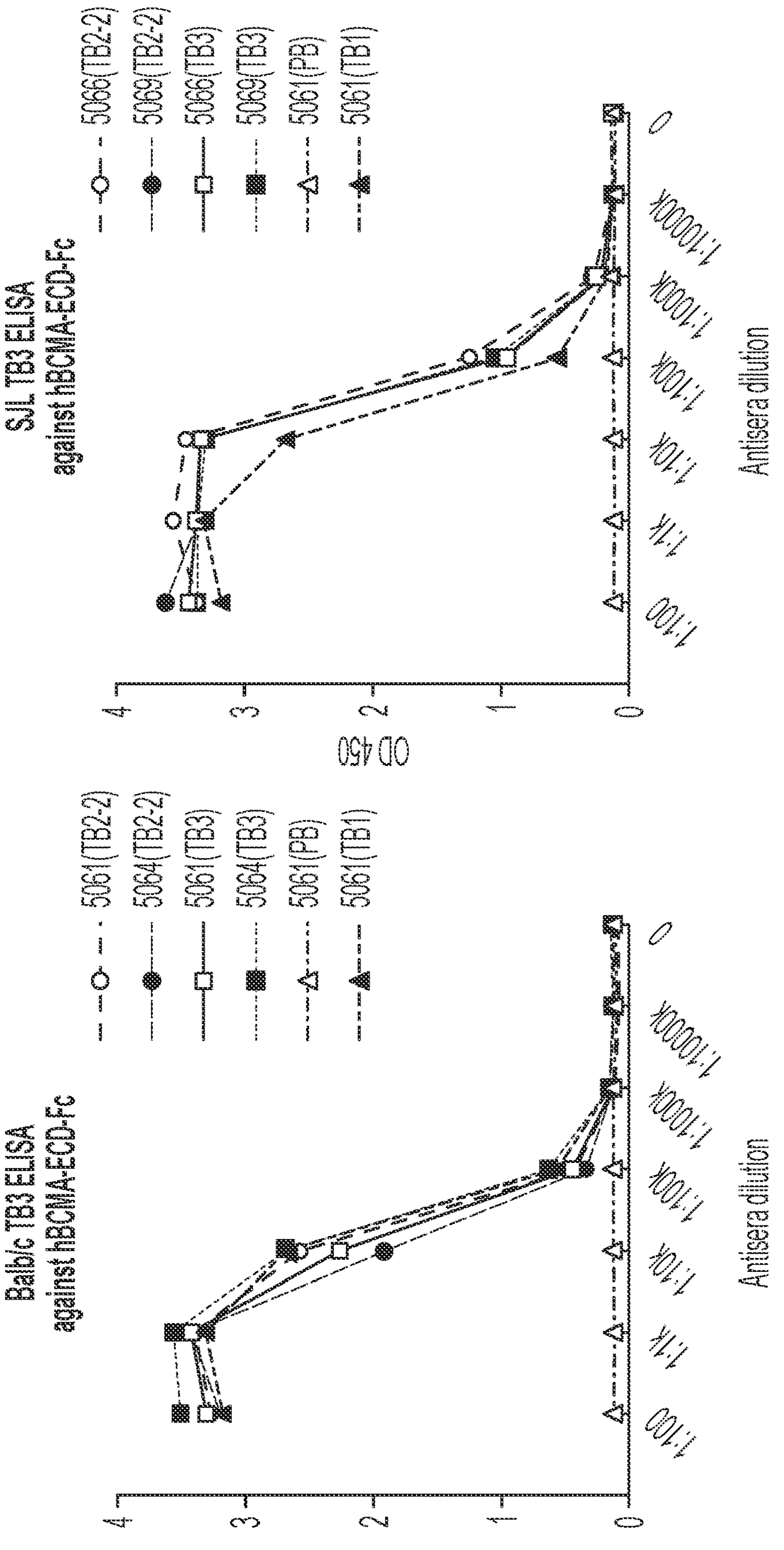
FIG. 5 shows ELISA analysis on the binding titers of mouse serum to hBCMA-ECD-Fc and cynoBCMA-ECD-Fc after the third booster immunization.
Figure 5:
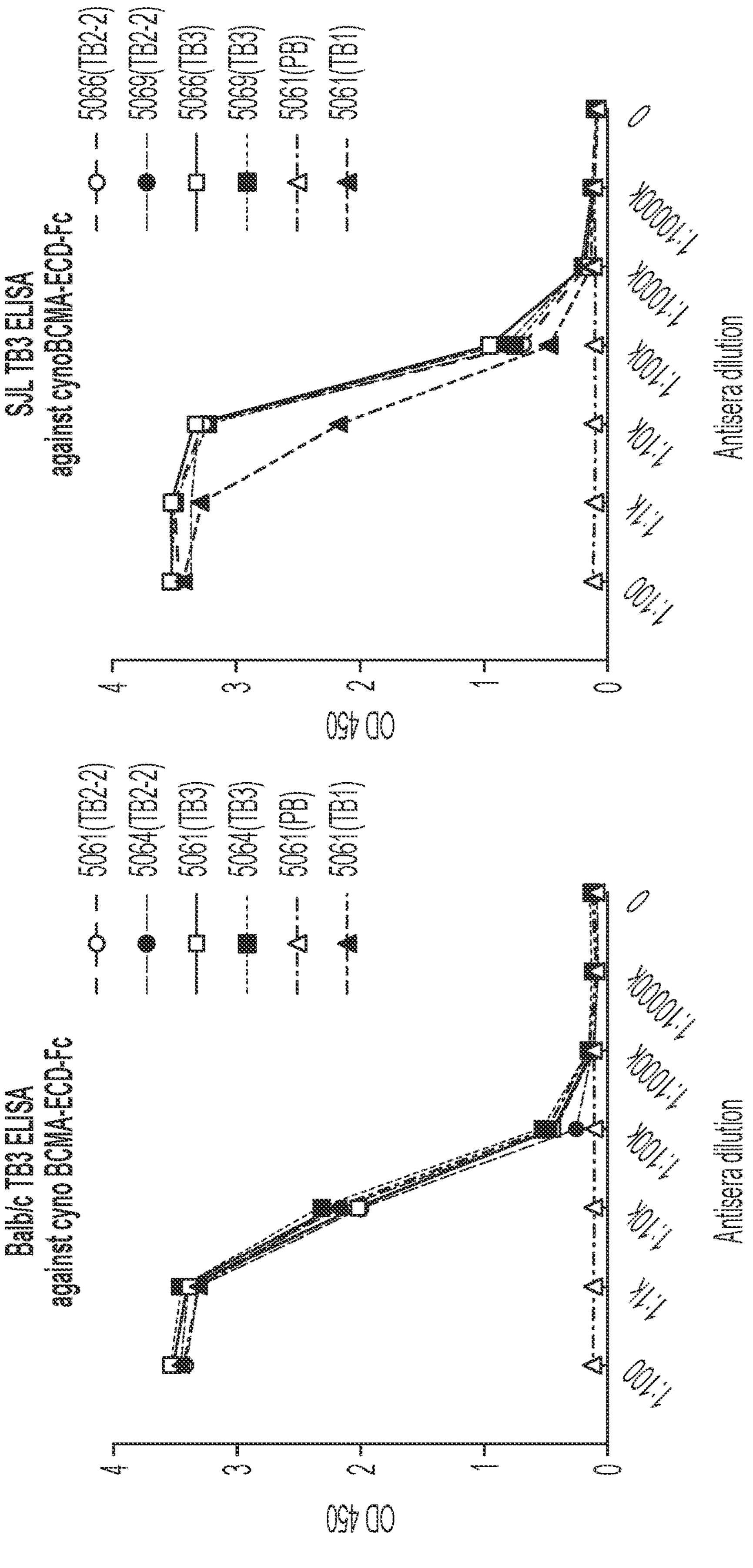

The ELISA analysis results of mouse titters after the third booster immunization are as shown in FIG. 5. The sera of four mice at a dilution of 1:10 k all had a desirable binding ability to hBCMA-ECD-Fc and cynoBCMA-ECD-Fc before and after immunization and had similar titers.

Figure 6:
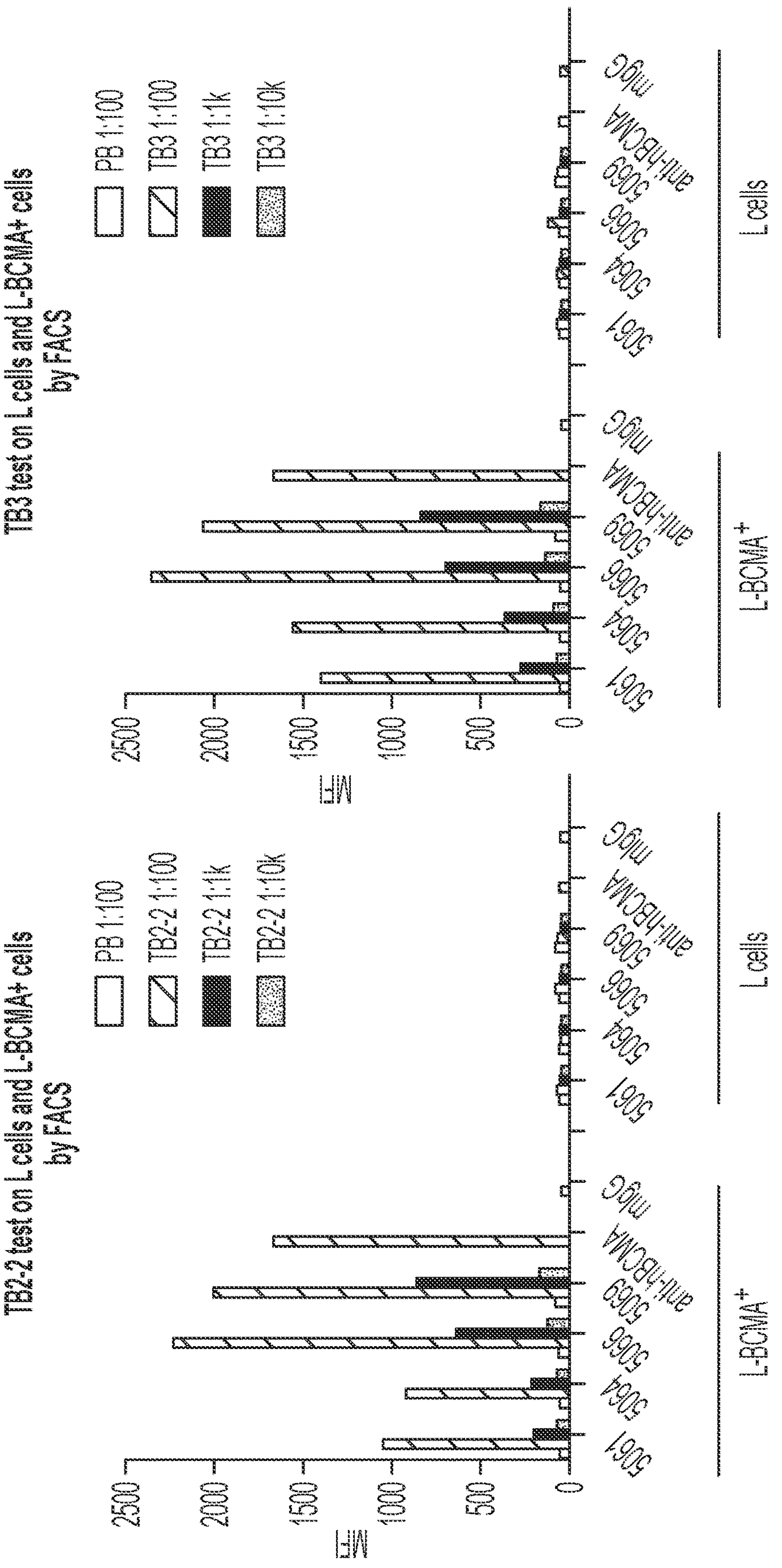
FIG. 6 shows flow cytometry analysis on the binding titers of mouse serum to L-BCMA+ and L cells before and after the third booster immunization.

The FACS detection results are as shown in FIG. 6. The sera of four mice at a dilution of 1:1,000 all bound to L-BCMA$^+$ cells. In the two mouse groups, Balb/c #5064 and SJL #5069 had the highest titers.

After the third booster immunization, Balb/c #5064 and SJL #5069 were selected to conduct the third fusion F0508, and Balb/c #5061 and SJL #5066 were selected to conduct the fourth fusion F0614.

Example 2 Screening of Hybridoma Cell Strains 2.1 Screening of Fusion F0109 Hybridoma Cells The cells after electrofusion were spread on 40 96-well plates. Among them, Balb/c #5065 was spread on plates #1 to #20, and SJL #5067 was spread on plates #21 to #40. Primary screening: ELISA detected the binding ability of the medium supernatant to hBCMA-ECD-Fc, a negative control group was NC-Fc, the set threshold value was Dvalue>0.8 and meanwhile OD450(hBCMA ECD-Fc)−OD450(hFc) >0.5, and 68 clones in total were obtained. After multiplication culture, secondary screening was conducted, 6G10 of Balb/c #5065 had a strong binding affinity to hBCMA-ECD-Fc, cynoBCMA-ECD-Fc and K562-BCMA$^+$ cells; 34D1 of SJL #5067 had a good binding affinity to K562-BCMA$^+$ cells. These two clones were selected as parent clones to conduct subclonal screening.

The monoclonals 6G10-1D7 and 6G10-1H2 and hybrid clones 6G10-1B11 and 6G10-1D3 derived from Balb/c #5065 and obtained from subclonal screening had a strong binding affinity to hBCMA-ECD-Fc, cynoBCMA-ECD-Fc and K562-BCMA$^+$; and the subclonal 34D1-2H2 derived from SJL #5067 had a strong binding affinity to hBCMA-ECD-Fc and K562-BCMA$^+$. The five clones were selected and cryopreserved. Clone 6G10-1D7 was selected to conduct antibody production in small batches.

2.2 Screening of Fusion F0227 Hybridoma Cells

From subclonal screening of fusion F0227, no positive clones that could bind to hBCMA-ECD-Fc and L-BCMA$^+$ cells were obtained.

2.3 Screening of Fusion F0508 Hybridoma Cells

The cells after electrofusion were spread on 40 96-well plates. Among them, Balb/c #5064 was spread on plates #81 to #100 and SJL #5069 was spread on plates #101 to #120.

Figure 7:
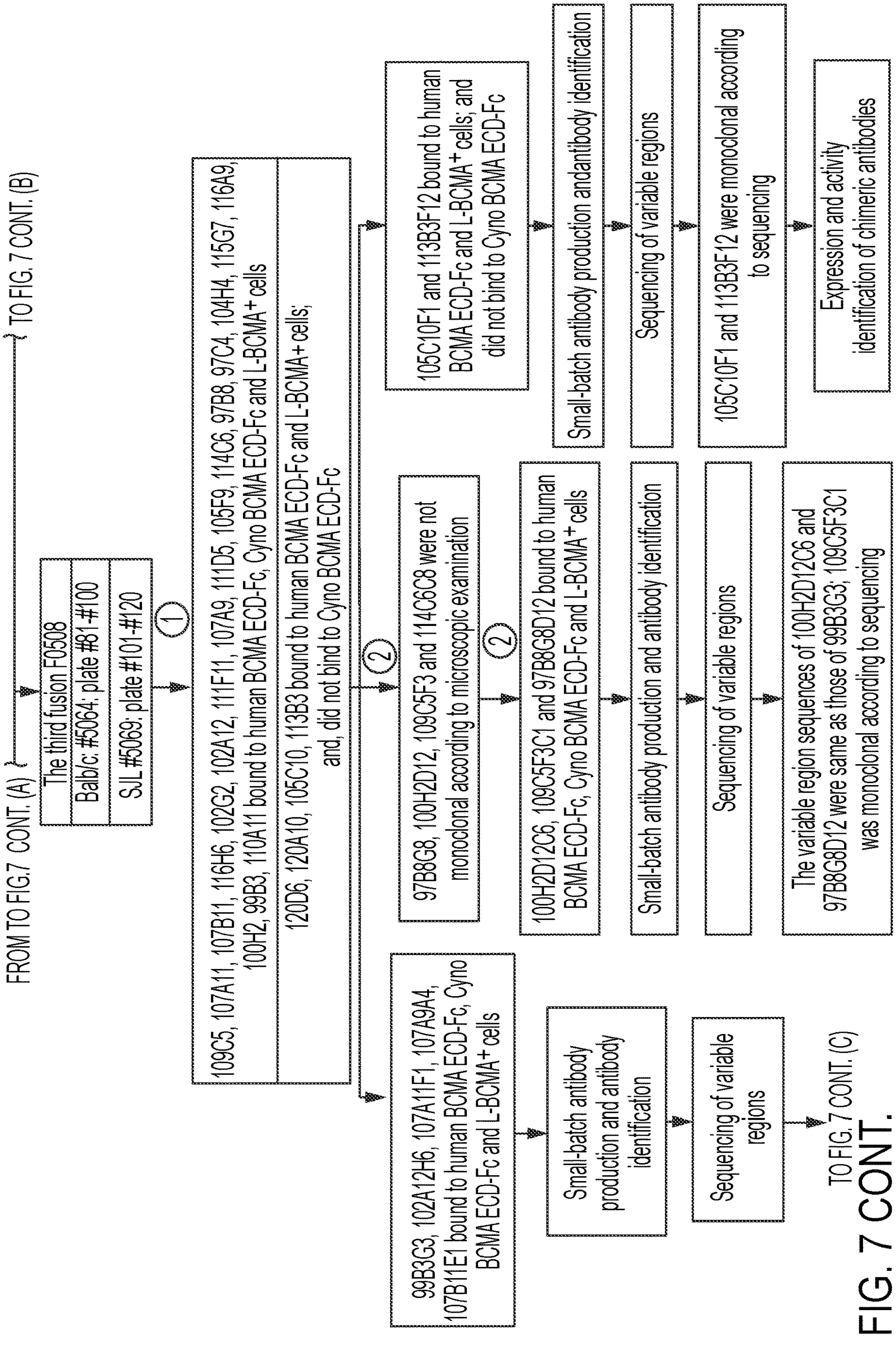
FIG. 7 shows a hybridoma cell screening process (all the selected clones do not bind to NC-Fc).
Figure 7:
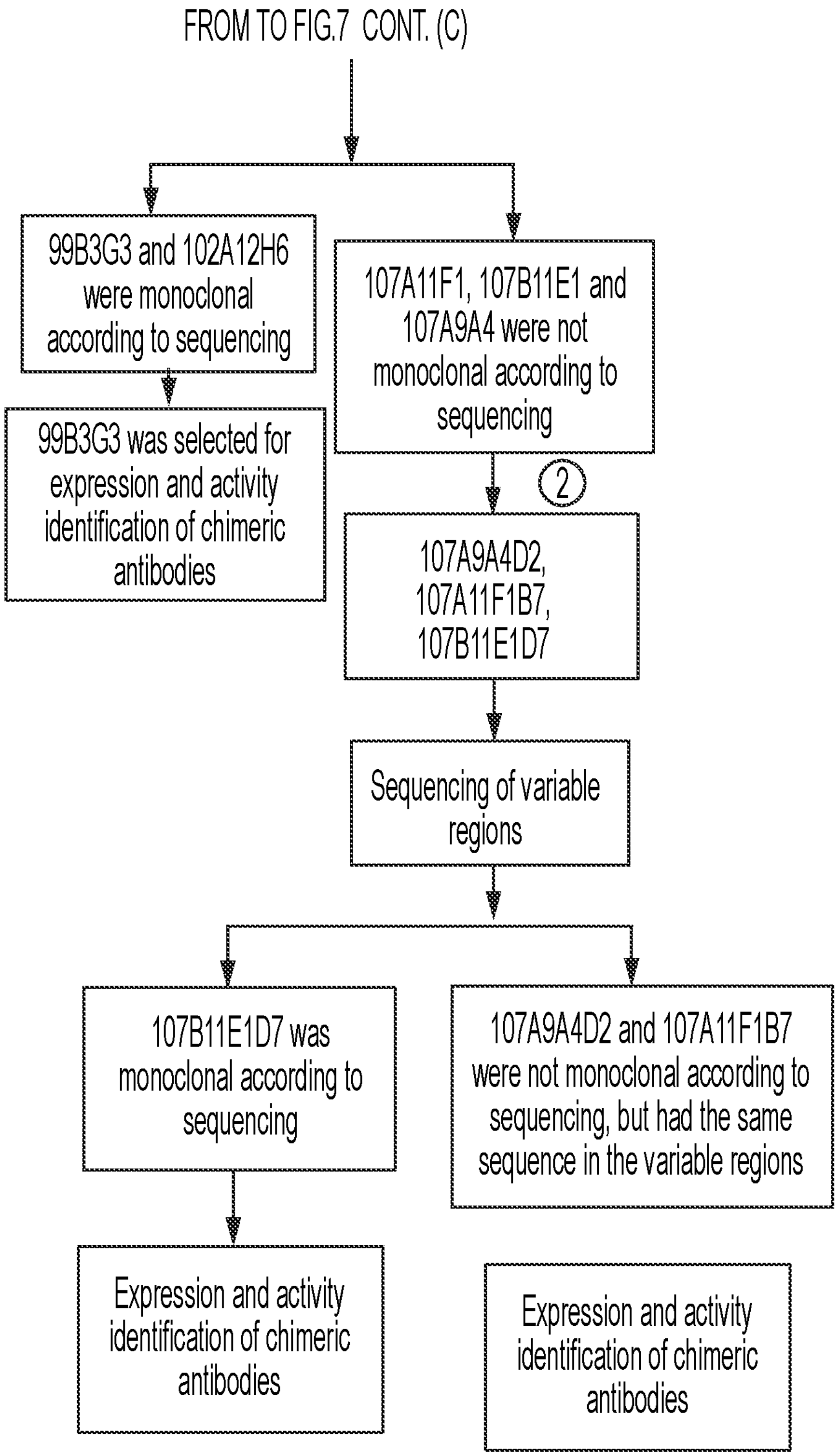

Primary screening: ELISA detected the binding affinity of the medium supernatant to hBCMA-ECD-Fc, a negative control group was NC-Fc, the set threshold value was Dvalue≥2, and 79 clones in total were obtained. After multiplication culture, secondary screening was conducted, and the obtained 19 clones (109C5, 107A11, 107B11, 116H6, 102G2, 102A12, 111F11, 107A9, 111D5, 105F9, 114C6, 97B8, 97C4, 104H4, 115G7, 116A9, 100H2, 99B3 and 110A11) all had a strong binding affinity to hBCMA-ECD-Fc, cynoBCMA-ECD-Fc and L-BCMA$^+$ cells; the obtained 4 clones (120D6, 120A10, 105C10 and 113B3) all had a strong binding affinity to hBCMA-ECD-Fc and L-BCMA$^+$ cells, and these 23 clones were used as parent clones to conduct subclonal screening, as shown in FIG. 7.

Each parent clone was spread on a 96-well plate to conduct subclonal screening. In primary screening, the subclonals of six clones 105F9, 111F11, 120D6, 104H4, 115G7 and 110A11 were all negative; 120A10 had a subclonal, which was negative in ELISA, while other clones were all negative. When 120A10 was screened before subcloning, it did not have cross-reactivity with machin BCMA, so this clone did not undergo secondary screening. The 96-well plates spread with the foregoing clones were cultured for two more days. Then ELISA screening was performed once again, and the screening result was still negative. Therefore, the subclonal screening of these seven parent clones was stopped.

The remaining 16 parent clones underwent secondary screening. Five subclones, 99B3G3, 102A12H6, 107A11F1, 107A9A4 and 107B11E1, obtained from screening all had a strong binding affinity to hBCMA-ECD-Fc, cynoBCMA-ECD-Fc and L-$BCMA^+$ cells and did not bind to NC-Fc. Two subclones, 105C10F1 and 113B3F12, both had a strong binding affinity to hBCMA-ECD-Fc and L-$BCMA^+$, and did not bind to cynoBCMA-ECD-Fc, NC-Fc. The foregoing seven subclones were selected to produce antibodies in small batches.

In addition, the four clones 97B8G8, 100H2D12, 109C5F3 and 114C6C8 were not monoclonal according to the microscopic examination and underwent the second round of subcloning. The results of the second round of primary subclonal screening are as follows. 114C6C8 did not generate a positive subclone, so this clone was no longer retained. Clones 97B8G8D12, 97B8G8E6, 97B8G8F7, 97B8G8G2, 100H2D12B10, 100H2D12C6, 100H2D12D5, 100H2D12H3, 109C5F3C1, 109C5F3D2, 109C5F3D4 and 109C5F3H3 were selected to undergo secondary screening. The results indicate that two obtained clones 100H2D12C6 and 109C5F3C1 both had a strong binding affinity to hBCMA-ECD-Fc, cynoBCMA-ECD-Fc and L-$BCMA^+$ cells and did not bind to NC-Fc. A clone that was generated, 97B8G8D12, had a strong binding affinity to hBCMA-ECD-Fc and cynoBCMA-ECD-Fc, and had a weak binding affinity to L-$BCMA^+$ cells. The foregoing three clones were selected to conduct antibody production in small batches.

As most of the subclones derived from clones 116A9, 111D5 and 116H6 had strong binding affinity to NC-hFc, FACS was used to screen all the subclones from the foregoing three clones: those from 116A9 were all negative clones; those from 116H6C10 were positive clones, but had strong binding affinity to NC-hFc; 10 subclones were selected from 111D5 to conduct secondary screening, and all the subclones had strong binding affinity to NC-hFc. Therefore, clones 116A9, 111D5 and 116H6, and subclones thereof were no longer retained.

Clones 97C4F2, 102G2B5, 102G2D1 and 102G2F3 did not bind to L-$BCMA^+$ cells, so they were no longer retained, either.

The sequencing results indicate that 107A11F1, 107B11E1 and 107A9A4 each had four heavy chains and a light chain, these three clones underwent the second round of subclonal screening. The results indicate that subclones 107A9A4D2, 107A11F1B7 and 107B11E1D7 of 107A11F1 had a strong binding affinity to hBCMA-ECD-Fc, cynoBCMA-ECD-Fc and L-$BCMA^+$ cells. These three clones were selected for sequencing; and subclones 107A9A4B2, 107A9A4D8, 107A9A4E9, 107A11F105, 107A11F1E6, 107A11F1E7, 107B11E1A8, 107B11E1B10 and 107B11E1C11 were cryopreserved.

2.4 Screening of Fusion F0614 Hybridoma Cells

The cells after electrofusion were spread on 40 96-well plates. Among them, Balb/c #5061 was spread on plates #121 to #140, and SJL #5066 was spread on plates #141 to #160. ELISA was used in the primary screening to detect the binding affinity of the medium supernatant to hBCMA-ECD-Fc, with the set threshold value being Dvalue≥0.8. 33 clones in total were obtained. After multiplication culture, a secondary screening was conducted. Five obtained clones (151A9, 156E11, 149H4, 143D6 and 154B8) all had a binding affinity to hBCMA-ECD-Fc, cynoBCMA-ECD-Fc and L-$BCMA^+$ and did not bind to NC-Fc. One obtained clone (152D8) had a strong binding affinity to hBCMA-ECD-Fc and L-$BCMA^+$ and did not bind to NC-Fc. These six clones were selected as parent clones to conduct subclonal screening.

Each parent clone was spread on a 96-well plate to conduct subclonal screening. The subclones of three clones 156E11, 149H4 and 154B8 were all negative, so no subcloning of these three parent clones underwent the secondary screening.

Subclones were selected from the remaining three parent clones to conduct the secondary screening. The results indicate that the three subclones, 143D6F4, 151A9A4 and 152D8E8, all had a strong binding affinity to hBCMA-ECD-Fc, cynoBCMA-ECD-Fc and L-$BCMA^+$ and did not bind to NC-Fc. These three subclones were selected for antibody production in small batches. 143D6D8 and 151A9F1 were cryopreserved.

2.5 Summary of Hybridoma Cell Screening Results

As shown in FIG. 7, four rounds of hybridoma cell fusion were conducted. After subclonal screening, 14 strains of hybridoma cells (6G10-1D7, 99B3G3, 102A12H6, 107A11F1, 107A9A4, 107B11E1, 100H2D12C6, 105C10F1, 113B3F12, 109C5F3C1, 97B8G8D12, 143D6F4, 151A9A4 and 152D8E8) were selected to undergo small-batch hybridoma antibody production and purification as well as sequencing of antibody variable regions.

The sequencing results indicate that the sequences of the antibody variable regions of 100H2D12C6 and 97B8G8D12 were the same as those of 99B3G3. 107A11F1, 107A9A4 and 107B11E1 were not monoclonal. These three hybridoma cells underwent the second round of subcloning. 107A9A4D2, 107A11F1B7 and 107B11E1D7 were selected to undergo sequencing of antibody variable regions. The antibody variable regions of 107A9A4D2 and 107A11F1B7 had the same sequence and each had a heavy chain and two light chains. The screening data of the foregoing hybridoma supernants are as shown in Table 6.

TABLE 6

Screening results of hybridoma cell supernants

| | ELISA (OD450 nm) | | | FACS (MFI) | |
|---|---|---|---|---|---|
| Clone | hBCMA-ECD-Fc | cynoBCMA-ECD-Fc | NC-Fc | $BCMA^+$ | $BCMA^-$ |
| 6G10-1D7 | 2.9 | 1.95 | 0.08 | 3882.8 | 104.9 |
| 99B3G3 | 3.68 | 3.65 | 0.14 | 1929.4 | 106.1 |
| 102A12H6 | 3.6 | 3.53 | 0.12 | 762.2 | 105.4 |
| 105C10F1 | 3.42 | 0.18 | 0.1 | 1958.2 | 104.9 |
| 107A11F1 | 3.63 | 3.65 | 0.1 | 4997.3 | 102.6 |
| 107B11E1 | 3.56 | 3.61 | 0.09 | 3521.4 | 105.9 |
| 107A9A4 | 3.33 | 3.61 | 0.09 | 2655.8 | 101.8 |
| 113B3F12 | 3.9 | 0.18 | 0.14 | 3888.1 | 102.5 |
| 100H2D12C6 | 3.37 | 3.48 | 0.13 | 1142.5 | 96.1 |
| 109C5F3C1 | 3.57 | 3.41 | 0.57 | 2891.9 | 101.1 |
| 143D6F4 | 3.26 | 3.4 | 0.2 | 1507.9 | 114.5 |
| 151A9A4 | 3.34 | 3.4 | 0.24 | 2915.3 | 103.9 |
| 152D8E8 | 3.35 | 3.31 | 0.23 | 1184.7 | 103.9 |

TABLE 6-continued

Screening results of hybridoma cell supernants

| | ELISA (OD450 nm) | | | FACS (MFI) | |
|---|---|---|---|---|---|
| | hBCMA- | cynoBCMA- | | | |
| Clone | ECD-Fc | ECD-Fc | NC-Fc | $BCMA^+$ | $BCMA^-$ |
| 97B8G8D12 | 3.06 | 3.37 | 0.13 | 357.5 | 95.8 |
| 107A9A4D2 | 3.5093 | 3.583 | 0.4596 | 4645.2 | 97.5 |
| 107A11F1B7 | 3.5267 | 3.5005 | 0.4413 | 5181 | 114.9 |
| 107B11E1D7 | 2.9167 | 3.5361 | 0.4431 | 3513.9 | 128.1 |

Figure 8:
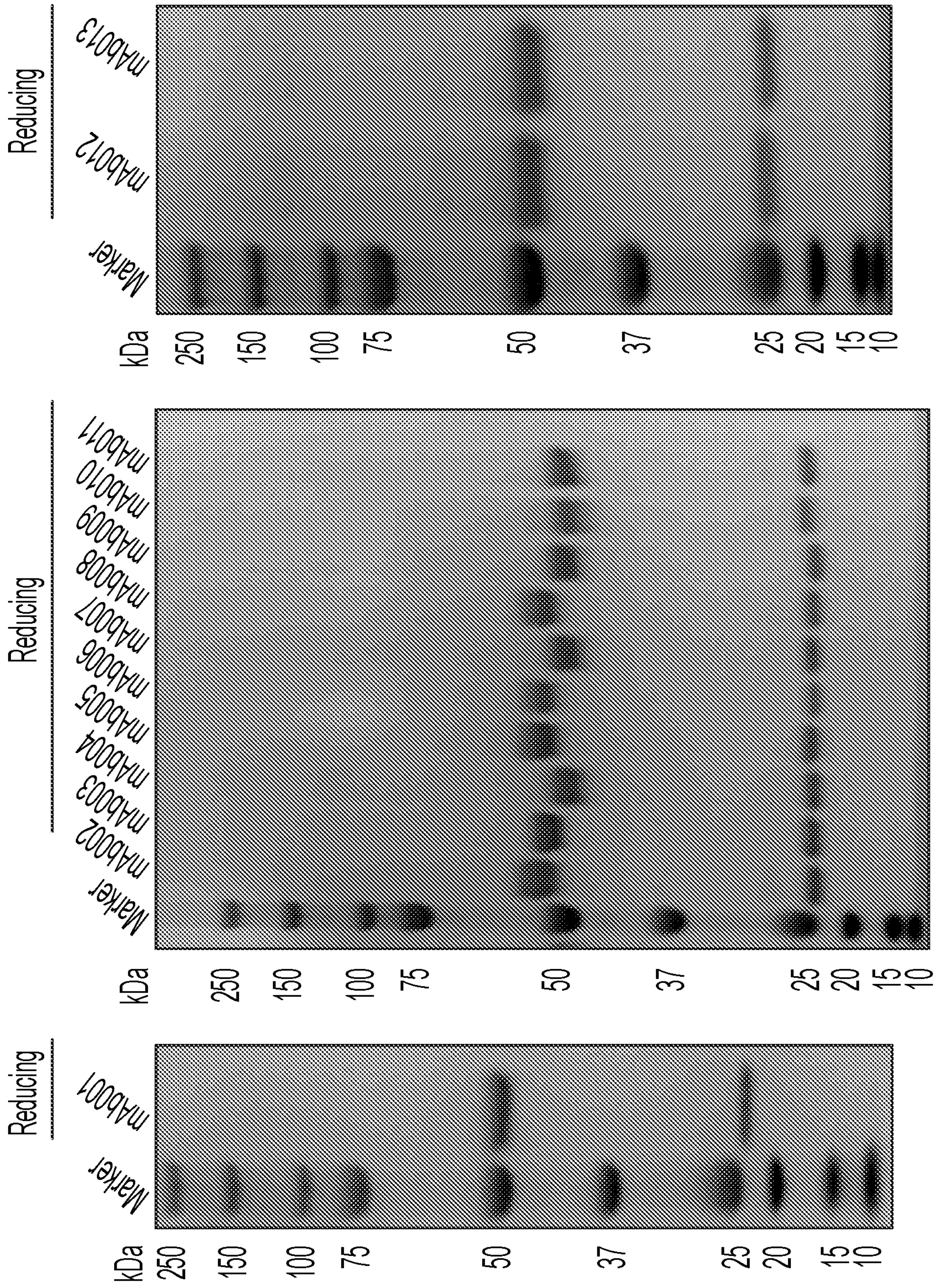
FIG. 8 shows SDS-PAGE analysis on small-batch antibody production and purification.

Example 3 Production and Purification of Hybridoma Antibodies 14 hybridoma cells in total were selected for antibody production in small batches. Among them, 97B8G8D12 did not produce antibodies. The remaining 13 clones all successfully generated corresponding antibodies, as shown in Table 7. SDS-PAGE results indicate that pure antibodies were obtained from purification, as shown in FIG. 8.

TABLE 7

Information about small-batch production and purification of antibodies

| Antibody No. | Clone | Subtype | conc (mg/ml) | Total amount (mg) | Animal origin |
|---|---|---|---|---|---|
| mAb001 | 6G10-1D7 | IgG1,κ | 0.847 | 5.929 | Balb/c #5065 |
| mAb002 | 99B3G3 | IgG1,κ | 0.847 | 7.1995 | Balb/c #5064 |
| mAb003 | 102A12H6 | IgG1,κ | 0.686 | 6.517 | SJL #5069 |
| mAb004 | 105C10F1 | IgG2b,κ | 0.861 | 10.332 | SJL #5069 |
| mAb005 | 107A11F1 | IgG2b,κ | 1.139 | 14.2375 | SJL #5069 |
| mAb006 | 107B11E1 | IgG1,κ | 0.993 | 11.4195 | SJL #5069 |
| mAb007 | 107A9A4 | IgG2b,κ | 2.248 | 30.348 | SJL #5069 |
| mAb008 | 113B3F12 | IgG2b,κ | 0.832 | 10.4 | SJL #5069 |
| mAb009 | 100H2D12C6 | IgG1,κ | 0.453 | 2.9445 | Balb/c #5064 |
| mAb010 | 109C5F3C1 | IgG2b,κ | 0.73 | 5.11 | SJL #5069 |
| mAb011 | 143D6F4 | IgG2b,κ | 0.73 | 10.95 | SJL #5066 |
| mAb012 | 151A9A4 | IgG2b,κ | 0.569 | 5.69 | SJL #5066 |
| mAb013 | 152D8E8 | IgG1,κ | 0.058 | 0.29 | SJL #5066 |

Example 4 Identification of Purified Hybridoma Antibodies 1.0 μg/ml hBCMA-ECD-Fc, cynoBCMA-ECD-Fc and hTACI-ECD-Fc were spread on plates to detect the specificity of hybridoma antibodies by ELISA.

Figure 9:
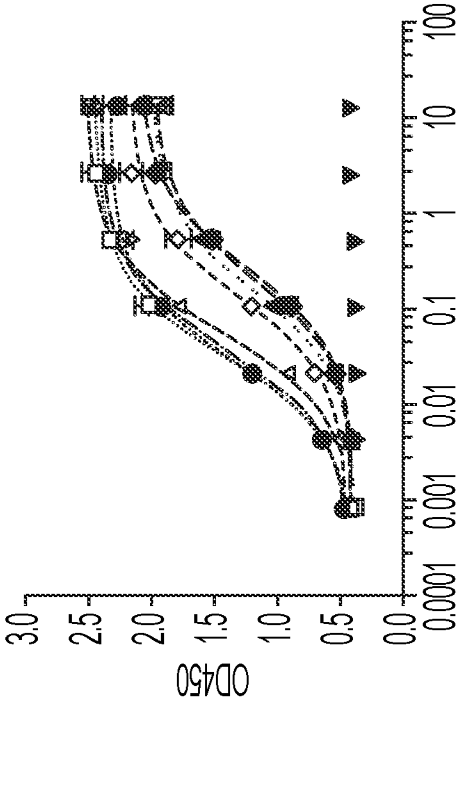
FIG. 9 shows ELISA analysis on the binding ability of a hybridoma antibody to hBCMA-ECD-Fc.
Figure 9:
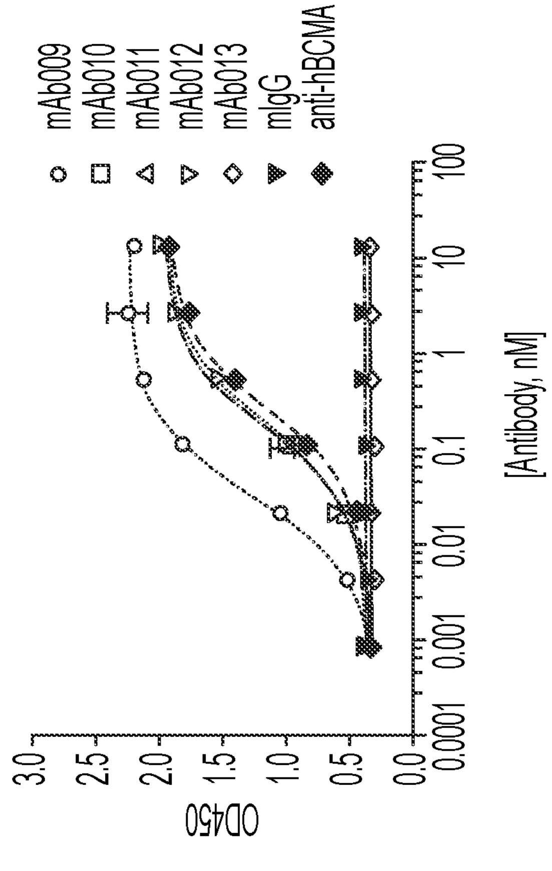
Figure 10:
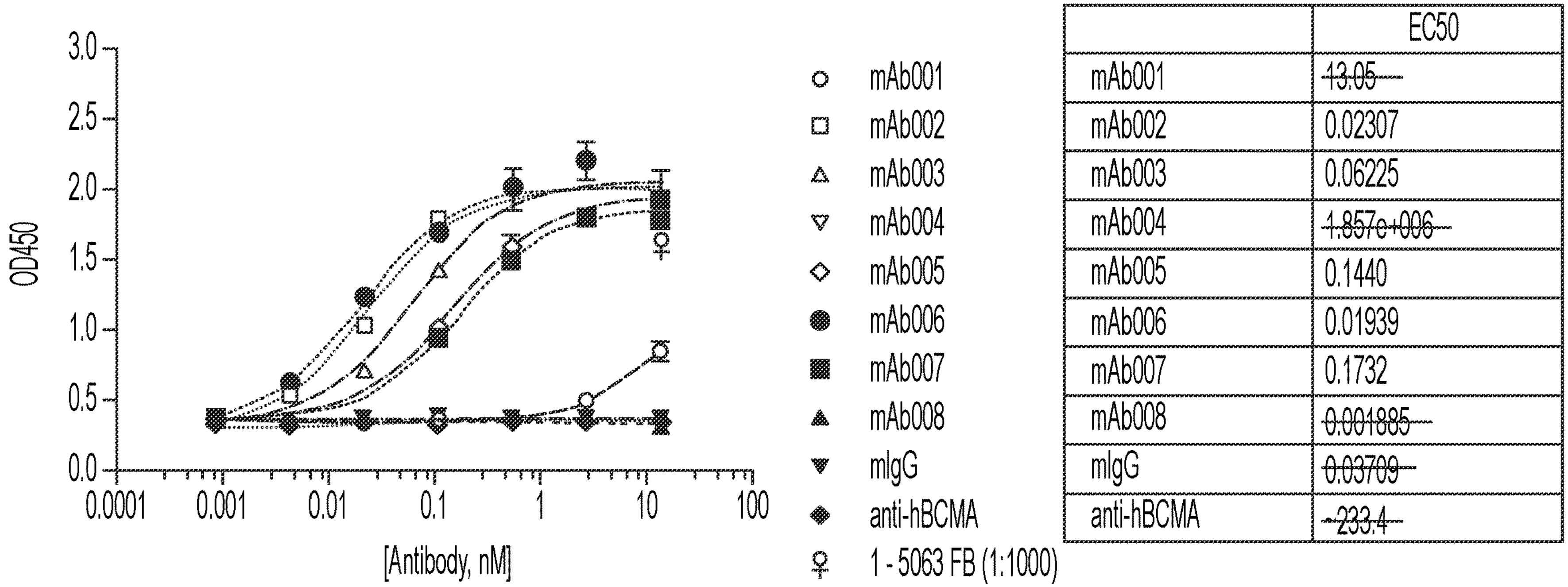
FIG. 10 shows ELISA analysis on the binding ability of a hybridoma antibody to cynoBCMA-ECD-Fc.
Figure 10:
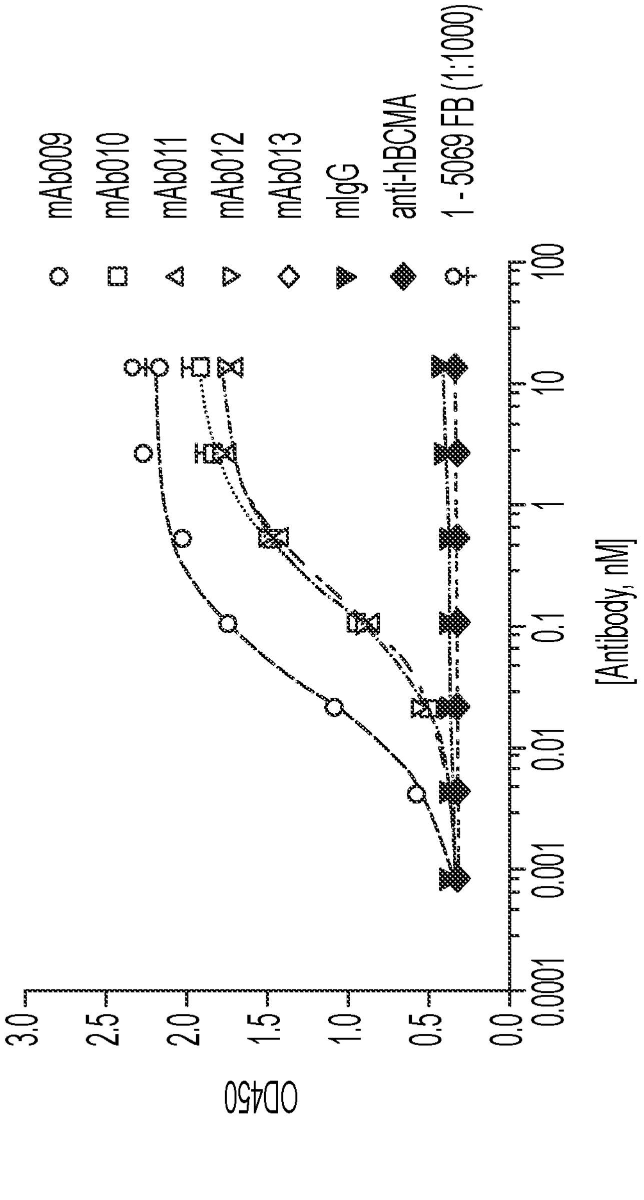
Figure 11:
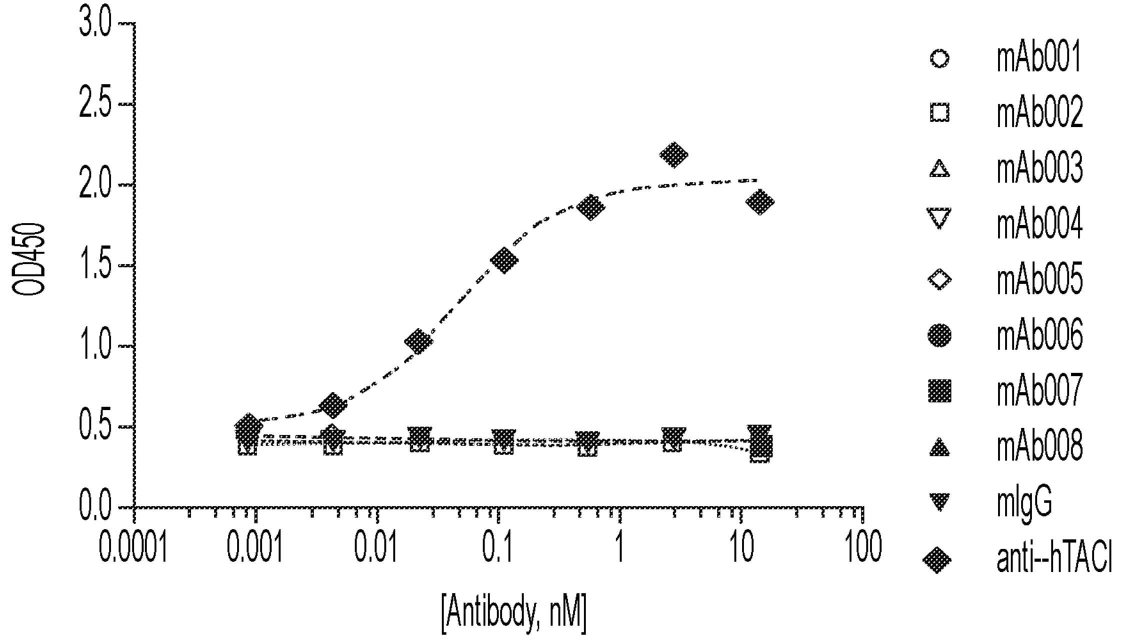
FIG. 11 shows ELISA analysis on the binding ability of a hybridoma antibody to hTACI-ECD-Fc.
Figure 11:
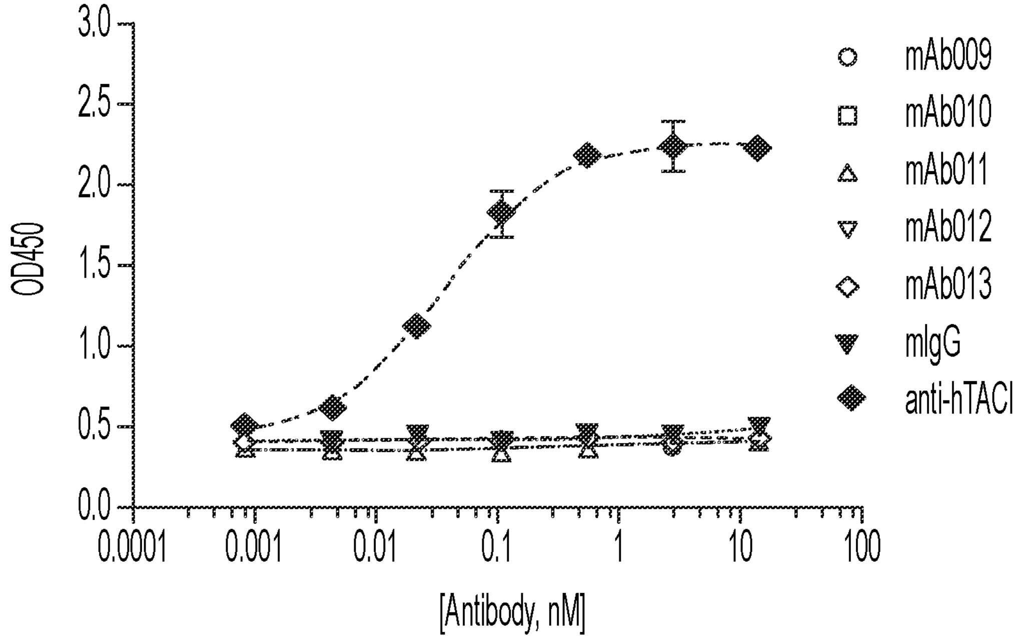

ELISA analysis results are shown in FIGS. 9-11. Purified hybridoma antibody mAb001(6G10-1D7) could bind to the extracellular domains of human BCMA, but had a weak binding affinity to the extracellular domains of machin BCMA. mAb001(6G10-1D7) bound to the extracellular domain of machin BCMA molecules only at a high concentration. mAb013(152D8E) did not bind to the extracellular domains of human BCMA and machin BCMA. mAb004 (105C10F1) and mAb008(13B3F12) could bind to the extracellular domains of human BCMA, but could not recognize the extracellular domains of machin BCMA. All other purified hybridoma antibodies could bind to the extracellular domains of human BCMA and machin BCMA. None of the hybridoma antibodies recognized hTACI-ECD-Fc. The EC50 for the binding of each antibody to hBCMA-ECD-Fc, cynoBCMA-ECD-Fc and hTACI-ECD-Fc is shown in Table 8.

TABLE 8

Analysis of binding specificity of hybridoma antibodies

| Anti-body No. | Clone | Subtype | EC50 (nM) hBCMA-ECD-Fc | cynoBCMA-ECD-Fc | hTACI-ECD-Fc |
|---|---|---|---|---|---|
| mAb001 | 6G10-1D7 | IgG1,κ | 0.034 | Low binding | No binding |
| mAb002 | 99B3G3 | IgG1,κ | 0.032 | 0.23 | No binding |
| mAb003 | 102A12H6 | IgG1,κ | 0.058 | 0.062 | No binding |
| mAb004 | 105C10F1 | IgG2b,κ | 0.038 | No binding | No binding |
| mAb005 | 107A11F1 | IgG2b,κ | 0.134 | 0.144 | No binding |
| mAb006 | 107B11E1 | IgG1,κ | 0.029 | 0.019 | No binding |
| mAb007 | 107A9A4 | IgG2b,κ | 0.21 | 0.17 | No binding |
| mAb008 | 113B3F12 | IgG2b,κ | 0.15 | No binding | No binding |
| mAb009 | 100H2D12C6 | IgG1,κ | 0.033 | 0.033 | No binding |
| mAb010 | 109C5F3C1 | IgG2c,κ | 0.18 | 0.18 | No binding |
| mAb011 | 143D6F4 | IgG2b,κ | 0.15 | 0.17 | No binding |
| mAb012 | 151A9A4 | IgG2b,κ | 0.17 | 0.15 | No binding |
| mAb013 | 152D8E8 | IgG1,κ | No binding | No binding | No binding |

Figure 12:
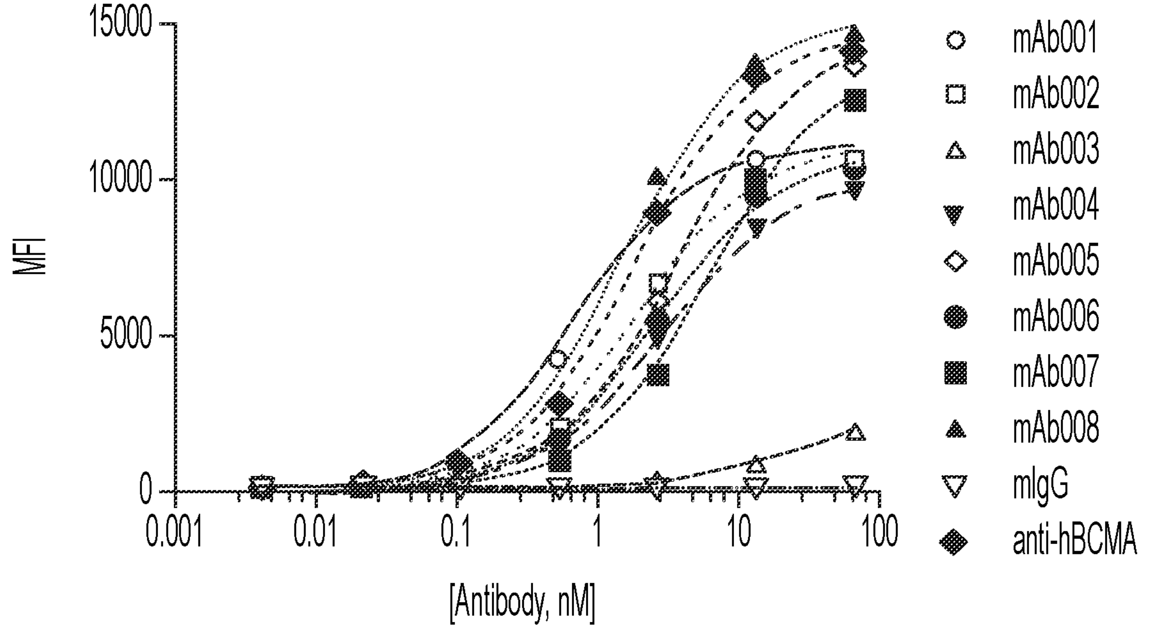
FIG. 12 shows flow cytometry analysis on the binding ability of a hybridoma antibody to L-BCMA+ cells.
Figure 12:
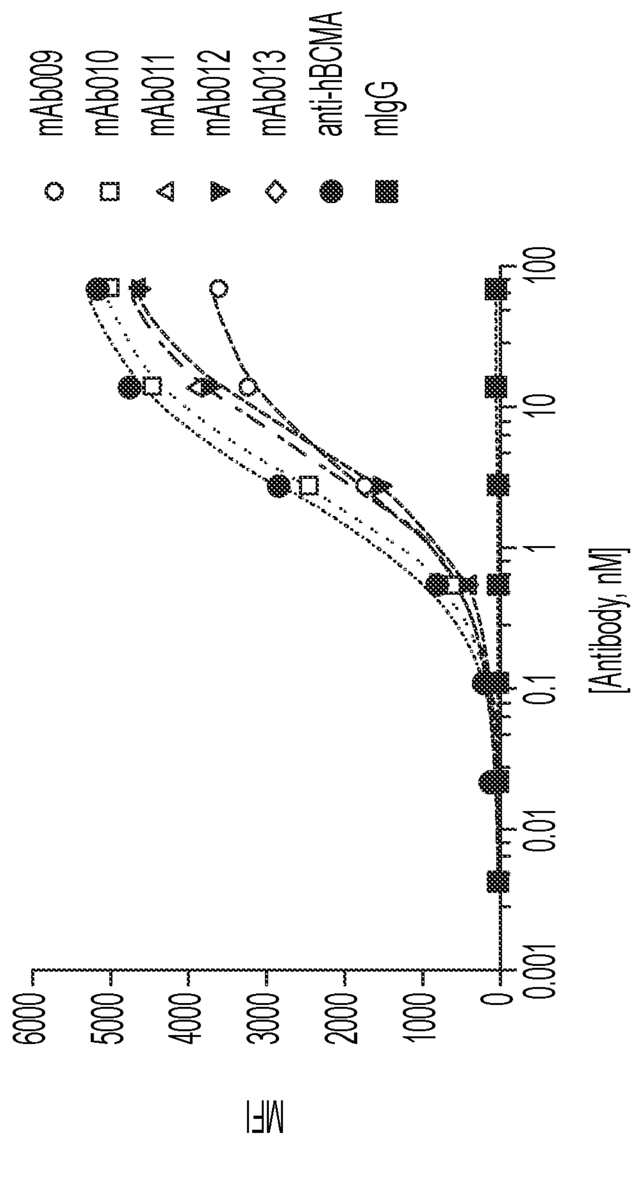
Figure 13:
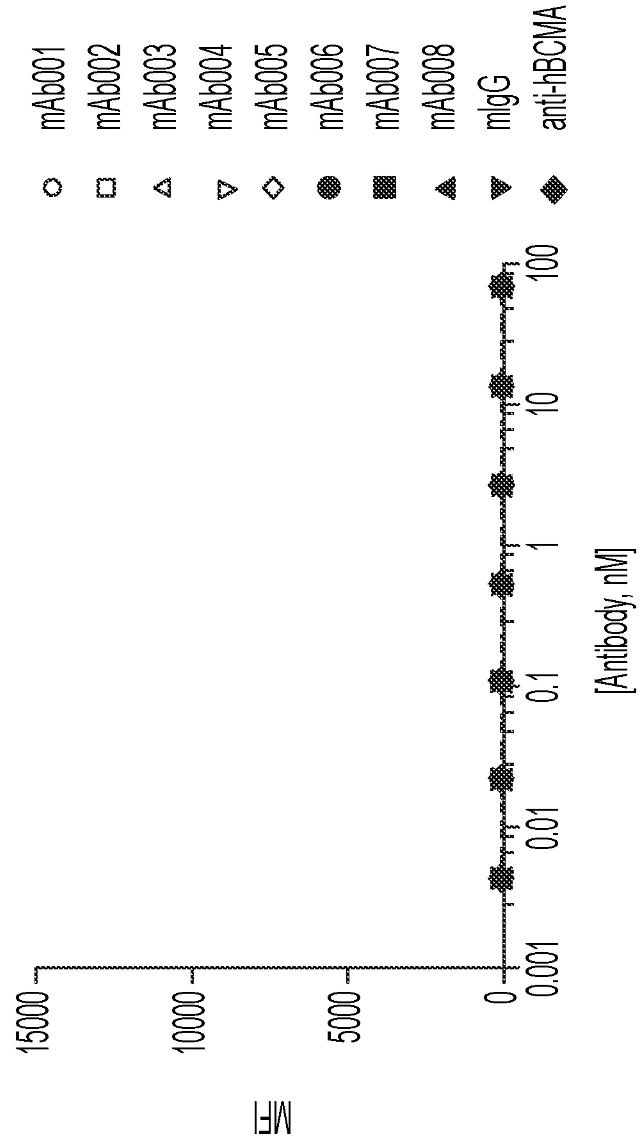
FIG. 13 shows flow cytometry analysis on the binding ability of a hybridoma antibody to L cells.
Figure 13:

The detection results of flow cytometry are as shown in FIGS. 12-13. Except mAb003 and mAb013, the remaining 11 hybridoma antibodies all had a desirable binding affinity to L-$BCMA^+$ cells and did not have non-specific binding to L cells.

Figure 14:
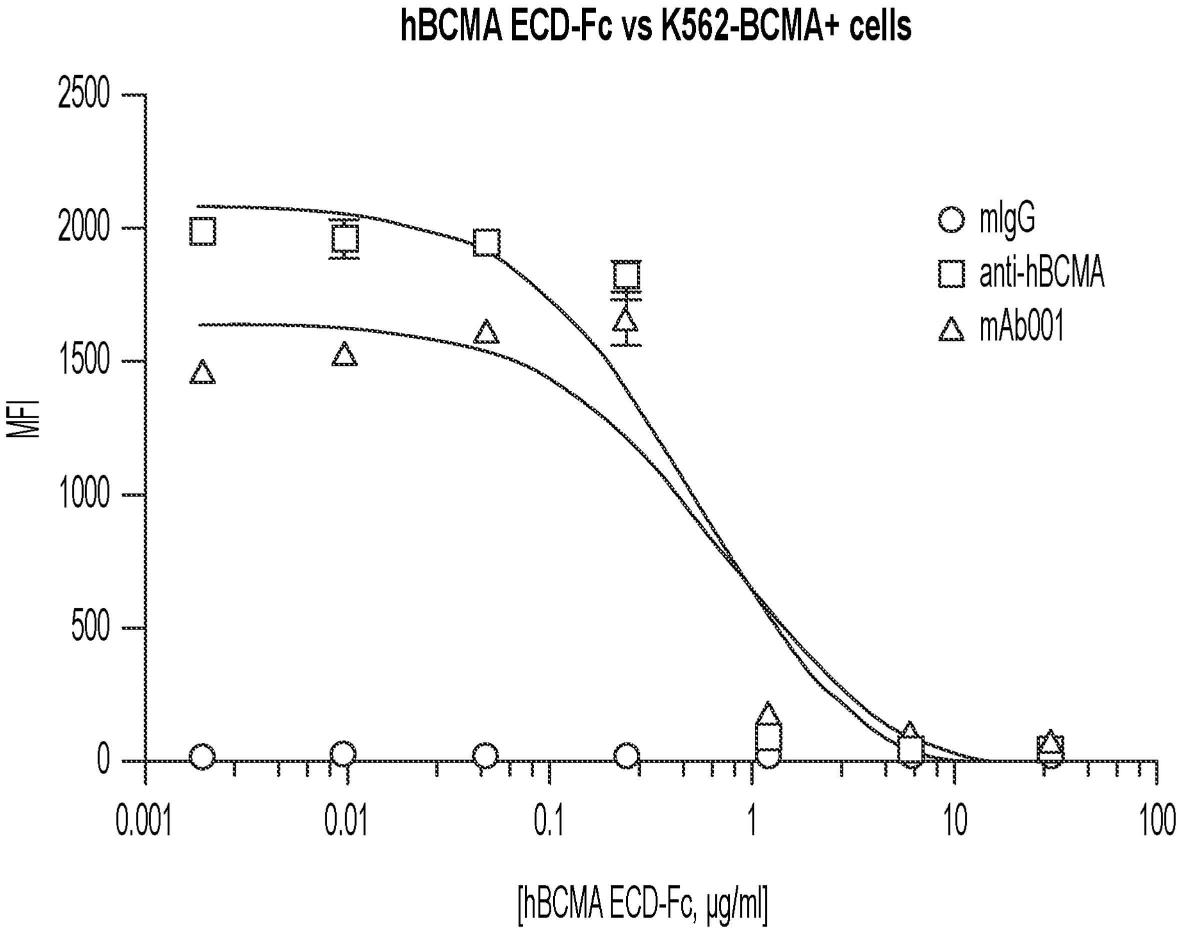
FIG. 14 shows flow cytometry analysis on the competitive binding of soluble BCMA to mAb001.
Figure 14:
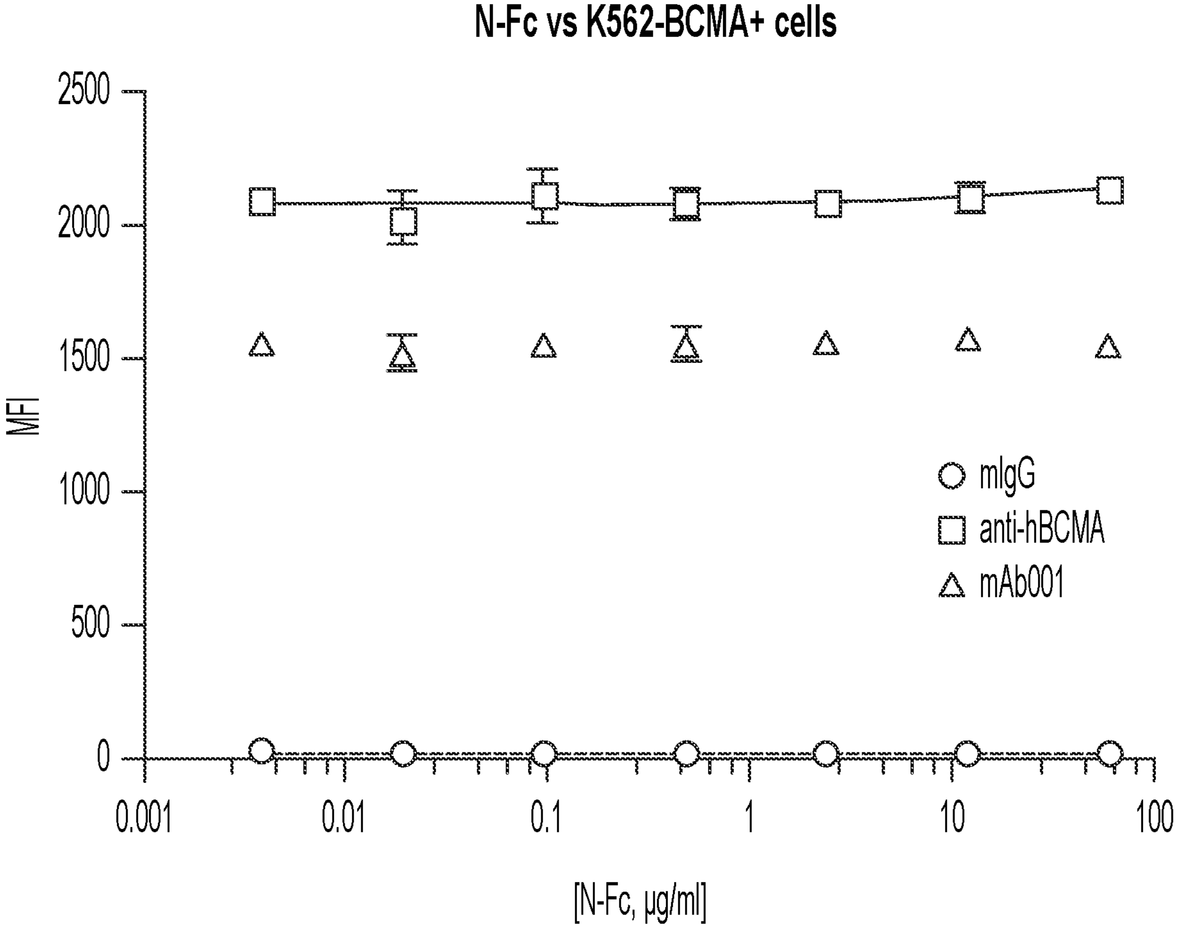
Figure 14:
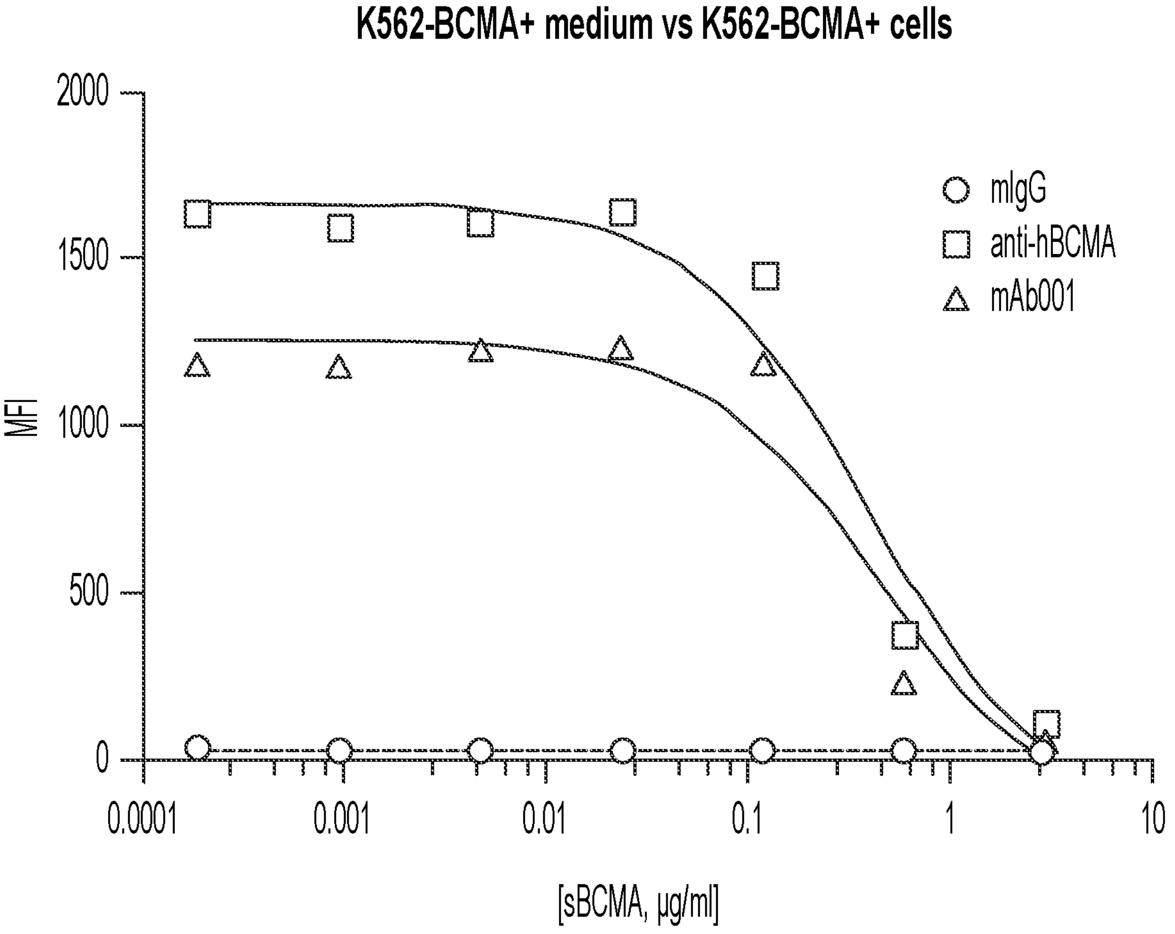
Figure 14:
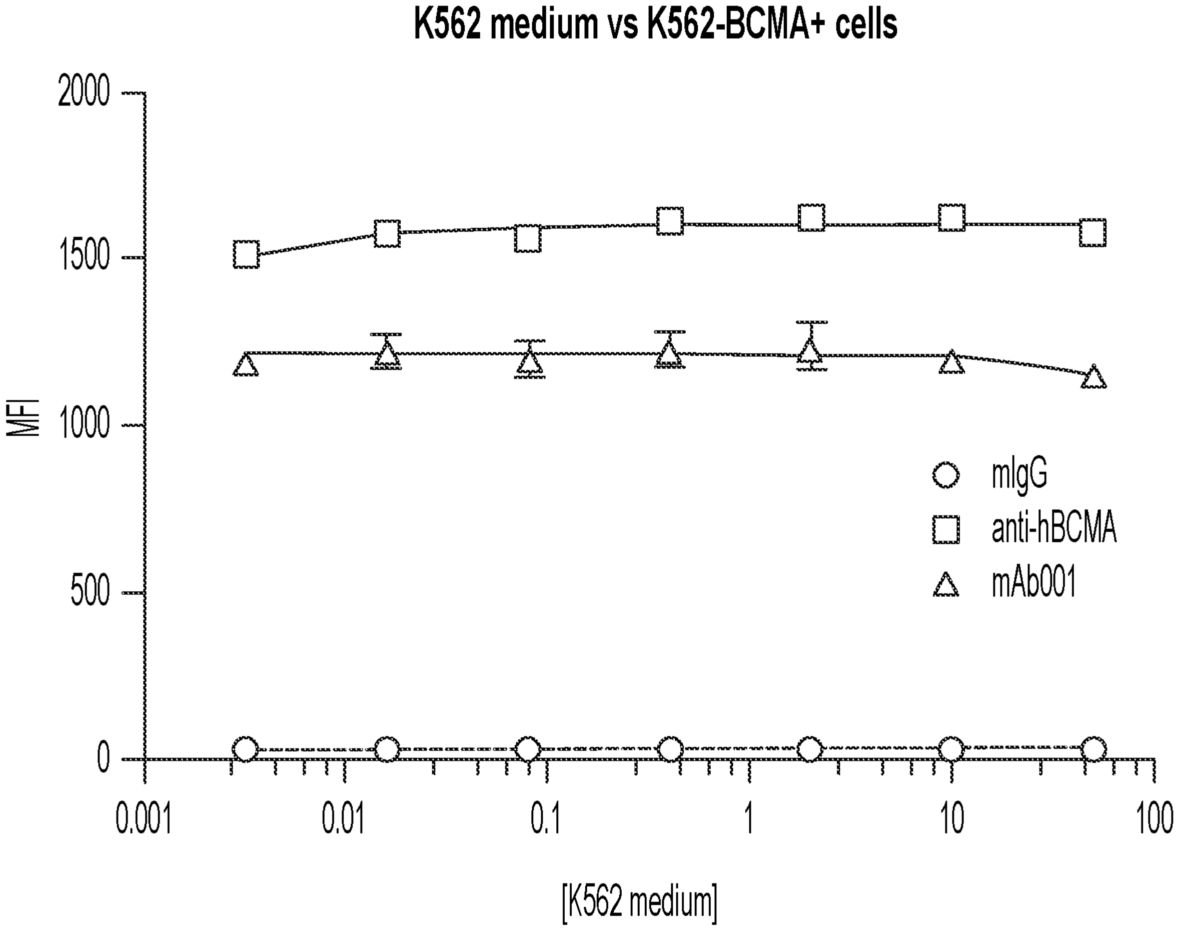
Figure 14:
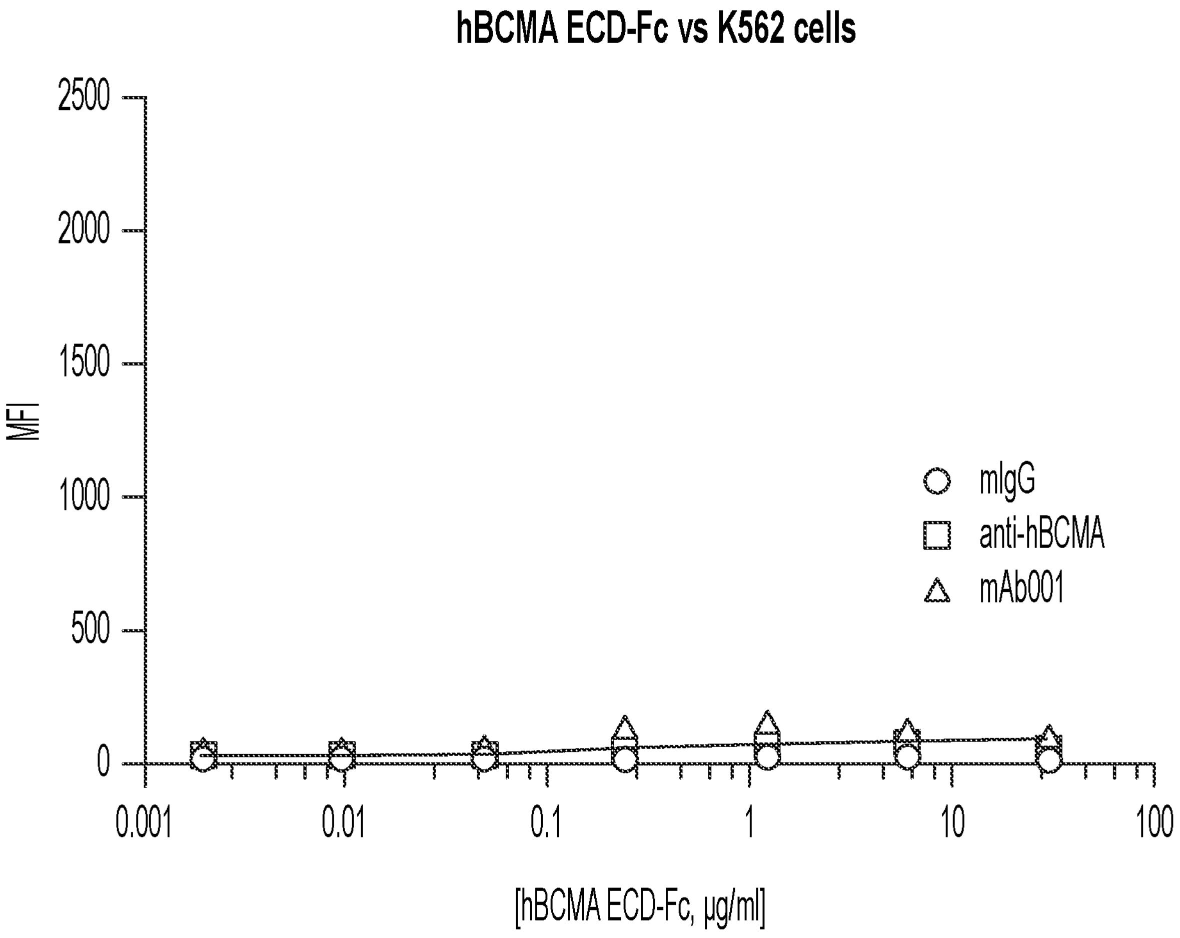
Figure 14:
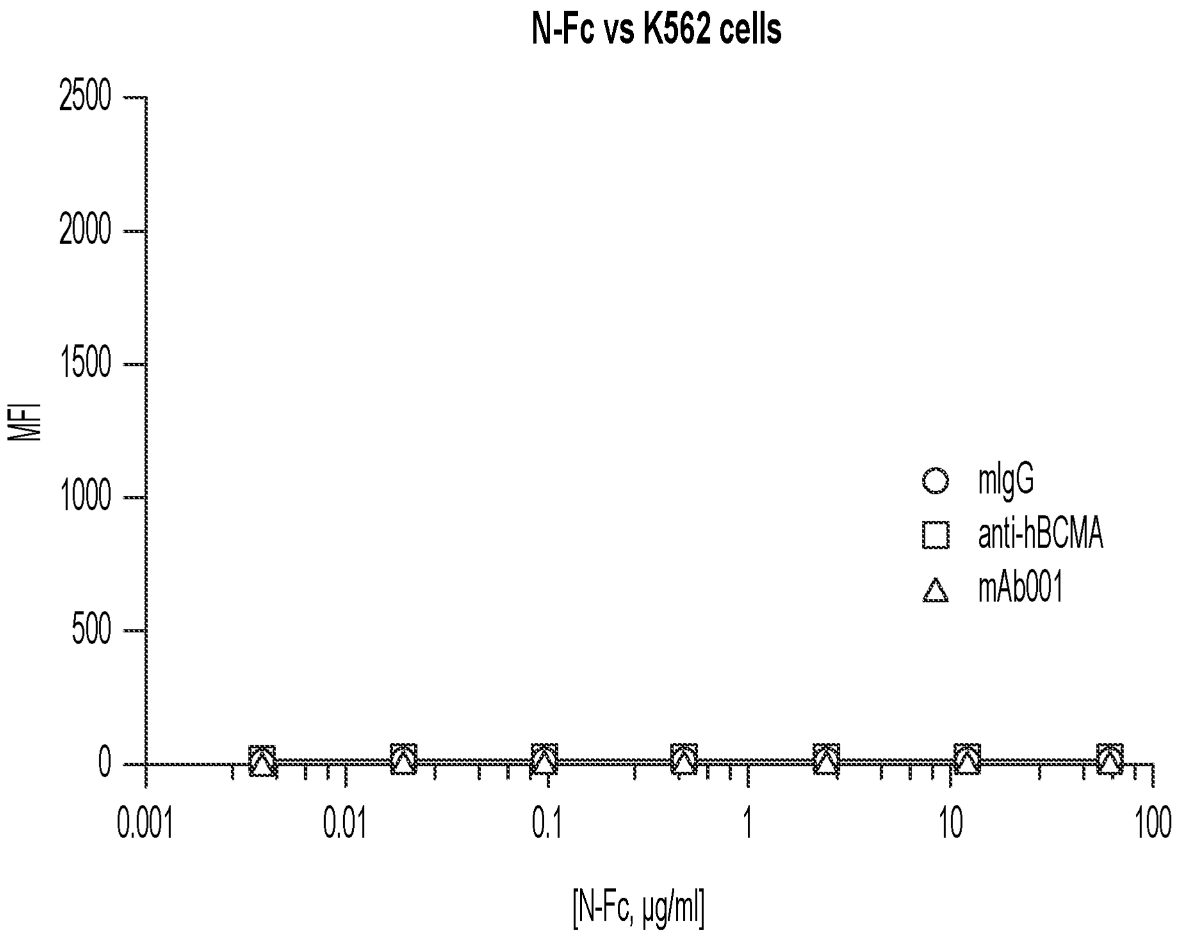

The analysis results of the competitive binding of hybridoma antibodies to soluble BCMA are as shown in FIG. 14. When the concentration of hBCMA-ECD-Fc was greater than 240 ng/ml, the binding of K562-$BCMA^+$ cells to mAb001 (final concentration EC80:1 μg/ml) could be competitively inhibited, with IC50 being 731 ng/ml and the corresponding molar ratio 1.7:1. When BCMA concentration of K562-$BCMA^+$ medium supernatant was grater than 120 ng/ml, the binding of K562-$BCMA^+$ cells to mAb001 (final concentration EC80:1 μg/ml) could be competitively inhibited, with IC50 being 466 ng/ml, and the corresponding molar ratio 10.4:1.

Example 5 Sequencing of Antibody Variable Regions 17 strains of hybridoma cells in total underwent sequencing of antibody variable regions. The sequencing results indicate that 12 strains of hybridoma cells were monoclonal: 6G10-1D7(CP01), 99B3G3(CP02), 102A12H6, 100H2D12C6, 105C10F1(CP03), 113B3F12, 109C5F3C1 (CP06), 97B8G8D12, 143D6F4(CP07), 151A9A4(CP08), 152D8E8(CP09) and 107B11E1D7(CP05). 99B3G3(CP02), 100H2D12C6 and 97B8G8D12 had the same sequence of the antibody variable regions. 5 strains of hybridoma cells were polyclonal: 107A11F1, 107A9A4, 107B11E1, 107A9A4D2 and 107A11F1B7 (CP04). 107A11F1, 107A9A4 and 107B11E1 each had four heavy chains and one light chain. 107A9A4D2 and 107A11F1B7(CP04) each had one heavy chain and two light chains with the same sequences.

Table 9 shows the sequences of the antibody variable regions.

TABLE 9

Nucleotide sequences encoding antibody variable regions

| Hybridoma No. | Nucleotide sequence encoding $V_H$ regions | Nucleotide sequence encoding $V_L$ regions |
|---|---|---|
| 6G10-1D7 (CP01) | SEQ ID NO: 1 | SEQ ID NO: 2 |
| 99B3G3 (CP02) | SEQ ID NO: 3 | SEQ ID NO: 4 |

TABLE 9-continued

| Nucleotide sequences encoding antibody variable regions | | |
|---|---|---|
| Hybridoma No. | Nucleotide sequence encoding $V_H$ regions | Nucleotide sequence encoding $V_L$ regions |
| 102A12H6 | SEQ ID NO: 5 | SEQ ID NO: 6 |
| 105C10F1 (CP03) | SEQ ID NO: 7 | SEQ ID NO: 8 |
| 107A11F1 | SEQ ID NO: 9 | SEQ ID NO: 13 |
| | SEQ ID NO: 10 | |
| | SEQ ID NO: 11 | |
| | SEQ ID NO: 12 | |
| 107B11E1 | SEQ ID NO: 14 | SEQ ID NO: 18 |
| | SEQ ID NO: 15 | |
| | SEQ ID NO: 16 | |
| | SEQ ID NO: 17 | |
| 107A9A4 | SEQ ID NO: 19 | SEQ ID NO: 23 |
| | SEQ ID NO: 20 | |
| | SEQ ID NO: 21 | |
| | SEQ ID NO: 22 | |
| 113B3F12 | SEQ ID NO: 24 | SEQ ID NO: 25 |
| 100H2D12C6 | SEQ ID NO: 3 | SEQ ID NO: 4 |
| 109C5F3C1 (CP06) | SEQ ID NO: 26 | SEQ ID NO: 27 |
| 143D6F4 (CP07) | SEQ ID NO: 28 | SEQ ID NO: 29 |
| 151A9A4 (CP08) | SEQ ID NO: 30 | SEQ ID NO: 31 |
| 152D8E8 (CP09) | SEQ ID NO: 32 | SEQ ID NO: 33 |
| 107A11F1B7 (CP04) | SEQ ID NO: 34 | SEQ ID NO: 35 |
| | | SEQ ID NO: 36 |
| 107A9A4D2 | SEQ ID NO: 34 | SEQ ID NO: 35 |
| | | SEQ ID NO: 36 |
| 107B11E1D7 (CP05) | SEQ ID NO: 37 | SEQ ID NO: 38 |
| 97B8G8D12 | SEQ ID NO: 3 | SEQ ID NO: 4 |

Example 6 Expression and Identification of Chimeric Antibodies

The antibody $V_H$ regions obtained from sequencing were cloned to an IgG1,κ recombinant antibody heavy chain expression vector, and the $V_L$ regions were cloned to an IgG1,κ recombinant antibody light chain expression vector to construct expression plasmids of chimeric antibodies. Five strains of monoclonal hybridoma cells (6G10-1D7, 99B3G3, 105C10F1, 113B3F12 and 107B11E1D7) and one strain of polyclonal hybridoma cells (107A9A4D2) were selected for expression of chimeric antibodies. Among them, 107A9A4D2VH was paired with 107A9A4D2VL-1 and 107A9A4D2VL-2, respectively for expression. The heavy and light chain sequences of the recombinantly expressed chimeric antibodies are as follows (the underlined parts are the antibody variable region sequences):

1. Hybridoma 6G10-1D7
>6G10-1D7VH heavy chain (SEQ ID NO: 39; $V_H$ is underlined):
MEFGLSWLFLVAILKGVQCEVQLQQSGPELVKPGASMKISCKASDYSFTDYIMTWV

KQSHGKNLEWIGLINPYNGGTTYNQKFKDKATFTVDKSSTTAYMDLLSLTSEDSAV

YYCARRGITTDYYTMDYWGQGTSVTVSSASTKGPSVFPLAPSSKSTSGGTAALGCLV

KDYFPEPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHE

ALHNHYTQKSLSLSPGK

>6G10-1D7VL light chain (SEQ ID NO: 40):
MDMRVPAQLLGLLLLWFPGSRCDIVMTQSQRFMSTSVGDRVSITCKASQSVGTAVA

WYQQTPGQFPKLLIYSTSNRYTGVPDRFTGSGSGTDFTLTISNMQSEDLADYFCQQY

STYPLTFGSGTKLELKRTVAAPSVFIFPPSDEQLKSGTASVVCLLNNFYPREAKVQWK

VDNALQSGNSQESVTEQDSKDSTYSLSSTLTLSKADYEKHKVYACEVTHQGLSSPVT

KSFNRGEC

2. Hybridoma 99B3G3
>99B3G3VH heavy chain (SEQ ID NO: 41; $V_H$ is underlined):
MEFGLSWLFLVAILKGVQCEVQLQQSGPVLVKPGASVKMSCKASGYTFTDLYMNW

VKQSHGKSLEWIGVINPYNGGTSYNQKFKAKATLTVDKSSITAYMELNSLTSEDSAV

YYCARGDSIYVMDYWGQGTSVTVSSASTKGPSVFPLAPSSKSTSGGTAALGCLVKD

YFPEPVTVSWNSGALTSGVHTFPAVLQSSGLYSLSSVVTVPSSSLGTQTYICNVNHKP

SNTKVDKKVEPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFYPSD

-continued

IAVEWESNGQPENNYKTTPPVLDSDGSFFLYSKLTVDKSRWQQGNVFSCSVMHEAL

HNHYTQKSLSLSPGK

>99B3G3VL light chain (SEQ ID NO: 42; $V_L$ is underlined):
MDMRVPAQLLGLLLLWFPGSRCDIVMTQSPSSLAMSVGQKVTMSCKSSQSLLNSSIQ

KNYLAWYQQKPGQSPKLLVYFASTRESGVPDRFIGSGSGTDFTLTISSVQAEDLADY

FCQQHYSSPLTFGAGTKLELKRTVAAPSVFIFPPSDEQLKSGTASVVCLLNNFYPREA

KVQWKVDNALQSGNSQESVTEQDSKDSTYSLSSTLTLSKADYEKHKVYACEVTHQ

GLSSPVTKSFNRGEC

3. Hybridoma 105C10F1
>105C10F1VH heavy chain (SEQ ID NO: 43; $V_H$ is underlined):
MEFGLSWLFLVAILKGVQCEVKLLQSGGGLVQPGGSLKLSCAASGIDFSRYWMSWV

RRAPGKGLEWIGEINPDSSTINYAPSLKDKFIISRDAAKNTLYLQMSKVRSEDTALYY

CATLYYDYDGDYAMDYWGQGTSVTVSSASTKGPSVFPLAPSSKSTSGGTAALGCLV

KDYFPEPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPEVTCV

WDVSHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHE

ALHNHYTQKSLSLSPGK

>105C10F1VL light chain (SEQ ID NO: 44; $V_L$ is underlined):
MDMRVPAQLLGLLLLWFPGSRCDIVMTPSQKFMSTSVGDRVSVTCKASQNVGTNV

AWYQQKPGQSPKALIYSASYRYSGVPDRFTGSGSGTDFTLTISNVQSEDLAEYFCQH

YNSYPFTFGSGTKLEIKRTVAAPSVFIFPPSDEQLKSGTASVVCLLNNFYPREAKVQW

KVDNALQSGNSQESVTEQDSKDSTYSLSSTLTLSKADYEKHKVYACEVTHQGLSSPV

TKSFNRGEC

4. Hybridoma 113B3F12
>113B3F12VH heavy chain (SEQ ID NO: 45; $V_H$ is underlined):
MEFGLSWLFLVAILKGVQCEVQLQQSGPVLVKPGASVKMSCKASGYTFTDYYMNW

VKQSHGKSLEWIGVINPYNGGTDYNQKFKGKATLTVDKSSSTAYMELNSLTSEDSA

VYYCARRRESYGTSYQGAYFDSWGQGTTLTVSSASTKGPSVFPLAPSSKSTSGGTAA

LGCLVKDYFPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKDTLMISRTP

EVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSRDELTKNQVSLTCLV

KGFYPSDIAVEWESNGQPENNYKTTPPVLDSDGSFFLYSKLTVDKSRWQQGNVFSCS

VMHEALHNHYTQKSLSLSPGK

>113B3F12VL light chain (SEQ ID NO: 46; $V_L$ is underlined):
MDMRVPAQLLGLLLLWFPGSRCDIQMTQTTSSLSASLGDRVTISCRASQDISNYLNW

YQQKPDGTVKLLIYYTSRLHSGVPSRFSGSGSGTDYSLSISDLEQEDIATYFCQQVITL

PWTFGGGTKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKS

FNRGEC

-continued

5. Hybridoma 107B11E1D7

>107B11E1D7VH heavy chain (SEQ ID NO: 47; $V_H$ is underlined):
MEFGLSWLFLVAILKGVQCEVQLQQSGPVLVKPGASVKMSCKASGYTFTDLYMNW

LKQSHGKRLEWIGVINPYNGGTSYNQKFKGKATLTVDKSSSTAYMDLNSLTSEDSA

VYYCARGDSIYVMDYWGQGTSFTVSSASTKGPSVFPLAPSSKSTSGGTAALGCLVK

DYFPEPVTVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSCSVMHEA

LHNHYTQKSLSLSPGK

>107B11E1D7VL light chain (SEQ ID NO: 48; $V_L$ is underlined):
MDMRVPAQLLGLLLLWFPGSRCENVLTQSPAIMSASPGEKVTMTCSASSSVSYMHW

YQQKSSTSPKLWIYDTSKLSSGVPGRFSGSGSGKSYSLTISSMEAEDVATYYCFQGSG

YPLFTFGSGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTK

SFNRGEC

6. Hybridoma 107A9A4D2

>107A9A4D2VH heavy chain (SEQ ID NO: 49; $V_H$ is underlined):
MEFGLSWLFLVAILKGVQCEVQLQQSGPVLVKPGASVKMSCKASGYTFTDLYMNW

LKQSHGKRLEWIGVINPYNGGTSYNQKFKGKATLTVDKSSSTAYMDLNSLTSEDSA

VYYCARGDSIYVMDYWGQGTSFTVSSASTKGPSVFPLAPSSKSTSGGTAALGCLVK

DYFPEPVTVSWNSGALTSGVHTFPAVLQSSGLYSLSSVVTVPSSSLGTQTYICNVNHK

PSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVFSCSVMHEA

LHNHYTQKSLSLSPGK

>107A9A4D2VL-1 light chain (SEQ ID NO: 50; $V_L$ is underlined):
MDMRVPAQLLGLLLLWFPGSRCENVLTQSPAIMSASPGEKVTMTCSASSSVSYMHW

YQQKSSTSPKLWIYDTSKLSSGVPGRFSGSGSGKSYSLTISSMEAEDVATYYCFQGSG

YPLFTFGSGTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQGLSSPVTK

SFNRGEC

>107A9A4D2VL-2 light chain (SEQ ID NO: 51; $V_L$ is underlined):
MDMRVPAQLLGLLLLWFPGSRCDIVMTQSPSSLAMSVGQKVTMSCKSSQSLLNSSIQ

KNYLAWYQQKPGQSPKLLIYFASTRESGVPDRFIGSGSGTDFTLTISSVQAEDLADYF

CQQHYSTPLTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGL

SSPVTKSFNRGEC

Example 7 Expression Identification of Chimeric Antibodies

Figure 15:
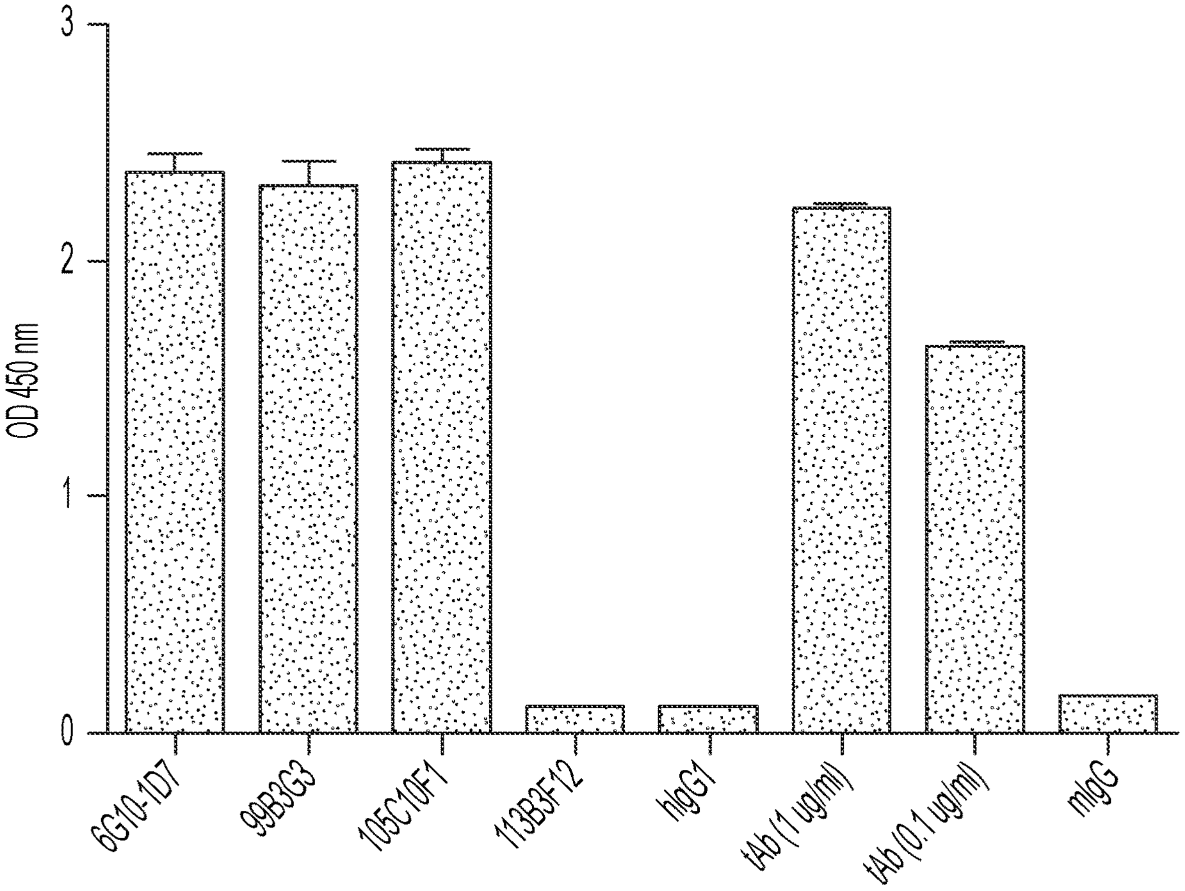
FIG. 15 shows ELISA analysis on the binding activity of a chimeric antibody to hBCMA-ECD-Fc.
Figure 15:
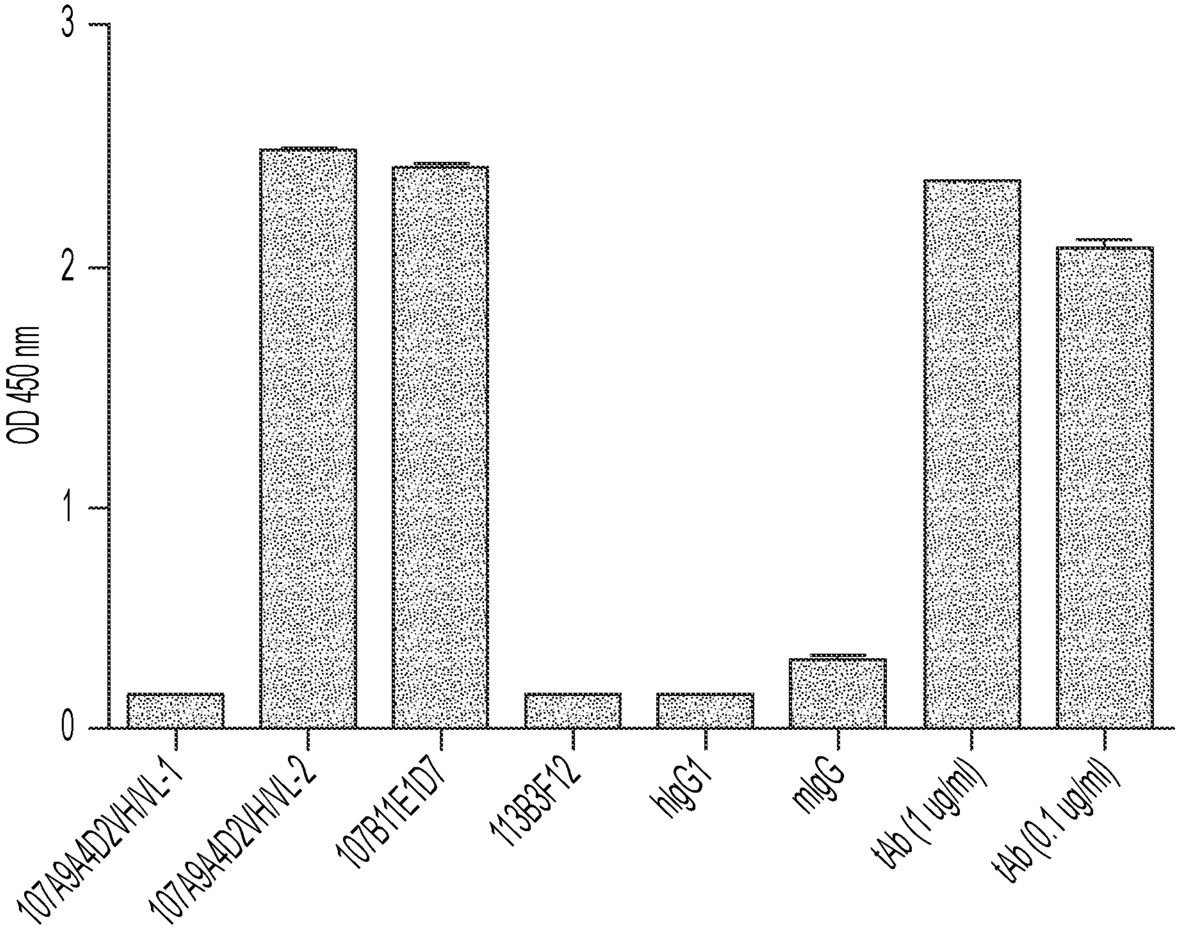
Figure 16:
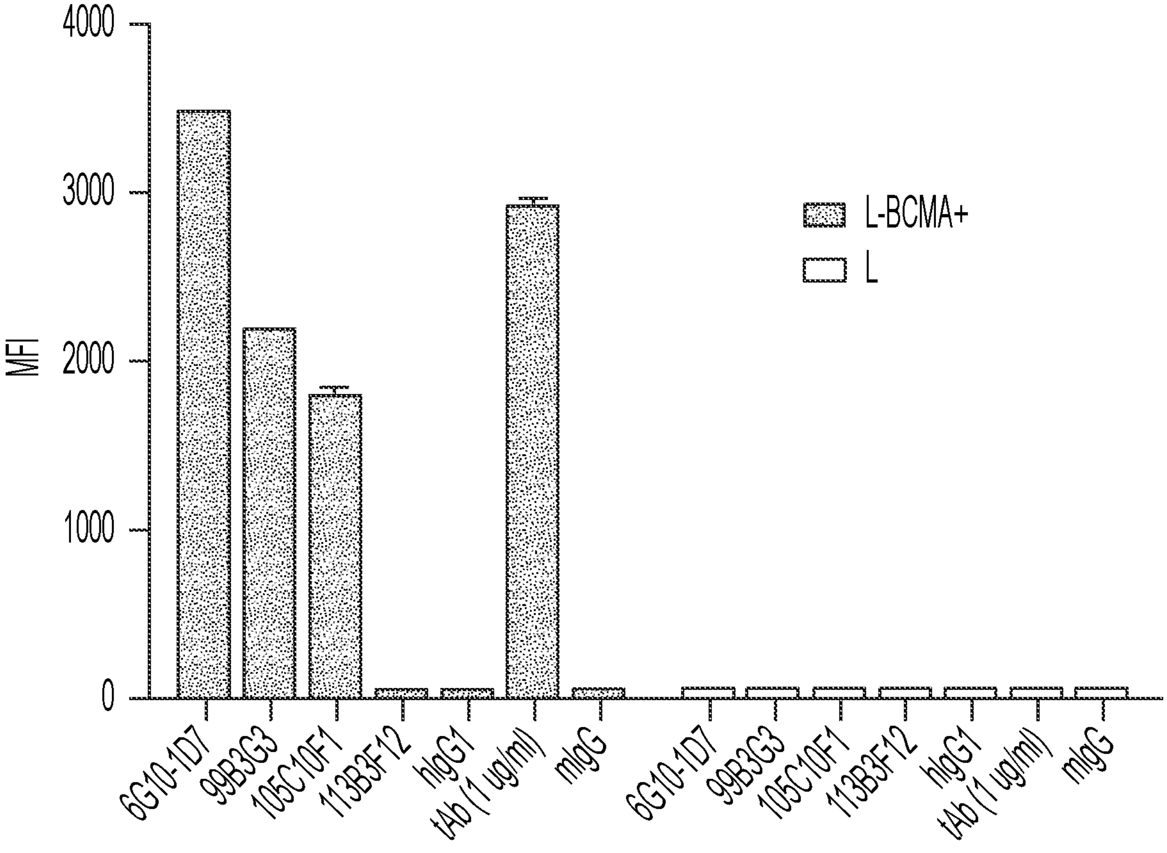
FIG. 16 shows flow cytometry analysis on the binding activity of a chimeric antibody to L-BCMA+ and L cells.
Figure 16:
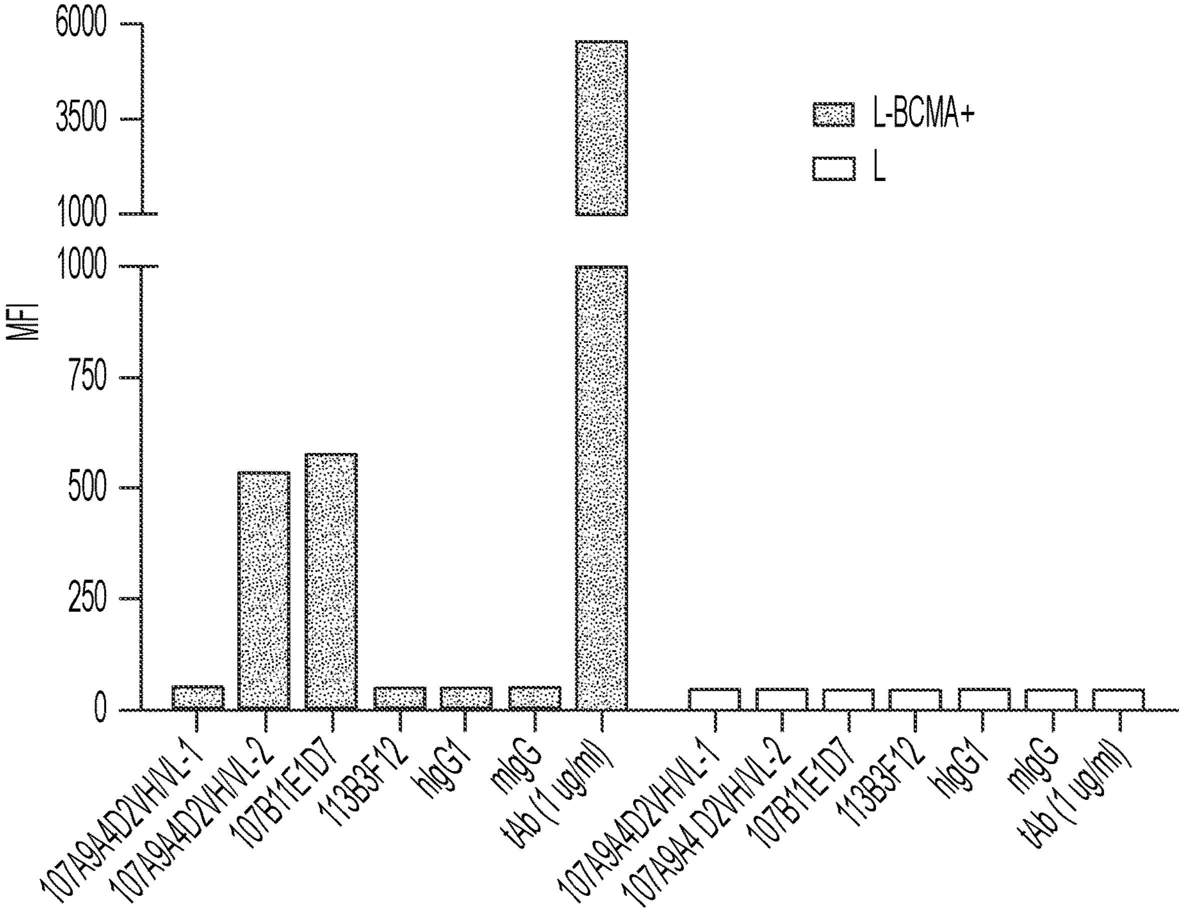

The results of ELISA analysis on the expression identification of chimeric antibodies are shown in FIG. 15. The results of flow cytometry detection are shown in FIG. 16. The chimeric antibodies of hybridoma 6G10-1D7, 99B3G3, 105C10F1 and 107B11E1D7 bound to the soluble extracellular domains of human BCMA molecules on the cell surface. The chimeric antibodies formed by pairing of the heavy chain 107A9A4D2VH and the light chain 107A9A4D2VL-2 of the hybridoma 107A9A4D2 all bound to the soluble extracellular domains of human BCMA molecules on the cell surface. The chimeric antibodies formed by pairing of 107A9A4D2VH and 107A9A4D2VL-1 did not bind to the soluble extracellular domains of human BCMA molecules on the cell surface. See Table 10 for detailed data.

TABLE 10

Detection results of the supernants of the chimeric antibodies

| | Elisa (OD450 nm) | FACS (MFI) | |
|---|---|---|---|
| Clone | hBCMA-ECD-Fc | L-BCMA$^+$ | L |
| 6G10-1D7 | 2.35 | 3467.5 | 31 |
| 99B3G3 | 2.3 | 2180 | 31 |
| 105C10F1 | 2.39 | 1801 | 32 |
| 113B3F12 | 0.09 | 37.5 | 32 |
| 107A9A4D2VH/VL-1 | 0.13 | 42.5 | 36 |
| 107A9A4D2VH/VL-2 | 2.45 | 525 | 35 |
| 107B11E1D7 | 2.38 | 565.5 | 34 |

Example 8 Construction of Lentiviral Expression Vectors Containing a CAR Structure The light chains and heavy chains of the nine antibodies obtained from the foregoing screening shown in Table 11 were used to construct 18 chimeric antigen receptors (CARs). The structure of a CAR comprises a signal peptide (leader sequence), an antigen-binding region, a linker region, a transmembrane domain, a costimulatory region, and a cytoplasmic signaling domain (e.g., a cytoplasmic signaling domain of CD3zeta), and the hinge region is as follows:

[CD8 LS]-[VL-Linker-VH]-[hinge-CD8TM]-[4-1BB]-[CD3zeta] or

[CD8 LS]-[VH-Linker-VL]-[hinge-CD8TM]-[4-1BB]-[CD3zeta]

TABLE 11

Chimeric antigen receptors constructed by using the VL and VH of the antibodies

| Clones | Re-named | VL-Linker-VH | VH-Linker-VL |
|---|---|---|---|
| 6G10-1D7 | CP01 | BCMA-CP01 | BCMA-CP01R |
| 99B3G3 | CP02 | BCMA-CP02 | BCMA-CP02R |
| 105C10F1 | CP03 | BCMA-CP03 | BCMA-CP03R |
| 107A11F1B7 | CP04 | BCMA-CP04 | BCMA-CP04R |
| 107B11E1D7 | CP05 | BCMA-CP05 | BCMA-CP05R |
| 109C5F3C1 | CP06 | BCMA-CP06 | BCMA-CP06R |
| 143D6F4 | CP07 | BCMA-CP07 | BCMA-CP07R |
| 151A9A4 | CP08 | BCMA-CP08 | BCMA-CP08R |
| 152D8E8 | CP09 | BCMA-CP09 | BCMA-CP09R |

Based on the sequences of the CARs constructed above, expression vectors were constructed through full-length DNA synthesis and cloning. The selected expression vectors were pWPT lentiviral vectors, and the cloning sites were BamH I and Sal I sites. The specific sequence of each CAR is as follows:

```
(1) The leader sequence (signal peptide) was the leader sequence of CD8 antigen:
MALPVTALLLPLALLLHAARP (SEQ ID NO: 52)

(2) Single-chain variable region light chain (VL) sequence derived from
BCMA-CP01 antibody:
DIVMTQSQRFMSTSVGDRVSITCKASQSVGTAVAWYQQTPGQFPKLLIYSTSNR
YTGVPDRFTGSGSGTDFTLTISNMQSEDLADYFCQQYSTYPLTFGSGTKLELK (SEQ
ID NO: 53)

(3) Single-chain variable region heavy chain (VH) sequence derived from
BCMA-CP01 antibody:
EVQLQQSGPELVKPGASMKISCKASDYSFTDYIMTWVKQSHGKNLEWIGLINPY
NGGTTYNQKFKDKATFTVDKSSTTAYMDLLSLTSEDSAVYYCARRGITTDYYTMDY
WGQGTSVTVSS (SEQ ID NO: 54)

(4) Single-chain variable region light chain (VL) sequence derived from
BCMA-CP02 antibody:
DIVMTQSPSSLAMSVGQKVTMSCKSSQSLLNSSIQKNYLAWYQQKPGQSPKLL
VYFASTRESGVPDRFIGSGSGTDFTLTISSVQAEDLADYFCQQHYSSPLTFGAGTKLE
LK (SEQ ID NO: 55)

(5) Single-chain variable region heavy chain (VH) sequence derived from
BCMA-CP02 antibody:
EVQLQQSGPVLVKPGASVKMSCKASGYTFTDLYMNWVKQSHGKSLEWIGVIN
PYNGGTSYNQKFKAKATLTVDKSSITAYMELNSLTSEDSAVYYCARGDSIYVMDYW
GQGTSVTVSS (SEQ ID NO: 56)

(6) Single-chain variable region light chain (VL) sequence derived from
BCMA-CP03 antibody:
DIVMTPSQKFMSTSVGDRVSVTCKASQNVGTNVAWYQQKPGQSPKALIYSASY
RYSGVPDRFTGSGSGTDFTLTISNVQSEDLAEYFCQHYNSYPFTFGSGTKLEIK (SEQ
ID NO: 57)

(7) Single-chain variable region heavy chain (VH) sequence derived from
BCMA-CP03 antibody:
EVKLLQSGGGLVQPGGSLKLSCAASGIDFSRYWMSWVRRAPGKGLEWIGEINP
DSSTINYAPSLKDKFIISRDAAKNTLYLQMSKVRSEDTALYYCATLYYDYDGDYAM
DYWGQGTSVTVSS (SEQ ID NO: 58)
```

-continued (8) Single-chain variable region light chain (VL) sequence derived from BCMA-CP04 antibody:
DIVMTQSPSSLAMSVGQKVTMSCKSSQSLLNSSIQKNYLAWYQQKPGQSPKLLI
YFASTRESGVPDRFIGSGSGTDFTLTISSVQAEDLADYFCQQHYSTPLTFGAGTKLEL
K (SEQ ID NO: 59)

(9) Single-chain variable region heavy chain (VH) sequence derived from BCMA-CP04 antibody:
EVQLQQSGPVLVKPGASVKMSCKASGYTFTDLYMNWLKQSHGKRLEWIGVIN
PYNGGTSYNQKFKGKATLTVDKSSSTAYMDLNSLTSEDSAVYYCARGDSIYVMDY
WGQGTSFTVSS (SEQ ID NO: 60)

(10) Single-chain variable region light chain (VL) sequence derived from BCMA-CP05 antibody:
ENVLTQSPAIMSASPGEKVTMTCSASSSVSYMHWYQQKSSTSPKLWIYDTSKLS
SGVPGRFSGSGSGKSYSLTISSMEAEDVATYYCFQGSGYPLFTFGSGTKLEIK (SEQ ID
NO: 61)

(11) Single-chain variable region heavy chain (VH) sequence derived from BCMA-CP05 antibody:
EVQLQQSGPVLVKPGASVKMSCKASGYTFTDLYMNWLKQSHGKRLEWIGVIN
PYNGGTSYNQKFKGKATLTVDKSSSTAYMDLNSLTSEDSAVYYCARGDSIYVMDY
WGQGTSFTVSS (SEQ ID NO: 62)

(12) Single-chain variable region light chain (VL) sequence derived from BCMA-CP06 antibody:
DIVMTQSPSSLALSVGQKVTMSCKSSQSLLDNSNQKHYLAWYQQKPGQSPKLL
VYFASTRESGVPDRFIGSGSGTDFTLTISSVQAEDLADYFCQQHYTAPLTFGAGTKLA
LK (SEQ ID NO: 63)

(13) Single-chain variable region heavy chain (VH) sequence derived from BCMA-CP06 antibody:
EVQLQQSGPVLVKPGASVKMSCKVSGYTFTDYYMNWVKQSHGKSLEWIGVIT
PYNGANRYNQKFKGKATLTVDKSSSTAYMEVSSLTSEDSAVYYCARGDSIYVMDY
WGQGTSVIVSS (SEQ ID NO: 64)

(14) Single-chain variable region light chain (VL) sequence derived from BCMA-CP07 antibody:
DIVMTQSPSSLAMSVGQKVTMSCKSSQSLLNSSIQKNYLAWYQQKPGQSPKLL
VYFASTRESGVPDRFIGSGSGTDFTLTISSVQAEDLADYFCQQHYSTPLTFGGGTKLE
LK (SEQ ID NO: 65)

(15) Single-chain variable region heavy chain (VH) sequence derived from BCMA-CP07 antibody:
EVQLQQSGPVLVKPGASVKMSCKASGYTFTDYSLNWVKQSHGKSLEWIGVVN
PYNGGTSHNQKFKGKATLTVDKSSSTAYMELNSLTSEDSAVYYCARPDSIYVMDYW
GQGTSVTVSS (SEQ ID NO: 66)

(16) Single-chain variable region light chain (VL) sequence derived from BCMA-CP08 antibody:
DIVMTQSPSSLAMSVGQKVTMSCKSSQSLLNSNIQKNYLAWYQQKPGQSPKLL
VYFASTRESGVPDRFIGSGSGTDFTLTISSVQAEDLADYFCQQHYSTPLTFGAGTKLE
LK (SEQ ID NO: 67)

(17) Single-chain variable region heavy chain (VH) sequence derived from BCMA-CP08 antibody:
EVQLQQSGPVLVKPGASVKMSCKASGYTFTDYSLNWVKQSHGKSLEWIGVVN
PYNGGTTYNQKFKGKATLTVDKSSSTAYMELNSLTSEDSAVYYCARPDSIYVMDSW
GQGTSVTVSS (SEQ ID NO: 68)

(18) Single-chain variable region light chain (VL) sequence derived from BCMA-CP09 antibody:
DIKMTQSPSSMYVSLGERVTITCKASQDINRNLSWFQQKPGKSPKTLIYRANRL
VDGVPLRFSGSGSGQDYSLTISSLEYEDMGIYYCLQYDEFPRTFGGGTKLEIK (SEQ
ID NO: 69)

(19) Single-chain variable region heavy chain (VH) sequence derived from BCMA-CP09 antibody:
QVTLKESGPGILQSSQTLSLTCSFSGFSLNTSGMGVNWIRQSSGKDLEWLAHIY
WNDDKRYNPSLKSRLTISKDTSRNQVFLRITSVDATDTATYFCCRSRLSFDYWGHGT
TLTVSS (SEQ ID NO: 70)

(20) Linker sequence between the heavy chains and light chains in the single-chain variable regions of BCMA-CP01/R, 02/R, 03/R, 04/R, 05/R, 06/R, 07/R, 08/R and 09/R is as follows:
GGGGSGGGGSGGGGS (SEQ ID NO: 71)

-continued

```
(21) Sequence of the hinge region (and linker region):
FVPVFLPAKPTTTPAPRPPTPAPTIASQPLSLRPEACRPAAGGAVHTRGLDFACD
(SEQ ID NO: 72)

(22) Sequence of a transmembrane domain, which is a CD8 (CD8TM)
transmembrane domain:
IYIWAPLAGTCGVLLLSLVITLYC (SEQ ID NO: 73)

(23) Sequence of an intracellular signaling motif from 4-1BB in the co-stimulatory
region:
KRGRKKLLYIFKQPFMRPVQTTQEEDGCSCRFPEEEEGGCEL (SEQ ID NO: 74)

(24) Sequence of an immunorecceptor tyrosine-based activation motif (ITAM) from
TCR complex in the cytoplasmic signaling region of CD3 zeta:
RVKFSRSADAPAYQQGQNQLYNELNLGRREEYDVLDKRRGRDPEMGGKPQR
RKNPQEGLYNELQKDKMAEAYSEIGMKGERRRGKGHDGLYQGLSTATKDTYDALH
MQALPPR (SEQ ID NO: 75)
```

Example 9 Preparation of CAR-T Cells (1) Healthy human venous blood was taken and isolation by the density gradient centrifugation was performed to obtain mononuclear cells (PBMCs).

(2) On Day 0, PBMCs were inoculated into cell culture flasks coated in advance with a CD3 monoclonal antibody (OKT3) at a final concentration of 5 μg/mL and Retronectin (purchased from TAKARA) at a final concentration of 10 μg/mL. The medium was CBMG-RC-09a cell medium containing 1% human albumin. Recombinant human interleukin 2 (CBMG-RC-05b) at a final concentration of 1000 U/mL was added. The medium was cultured in a $CO_2$ incubator at 37° C. and saturated humidity of 5%.

(3) On Day 1, the supernatant of the cultured PBMCs was slowly removed, fresh CBMG-RC-09a cell medium containing 1% human albumin was added. Recombinant human interleukin 2 (CBMG-RC-05b) was added to the medium to a final concentration of 1000 U/mL. The cells continued to be cultured in a $CO_2$ incubator at 37° C. and saturated humidity of 5%.

(4) On Day 3, fresh culture medium, concentrated and purified CAR-BCMAs lentiviruses, protamine sulfate (12 μg/ml), and CBMG-RC-05b at a final concentration of 1000 U/mL were added. After transduction in a 37° C., 5% $CO_2$ incubator for 12 hours, the culture solution was discarded, fresh medium was added, and culturing was continued in the 37° C., 5% $CO_2$ incubator.

(5) From Day 6 on, CART-BCMAs cells were used for desired activity tests.

Example 10 Detection of the Integration Rates of CAR Genes in T Cell Genomes and the Expression Levels of Proteins Encoded by the CAR Genes on the Membrane Surface Using $0.5\times10^6$ CART-BCMAs cells cultured for 7 days in Example 9, after staining of recombinant human BCMA protein Fc fragment, the expression levels of CAR-BCMA proteins on the T cell membrane surface were analyzed on a flow cytometer.

Figure 17:
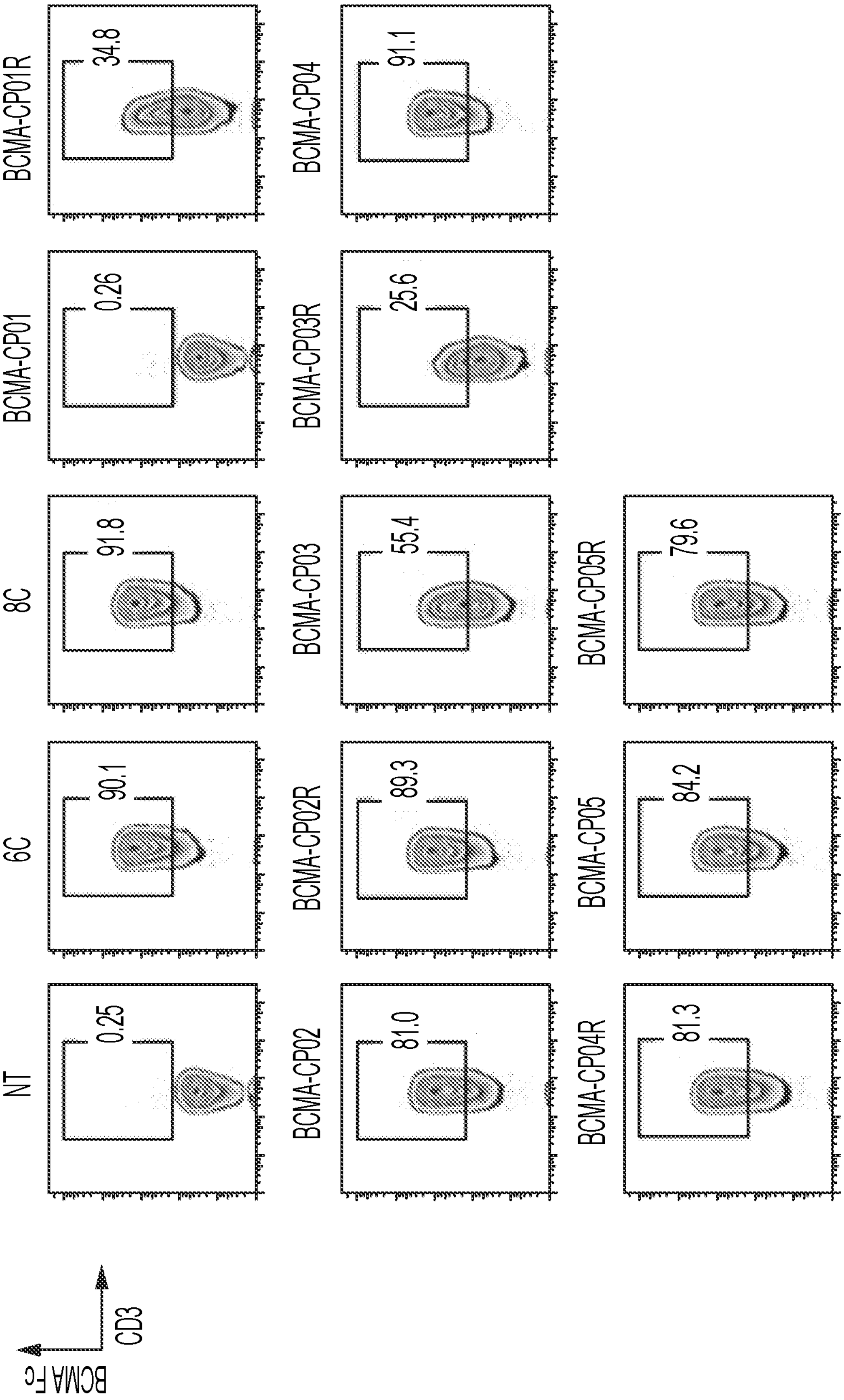
FIG. 17 shows the detection of the transfection efficiency of engineered T cells targeting a human BCMA chimeric antigen receptor. The recombinant human BCMA protein Fc fragment staining method identifies the expression level of a CAR gene-encoded protein on the cell membrane surface in the CART-BCMAs cells cultured for seven days.
Figure 17:
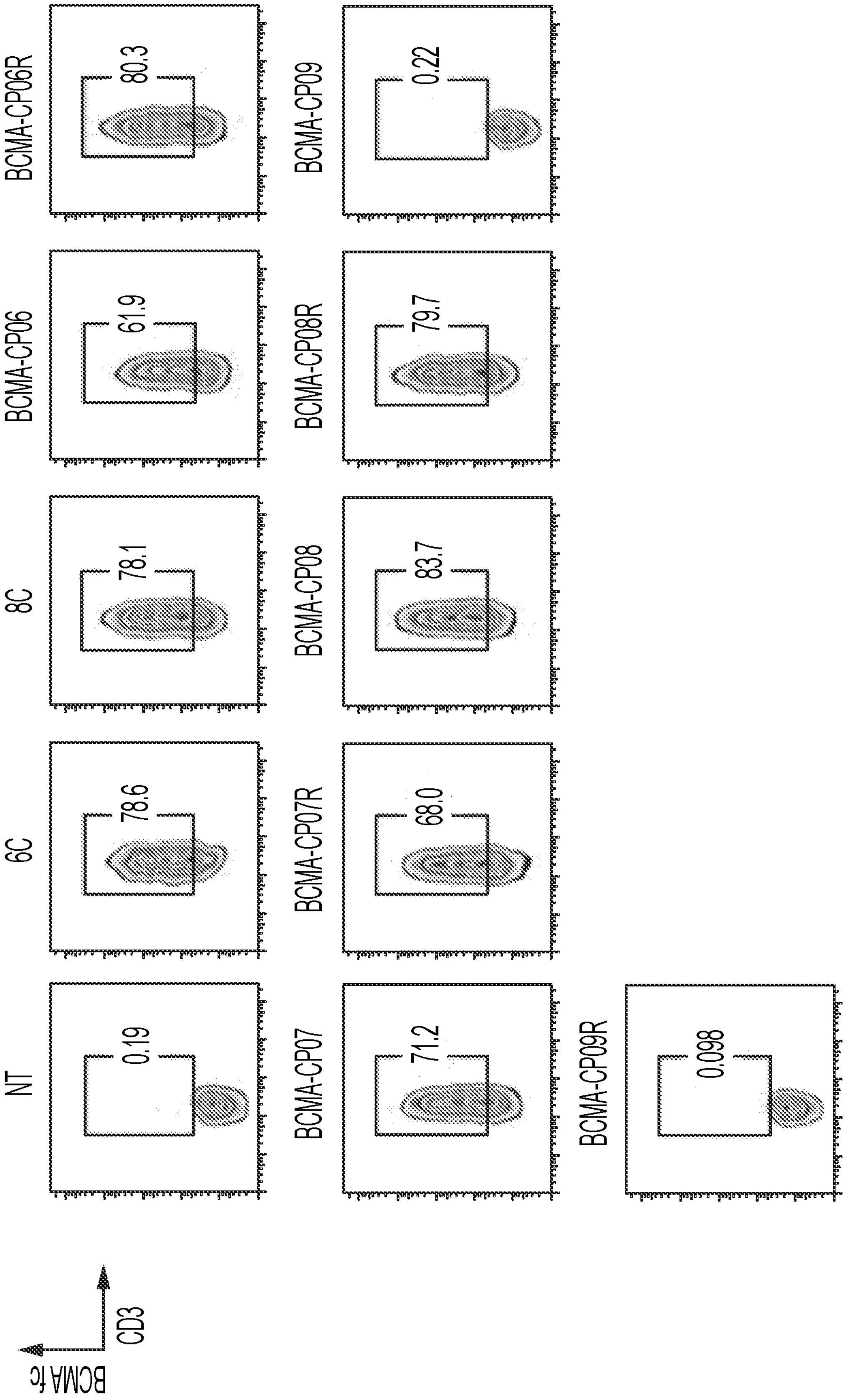

The results are shown in FIG. 17. Except that BCMA-CP01, CP09, and CP09R, the three CAR-T lentiviruses, did not have a transfection rate, the other 15 BCMA-CP CAR-T cells all had a relatively high T cell surface expression of CAR after seven days of transduction. 6C and 8C were positive controls.

Example 11 Detection of CART-BCMAs In Vitro Activation Ability

The CART-BCMAs cells cultured for seven days in Example 9 were used to detect proteins CD137 and IFNγ, the cell activation level indicators. $1\times10^5$ CART-BCMA cells cultured for seven days were cultured with human BCMA-positive A549-BCMA-1D6, MM.1S, RPMI822 6 tumor cell line, monkey BCMA-positive A549-BCMA-M, BCMA-negative A549 tumor cell line or addition-free tumor cells, respectively, in 200 μl of CBMG-RC-09a medium at a ratio of 1:1 for 18 h. Then the expression level of CD137 on the T cell membrane surface was detected by flow cytometry, and the secretion level of IFNγ in the culture supernatant was detected by ELISA.

Figure 18:
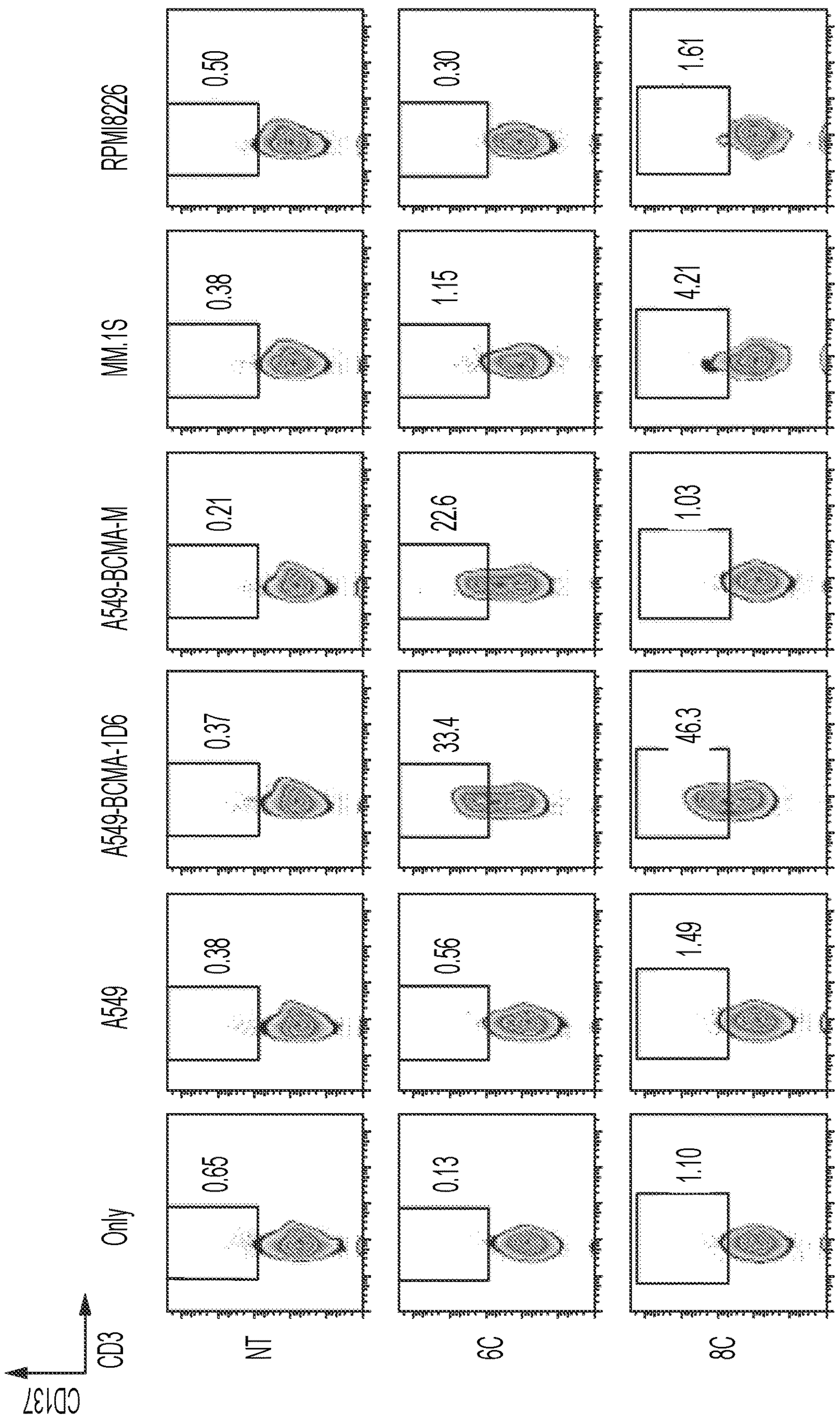
FIG. 18 shows the expression level of CD137 on the T cell membrane surface detected by flow cytometry.
Figure 18:
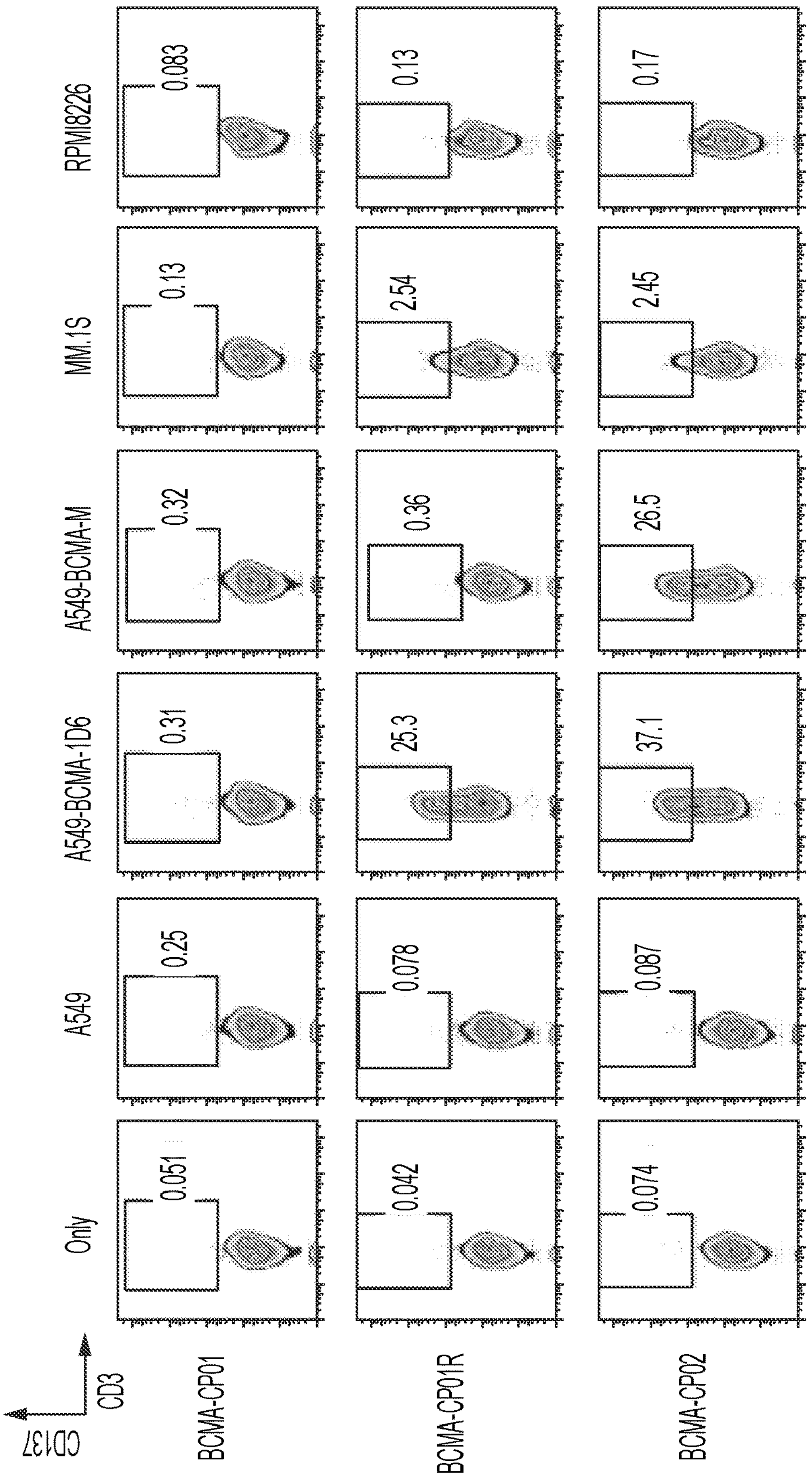
Figure 18:
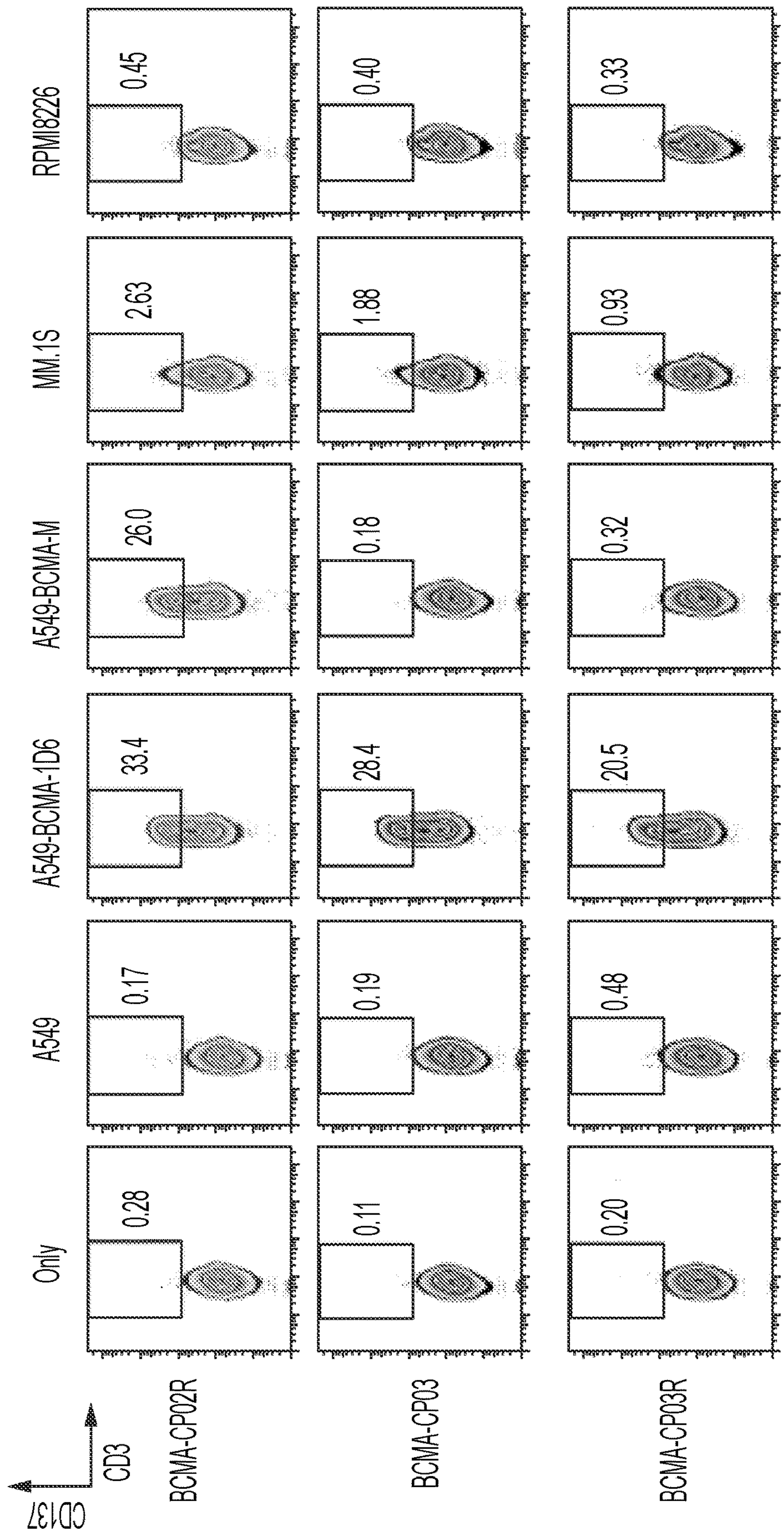
Figure 18:
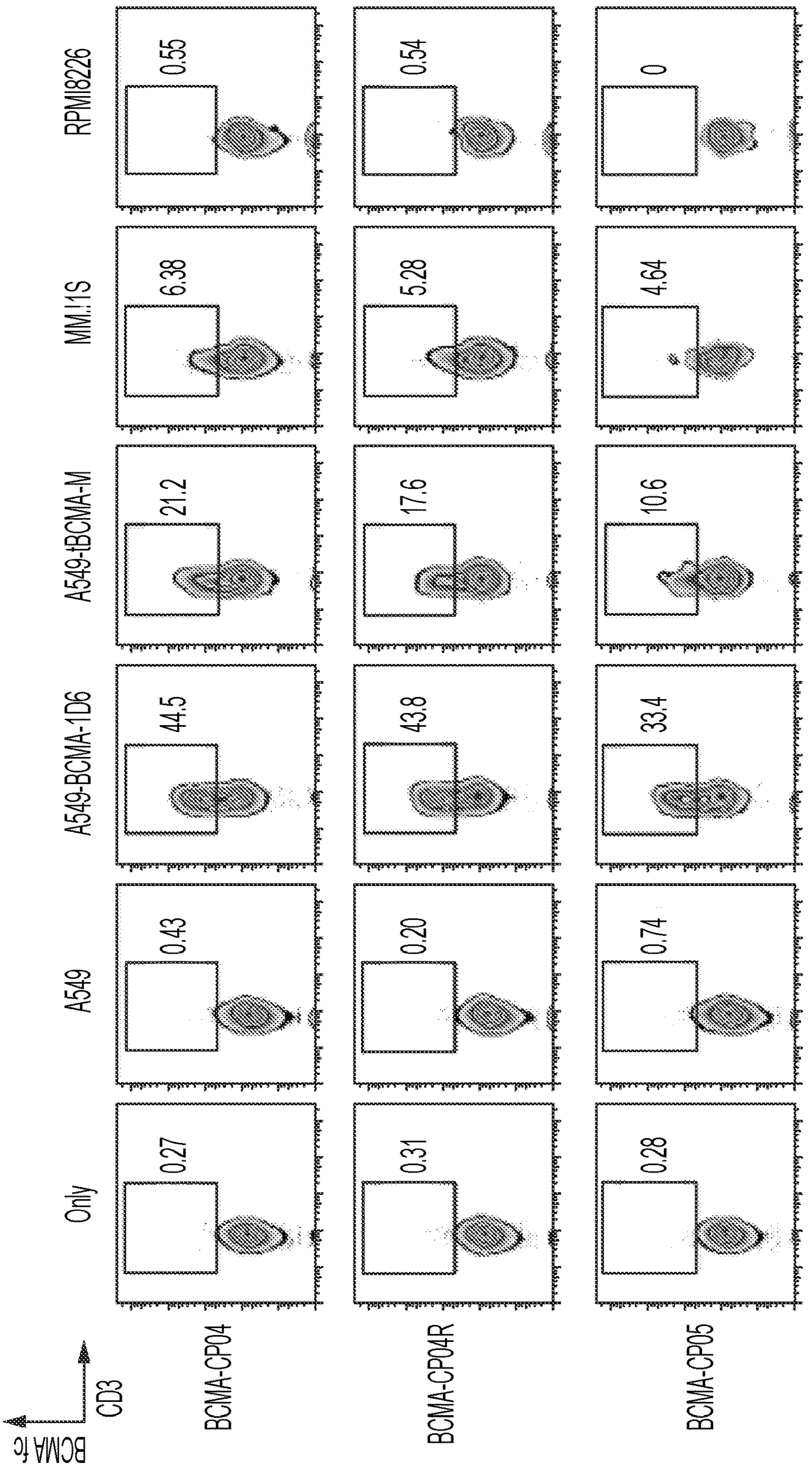
Figure 18:
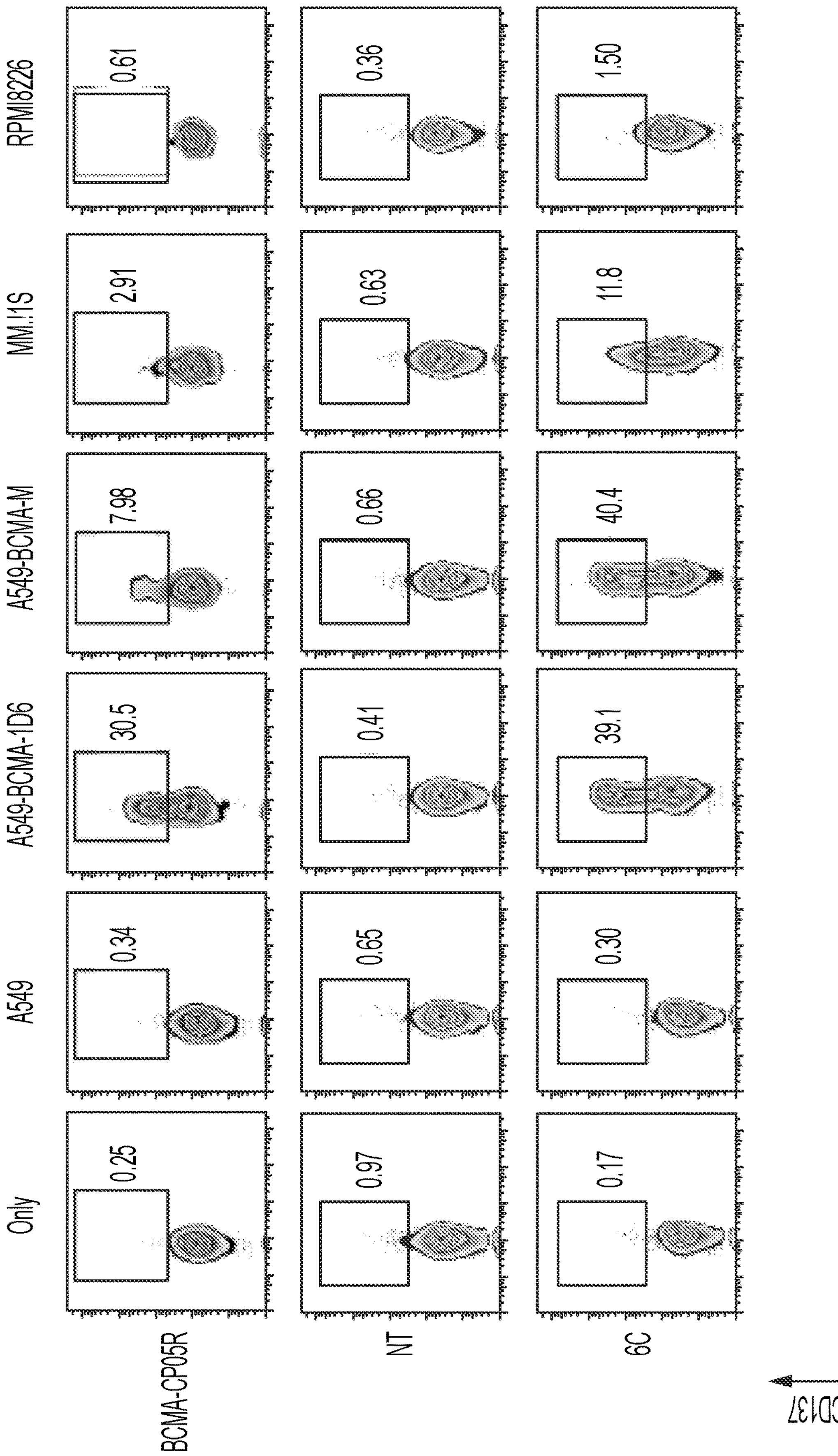
Figure 18:
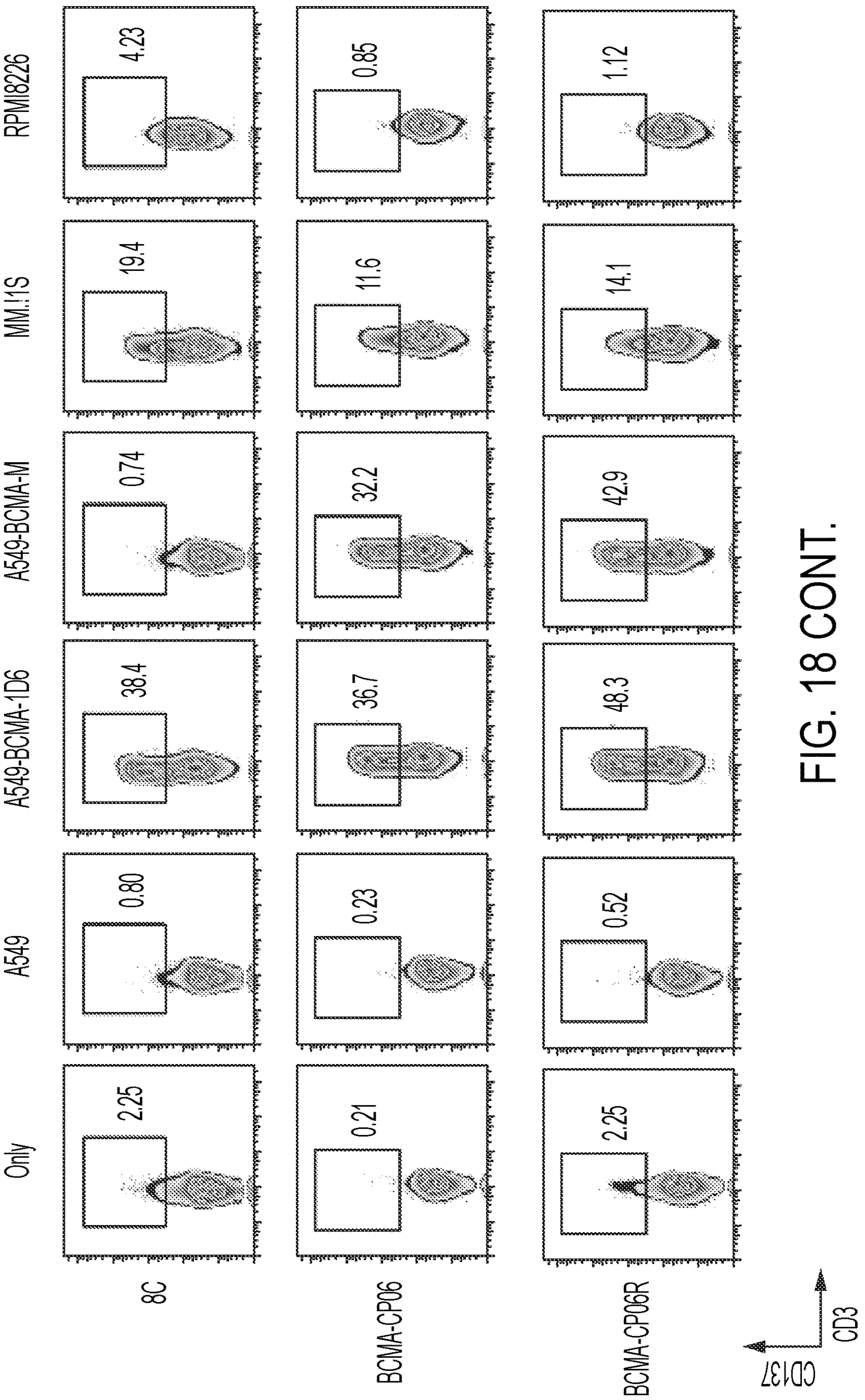
Figure 18:
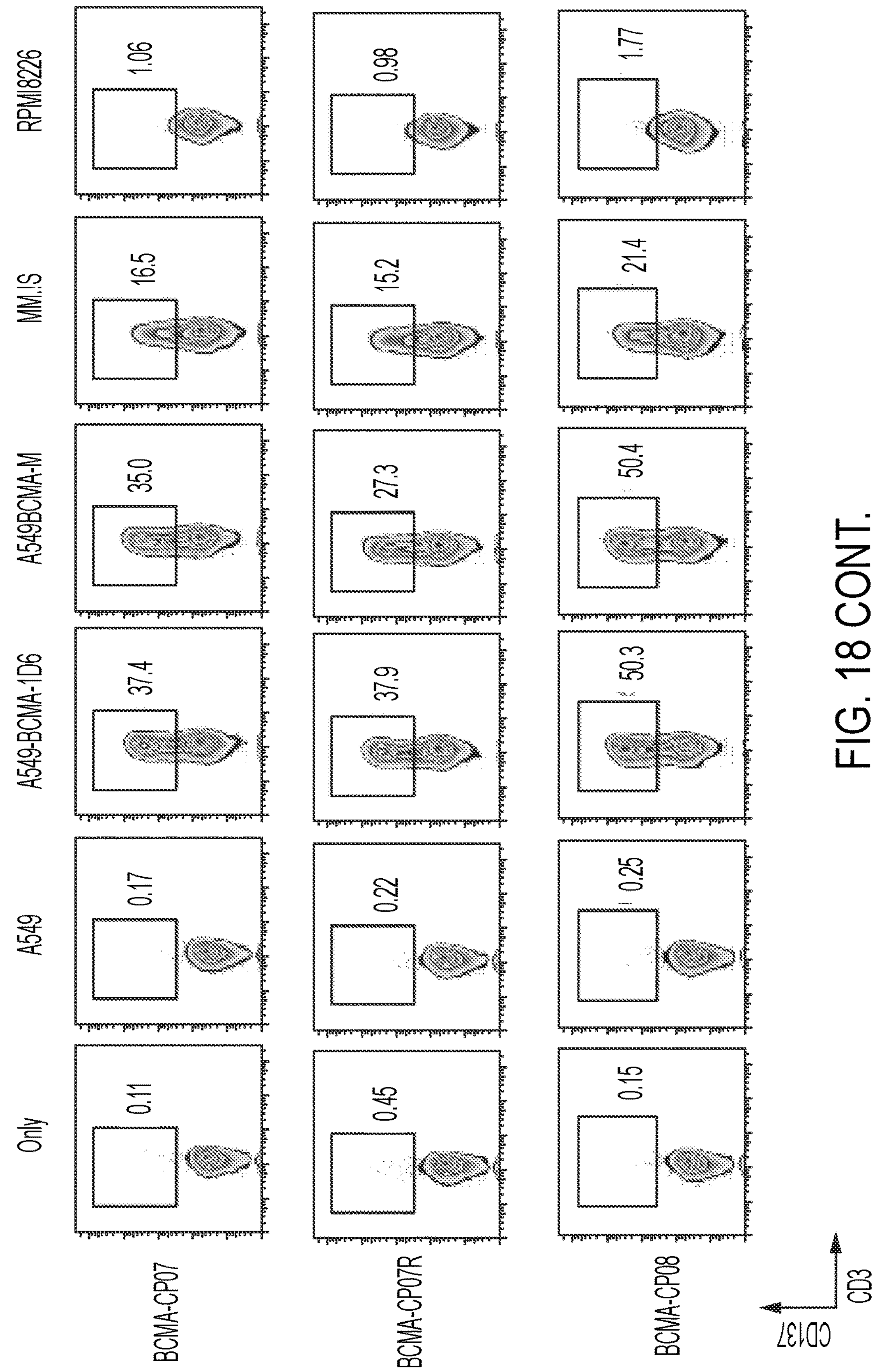
Figure 18:
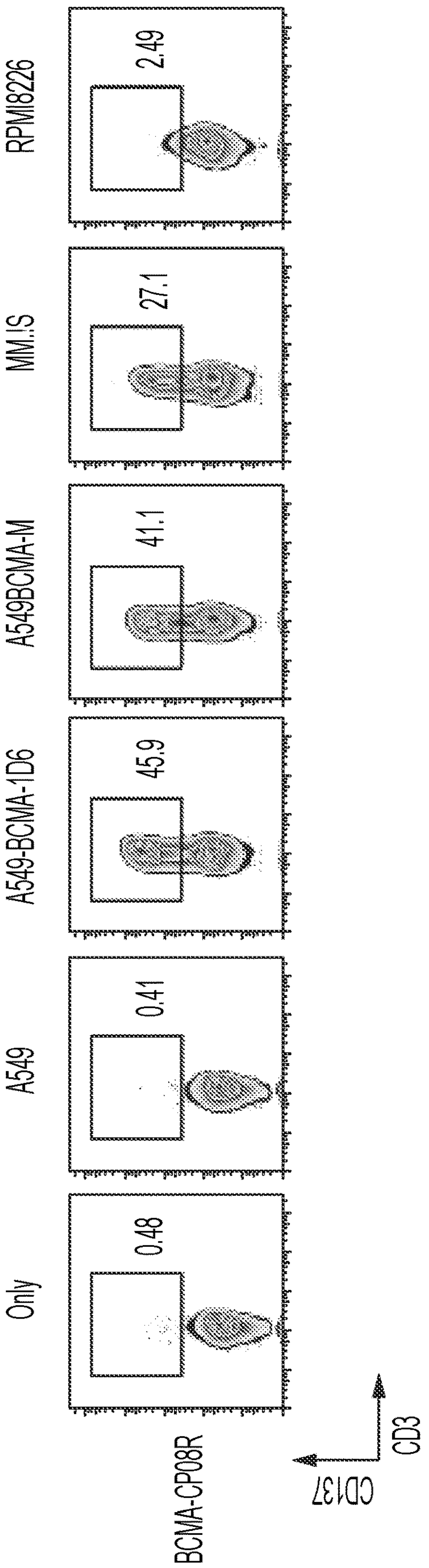
Figure 19:
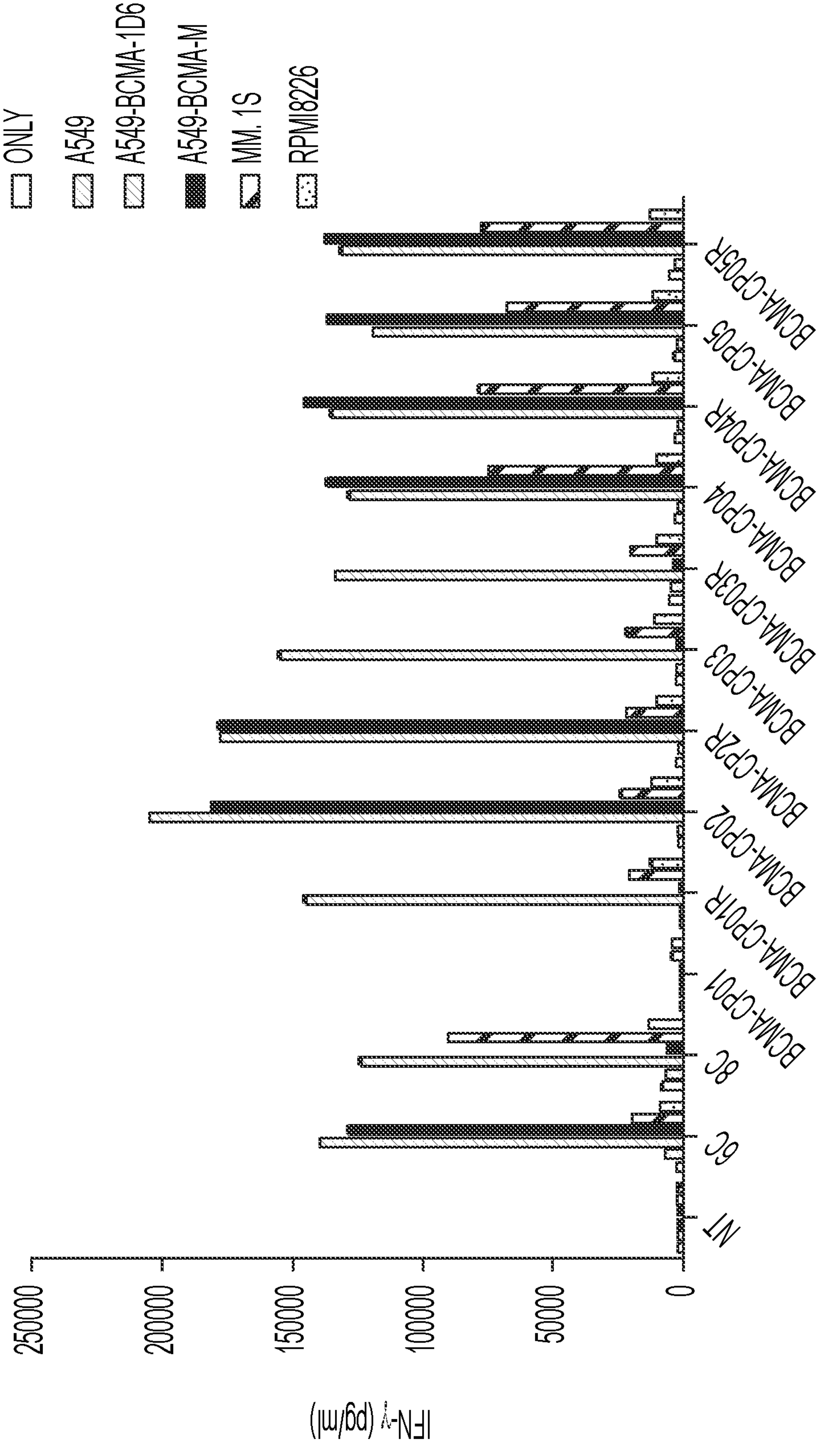
FIG. 19 shows the secretion level of IFNγ in the culture supernatant detected by the ELISA method.
Figure 19:
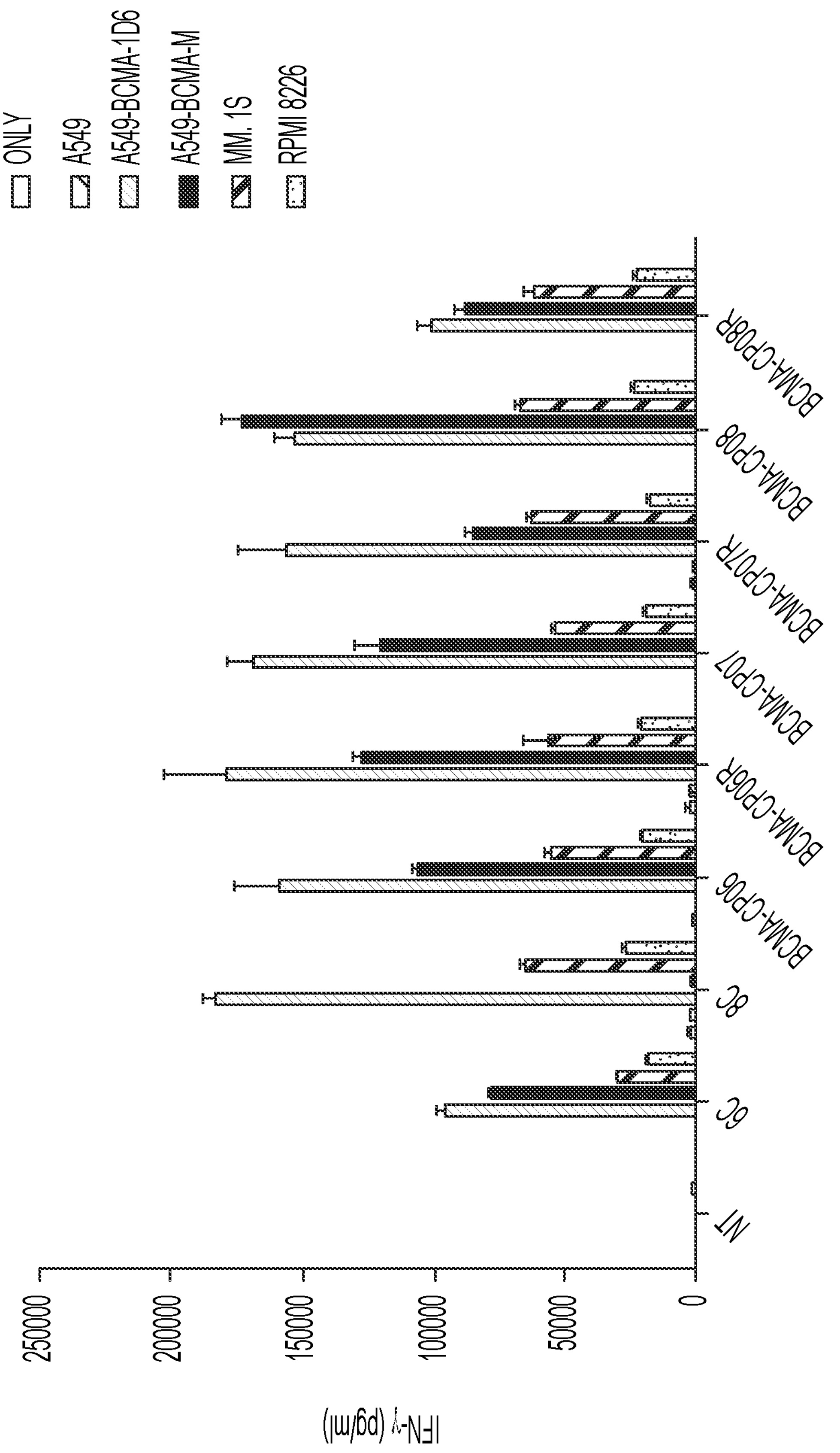

The results are as shown in FIGS. 18 and 19. BCMA-CP01R, CP03 and CP03R showed a high-specificity IFN-γ release ability and CD137 activation-specific up-regulation expression to A549-BCMA-1D6 cells only. BCMA-CP02/R, CP04/R and CP05/R showed a high-specificity IFN-γ release ability and CD137 activation-specific up-regulation expression to both A549-BCMA-1D6 and A549-BCMA-M cells.

Example 12 Detection of Cytotoxicity of CART-BCMAs Cells Towards Target Cells RTCA (real-time cellular analysis) was performed to detect the cytotoxicity of the CART cells (BCMA-CP01/R-05/R) cultured for 14 days and the CART cells (BCMA-CP06/R-09/R) cultured for 12 days in Example 9 towards target cells. After they were co-cultured with BCMA-negative cells (A549), human BCMA-positive self-constructed cells A549-BCMA-1D6, or monkey BCMA-positive self-constructed cells A549-BCMA-M at the ratios shown in FIG. 4 in 200 μl of CBMG-RC-09a medium, respectively for 8 h, the cytotoxicities of the CART cells towards each target cell were analyzed.

Figure 20:
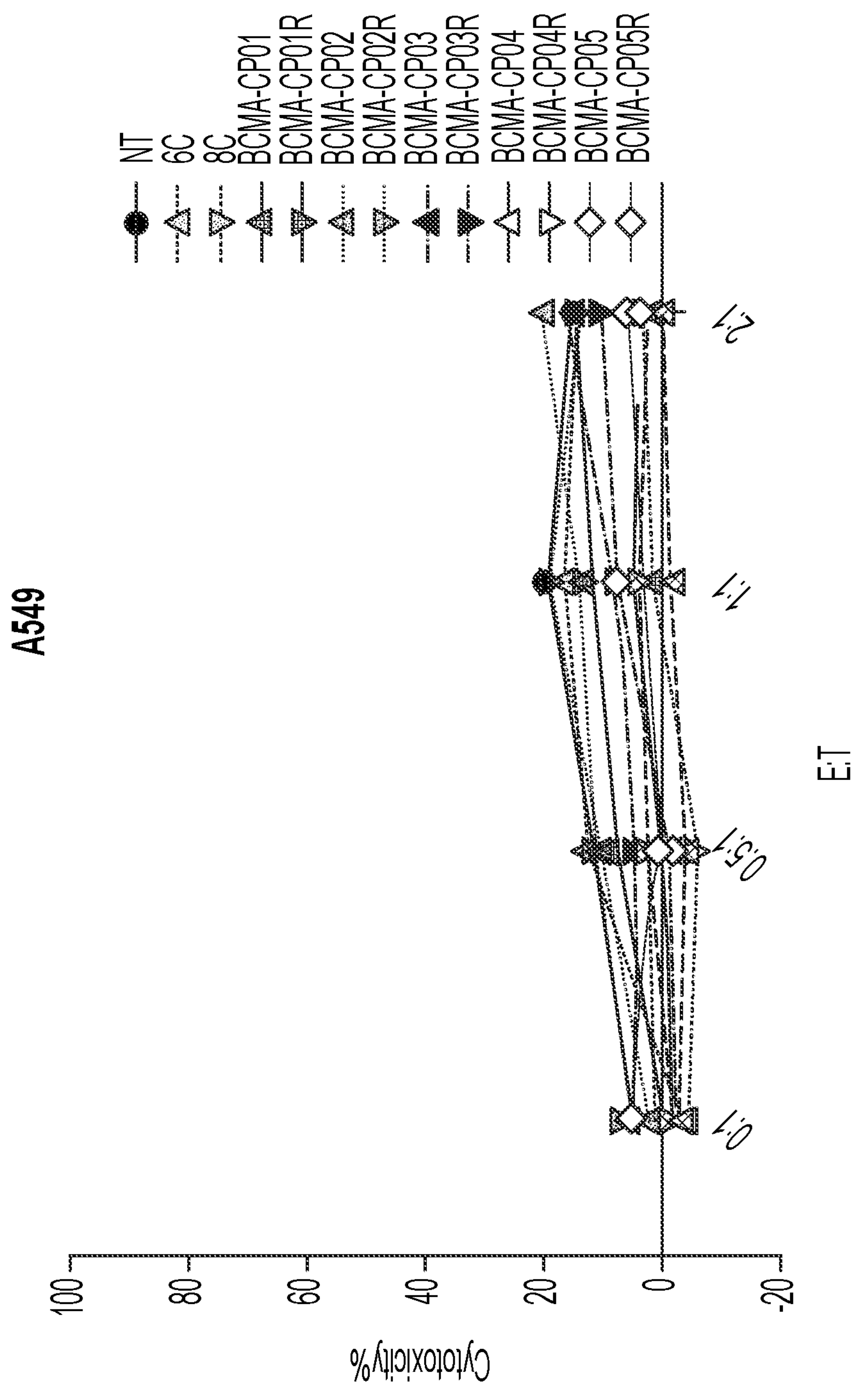
FIG. 20 shows the RTCA real-time label-free cell analysis to detect the killing effect of CART-BCMAs on target cells. The human BCMA-positive A549-BCMA-1D6 tumor cell line, the monkey BCMA-positive A549-BCMA-M tumor cell line, and the BCMA-negative A549 tumor cell line are co-cultured in 200 μl of CBMG-RC-09a medium, according to different effector target ratios for 8 h, and then the killing rate was calculated.
Figure 20:
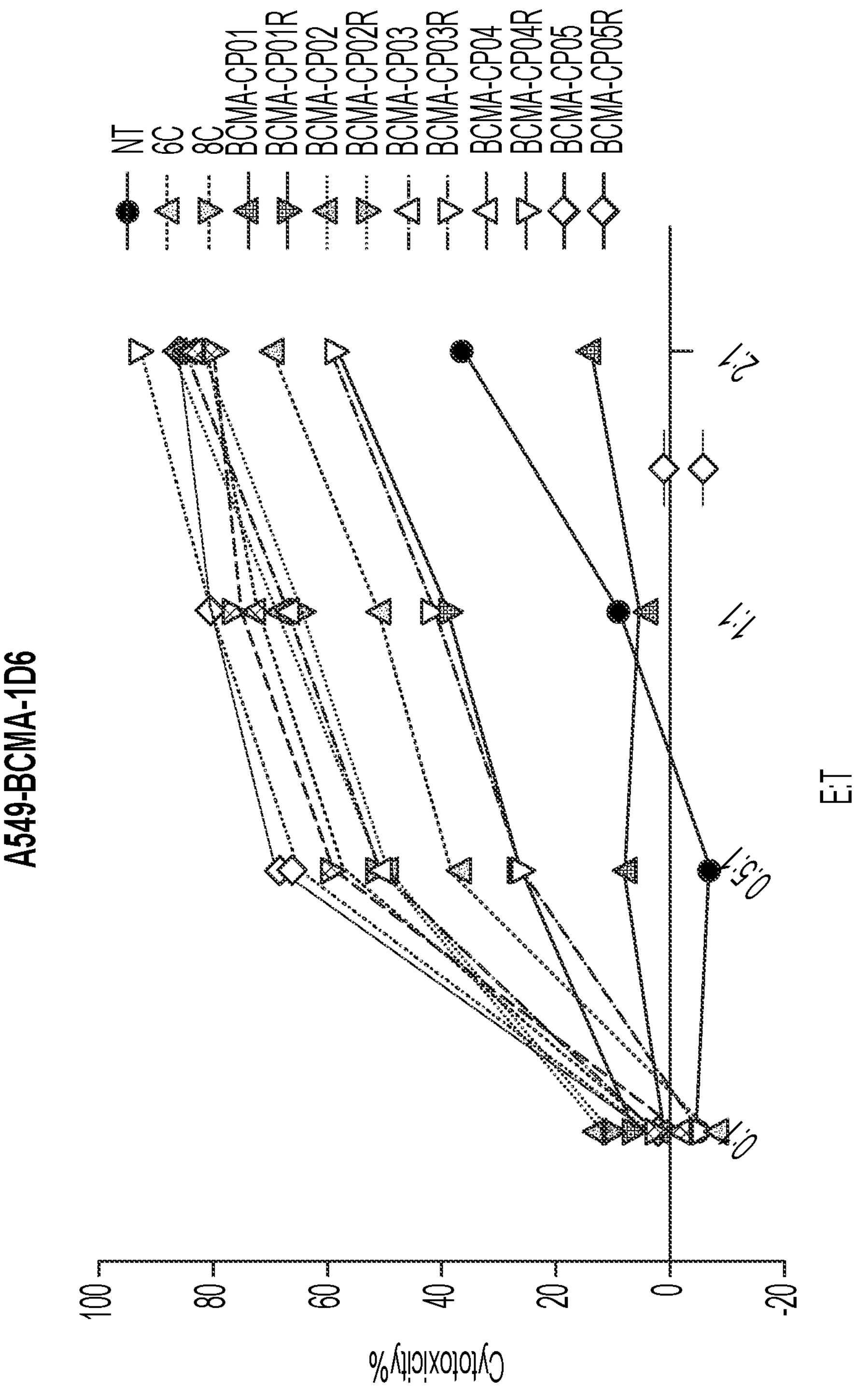
Figure 20:
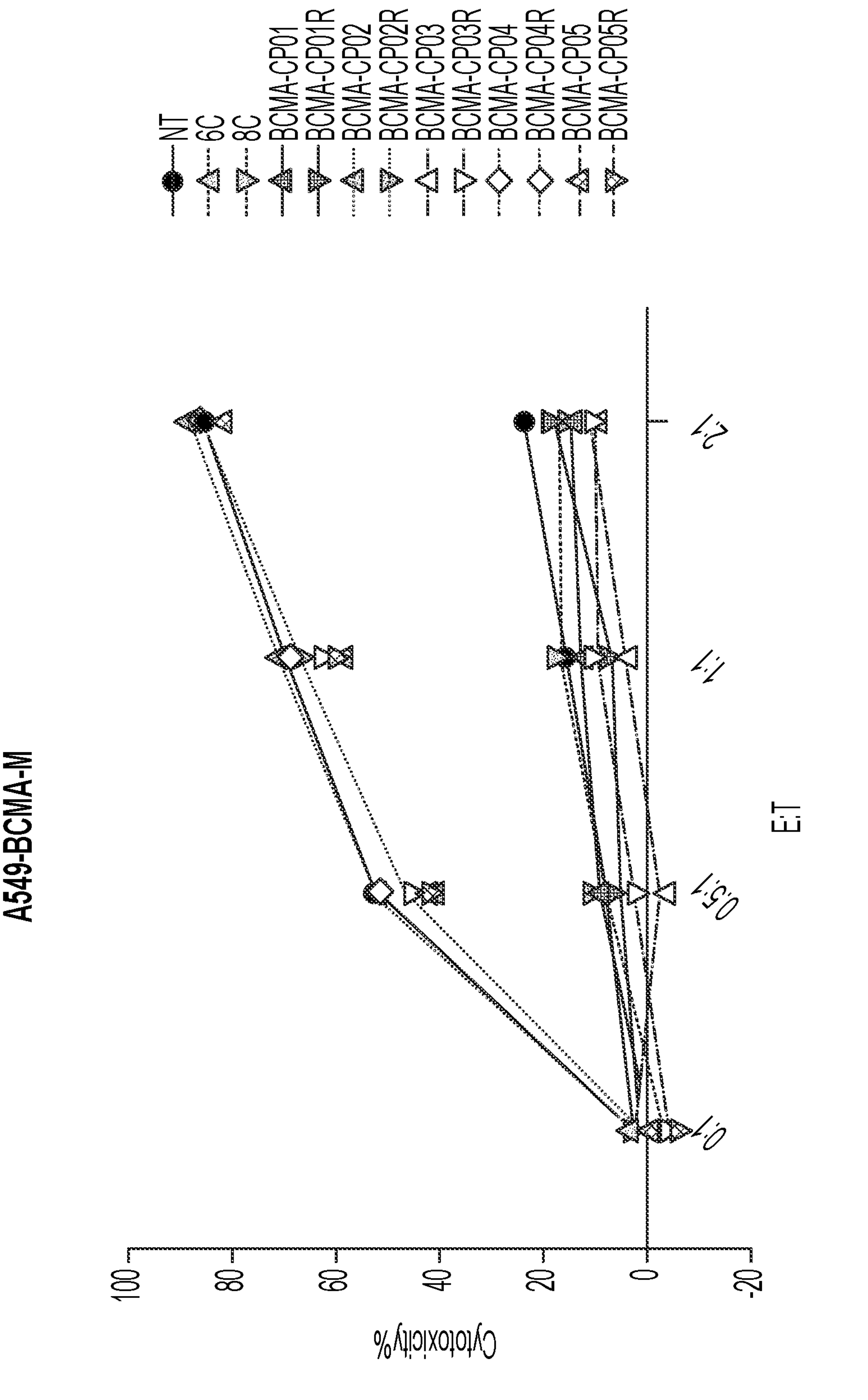
Figure 20:
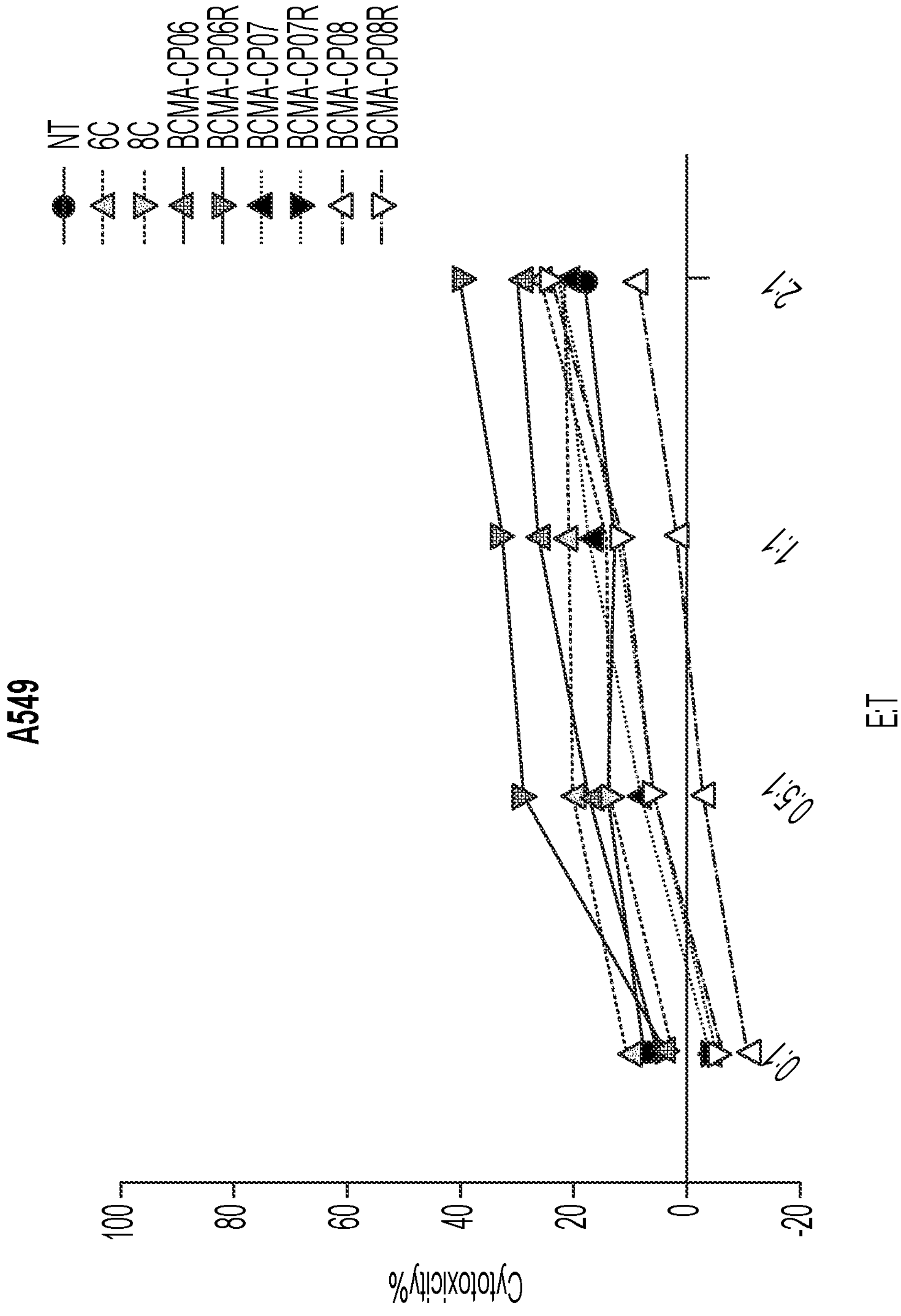
Figure 20:
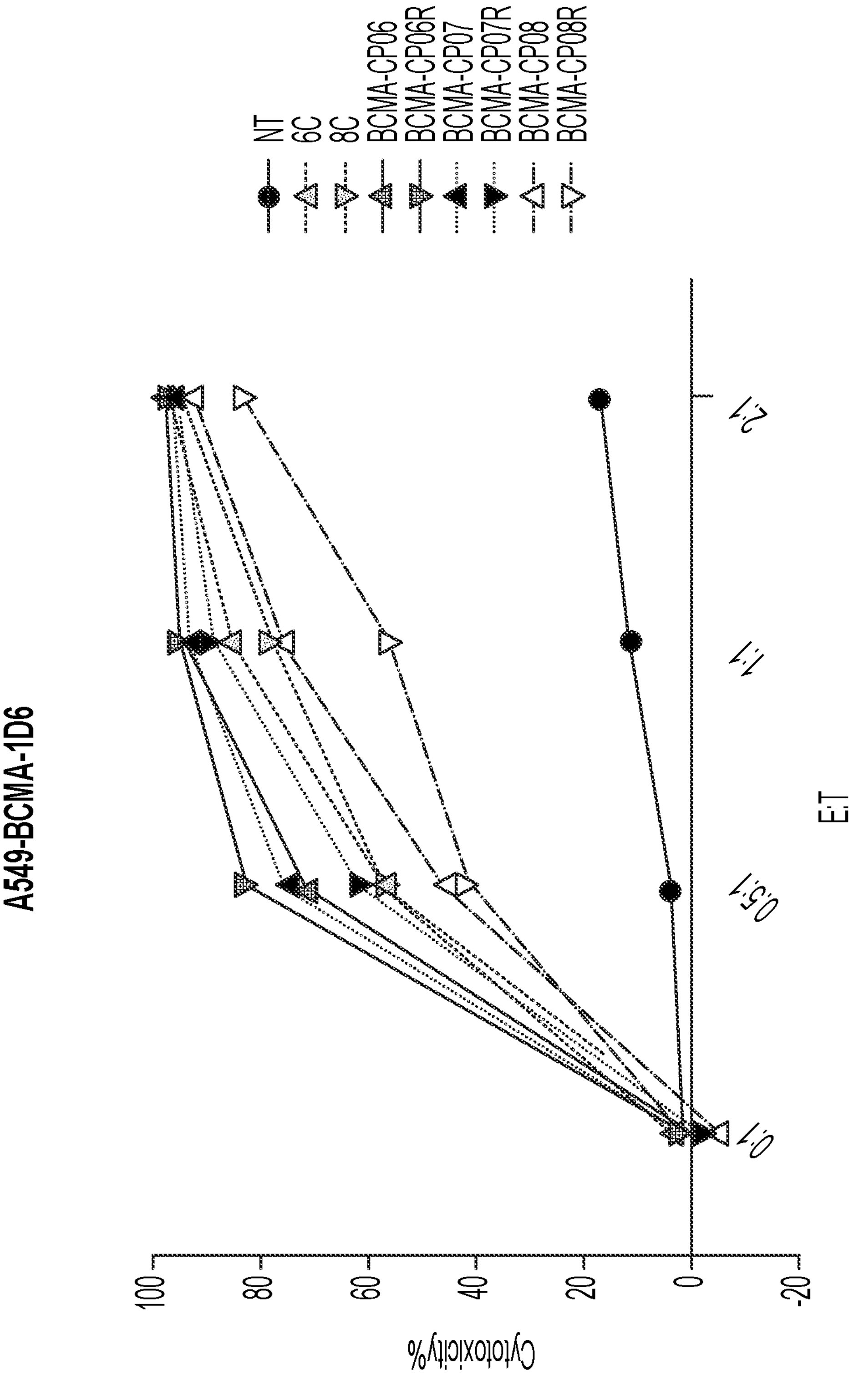
Figure 20:
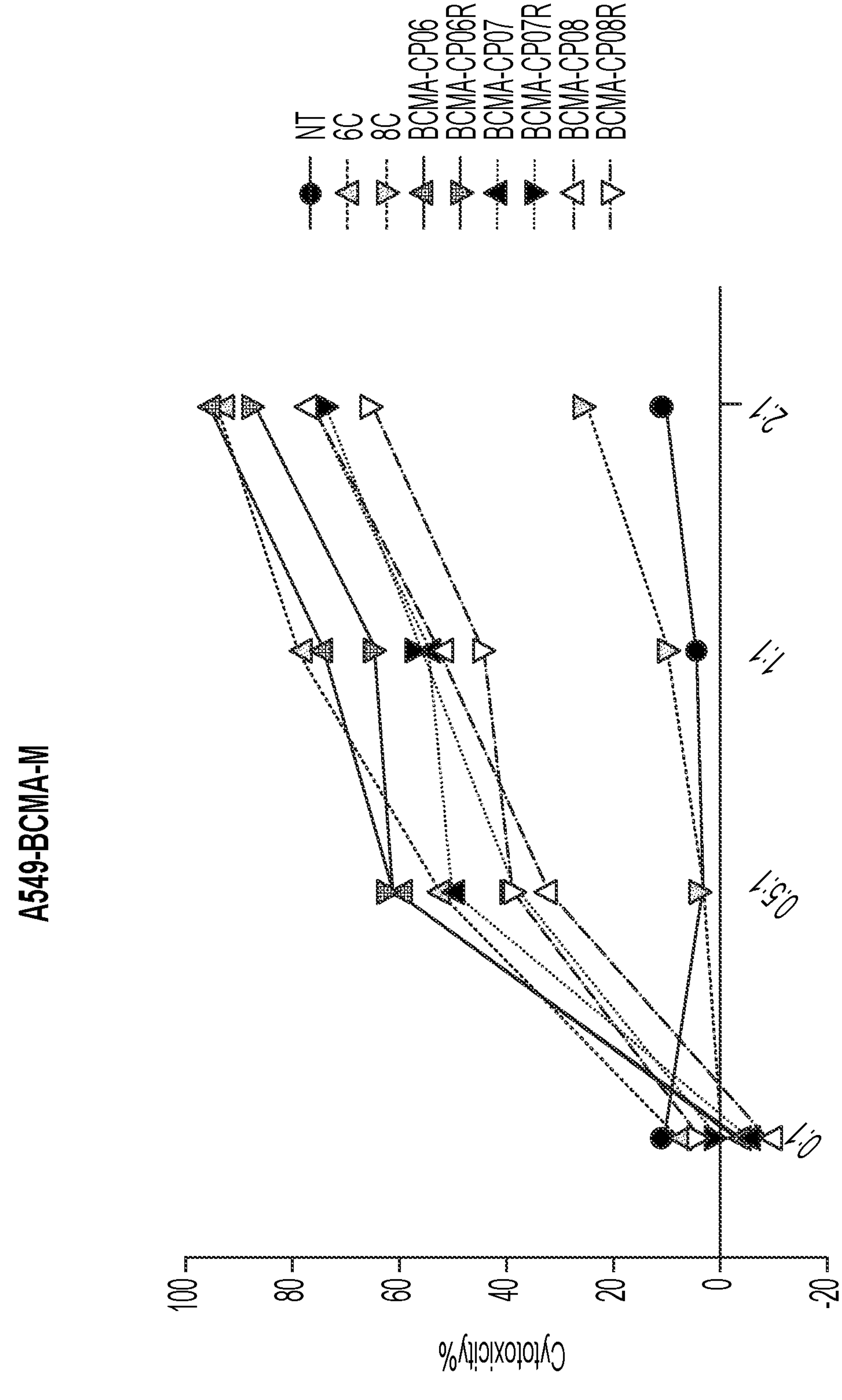

The results are shown in FIG. 20. BCMA-CP01R, CP03 and CP03R had strong cytotoxicity towards A549-BCMA-1D6. BCMA-CP02/R, 04/R and 05/R had strong cytotoxicity towards A549-BCMA-1D6 and A549-BCMA-M cells and did not have a significant killing effect on negative target cells A549. The untransduced control group (NT) also did not have a significant killing effect on the target cells.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

What is claimed is:

1. An anti-BCMA antibody, or an antigen-binding portion thereof, comprising a light chain variable region ($V_L$) and a heavy chain variable region ($V_H$), wherein the light chain variable region comprises three CDRs, CDR1, CDR2 and CDR3, having amino acid sequences comprising the amino acid sequences set forth in SEQ ID NOs: 118, 119 and 120, respectively; and wherein the heavy chain variable region comprises three complementarity determining regions (CDRs), CDR1, CDR2 and CDR3, having amino acid sequences comprising the amino acid sequences set forth in SEQ ID NOs: 121, 122 and 123, respectively.

2. An anti-BCMA antibody or antigen-binding portion thereof, comprising a light chain variable region ($V_L$) and a heavy chain variable region ($V_H$), wherein the $V_L$ and $V_H$ have amino acid sequences comprising the amino acid sequences set forth in SEQ ID NO: 67 and SEQ ID NO: 68, respectively.

3. The antibody or antigen-binding portion thereof of claim 1, wherein the antibody or antigen-binding portion thereof is selected from the group consisting of: (a) a whole immunoglobulin molecule; (b) an scFv; (c) a Fab fragment; (d) an F(ab')2; and (e) a disulfide linked Fv.

4. A composition comprising the antibody or antigen-binding portion thereof of claim 1, and a pharmaceutically acceptable carrier.

5. A chimeric antigen receptor (CAR), comprising an anti-BCMA antigen-binding region which comprises a light chain variable region ($V_L$) and a heavy chain variable region ($V_H$), the $V_L$ comprising three CDRs, CDR1, CDR2 and CDR3, having amino acid sequences comprising the amino acid sequences set forth in SEQ ID NOs: 118, 119 and 120, respectively; the $V_H$ comprising three complementarity determining regions (CDRs), CDR1, CDR2 and CDR3, having amino acid sequences comprising the amino acid sequences set forth in SEQ ID NOs: 121, 122 and 123, respectively.

6. A chimeric antigen receptor (CAR), comprising an anti-BCMA antigen-binding region which comprises a light chain variable region ($V_L$) and a heavy chain variable region ($V_H$), wherein the $V_L$ and $V_H$ have amino acid sequences comprising the amino acid sequences set forth in SEQ ID NO: 67 and SEQ ID NO: 68, respectively.

7. The CAR of claim 5, wherein the anti-BCMA antigen-binding region is a single-chain variable fragment (scFv) that specifically binds BCMA.

8. The CAR of claim 5, wherein the CAR further comprises one or more of the following:

(a) a signal peptide, (b) a hinge region, (c) a transmembrane domain, (d) a co-stimulatory region, and (e) a cytoplasmic signaling domain.

9. The CAR of claim 8, wherein the co-stimulatory region comprises a co-stimulatory region of 4-1BB (CD137), CD28, OX40, CD2, CD7, CD27, CD30, CD40, CD70, CD134, PD1, Dap10, CDS, ICAM-1, LFA-1 (CD11a/CD18), ICOS (CD278), NKG2D, GITR, TLR2, or combinations thereof.

10. The CAR of claim 8, wherein the cytoplasmic signaling domain comprises a cytoplasmic signaling domain of CD3ζ.

11. The CAR of claim 8, wherein the hinge region comprises a hinge region of Ig4, CD8, CD28, CD137, or combinations thereof.

12. The CAR of claim 8, wherein the transmembrane domain comprises a transmembrane domain of CD8, CD28, CD3ε, CD45, CD4, CD5, CD9, CD16, CD22, CD33, CD37, CD64, CD80, CD86, CD134, CD137, CD154, or combinations thereof.

13. An immune cell expressing the CAR of claim 5.

14. The immune cell of claim 13, wherein the immune cell is a T cell, a natural killer (NK) cell, a natural killer T cell, a lymphoid progenitor cell, a hematopoietic stem cell, a stem cell, a macrophage, or a dendritic cell.

* * * * *

SEQUENCE LISTING

<160> NUMBER OF SEQ ID NOS: 129

<210> SEQ ID NO 1
<211> LENGTH: 363
<212> TYPE: DNA
<213> ORGANISM: Mus musculus

<400> SEQUENCE: 1
gaggtccagc tgcaacagtc tggacctgaa ctggtgaagc ctggagcttc aatgaagata 60
tcctgcaagg cttctgatta ctcattcact gactacatca tgacctgggt gaagcagagc 120
catggaaaga accttgagtg gattggactt attaatcctt acaatggtgg tactacctac 180
aaccagaagt tcaaggacaa ggccacattt actgtagaca agtcctccac cacagcctac 240
atggacctcc tcagtctgac atctgaggac tctgcagtct attactgtgc aagaaggggg 300
attacgacgg attactatac tatggactac tggggtcaag gaacctcagt caccgtctcc 360
tca 363

<210> SEQ ID NO 2
<211> LENGTH: 321
<212> TYPE: DNA
<213> ORGANISM: Mus musculus

<400> SEQUENCE: 2
gacattgtga tgacccagtc tcaaagattc atgtccacat cagtaggaga cagggtcagc 60
atcacctgca aggccagtca gagtgtgggt actgctgtag cctggtatca acagacacca 120
ggacaattcc ctaaacttct gatttactcg acatccaatc gatacactgg agtccctgat 180
cgcttcacag gcagtggatc tgggacagat ttcactctca ccatcagcaa tatgcagtct 240
gaagacctgg cagattattt ctgccaacaa tatagcacct atccgctcac gttcggttct 300
gggaccaagc tggagctgaa a 321

<210> SEQ ID NO 3
<211> LENGTH: 354
<212> TYPE: DNA
<213> ORGANISM: Mus musculus

<400> SEQUENCE: 3
gaggtccagc tgcaacagtc tggacctgtg ctggtgaagc ctggggcttc agtgaagatg 60
tcctgtaagg cttctggata cacattcact gacctctata tgaactgggt gaagcagagt 120
catggaaaga gccttgagtg gattggagtt attaatcctt acaacggtgg tacaagctac 180
aaccagaaat tcaaggccaa ggccacattg actgttgaca agtcctccat cacagcctac 240
atggagctca acagcctgac atctgaggac tctgcagtct attactgtgc aagaggtgat 300
agtatctatg tcatggacta ctggggtcaa ggaacctcag tcaccgtctc ctca 354

<210> SEQ ID NO 4

-continued

<211> LENGTH: 339
<212> TYPE: DNA
<213> ORGANISM: Mus musculus

<400> SEQUENCE: 4
gacattgtga tgacacagtc tccatcctcc ctggctatgt cagtaggaca gaaggtcact 60
atgagctgca agtccagtca gagcctttta aatagtagca ttcaaaagaa ctatttggcc 120
tggtaccagc agaaaccagg acagtctcct aaacttctgg tatactttgc atccactagg 180
gaatctgggg tccctgatcg cttcataggc agtggatctg ggacagattt cactcttacc 240
atcagcagtg tgcaggctga agacctggca gattacttct gtcagcaaca ttatagcagt 300
ccgctcacgt tcggtgctgg gaccaagctg gagctgaaa 339

<210> SEQ ID NO 5
<211> LENGTH: 354
<212> TYPE: DNA
<213> ORGANISM: Mus musculus

<400> SEQUENCE: 5
gaggtccagc tgcagcagtc tggacctgag ctggtgaagc ctggggcttc agtgaagata 60
tcctgcaagg cttctggtta ctcattcact ggctactata tgaactgggt gaagcaaagt 120
cctgaaaaga gccttgagtg gattggagag attaattcta gcactggtgg tactacgtac 180
aaccagaagt tcaaggccaa ggccacaatg actgtagaca aatcctccaa cacagcctac 240
atggagctca agagcctgac atctgaggac tctgcagtct attattgtcg gtactacggt 300
agtgactggc acttcgatgt ctggggcaca gggaccacgg tcaccgtctc ctca 354

<210> SEQ ID NO 6
<211> LENGTH: 318
<212> TYPE: DNA
<213> ORGANISM: Mus musculus

<400> SEQUENCE: 6
caaattgttc tcacccagtc tccagcactc atgtctgcat ctccagggga gaaggtcacc 60
atgacctgca gtgccagctc aagtgtaagt tacatgtact ggtaccagca gaagccaaga 120
tcctccccca aaccctggat ttatctcaca tccagcctgg cttctggagt ccctgctcgc 180
ttcagtggca gtgggtctgg gacctcttac tctctcacaa tcagcaccat ggaggctgaa 240
gatgctgcca cttattactg ccagcagtgg agtagtgacc cactcacgtt cggtgctggg 300
accaagctgg agctgaaa 318

<210> SEQ ID NO 7
<211> LENGTH: 366
<212> TYPE: DNA
<213> ORGANISM: Mus musculus

<400> SEQUENCE: 7
gaggtgaagc ttctccagtc tggaggtggc ctggtgcagc ctggaggatc cctgaaactc 60
tcctgtgcag cctcaggaat cgattttagt agatactgga tgagttgggt tcggcgggct 120
ccagggaaag gactagaatg gattggagaa attaatccag atagcagtac aataaactat 180
gcaccatctc taaaggataa attcatcatc tccagagacg ccgccaaaaa tacgctgtac 240
ctgcaaatga gcaaagtgag atctgaggac acagcccttt attactgtgc aaccctctac 300
tatgattacg acggcgacta tgctatggac tactggggtc aaggaacctc agtcaccgtc 360
tcctca 366

-continued

<210> SEQ ID NO 8
<211> LENGTH: 321
<212> TYPE: DNA
<213> ORGANISM: Mus musculus

<400> SEQUENCE: 8
gacattgtga tgaccccgtc tcaaaaattc atgtccacct cagtaggaga cagggtcagc 60
gtcacctgta aggccagtca gaatgtgggt actaatgtag cctggtatca acagaaacca 120
gggcaatctc ctaaagcact gatttactcg gcatcctacc ggtacagtgg agtccctgat 180
cgcttcacag gcagtggatc tgggacagat ttcactctca ccatcagcaa tgtgcagtct 240
gaagacttgg cagagtattt ctgtcagcat tataacagct atccattcac gttcggctcg 300
gggacaaagt tggaaataaa a 321

<210> SEQ ID NO 9
<211> LENGTH: 375
<212> TYPE: DNA
<213> ORGANISM: Mus musculus

<400> SEQUENCE: 9
gaggtccagc tgcaacagtc tggacctgtg ctggtgaagc ctggggcttc agtgaagatg 60
tcctgtaagg cttctggata cacattcact gactactata tgaactgggt gaagcagagc 120
catggaaaga gccttgagtg gattggagtt attaatcctt acaacggtgg tactgactac 180
aaccagaagt tcaagggcaa ggccacattg actgttgaca agtcctccag cacagcctac 240
atggagctca acagcctgac atctgaggac tctgcagtct attactgtgc aagaagaaga 300
gaatcctacg gtactagcta ccagggggct tactttgact cctggggcca aggcaccact 360
ctcacagtct cctca 375

<210> SEQ ID NO 10
<211> LENGTH: 354
<212> TYPE: DNA
<213> ORGANISM: Mus musculus

<400> SEQUENCE: 10
gaggtccagc tgcaacagtc tggacctgtg ctggtgaagc ctggggcttc agtgaagatg 60
tcctgtaagg cttctggata tacattcact gacctctata tgaactggtt gaagcagagc 120
catggaaagc gccttgagtg gattggagtt attaatcctt acaacggtgg tactagctac 180
aaccagaagt tcaagggcaa ggccacattg actgttgaca agtcctccag cacagcctac 240
atggacctca acagcctgac atctgaggac tctgcagtct attactgtgc aagaggtgat 300
agtatctatg ttatggacta ctggggtcaa ggaacctcat tcaccgtctc ctca 354

<210> SEQ ID NO 11
<211> LENGTH: 363
<212> TYPE: DNA
<213> ORGANISM: Mus musculus

<400> SEQUENCE: 11
caggtgcagc tgaagcagtc aggacctggc ctagtgcagc cctcacagag cctgtccatc 60
acctgcacag tctctggttt ctcattaact agttatggtg tacactgggt tcgccagtct 120
ccaggaaagg gtctggagtg gctgggagtg atatggaatg gtggaagtac agactataat 180
gcagctttca tatccagact gagcatcagc aaggacaatt ccaagagcca agttttcttt 240

-continued aaaatgaaca gtctgcaagc tgatgacaca gccatatatt actgtgccag aaggaactac 300
ggtagtacct attactttgg tatggactac tggggtcaag gaacctcagt caccgtctcc 360
tca 363

<210> SEQ ID NO 12
<211> LENGTH: 354
<212> TYPE: DNA
<213> ORGANISM: Mus musculus

<400> SEQUENCE: 12
caggtccaac tgcagcagcc tggggctgag cttgtgaagc ctggggcttc agtgaagctg 60
tcctgcaagg cttctggcta caccttcacc agccattgga tgcagtgggt aaaacagagg 120
cctggacagg gccttgagtg gatcggagag attgatcctt ctgataactc tgctgactat 180
aatcaaaagt tcaagggcag ggtcacattg actgtagaca cgtcctccag cacaacctac 240
atgcagctca gcagcctgac atctgaggac tctgcggtct attactgtgc aagagagatt 300
agtacggtag ggtttactta ctggggccaa gggactctgg tcactgtctc tgca 354

<210> SEQ ID NO 13
<211> LENGTH: 321
<212> TYPE: DNA
<213> ORGANISM: Mus musculus

<400> SEQUENCE: 13
gaaaatgttc tcacccagtc tccagcaatc atgtctgcat ctccagggga aaaggtcacc 60
atgacctgca gtgccagctc aagtgtaagt tacatgcact ggtaccagca gaagtcaagc 120
acctccccca aactctggat ttatgacaca tccaaactgt cttctggagt cccaggtcgc 180
ttcagtggca gtgggtctgg aaagtcttac tctctcacga tcagcagcat ggaggctgaa 240
gatgttgcca cttattactg ttttcagggg agtgggtacc cactattcac gttcggctcg 300
gggacaaagt tggaaataaa a 321

<210> SEQ ID NO 14
<211> LENGTH: 363
<212> TYPE: DNA
<213> ORGANISM: Mus musculus

<400> SEQUENCE: 14
caggtgcagc tgaagcagtc aggacctggc ctagtgcagc cctcacagag cctgtccatc 60
acctgcacag tctctggttt ctcattaact agttatggtg tacactgggt tcgccagtct 120
ccaggaaagg gtctggagtg gctgggagtg atatggaatg gtggaagtac agactataat 180
gcagctttca tatccagact gagcatcagc aaggacaatt ccaagagcca agttttcttt 240
aaaatgaaca gtctgcaagc tgatgacaca gccatatatt actgtgccag aaggaactac 300
ggtagtacct attactttgg tatggactac tggggtcaag gaacctcagt caccgtctcc 360
tca 363

<210> SEQ ID NO 15
<211> LENGTH: 357
<212> TYPE: DNA
<213> ORGANISM: Mus musculus

<400> SEQUENCE: 15
cagatccagt tggtacagtc tggacctgag ctgaagaagc ctggagagac agtcaagatc 60
tcctgcaagg cttctgggta taccttcaca acctatggaa tgagctgggt gaaacaggct 120

-continued

```
ccaggaaagg gtttaaagtg gatgggctgg ataaacacct actctggagt gccaacatat    180

ggtgatgact tcaagggacg gtttgccttc tctttggaaa cctctgccag cactgcctat    240

ttgcagatca acaacctcaa aaatgaggac acggctacat atttctgtgt aagatattac    300

tacggtagta ccccgtttgc ttactggggc caagggactc tggtcactgt ctctgca       357
```

<210> SEQ ID NO 16
<211> LENGTH: 360
<212> TYPE: DNA
<213> ORGANISM: Mus musculus

<400> SEQUENCE: 16

```
caggtccaac tgcagcagcc tggggctgag cttgtgaagc ctggggcttc agtgaggctg     60

tcctgcaagg cttctggcta caccttcacc agctactgga tgcactgggt gaagcagagg    120

cctggacgag gccttgagtg gattggaagg attgatccta atagtggtgg tactaagtac    180

aatgagaagt tcaagagcaa ggccacactg actgtagaca aaccctccag cacagcctac    240

atgcagctca gcagcctgac atctgaggac tctgcggtct attattgtgc aagaaatggg    300

gtagtagttt cgtactactt tgactactgg ggccaaggca ccactctcac agtctcctca    360
```

<210> SEQ ID NO 17
<211> LENGTH: 336
<212> TYPE: DNA
<213> ORGANISM: Mus musculus

<400> SEQUENCE: 17

```
gatgtacagc ttcaggagtc aggacctggc ctcgtgaaac cttctcagtc tctgtctctc     60

acctgctctg tcactggcta ctccatcacc agtgattatt tctggagctg gatccggcag    120

tttccaggaa acaaaatgga atggatgggc tacattagtt acgatggtcg caataactac    180

aacccatctc tcaaaaatcg aatctccatc actcgtgaca catctaagaa ccagtttttc    240

ctgaagttga attctgtgac ttctgaggac acagccacgt attactgtgc aagacatgac    300

ttctggggcc aaggcaccac tctcacagtc tcctca                              336
```

<210> SEQ ID NO 18
<211> LENGTH: 321
<212> TYPE: DNA
<213> ORGANISM: Mus musculus

<400> SEQUENCE: 18

```
aatattgtgg tgacccagac tcccaaattc ctgcttgtat caccaggaga cagggttacc     60

ataacctgca aggccagtca gagtgtgagt aatgatgtgg cttggtacca acagaagcca    120

gggcagtctc ctaaactgct gatatactat gcatccaatc gctatactgg agtccctgat    180

cgcttcactg gcagtggata tgggacggat ttcactttca ccatcagcac tgtgcaggct    240

gaagacctgg cagtttattt ctgtcagcag gattatagct ctccgctcac gttcggtgct    300

gggaccaagc tggagctgaa a                                              321
```

<210> SEQ ID NO 19
<211> LENGTH: 354
<212> TYPE: DNA
<213> ORGANISM: Mus musculus

<400> SEQUENCE: 19

```
gaggtccagc tgcaacagtc tggacctgtg ctggtgaagc ctggggcttc agtgaagatg     60
```

-continued

```
tcctgtaagg cttctggata tacattcact gacctctata tgaactggtt gaagcagagc    120

catggaaagc gccttgagtg gattggagtt attaatcctt acaacggtgg tactagctac    180

aaccagaagt tcaagggcaa ggccacattg actgttgaca agtcctccag cacagcctac    240

atggacctca acagcctgac atctgaggac tctgcagtct attactgtgc aagaggtgat    300

agtatctatg ttatggacta ctggggtcaa ggaacctcat tcaccgtctc ctca          354
```

<210> SEQ ID NO 20
<211> LENGTH: 363
<212> TYPE: DNA
<213> ORGANISM: Mus musculus

<400> SEQUENCE: 20

```
caggtgcagc tgaagcagtc aggacctggc ctagtgcagc cctcacagag cctgtccatc     60

acctgcacag tctctggttt ctcattaact agttatggtg tacactgggt tcgccagtct    120

ccaggaaagg gtctggagtg gctgggagtg atatggaatg gtggaagtac agactataat    180

gcagctttca tatccagact gagcatcagc aaggacaatt ccaagagcca agttttcttt    240

aaaatgaaca gtctgcaagc tgatgacaca gccatatatt actgtgccag aaggaactac    300

ggtagtacct attactttgg tatggactac tggggtcaag gaacctcagt caccgtctcc    360

tca                                                                  363
```

<210> SEQ ID NO 21
<211> LENGTH: 360
<212> TYPE: DNA
<213> ORGANISM: Mus musculus

<400> SEQUENCE: 21

```
caggtccaac tgcagcagcc tggggctgag cttgtgaagc ctggggcttc agtgaggctg     60

tcctgcaagg cttctggcta caccttcacc agctactgga tgcactgggt gaagcagagg    120

cctggacgag gccttgagtg gattggaagg attgatccta atagtggtgg tactaagtac    180

aatgagaagt tcaagagcaa ggccacactg actgtagaca aaccctccag cacagcctac    240

atgcagctca gcagcctgac atctgaggac tctgcggtct attattgtgc aagaaatggg    300

gtagtagttt cgtactactt tgactactgg ggccaaggca ccactctcac agtctcctca    360
```

<210> SEQ ID NO 22
<211> LENGTH: 351
<212> TYPE: DNA
<213> ORGANISM: Mus musculus

<400> SEQUENCE: 22

```
gaggtgaagc ttctccagtc tggaggtggc ctggtgcagc ctggaggatc cctgaaactc     60

tcctgtgcag cctcaggaat cgattttagt agatactgga tgagttgggt tcggcgggct    120

ccagggaaag gactagaatg gattggagaa attaatccag atagcagtac aataaactat    180

gcaccatctc taaaggataa attcatcatc tccagagaca acgccaaaaa tacgctgtac    240

ctgcaaatga gcaaagtgag atctgaggac acagtccttt attactgtgc aagagataat    300

atggggtact tcgatgtctg gggcacaggg accacggtca ccgtctcctc a             351
```

<210> SEQ ID NO 23
<211> LENGTH: 339
<212> TYPE: DNA
<213> ORGANISM: Mus musculus

<400> SEQUENCE: 23

-continued

```
gacattgtga tgacacagtc tccatcctcc ctggctatgt cagtaggaca gaaggtcact     60

atgagctgca agtccagtca gagcctttta aatagtagca ttcaaaagaa ctatttggcc    120

tggtaccagc agaaaccagg acagtctcct aaacttctga tatactttgc atccactagg    180

gaatctgggg tccctgatcg cttcataggc agtggatctg ggacagattt cactcttacc    240

atcagcagtg tgcaggctga agacctggca gattacttct gtcagcaaca ttatagcact    300

ccgctcacgt tcggtgctgg gaccaagctg gagctgaaa                           339


<210> SEQ ID NO 24
<211> LENGTH: 375
<212> TYPE: DNA
<213> ORGANISM: Mus musculus

<400> SEQUENCE: 24

gaggtccagc tgcaacagtc tggacctgtg ctggtgaagc ctggggcttc agtgaagatg     60

tcctgtaagg cttctggata cacattcact gactactata tgaactgggt gaagcagagc    120

catggaaaga gccttgagtg gattggagtt attaatcctt acaacggtgg tactgactac    180

aaccagaagt tcaagggcaa ggccacattg actgttgaca agtcctccag cacagcctac    240

atggagctca acagcctgac atctgaggac tctgcagtct attactgtgc aagaagaaga    300

gaatcctacg gtactagcta ccagggggct tactttgact cctggggcca aggcaccact    360

ctcacagtct cctca                                                     375


<210> SEQ ID NO 25
<211> LENGTH: 321
<212> TYPE: DNA
<213> ORGANISM: Mus musculus

<400> SEQUENCE: 25

gatatccaga tgacacagac tacatcctcc ctgtctgcct ctctgggaga cagagtcacc     60

atcagttgca gggcaagtca ggacattagc aattatttaa actggtatca gcagaaacca    120

gatggaactg ttaaactcct gatctactac acatcaagat tacactcagg agtcccatca    180

aggttcagtg gcagtgggtc tggaacagat tattctctca gcattagcga cctggagcaa    240

gaagatattg ccacttactt ttgccaacag gttattacgc ttccgtggac gttcggtgga    300

ggcaccaagc tggaaatcaa a                                              321


<210> SEQ ID NO 26
<211> LENGTH: 354
<212> TYPE: DNA
<213> ORGANISM: Mus musculus

<400> SEQUENCE: 26

gaggtccagc tgcaacagtc tggacctgtg ctggtgaagc ctggggcttc agtgaagatg     60

tcctgtaagg tttctggata cacattcact gactactata tgaactgggt gaagcagagc    120

catggaaaga gccttgaatg gattggagtt attactcctt acaacggtgc taataggtac    180

aaccagaaat tcaagggcaa ggccacattg actgttgaca agtcctccag cacagcctac    240

atggaggtct ccagcctgac atcggaggac tctgcagtct attactgtgc aagaggtgat    300

agtatatatg ttatggacta ttggggtcaa ggaacctcag tcatcgtctc ctca          354


<210> SEQ ID NO 27
<211> LENGTH: 339
<212> TYPE: DNA
```

<213> ORGANISM: Mus musculus

<400> SEQUENCE: 27
gacattgtga tgacacagtc tccatcctcc ctggctctgt cagtaggaca gaaggtcact 60
atgagctgca agtccagtca gagcctttta gataattcca atcaaaagca ctatttggcc 120
tggtaccagc agaaaccagg acagtctcct aaacttctgg tatactttgc atccactagg 180
gaatctgggg tccctgatcg cttcataggc agtggctctg ggacagattt cactcttacc 240
atcagcagtg tgcaggctga agacctggca gattacttct gtcagcagca ttataccgct 300
ccgctcacgt tcggtgctgg gaccaagctg gcgctgaaa 339

<210> SEQ ID NO 28
<211> LENGTH: 354
<212> TYPE: DNA
<213> ORGANISM: Mus musculus

<400> SEQUENCE: 28
gaggtccagc tgcaacagtc tggacctgtg ctggtgaagc ctggggcttc agtgaagatg 60
tcctgtaagg cttctggata cacattcact gactactctt tgaactgggt gaagcagagc 120
catggaaaaa gccttgagtg gattggagtt gttaatcctt acaacggtgg tactagccac 180
aaccagaagt tcaagggcaa ggccacattg actgttgaca agtcctccag cacagcctac 240
atggagctca acagcctgac atctgaggac tctgcagtct attactgtgc aagacccgat 300
agtatatatg ttatggacta ctggggtcaa ggaacctcag tcaccgtctc ctca 354

<210> SEQ ID NO 29
<211> LENGTH: 339
<212> TYPE: DNA
<213> ORGANISM: Mus musculus

<400> SEQUENCE: 29
gacattgtga tgacacagtc tccatcctcc ctggctatgt cagtaggaca gaaggtcact 60
atgagctgca agtccagtca gagcctttta aatagtagca ttcaaaagaa ctatttggcc 120
tggtaccagc agaaaccagg acagtctcct aaacttctgg tatactttgc atccactagg 180
gaatctgggg tccctgatcg cttcataggc agtggatctg ggacagattt cactcttacc 240
atcagcagtg tgcaggctga agacctggca gattacttct gtcagcaaca ttatagcact 300
ccgctcacgt tcggtggtgg gaccaagctg gagctgaaa 339

<210> SEQ ID NO 30
<211> LENGTH: 354
<212> TYPE: DNA
<213> ORGANISM: Mus musculus

<400> SEQUENCE: 30
gaggtccaac tgcaacagtc tggacctgtg ctggtgaagc ctggggcttc agtgaagatg 60
tcctgtaagg cttctggata cacattcact gactactctc tgaactgggt gaagcagagc 120
catggaaaga gccttgagtg gattggagtt gttaatcctt acaacggtgg tactacctac 180
aaccagaagt tcaagggcaa ggccacattg actgttgaca agtcctccag cacagcctac 240
atggagctca acagcctgac atctgaggac tctgcagtct attactgtgc aagacccgat 300
agtatctatg ttatggactc ctggggtcaa ggaacctcag tcaccgtctc ctca 354

<210> SEQ ID NO 31
<211> LENGTH: 339

-continued

<212> TYPE: DNA
<213> ORGANISM: Mus musculus

<400> SEQUENCE: 31
gacattgtga tgacacagtc tccatcctcc ctggctatgt cagtaggaca gaaggtcact 60
atgagctgca agtccagtca gagcctttta aatagtaaca ttcaaaagaa ctatttggcc 120
tggtaccagc agaaaccagg acagtctcct aaacttctgg tatactttgc atccactagg 180
gaatctgggg tccctgatcg cttcataggc agtggatctg ggacagattt cactcttacc 240
atcagcagtg tgcaggctga agacctggca gattacttct gtcagcaaca ttatagcact 300
ccgctcacgt tcggtgctgg gaccaagctg gagctgaaa 339

<210> SEQ ID NO 32
<211> LENGTH: 351
<212> TYPE: DNA
<213> ORGANISM: Mus musculus

<400> SEQUENCE: 32
caggttactc tgaaagagtc tggccctggg attttgcagt cctcccagac cctcagtctg 60
acctgttctt tttctgggtt ttcgctgaac acctctggta tgggtgtgaa ctggattcgt 120
cagtcttcag gaaaggatct ggagtggctg gcacacattt actggaatga tgacaagcgc 180
tataatccat ccctgaagag ccggctcaca atttccaagg acacctccag aaatcaggtc 240
ttcctcagga tcaccagtgt ggacgctaca gacactgcca cttatttctg ttgtcgaagt 300
agactctcct ttgactactg gggccacggc accactctca cagtctcctc a 351

<210> SEQ ID NO 33
<211> LENGTH: 321
<212> TYPE: DNA
<213> ORGANISM: Mus musculus

<400> SEQUENCE: 33
gacatcaaga tgacccagtc tccatcttcc atgtatgtat ctctaggaga gagagtcact 60
atcacttgca aggcgagtca ggacattaat aggaatttaa gctggttcca gcagaaacca 120
gggaaatctc ctaagaccct gatctatcgt gcaaacagat tggtagatgg ggtcccatta 180
aggttcagtg gcagtggatc tgggcaagat tattctctca ccatcagcag cctggagtat 240
gaagatatgg gaatttatta ttgtctacag tatgatgagt ttcctcggac gttcggtgga 300
ggcaccaagt tggaaatcaa a 321

<210> SEQ ID NO 34
<211> LENGTH: 354
<212> TYPE: DNA
<213> ORGANISM: Mus musculus

<400> SEQUENCE: 34
gaggtccagc tgcaacagtc tggacctgtg ctggtgaagc ctggggcttc agtgaagatg 60
tcctgtaagg cttctggata tacattcact gacctctata tgaactggtt gaagcagagc 120
catggaaagc gccttgagtg gattggagtt attaatcctt acaacggtgg tactagctac 180
aaccagaagt tcaagggcaa ggccacattg actgttgaca agtcctccag cacagcctac 240
atggacctca acagcctgac atctgaggac tctgcagtct attactgtgc aagaggtgat 300
agtatctatg ttatggacta ctggggtcaa ggaacctcat tcaccgtctc ctca 354

<210> SEQ ID NO 35

<211> LENGTH: 321
<212> TYPE: DNA
<213> ORGANISM: Mus musculus

<400> SEQUENCE: 35
gaaaatgttc tcacccagtc tccagcaatc atgtctgcat ctccagggga aaaggtcacc 60
atgacctgca gtgccagctc aagtgtaagt tacatgcact ggtaccagca gaagtcaagc 120
acctccccca aactctggat ttatgacaca tccaaactgt cttctggagt cccaggtcgc 180
ttcagtggca gtgggtctgg aaagtcttac tctctcacga tcagcagcat ggaggctgaa 240
gatgttgcca cttattactg ttttcagggg agtgggtacc cactattcac gttcggctcg 300
gggacaaagt tggaaataaa a 321

<210> SEQ ID NO 36
<211> LENGTH: 339
<212> TYPE: DNA
<213> ORGANISM: Mus musculus

<400> SEQUENCE: 36
gacattgtga tgacacagtc tccatcctcc ctggctatgt cagtaggaca gaaggtcact 60
atgagctgca agtccagtca gagcctttta aatagtagca ttcaaaagaa ctatttggcc 120
tggtaccagc agaaaccagg acagtctcct aaacttctga tatactttgc atccactagg 180
gaatctgggg tccctgatcg cttcataggc agtggatctg ggacagattt cactcttacc 240
atcagcagtg tgcaggctga agacctggca gattacttct gtcagcaaca ttatagcact 300
ccgctcacgt tcggtgctgg gaccaagctg gagctgaaa 339

<210> SEQ ID NO 37
<211> LENGTH: 354
<212> TYPE: DNA
<213> ORGANISM: Mus musculus

<400> SEQUENCE: 37
gaggtccagc tgcaacagtc tggacctgtg ctggtgaagc ctggggcttc agtgaagatg 60
tcctgtaagg tttctggata cacattcact gactactata tgaactgggt gaagcagagc 120
catggaaaga gccttgaatg gattggaatt attactcctt acaacggtgc tactaactac 180
aaccagaagt tcaagggcaa ggccacattg actgttgaca agtcctccag cacagcctac 240
atggagctca acagcctgac atctgaagac tctgcagtct attactgtgc aagaggtgat 300
agtatctatg ttatggacta ttggggtcaa ggaacctcag tcaccgtctc ctca 354

<210> SEQ ID NO 38
<211> LENGTH: 339
<212> TYPE: DNA
<213> ORGANISM: Mus musculus

<400> SEQUENCE: 38
gacattgtga tgacacagtc tccatcctcc ctggctatgt cagtaggaca gaaggtcact 60
atgagctgca agtccagtca gagcctttta aatagtggca atcaaaagaa ctatttggcc 120
tggtaccagc agaaaccagg acagtctcct aaacttctgg tatactttgc atccactagg 180
gaatctgggg tccccgatcg cttcataggc agtgactctg ggacagattt cactcttacc 240
atcagcagtg tgcaggctga agacctggca gattacttct gtcagcaaca ttataccgct 300
ccgctcacgt tcggtgctgg gaccaagctg gagctgaaa 339

-continued

<210> SEQ ID NO 39
<211> LENGTH: 470
<212> TYPE: PRT
<213> ORGANISM: Artificial Sequence
<220> FEATURE:
<223> OTHER INFORMATION: Synthetic

<400> SEQUENCE: 39

```
Met Glu Phe Gly Leu Ser Trp Leu Phe Leu Val Ala Ile Leu Lys Gly
1               5                   10                  15

Val Gln Cys Glu Val Gln Leu Gln Gln Ser Gly Pro Glu Leu Val Lys
            20                  25                  30

Pro Gly Ala Ser Met Lys Ile Ser Cys Lys Ala Ser Asp Tyr Ser Phe
        35                  40                  45

Thr Asp Tyr Ile Met Thr Trp Val Lys Gln Ser His Gly Lys Asn Leu
    50                  55                  60

Glu Trp Ile Gly Leu Ile Asn Pro Tyr Asn Gly Gly Thr Thr Tyr Asn
65                  70                  75                  80

Gln Lys Phe Lys Asp Lys Ala Thr Phe Thr Val Asp Lys Ser Ser Thr
                85                  90                  95

Thr Ala Tyr Met Asp Leu Leu Ser Leu Thr Ser Glu Asp Ser Ala Val
            100                 105                 110

Tyr Tyr Cys Ala Arg Arg Gly Ile Thr Thr Asp Tyr Tyr Thr Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
```

```
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 40
<211> LENGTH: 236
<212> TYPE: PRT
<213> ORGANISM: Artificial Sequence
<220> FEATURE:
<223> OTHER INFORMATION: Synthetic

<400> SEQUENCE: 40

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Gln Arg Phe
            20                  25                  30

Met Ser Thr Ser Val Gly Asp Arg Val Ser Ile Thr Cys Lys Ala Ser
        35                  40                  45

Gln Ser Val Gly Thr Ala Val Ala Trp Tyr Gln Gln Thr Pro Gly Gln
    50                  55                  60

Phe Pro Lys Leu Leu Ile Tyr Ser Thr Ser Asn Arg Tyr Thr Gly Val
65                  70                  75                  80

Pro Asp Arg Phe Thr Gly Ser Gly Ser Gly Thr Asp Phe Thr Leu Thr
                85                  90                  95

Ile Ser Asn Met Gln Ser Glu Asp Leu Ala Asp Tyr Phe Cys Gln Gln
            100                 105                 110

Tyr Ser Thr Tyr Pro Leu Thr Phe Gly Ser Gly Thr Lys Leu Glu Leu
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 41
<211> LENGTH: 467
<212> TYPE: PRT
```

-continued

<213> ORGANISM: Artificial Sequence
<220> FEATURE:
<223> OTHER INFORMATION: Synthetic

<400> SEQUENCE: 41

```
Met Glu Phe Gly Leu Ser Trp Leu Phe Leu Val Ala Ile Leu Lys Gly
1               5                   10                  15

Val Gln Cys Glu Val Gln Leu Gln Gln Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Leu Tyr Met Asn Trp Val Lys Gln Ser His Gly Lys Ser Leu
    50                  55                  60

Glu Trp Ile Gly Val Ile Asn Pro Tyr Asn Gly Gly Thr Ser Tyr Asn
65                  70                  75                  80

Gln Lys Phe Lys Ala Lys Ala Thr Leu Thr Val Asp Lys Ser Ser Ile
                85                  90                  95

Thr Ala Tyr Met Glu Leu Asn Ser Leu Thr Ser Glu Asp Ser Ala Val
            100                 105                 110

Tyr Tyr Cys Ala Arg Gly Asp Ser Ile Tyr Val Met Asp Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
```

-continued 385 390 395 400

Trp Glu Ser Asn Gly Gln Pro Glu Asn Asn Tyr Lys Thr Thr Pro Pro
405 410 415

Val Leu Asp Ser Asp Gly Ser Phe Phe Leu Tyr Ser Lys Leu Thr Val
420 425 430

Asp Lys Ser Arg Trp Gln Gln Gly Asn Val Phe Ser Cys Ser Val Met
435 440 445

His Glu Ala Leu His Asn His Tyr Thr Gln Lys Ser Leu Ser Leu Ser
450 455 460

Pro Gly Lys
465

<210> SEQ ID NO 42
<211> LENGTH: 242
<212> TYPE: PRT
<213> ORGANISM: Artificial Sequence
<220> FEATURE:
<223> OTHER INFORMATION: Synthetic

<400> SEQUENCE: 42

Met Asp Met Arg Val Pro Ala Gln Leu Leu Gly Leu Leu Leu Leu Trp
1 5 10 15

Phe Pro Gly Ser Arg Cys Asp Ile Val Met Thr Gln Ser Pro Ser Ser
20 25 30

Leu Ala Met Ser Val Gly Gln Lys Val Thr Met Ser Cys Lys Ser Ser
35 40 45

Gln Ser Leu Leu Asn Ser Ser Ile Gln Lys Asn Tyr Leu Ala Trp Tyr
50 55 60

Gln Gln Lys Pro Gly Gln Ser Pro Lys Leu Leu Val Tyr Phe Ala Ser
65 70 75 80

Thr Arg Glu Ser Gly Val Pro Asp Arg Phe Ile Gly Ser Gly Ser Gly
85 90 95

Thr Asp Phe Thr Leu Thr Ile Ser Ser Val Gln Ala Glu Asp Leu Ala
100 105 110

Asp Tyr Phe Cys Gln Gln His Tyr Ser Ser Pro Leu Thr Phe Gly Ala
115 120 125

Gly Thr Lys Leu Glu Leu Lys Arg Thr Val Ala Ala Pro Ser Val Phe
130 135 140

Ile Phe Pro Pro Ser Asp Glu Gln Leu Lys Ser Gly Thr Ala Ser Val
145 150 155 160

Val Cys Leu Leu Asn Asn Phe Tyr Pro Arg Glu Ala Lys Val Gln Trp
165 170 175

Lys Val Asp Asn Ala Leu Gln Ser Gly Asn Ser Gln Glu Ser Val Thr
180 185 190

Glu Gln Asp Ser Lys Asp Ser Thr Tyr Ser Leu Ser Ser Thr Leu Thr
195 200 205

Leu Ser Lys Ala Asp Tyr Glu Lys His Lys Val Tyr Ala Cys Glu Val
210 215 220

Thr His Gln Gly Leu Ser Ser Pro Val Thr Lys Ser Phe Asn Arg Gly
225 230 235 240

Glu Cys

<210> SEQ ID NO 43
<211> LENGTH: 471
<212> TYPE: PRT
<213> ORGANISM: Artificial Sequence
<220> FEATURE:
<223> OTHER INFORMATION: Synthetic

<400> SEQUENCE: 43

```
Met Glu Phe Gly Leu Ser Trp Leu Phe Leu Val Ala Ile Leu Lys Gly
1               5                   10                  15

Val Gln Cys Glu Val Lys Leu Leu Gln Ser Gly Gly Gly Leu Val Gln
            20                  25                  30

Pro Gly Gly Ser Leu Lys Leu Ser Cys Ala Ala Ser Gly Ile Asp Phe
        35                  40                  45

Ser Arg Tyr Trp Met Ser Trp Val Arg Arg Ala Pro Gly Lys Gly Leu
    50                  55                  60

Glu Trp Ile Gly Glu Ile Asn Pro Asp Ser Ser Thr Ile Asn Tyr Ala
65                  70                  75                  80

Pro Ser Leu Lys Asp Lys Phe Ile Ile Ser Arg Asp Ala Ala Lys Asn
                85                  90                  95

Thr Leu Tyr Leu Gln Met Ser Lys Val Arg Ser Glu Asp Thr Ala Leu
            100                 105                 110

Tyr Tyr Cys Ala Thr Leu Tyr Tyr Asp Tyr Asp Gly Asp Tyr Ala Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Lys Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400
```

Ile Ala Val Glu Trp Glu Ser Asn Gly Gln Pro Glu Asn Asn Tyr Lys
405 410 415

Thr Thr Pro Pro Val Leu Asp Ser Asp Gly Ser Phe Phe Leu Tyr Ser
420 425 430

Lys Leu Thr Val Asp Lys Ser Arg Trp Gln Gln Gly Asn Val Phe Ser
435 440 445

Cys Ser Val Met His Glu Ala Leu His Asn His Tyr Thr Gln Lys Ser
450 455 460

Leu Ser Leu Ser Pro Gly Lys
465 470

<210> SEQ ID NO 44
<211> LENGTH: 236
<212> TYPE: PRT
<213> ORGANISM: Artificial Sequence
<220> FEATURE:
<223> OTHER INFORMATION: Synthetic

<400> SEQUENCE: 44

Met Asp Met Arg Val Pro Ala Gln Leu Leu Gly Leu Leu Leu Leu Trp
1 5 10 15

Phe Pro Gly Ser Arg Cys Asp Ile Val Met Thr Pro Ser Gln Lys Phe
20 25 30

Met Ser Thr Ser Val Gly Asp Arg Val Ser Val Thr Cys Lys Ala Ser
35 40 45

Gln Asn Val Gly Thr Asn Val Ala Trp Tyr Gln Gln Lys Pro Gly Gln
50 55 60

Ser Pro Lys Ala Leu Ile Tyr Ser Ala Ser Tyr Arg Tyr Ser Gly Val
65 70 75 80

Pro Asp Arg Phe Thr Gly Ser Gly Ser Gly Thr Asp Phe Thr Leu Thr
85 90 95

Ile Ser Asn Val Gln Ser Glu Asp Leu Ala Glu Tyr Phe Cys Gln His
100 105 110

Tyr Asn Ser Tyr Pro Phe Thr Phe Gly Ser Gly Thr Lys Leu Glu Ile
115 120 125

Lys Arg Thr Val Ala Ala Pro Ser Val Phe Ile Phe Pro Pro Ser Asp
130 135 140

Glu Gln Leu Lys Ser Gly Thr Ala Ser Val Val Cys Leu Leu Asn Asn
145 150 155 160

Phe Tyr Pro Arg Glu Ala Lys Val Gln Trp Lys Val Asp Asn Ala Leu
165 170 175

Gln Ser Gly Asn Ser Gln Glu Ser Val Thr Glu Gln Asp Ser Lys Asp
180 185 190

Ser Thr Tyr Ser Leu Ser Ser Thr Leu Thr Leu Ser Lys Ala Asp Tyr
195 200 205

Glu Lys His Lys Val Tyr Ala Cys Glu Val Thr His Gln Gly Leu Ser
210 215 220

Ser Pro Val Thr Lys Ser Phe Asn Arg Gly Glu Cys
225 230 235

<210> SEQ ID NO 45
<211> LENGTH: 474
<212> TYPE: PRT
<213> ORGANISM: Artificial Sequence
<220> FEATURE:
<223> OTHER INFORMATION: Synthetic -continued

<400> SEQUENCE: 45

```
Met Glu Phe Gly Leu Ser Trp Leu Phe Leu Val Ala Ile Leu Lys Gly
1               5                   10                  15

Val Gln Cys Glu Val Gln Leu Gln Gln Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Val Ile Asn Pro Tyr Asn Gly Gly Thr Asp Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Asn Ser Leu Thr Ser Glu Asp Ser Ala Val
            100                 105                 110

Tyr Tyr Cys Ala Arg Arg Arg Glu Ser Tyr Gly Thr Ser Tyr Gln Gly
        115                 120                 125

Ala Tyr Phe Asp Ser Trp Gly Gln Gly Thr Thr Leu Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415
```

```
Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470


<210> SEQ ID NO 46
<211> LENGTH: 236
<212> TYPE: PRT
<213> ORGANISM: Artificial Sequence
<220> FEATURE:
<223> OTHER INFORMATION: Synthetic

<400> SEQUENCE: 46

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Asn Tyr Leu Asn Trp Tyr Gln Gln Lys Pro Asp Gly
    50                  55                  60

Thr Val Lys Leu Leu Ile Tyr Tyr Thr Ser Arg Leu His Ser Gly Val
65                  70                  75                  80

Pro Ser Arg Phe Ser Gly Ser Gly Ser Gly Thr Asp Tyr Ser Leu Ser
                85                  90                  95

Ile Ser Asp Leu Glu Gln Glu Asp Ile Ala Thr Tyr Phe Cys Gln Gln
            100                 105                 110

Val Ile Thr Leu Pro Trp Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 47
<211> LENGTH: 467
<212> TYPE: PRT
<213> ORGANISM: Artificial Sequence
<220> FEATURE:
<223> OTHER INFORMATION: Synthetic

<400> SEQUENCE: 47

Met Glu Phe Gly Leu Ser Trp Leu Phe Leu Val Ala Ile Leu Lys Gly
```

-continued

```
1               5                   10                  15

Val Gln Cys Glu Val Gln Leu Gln Gln Ser Gly Pro Val Leu Val Lys
            20                  25                  30

Pro Gly Ala Ser Val Lys Met Ser Cys Lys Ala Ser Gly Tyr Thr Phe
        35                  40                  45

Thr Asp Leu Tyr Met Asn Trp Leu Lys Gln Ser His Gly Lys Arg Leu
    50                  55                  60

Glu Trp Ile Gly Val Ile Asn Pro Tyr Asn Gly Gly Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Asp Leu Asn Ser Leu Thr Ser Glu Asp Ser Ala Val
            100                 105                 110

Tyr Tyr Cys Ala Arg Gly Asp Ser Ile Tyr Val Met Asp Tyr Trp Gly
        115                 120                 125

Gln Gly Thr Ser Phe Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430
```

Asp Lys Ser Arg Trp Gln Gln Gly Asn Val Phe Ser Cys Ser Val Met
435 440 445

His Glu Ala Leu His Asn His Tyr Thr Gln Lys Ser Leu Ser Leu Ser
450 455 460

Pro Gly Lys
465

<210> SEQ ID NO 48
<211> LENGTH: 236
<212> TYPE: PRT
<213> ORGANISM: Artificial Sequence
<220> FEATURE:
<223> OTHER INFORMATION: Synthetic

<400> SEQUENCE: 48

Met Asp Met Arg Val Pro Ala Gln Leu Leu Gly Leu Leu Leu Leu Trp
1 5 10 15

Phe Pro Gly Ser Arg Cys Glu Asn Val Leu Thr Gln Ser Pro Ala Ile
20 25 30

Met Ser Ala Ser Pro Gly Glu Lys Val Thr Met Thr Cys Ser Ala Ser
35 40 45

Ser Ser Val Ser Tyr Met His Trp Tyr Gln Gln Lys Ser Ser Thr Ser
50 55 60

Pro Lys Leu Trp Ile Tyr Asp Thr Ser Lys Leu Ser Ser Gly Val Pro
65 70 75 80

Gly Arg Phe Ser Gly Ser Gly Ser Gly Lys Ser Tyr Ser Leu Thr Ile
85 90 95

Ser Ser Met Glu Ala Glu Asp Val Ala Thr Tyr Tyr Cys Phe Gln Gly
100 105 110

Ser Gly Tyr Pro Leu Phe Thr Phe Gly Ser Gly Thr Lys Leu Glu Ile
115 120 125

Lys Arg Thr Val Ala Ala Pro Ser Val Phe Ile Phe Pro Pro Ser Asp
130 135 140

Glu Gln Leu Lys Ser Gly Thr Ala Ser Val Val Cys Leu Leu Asn Asn
145 150 155 160

Phe Tyr Pro Arg Glu Ala Lys Val Gln Trp Lys Val Asp Asn Ala Leu
165 170 175

Gln Ser Gly Asn Ser Gln Glu Ser Val Thr Glu Gln Asp Ser Lys Asp
180 185 190

Ser Thr Tyr Ser Leu Ser Ser Thr Leu Thr Leu Ser Lys Ala Asp Tyr
195 200 205

Glu Lys His Lys Val Tyr Ala Cys Glu Val Thr His Gln Gly Leu Ser
210 215 220

Ser Pro Val Thr Lys Ser Phe Asn Arg Gly Glu Cys
225 230 235

<210> SEQ ID NO 49
<211> LENGTH: 467
<212> TYPE: PRT
<213> ORGANISM: Artificial Sequence
<220> FEATURE:
<223> OTHER INFORMATION: Synthetic

<400> SEQUENCE: 49

Met Glu Phe Gly Leu Ser Trp Leu Phe Leu Val Ala Ile Leu Lys Gly
1 5 10 15

Val Gln Cys Glu Val Gln Leu Gln Gln Ser Gly Pro Val Leu Val Lys

-continued

```
            20                  25                  30

Pro Gly Ala Ser Val Lys Met Ser Cys Lys Ala Ser Gly Tyr Thr Phe
        35                  40                  45

Thr Asp Leu Tyr Met Asn Trp Leu Lys Gln Ser His Gly Lys Arg Leu
    50                  55                  60

Glu Trp Ile Gly Val Ile Asn Pro Tyr Asn Gly Gly Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Asp Leu Asn Ser Leu Thr Ser Glu Asp Ser Ala Val
            100                 105                 110

Tyr Tyr Cys Ala Arg Gly Asp Ser Ile Tyr Val Met Asp Tyr Trp Gly
        115                 120                 125

Gln Gly Thr Ser Phe Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445
```

His Glu Ala Leu His Asn His Tyr Thr Gln Lys Ser Leu Ser Leu Ser
    450                 455                 460

Pro Gly Lys
465

<210> SEQ ID NO 50
<211> LENGTH: 236
<212> TYPE: PRT
<213> ORGANISM: Artificial Sequence
<220> FEATURE:
<223> OTHER INFORMATION: Synthetic

<400> SEQUENCE: 50

Met Asp Met Arg Val Pro Ala Gln Leu Leu Gly Leu Leu Leu Leu Trp
1               5                   10                  15

Phe Pro Gly Ser Arg Cys Glu Asn Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Ser Tyr Met His Trp Tyr Gln Gln Lys Ser Ser Thr Ser
    50                  55                  60

Pro Lys Leu Trp Ile Tyr Asp Thr Ser Lys Leu Ser Ser Gly Val Pro
65                  70                  75                  80

Gly Arg Phe Ser Gly Ser Gly Ser Gly Lys Ser Tyr Ser Leu Thr Ile
                85                  90                  95

Ser Ser Met Glu Ala Glu Asp Val Ala Thr Tyr Tyr Cys Phe Gln Gly
            100                 105                 110

Ser Gly Tyr Pro Leu Phe Thr Phe Gly Ser Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 51
<211> LENGTH: 242
<212> TYPE: PRT
<213> ORGANISM: Artificial Sequence
<220> FEATURE:
<223> OTHER INFORMATION: Synthetic

<400> SEQUENCE: 51

Met Asp Met Arg Val Pro Ala Gln Leu Leu Gly Leu Leu Leu Leu Trp
1               5                   10                  15

Phe Pro Gly Ser Arg Cys Asp Ile Val Met Thr Gln Ser Pro Ser Ser
            20                  25                  30

Leu Ala Met Ser Val Gly Gln Lys Val Thr Met Ser Cys Lys Ser Ser

```
        35                  40                  45

Gln Ser Leu Leu Asn Ser Ser Ile Gln Lys Asn Tyr Leu Ala Trp Tyr
    50                  55                  60

Gln Gln Lys Pro Gly Gln Ser Pro Lys Leu Leu Ile Tyr Phe Ala Ser
65                  70                  75                  80

Thr Arg Glu Ser Gly Val Pro Asp Arg Phe Ile Gly Ser Gly Ser Gly
                85                  90                  95

Thr Asp Phe Thr Leu Thr Ile Ser Ser Val Gln Ala Glu Asp Leu Ala
            100                 105                 110

Asp Tyr Phe Cys Gln Gln His Tyr Ser Thr Pro Leu Thr Phe Gly Ala
        115                 120                 125

Gly Thr Lys Leu Glu Leu Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys


<210> SEQ ID NO 52
<211> LENGTH: 21
<212> TYPE: PRT
<213> ORGANISM: Artificial Sequence
<220> FEATURE:
<223> OTHER INFORMATION: Synthetic

<400> SEQUENCE: 52

Met Ala Leu Pro Val Thr Ala Leu Leu Leu Pro Leu Ala Leu Leu Leu
1               5                   10                  15

His Ala Ala Arg Pro
            20


<210> SEQ ID NO 53
<211> LENGTH: 107
<212> TYPE: PRT
<213> ORGANISM: Artificial Sequence
<220> FEATURE:
<223> OTHER INFORMATION: Synthetic

<400> SEQUENCE: 53

Asp Ile Val Met Thr Gln Ser Gln Arg Phe Met Ser Thr Ser Val Gly
1               5                   10                  15

Asp Arg Val Ser Ile Thr Cys Lys Ala Ser Gln Ser Val Gly Thr Ala
            20                  25                  30

Val Ala Trp Tyr Gln Gln Thr Pro Gly Gln Phe Pro Lys Leu Leu Ile
        35                  40                  45

Tyr Ser Thr Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
```

-continued

```
65                  70                  75                  80

Glu Asp Leu Ala Asp Tyr Phe Cys Gln Gln Tyr Ser Thr Tyr Pro Leu
                85                  90                  95

Thr Phe Gly Ser Gly Thr Lys Leu Glu Leu Lys
            100                 105


<210> SEQ ID NO 54
<211> LENGTH: 121
<212> TYPE: PRT
<213> ORGANISM: Artificial Sequence
<220> FEATURE:
<223> OTHER INFORMATION: Synthetic

<400> SEQUENCE: 54

Glu Val Gln Leu Gln Gln Ser Gly Pro Glu Leu Val Lys Pro Gly Ala
1               5                   10                  15

Ser Met Lys Ile Ser Cys Lys Ala Ser Asp Tyr Ser Phe Thr Asp Tyr
            20                  25                  30

Ile Met Thr Trp Val Lys Gln Ser His Gly Lys Asn Leu Glu Trp Ile
        35                  40                  45

Gly Leu Ile Asn Pro Tyr Asn Gly Gly Thr Thr Tyr Asn Gln Lys Phe
    50                  55                  60

Lys Asp Lys Ala Thr Phe Thr Val Asp Lys Ser Ser Thr Thr Ala Tyr
65                  70                  75                  80

Met Asp Leu Leu Ser Leu Thr Ser Glu Asp Ser Ala Val Tyr Tyr Cys
                85                  90                  95

Ala Arg Arg Gly Ile Thr Thr Asp Tyr Tyr Thr Met Asp Tyr Trp Gly
            100                 105                 110

Gln Gly Thr Ser Val Thr Val Ser Ser
        115                 120


<210> SEQ ID NO 55
<211> LENGTH: 113
<212> TYPE: PRT
<213> ORGANISM: Artificial Sequence
<220> FEATURE:
<223> OTHER INFORMATION: Synthetic

<400> SEQUENCE: 55

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Ile Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ser Pro Leu Thr Phe Gly Ala Gly Thr Lys Leu Glu Leu
            100                 105                 110

Lys


<210> SEQ ID NO 56
<211> LENGTH: 118
<212> TYPE: PRT
```

<213> ORGANISM: Artificial Sequence
<220> FEATURE:
<223> OTHER INFORMATION: Synthetic

<400> SEQUENCE: 56

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Leu
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Gly Thr Ser Tyr Asn Gln Lys Phe
    50                  55                  60

Lys Ala Lys Ala Thr Leu Thr Val Asp Lys Ser Ser Ile Thr Ala Tyr
65                  70                  75                  80

Met Glu Leu Asn Ser Leu Thr Ser Glu Asp Ser Ala Val Tyr Tyr Cys
                85                  90                  95

Ala Arg Gly Asp Ser Ile Tyr Val Met Asp Tyr Trp Gly Gln Gly Thr
            100                 105                 110

Ser Val Thr Val Ser Ser
        115
```

<210> SEQ ID NO 57
<211> LENGTH: 107
<212> TYPE: PRT
<213> ORGANISM: Artificial Sequence
<220> FEATURE:
<223> OTHER INFORMATION: Synthetic

<400> SEQUENCE: 57

```
Asp Ile Val Met Thr Pro Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln His Tyr Asn Ser Tyr Pro Phe
                85                  90                  95

Thr Phe Gly Ser Gly Thr Lys Leu Glu Ile Lys
            100                 105
```

<210> SEQ ID NO 58
<211> LENGTH: 122
<212> TYPE: PRT
<213> ORGANISM: Artificial Sequence
<220> FEATURE:
<223> OTHER INFORMATION: Synthetic

<400> SEQUENCE: 58

```
Glu Val Lys Leu Leu Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45
```

Gly Glu Ile Asn Pro Asp Ser Ser Thr Ile Asn Tyr Ala Pro Ser Leu
50 55 60

Lys Asp Lys Phe Ile Ile Ser Arg Asp Ala Ala Lys Asn Thr Leu Tyr
65 70 75 80

Leu Gln Met Ser Lys Val Arg Ser Glu Asp Thr Ala Leu Tyr Tyr Cys
85 90 95

Ala Thr Leu Tyr Tyr Asp Tyr Asp Gly Asp Tyr Ala Met Asp Tyr Trp
100 105 110

Gly Gln Gly Thr Ser Val Thr Val Ser Ser
115 120

<210> SEQ ID NO 59
<211> LENGTH: 113
<212> TYPE: PRT
<213> ORGANISM: Artificial Sequence
<220> FEATURE:
<223> OTHER INFORMATION: Synthetic

<400> SEQUENCE: 59

Asp Ile Val Met Thr Gln Ser Pro Ser Ser Leu Ala Met Ser Val Gly
1 5 10 15

Gln Lys Val Thr Met Ser Cys Lys Ser Ser Gln Ser Leu Leu Asn Ser
20 25 30

Ser Ile Gln Lys Asn Tyr Leu Ala Trp Tyr Gln Gln Lys Pro Gly Gln
35 40 45

Ser Pro Lys Leu Leu Ile Tyr Phe Ala Ser Thr Arg Glu Ser Gly Val
50 55 60

Pro Asp Arg Phe Ile Gly Ser Gly Ser Gly Thr Asp Phe Thr Leu Thr
65 70 75 80

Ile Ser Ser Val Gln Ala Glu Asp Leu Ala Asp Tyr Phe Cys Gln Gln
85 90 95

His Tyr Ser Thr Pro Leu Thr Phe Gly Ala Gly Thr Lys Leu Glu Leu
100 105 110

Lys

<210> SEQ ID NO 60
<211> LENGTH: 118
<212> TYPE: PRT
<213> ORGANISM: Artificial Sequence
<220> FEATURE:
<223> OTHER INFORMATION: Synthetic

<400> SEQUENCE: 60

Glu Val Gln Leu Gln Gln Ser Gly Pro Val Leu Val Lys Pro Gly Ala
1 5 10 15

Ser Val Lys Met Ser Cys Lys Ala Ser Gly Tyr Thr Phe Thr Asp Leu
20 25 30

Tyr Met Asn Trp Leu Lys Gln Ser His Gly Lys Arg Leu Glu Trp Ile
35 40 45

Gly Val Ile Asn Pro Tyr Asn Gly Gly Thr Ser Tyr Asn Gln Lys Phe
50 55 60

Lys Gly Lys Ala Thr Leu Thr Val Asp Lys Ser Ser Ser Thr Ala Tyr
65 70 75 80

Met Asp Leu Asn Ser Leu Thr Ser Glu Asp Ser Ala Val Tyr Tyr Cys
85 90 95

Ala Arg Gly Asp Ser Ile Tyr Val Met Asp Tyr Trp Gly Gln Gly Thr
100 105 110

```
Ser Phe Thr Val Ser Ser
        115


<210> SEQ ID NO 61
<211> LENGTH: 107
<212> TYPE: PRT
<213> ORGANISM: Artificial Sequence
<220> FEATURE:
<223> OTHER INFORMATION: Synthetic

<400> SEQUENCE: 61

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ser Ser Gly Val Pro Gly Arg Phe Ser Gly Ser
    50                  55                  60

Gly Ser Gly Lys Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Phe
                85                  90                  95

Thr Phe Gly Ser Gly Thr Lys Leu Glu Ile Lys
            100                 105


<210> SEQ ID NO 62
<211> LENGTH: 118
<212> TYPE: PRT
<213> ORGANISM: Artificial Sequence
<220> FEATURE:
<223> OTHER INFORMATION: Synthetic

<400> SEQUENCE: 62

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Leu
            20                  25                  30

Tyr Met Asn Trp Leu Lys Gln Ser His Gly Lys Arg Leu Glu Trp Ile
        35                  40                  45

Gly Val Ile Asn Pro Tyr Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Arg Gly Asp Ser Ile Tyr Val Met Asp Tyr Trp Gly Gln Gly Thr
            100                 105                 110

Ser Phe Thr Val Ser Ser
        115


<210> SEQ ID NO 63
<211> LENGTH: 113
<212> TYPE: PRT
<213> ORGANISM: Artificial Sequence
<220> FEATURE:
<223> OTHER INFORMATION: Synthetic

<400> SEQUENCE: 63
```

Asp Ile Val Met Thr Gln Ser Pro Ser Ser Leu Ala Leu Ser Val Gly
1 5 10 15

Gln Lys Val Thr Met Ser Cys Lys Ser Ser Gln Ser Leu Leu Asp Asn
20 25 30

Ser Asn Gln Lys His Tyr Leu Ala Trp Tyr Gln Gln Lys Pro Gly Gln
35 40 45

Ser Pro Lys Leu Leu Val Tyr Phe Ala Ser Thr Arg Glu Ser Gly Val
50 55 60

Pro Asp Arg Phe Ile Gly Ser Gly Ser Gly Thr Asp Phe Thr Leu Thr
65 70 75 80

Ile Ser Ser Val Gln Ala Glu Asp Leu Ala Asp Tyr Phe Cys Gln Gln
85 90 95

His Tyr Thr Ala Pro Leu Thr Phe Gly Ala Gly Thr Lys Leu Ala Leu
100 105 110

Lys

<210> SEQ ID NO 64
<211> LENGTH: 118
<212> TYPE: PRT
<213> ORGANISM: Artificial Sequence
<220> FEATURE:
<223> OTHER INFORMATION: Synthetic

<400> SEQUENCE: 64

Glu Val Gln Leu Gln Gln Ser Gly Pro Val Leu Val Lys Pro Gly Ala
1 5 10 15

Ser Val Lys Met Ser Cys Lys Val Ser Gly Tyr Thr Phe Thr Asp Tyr
20 25 30

Tyr Met Asn Trp Val Lys Gln Ser His Gly Lys Ser Leu Glu Trp Ile
35 40 45

Gly Val Ile Thr Pro Tyr Asn Gly Ala Asn Arg Tyr Asn Gln Lys Phe
50 55 60

Lys Gly Lys Ala Thr Leu Thr Val Asp Lys Ser Ser Ser Thr Ala Tyr
65 70 75 80

Met Glu Val Ser Ser Leu Thr Ser Glu Asp Ser Ala Val Tyr Tyr Cys
85 90 95

Ala Arg Gly Asp Ser Ile Tyr Val Met Asp Tyr Trp Gly Gln Gly Thr
100 105 110

Ser Val Ile Val Ser Ser
115

<210> SEQ ID NO 65
<211> LENGTH: 113
<212> TYPE: PRT
<213> ORGANISM: Artificial Sequence
<220> FEATURE:
<223> OTHER INFORMATION: Synthetic

<400> SEQUENCE: 65

Asp Ile Val Met Thr Gln Ser Pro Ser Ser Leu Ala Met Ser Val Gly
1 5 10 15

Gln Lys Val Thr Met Ser Cys Lys Ser Ser Gln Ser Leu Leu Asn Ser
20 25 30

Ser Ile Gln Lys Asn Tyr Leu Ala Trp Tyr Gln Gln Lys Pro Gly Gln
35 40 45

Ser Pro Lys Leu Leu Val Tyr Phe Ala Ser Thr Arg Glu Ser Gly Val
50 55 60

```
Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Gly Gly Thr Lys Leu Glu Leu
            100                 105                 110

Lys
```

<210> SEQ ID NO 66
<211> LENGTH: 118
<212> TYPE: PRT
<213> ORGANISM: Artificial Sequence
<220> FEATURE:
<223> OTHER INFORMATION: Synthetic

<400> SEQUENCE: 66

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Ser Leu Asn Trp Val Lys Gln Ser His Gly Lys Ser Leu Glu Trp Ile
        35                  40                  45

Gly Val Val Asn Pro Tyr Asn Gly Gly Thr Ser His Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Pro Asp Ser Ile Tyr Val Met Asp Tyr Trp Gly Gln Gly Thr
            100                 105                 110

Ser Val Thr Val Ser Ser
        115
```

<210> SEQ ID NO 67
<211> LENGTH: 113
<212> TYPE: PRT
<213> ORGANISM: Artificial Sequence
<220> FEATURE:
<223> OTHER INFORMATION: Synthetic

<400> SEQUENCE: 67

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Asn Ile Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys
```

<210> SEQ ID NO 68
<211> LENGTH: 118
<212> TYPE: PRT
<213> ORGANISM: Artificial Sequence
<220> FEATURE:
<223> OTHER INFORMATION: Synthetic

<400> SEQUENCE: 68

```
Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Ser Leu Asn Trp Val Lys Gln Ser His Gly Lys Ser Leu Glu Trp Ile
        35                  40                  45

Gly Val Val Asn Pro Tyr Asn Gly Gly Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Pro Asp Ser Ile Tyr Val Met Asp Ser Trp Gly Gln Gly Thr
            100                 105                 110

Ser Val Thr Val Ser Ser
        115
```

<210> SEQ ID NO 69
<211> LENGTH: 107
<212> TYPE: PRT
<213> ORGANISM: Artificial Sequence
<220> FEATURE:
<223> OTHER INFORMATION: Synthetic

<400> SEQUENCE: 69

```
Asp Ile Lys Met Thr Gln Ser Pro Ser Ser Met Tyr Val Ser Leu Gly
1               5                   10                  15

Glu Arg Val Thr Ile Thr Cys Lys Ala Ser Gln Asp Ile Asn Arg Asn
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Leu Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105
```

<210> SEQ ID NO 70
<211> LENGTH: 117
<212> TYPE: PRT
<213> ORGANISM: Artificial Sequence
<220> FEATURE:
<223> OTHER INFORMATION: Synthetic

<400> SEQUENCE: 70

```
Gln Val Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Asn Thr Ser
            20                  25                  30
```

Gly Met Gly Val Asn Trp Ile Arg Gln Ser Ser Gly Lys Asp Leu Glu
35 40 45

Trp Leu Ala His Ile Tyr Trp Asn Asp Asp Lys Arg Tyr Asn Pro Ser
50 55 60

Leu Lys Ser Arg Leu Thr Ile Ser Lys Asp Thr Ser Arg Asn Gln Val
65 70 75 80

Phe Leu Arg Ile Thr Ser Val Asp Ala Thr Asp Thr Ala Thr Tyr Phe
85 90 95

Cys Cys Arg Ser Arg Leu Ser Phe Asp Tyr Trp Gly His Gly Thr Thr
100 105 110

Leu Thr Val Ser Ser
115

<210> SEQ ID NO 71
<211> LENGTH: 15
<212> TYPE: PRT
<213> ORGANISM: Artificial Sequence
<220> FEATURE:
<223> OTHER INFORMATION: Synthetic

<400> SEQUENCE: 71

Gly Gly Gly Gly Ser Gly Gly Gly Gly Ser Gly Gly Gly Gly Ser
1 5 10 15

<210> SEQ ID NO 72
<211> LENGTH: 55
<212> TYPE: PRT
<213> ORGANISM: Artificial Sequence
<220> FEATURE:
<223> OTHER INFORMATION: Synthetic

<400> SEQUENCE: 72

Phe Val Pro Val Phe Leu Pro Ala Lys Pro Thr Thr Thr Pro Ala Pro
1 5 10 15

Arg Pro Pro Thr Pro Ala Pro Thr Ile Ala Ser Gln Pro Leu Ser Leu
20 25 30

Arg Pro Glu Ala Cys Arg Pro Ala Ala Gly Gly Ala Val His Thr Arg
35 40 45

Gly Leu Asp Phe Ala Cys Asp
50 55

<210> SEQ ID NO 73
<211> LENGTH: 24
<212> TYPE: PRT
<213> ORGANISM: Artificial Sequence
<220> FEATURE:
<223> OTHER INFORMATION: Synthetic

<400> SEQUENCE: 73

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 74
<211> LENGTH: 42
<212> TYPE: PRT
<213> ORGANISM: Artificial Sequence
<220> FEATURE:
<223> OTHER INFORMATION: Synthetic

<400> SEQUENCE: 74

-continued

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 75
<211> LENGTH: 113
<212> TYPE: PRT
<213> ORGANISM: Artificial Sequence
<220> FEATURE:
<223> OTHER INFORMATION: Synthetic

<400> SEQUENCE: 75

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 76
<211> LENGTH: 11
<212> TYPE: PRT
<213> ORGANISM: Mus musculus

<400> SEQUENCE: 76

```
Lys Ala Ser Gln Ser Val Gly Thr Ala Val Ala
1               5                   10
```

<210> SEQ ID NO 77
<211> LENGTH: 7
<212> TYPE: PRT
<213> ORGANISM: Mus musculus

<400> SEQUENCE: 77

```
Ser Thr Ser Asn Arg Tyr Thr
1               5
```

<210> SEQ ID NO 78
<211> LENGTH: 9
<212> TYPE: PRT
<213> ORGANISM: Mus musculus

<400> SEQUENCE: 78

```
Gln Gln Tyr Ser Thr Tyr Pro Leu Thr
1               5
```

<210> SEQ ID NO 79
<211> LENGTH: 5

<212> TYPE: PRT
<213> ORGANISM: Mus musculus

<400> SEQUENCE: 79

Asp Tyr Ile Met Thr
1 5

<210> SEQ ID NO 80
<211> LENGTH: 17
<212> TYPE: PRT
<213> ORGANISM: Mus musculus

<400> SEQUENCE: 80

Leu Ile Asn Pro Tyr Asn Gly Gly Thr Thr Tyr Asn Gln Lys Phe Lys
1 5 10 15

Asp

<210> SEQ ID NO 81
<211> LENGTH: 12
<212> TYPE: PRT
<213> ORGANISM: Mus musculus

<400> SEQUENCE: 81

Arg Gly Ile Thr Thr Asp Tyr Tyr Thr Met Asp Tyr
1 5 10

<210> SEQ ID NO 82
<211> LENGTH: 17
<212> TYPE: PRT
<213> ORGANISM: Mus musculus

<400> SEQUENCE: 82

Lys Ser Ser Gln Ser Leu Leu Asn Ser Ser Ile Gln Lys Asn Tyr Leu
1 5 10 15

Ala

<210> SEQ ID NO 83
<211> LENGTH: 7
<212> TYPE: PRT
<213> ORGANISM: Mus musculus

<400> SEQUENCE: 83

Phe Ala Ser Thr Arg Glu Ser
1 5

<210> SEQ ID NO 84
<211> LENGTH: 9
<212> TYPE: PRT
<213> ORGANISM: Mus musculus

<400> SEQUENCE: 84

Gln Gln His Tyr Ser Ser Pro Leu Thr
1 5

<210> SEQ ID NO 85
<211> LENGTH: 5
<212> TYPE: PRT
<213> ORGANISM: Mus musculus

<400> SEQUENCE: 85

Asp Leu Tyr Met Asn
1 5

<210> SEQ ID NO 86
<211> LENGTH: 17
<212> TYPE: PRT
<213> ORGANISM: Mus musculus

<400> SEQUENCE: 86

Val Ile Asn Pro Tyr Asn Gly Gly Thr Ser Tyr Asn Gln Lys Phe Lys
1 5 10 15

Ala

<210> SEQ ID NO 87
<211> LENGTH: 9
<212> TYPE: PRT
<213> ORGANISM: Mus musculus

<400> SEQUENCE: 87

Gly Asp Ser Ile Tyr Val Met Asp Tyr
1 5

<210> SEQ ID NO 88
<211> LENGTH: 11
<212> TYPE: PRT
<213> ORGANISM: Mus musculus

<400> SEQUENCE: 88

Lys Ala Ser Gln Asn Val Gly Thr Asn Val Ala
1 5 10

<210> SEQ ID NO 89
<211> LENGTH: 7
<212> TYPE: PRT
<213> ORGANISM: Mus musculus

<400> SEQUENCE: 89

Ser Ala Ser Tyr Arg Tyr Ser
1 5

<210> SEQ ID NO 90
<211> LENGTH: 9
<212> TYPE: PRT
<213> ORGANISM: Mus musculus

<400> SEQUENCE: 90

Gln His Tyr Asn Ser Tyr Pro Phe Thr
1 5

<210> SEQ ID NO 91
<211> LENGTH: 5
<212> TYPE: PRT
<213> ORGANISM: Mus musculus

<400> SEQUENCE: 91

Arg Tyr Trp Met Ser
1 5

<210> SEQ ID NO 92
<211> LENGTH: 17
<212> TYPE: PRT
<213> ORGANISM: Mus musculus

<400> SEQUENCE: 92

Glu Ile Asn Pro Asp Ser Ser Thr Ile Asn Tyr Ala Pro Ser Leu Lys
1 5 10 15

Asp

<210> SEQ ID NO 93
<211> LENGTH: 13
<212> TYPE: PRT
<213> ORGANISM: Mus musculus

<400> SEQUENCE: 93

Leu Tyr Tyr Asp Tyr Asp Gly Asp Tyr Ala Met Asp Tyr
1               5                   10

<210> SEQ ID NO 94
<211> LENGTH: 17
<212> TYPE: PRT
<213> ORGANISM: Mus musculus

<400> SEQUENCE: 94

Lys Ser Ser Gln Ser Leu Leu Asn Ser Ser Ile Gln Lys Asn Tyr Leu
1               5                   10                  15

Ala

<210> SEQ ID NO 95
<211> LENGTH: 7
<212> TYPE: PRT
<213> ORGANISM: Mus musculus

<400> SEQUENCE: 95

Phe Ala Ser Thr Arg Glu Ser
1               5

<210> SEQ ID NO 96
<211> LENGTH: 9
<212> TYPE: PRT
<213> ORGANISM: Mus musculus

<400> SEQUENCE: 96

Gln Gln His Tyr Ser Thr Pro Leu Thr
1               5

<210> SEQ ID NO 97
<211> LENGTH: 5
<212> TYPE: PRT
<213> ORGANISM: Mus musculus

<400> SEQUENCE: 97

Asp Leu Tyr Met Asn
1               5

<210> SEQ ID NO 98
<211> LENGTH: 17
<212> TYPE: PRT
<213> ORGANISM: Mus musculus

<400> SEQUENCE: 98

Val Ile Asn Pro Tyr Asn Gly Gly Thr Ser Tyr Asn Gln Lys Phe Lys
1               5                   10                  15

Gly

<210> SEQ ID NO 99
<211> LENGTH: 9
<212> TYPE: PRT
<213> ORGANISM: Mus musculus

<400> SEQUENCE: 99

-continued

Gly Asp Ser Ile Tyr Val Met Asp Tyr
1 5

<210> SEQ ID NO 100
<211> LENGTH: 10
<212> TYPE: PRT
<213> ORGANISM: Mus musculus

<400> SEQUENCE: 100

Ser Ala Ser Ser Ser Val Ser Tyr Met His
1 5 10

<210> SEQ ID NO 101
<211> LENGTH: 7
<212> TYPE: PRT
<213> ORGANISM: Mus musculus

<400> SEQUENCE: 101

Asp Thr Ser Lys Leu Ser Ser
1 5

<210> SEQ ID NO 102
<211> LENGTH: 10
<212> TYPE: PRT
<213> ORGANISM: Mus musculus

<400> SEQUENCE: 102

Phe Gln Gly Ser Gly Tyr Pro Leu Phe Thr
1 5 10

<210> SEQ ID NO 103
<211> LENGTH: 5
<212> TYPE: PRT
<213> ORGANISM: Mus musculus

<400> SEQUENCE: 103

Asp Leu Tyr Met Asn
1 5

<210> SEQ ID NO 104
<211> LENGTH: 17
<212> TYPE: PRT
<213> ORGANISM: Mus musculus

<400> SEQUENCE: 104

Val Ile Asn Pro Tyr Asn Gly Gly Thr Ser Tyr Asn Gln Lys Phe Lys
1 5 10 15

Gly

<210> SEQ ID NO 105
<211> LENGTH: 9
<212> TYPE: PRT
<213> ORGANISM: Mus musculus

<400> SEQUENCE: 105

Gly Asp Ser Ile Tyr Val Met Asp Tyr
1 5

<210> SEQ ID NO 106
<211> LENGTH: 17
<212> TYPE: PRT
<213> ORGANISM: Mus musculus

<400> SEQUENCE: 106

-continued

```
Lys Ser Ser Gln Ser Leu Leu Asp Asn Ser Asn Gln Lys His Tyr Leu
1               5                   10                  15

Ala


<210> SEQ ID NO 107
<211> LENGTH: 7
<212> TYPE: PRT
<213> ORGANISM: Mus musculus

<400> SEQUENCE: 107

Phe Ala Ser Thr Arg Glu Ser
1               5


<210> SEQ ID NO 108
<211> LENGTH: 9
<212> TYPE: PRT
<213> ORGANISM: Mus musculus

<400> SEQUENCE: 108

Gln Gln His Tyr Thr Ala Pro Leu Thr
1               5


<210> SEQ ID NO 109
<211> LENGTH: 5
<212> TYPE: PRT
<213> ORGANISM: Mus musculus

<400> SEQUENCE: 109

Asp Tyr Tyr Met Asn
1               5


<210> SEQ ID NO 110
<211> LENGTH: 17
<212> TYPE: PRT
<213> ORGANISM: Mus musculus

<400> SEQUENCE: 110

Val Ile Thr Pro Tyr Asn Gly Ala Asn Arg Tyr Asn Gln Lys Phe Lys
1               5                   10                  15

Gly


<210> SEQ ID NO 111
<211> LENGTH: 9
<212> TYPE: PRT
<213> ORGANISM: Mus musculus

<400> SEQUENCE: 111

Gly Asp Ser Ile Tyr Val Met Asp Tyr
1               5


<210> SEQ ID NO 112
<211> LENGTH: 17
<212> TYPE: PRT
<213> ORGANISM: Mus musculus

<400> SEQUENCE: 112

Lys Ser Ser Gln Ser Leu Leu Asn Ser Ser Ile Gln Lys Asn Tyr Leu
1               5                   10                  15

Ala


<210> SEQ ID NO 113
<211> LENGTH: 7
<212> TYPE: PRT
```

<213> ORGANISM: Mus musculus

<400> SEQUENCE: 113

Phe Ala Ser Thr Arg Glu Ser
1 5

<210> SEQ ID NO 114
<211> LENGTH: 9
<212> TYPE: PRT
<213> ORGANISM: Mus musculus

<400> SEQUENCE: 114

Gln Gln His Tyr Ser Thr Pro Leu Thr
1 5

<210> SEQ ID NO 115
<211> LENGTH: 5
<212> TYPE: PRT
<213> ORGANISM: Mus musculus

<400> SEQUENCE: 115

Asp Tyr Ser Leu Asn
1 5

<210> SEQ ID NO 116
<211> LENGTH: 17
<212> TYPE: PRT
<213> ORGANISM: Mus musculus

<400> SEQUENCE: 116

Val Val Asn Pro Tyr Asn Gly Gly Thr Ser His Asn Gln Lys Phe Lys
1 5 10 15

Gly

<210> SEQ ID NO 117
<211> LENGTH: 9
<212> TYPE: PRT
<213> ORGANISM: Mus musculus

<400> SEQUENCE: 117

Pro Asp Ser Ile Tyr Val Met Asp Tyr
1 5

<210> SEQ ID NO 118
<211> LENGTH: 17
<212> TYPE: PRT
<213> ORGANISM: Mus musculus

<400> SEQUENCE: 118

Lys Ser Ser Gln Ser Leu Leu Asn Ser Asn Ile Gln Lys Asn Tyr Leu
1 5 10 15

Ala

<210> SEQ ID NO 119
<211> LENGTH: 7
<212> TYPE: PRT
<213> ORGANISM: Mus musculus

<400> SEQUENCE: 119

Phe Ala Ser Thr Arg Glu Ser
1 5

<210> SEQ ID NO 120

-continued

<211> LENGTH: 9
<212> TYPE: PRT
<213> ORGANISM: Mus musculus

<400> SEQUENCE: 120

Gln Gln His Tyr Ser Thr Pro Leu Thr
1               5

<210> SEQ ID NO 121
<211> LENGTH: 5
<212> TYPE: PRT
<213> ORGANISM: Mus musculus

<400> SEQUENCE: 121

Asp Tyr Ser Leu Asn
1               5

<210> SEQ ID NO 122
<211> LENGTH: 17
<212> TYPE: PRT
<213> ORGANISM: Mus musculus

<400> SEQUENCE: 122

Val Val Asn Pro Tyr Asn Gly Gly Thr Thr Tyr Asn Gln Lys Phe Lys
1               5                   10                  15

Gly

<210> SEQ ID NO 123
<211> LENGTH: 9
<212> TYPE: PRT
<213> ORGANISM: Mus musculus

<400> SEQUENCE: 123

Pro Asp Ser Ile Tyr Val Met Asp Ser
1               5

<210> SEQ ID NO 124
<211> LENGTH: 11
<212> TYPE: PRT
<213> ORGANISM: Mus musculus

<400> SEQUENCE: 124

Lys Ala Ser Gln Asp Ile Asn Arg Asn Leu Ser
1               5                   10

<210> SEQ ID NO 125
<211> LENGTH: 7
<212> TYPE: PRT
<213> ORGANISM: Mus musculus

<400> SEQUENCE: 125

Arg Ala Asn Arg Leu Val Asp
1               5

<210> SEQ ID NO 126
<211> LENGTH: 9
<212> TYPE: PRT
<213> ORGANISM: Mus musculus

<400> SEQUENCE: 126

Leu Gln Tyr Asp Glu Phe Pro Arg Thr
1               5

<210> SEQ ID NO 127

-continued

```
<211> LENGTH: 7
<212> TYPE: PRT
<213> ORGANISM: Mus musculus

<400> SEQUENCE: 127

Thr Ser Gly Met Gly Val Asn
1               5


<210> SEQ ID NO 128
<211> LENGTH: 16
<212> TYPE: PRT
<213> ORGANISM: Mus musculus

<400> SEQUENCE: 128

His Ile Tyr Trp Asn Asp Asp Lys Arg Tyr Asn Pro Ser Leu Lys Ser
1               5                   10                  15


<210> SEQ ID NO 129
<211> LENGTH: 7
<212> TYPE: PRT
<213> ORGANISM: Mus musculus

<400> SEQUENCE: 129

Ser Arg Leu Ser Phe Asp Tyr
1               5
```